(12) United States Patent
Ackermann et al.

(10) Patent No.: US 6,242,644 B1
(45) Date of Patent: Jun. 5, 2001

(54) N-(4-CARBAMIMIDOYL-PHENYL)-GLYCINE DERIVATIVES

(75) Inventors: Jean Ackermann, Riehen; Leo Alig, Kaiseraugst, both of (CH); Alexander Chucholowski, Grenzach-Wyhlen (DE); Katrin Groebke, Basle; Kurt Hilpert, Hofstetten, both of (CH); Holger Kuehne, Grenzach-Wyhlen (DE); Ulrike Obst, Grenzach-Wyhlen (DE); Lutz Weber, Grenzach-Wyhlen (DE); Hans Peter Wessel, Heitersheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/460,901

(22) Filed: Dec. 14, 1999

(30) Foreign Application Priority Data

Dec. 14, 1998 (EP) .................................................. 98123721

(51) Int. Cl.[7] ........................ C07C 243/18; C07C 251/16
(52) U.S. Cl. ........................ 562/439; 562/430; 562/433; 564/147; 564/157; 564/225; 564/244; 564/247
(58) Field of Search ................................. 564/147, 157, 564/225, 244, 247; 562/439, 430, 433

(56) References Cited

FOREIGN PATENT DOCUMENTS

| 2 255 180 | 4/1999 | (CA) . |
|---|---|---|
| 588655 | 3/1994 | (EP) . |
| 0739886 | * 10/1996 | (EP) . |
| 760364 | 3/1997 | (EP) . |
| 921116 | 6/1999 | (EP) . |
| 96/37464 | * 10/1996 | (WO) . |
| WO 9730971 | 8/1997 | (WO) . |
| WO 9941231 | 8/1999 | (WO) . |

OTHER PUBLICATIONS

Synthesis, Folkmann et al., (1990) pp. 1159–1166.
J.Med. Chem., Alexander et al., (1988) 31, pp. 318–322.

* cited by examiner

Primary Examiner—Alan L. Rotman
Assistant Examiner—Rita Desai
(74) Attorney, Agent, or Firm—George W. Johnston; William H. Epstein; John P. Parise

(57) ABSTRACT

The invention is concerned with novel N-(4-carbamimidoyl-phenyl)-glycine derivatives of the formula:

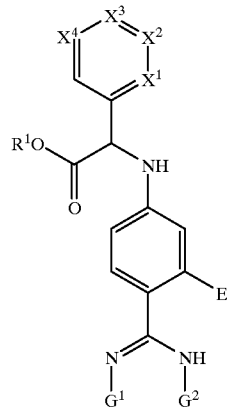

wherein $R^1$, E, $X^1$ to $X^4$ and $G^1$ and $G^2$ are as defined in the description and the claims, as well as hydrates or solvates and physiologically usable salts thereof.

22 Claims, No Drawings

N-(4-CARBAMIMIDOYL-PHENYL)-GLYCINE DERIVATIVES

BACKGROUND OF THE INVENTION

1. Field

The invention relates to N-(4-carbamimidoyl-phenyl)-glycine derivatives and methods for preparing and using such derivatives for treating diseases such as thrombosis, apoplexy, cardiac infarction, inflammation and arteriosclerosis, which are associated with coagulation factors Xa, IXa and thrombin.

2. Description

There is a continuing effort to identify compounds that inhibit the formation of coagulation factors Xa, IXa and thrombin induced by factor VIIa and tissue factor. The subject invention provides new compounds that are useful and have activity for this purpose.

SUMMARY OF THE INVENTION

The subject invention provides a compound of the formula:

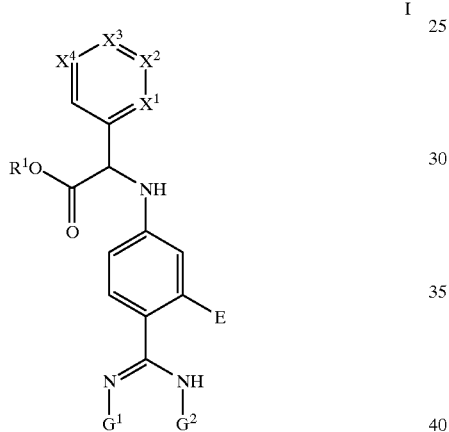

I wherein $R^1$ is hydrogen or the residue of an ester group that is cleavable under physiological conditions;

E is hydrogen or hydroxy;

three of the symbols $X^1$ to $X^4$, independent of each another, are each a group $C(R^a)$, $C(R^b)$ or $C(R^c)$ and the fourth symbol is a group $C(R^d)$ or N;

$R^a$ to $R^d$, independent of each other, are each hydrogen, alkenyl, alkenylcarbonyloxyalkoxy, alkenyloxy, alkynyl, alkynyloxy, alkoxy, alkoxyalkenyl, alkoxyalkoxy, alkoxyalkyl, alkoxyalkyl(alkyl)aminoalkyl, alkoxyalkylcarboxamido, alkoxycarbonyl, alkoxycarbonylalkoxy, alkoxycarbonylalkyl, alkoxycarbonylalkylcarboxamido, alkoxycarbonylarylalkoxy, alkoxycarbonylaryloxy, alkoxycarbonylcarboxamido, alkyl, alkyl(alkylcarbonyl)amino, alkylcarbonyl, alkylcarbonylalkoxy, alkylcarbonyloxyalkoxy, alkylcarboxamido, alkylcarboxamidoalkoxy, alkylsulphanyl, alkylsulphanylalkoxy, alkylsulphinyl, alkylsulphonyl, alkylsulphonylamino, alkylsulphonylaminoalkoxy, alkylureidyl, alkylthioureidyl, amino, aminoalkoxy, aryl, arylalkenyl, arylalkynyl, arylalkoxy, arylalkoxyalkoxy, arylalkyl, arylalkylcarboxamido, arylcarbonylalkoxy, arylcarboxamido, arylcarboxamidoalkoxy, aryloxy, aryloxyalkoxy, arylsulphonylamino, arylsulphonylaminoalkoxy, carboxy, carboxyalkyl, carboxyalkylcarboxamido, carboxyalkoxy, carboxyarylalkoxy, carboxyaryloxy, carboxycarboxamido, carbamoylalkoxy, cycloalkyl, cycloalkoxy, cycloalkylalkoxy, cycloalkylamino, cycloalkylaminoalkyl, cycloalkylaminocarbonyloxy, cycloalkylcarbamoylalkoxy, cycloalkylcarboxamido, dihydroxyalkoxy, halogen, haloalkenyl, haloalkoxy, haloalkyl, hydroxy, hydroxyalkoxy, hydroxyalkoxyalkoxy, hydroxyalkyl, hydroxycycloalkoxy, hydroxycycloalkylamino, mono- or di-alkylamino, mono- or di-alkylaminoalkoxy, mono- or di-alkylaminoalkyl, mono- or di-alkylaminocarbonylalkoxy, 2,2,2-trifluoroacetylaminoalkoxy, or an unsubstituted or substituted heterocyclic substituent selected from the group consisting of azepanylcarbonylalkoxy, benzoimidazolyl, morpholinylalkoxy, morpholinylalkyl, morpholinyloxoalkoxy, piperidinylalkoxy, piperidinylamino, piperidinylaminoalkyl, piperidinyloxy, alkylsulphonylpiperidinyloxy, furanylalkoxy, 1,3-dioxo-1,3-dihydroisoindolylalkyl, imidazolyl, imidazolylalkyl, isothiazolyloxy, dihydroisoxazolyl, piperazinyl, piperazinylalkyl, pyridinylaminoalkyl, bis-pyridinylalkylamino, pyridinyloxy, pyrimidinylaminoalkylazepanylideneamino, pyrrolidinyl, pyrrolidinylalkoxy, pyrrolidinylalkyl, pyrrolidinyloxy, pyrrolidinyloxoalkoxy, oxopyrrolidinylalkoxy, oxadiazolyl, tetrahydrofuranylalkoxy, tetrahydrofuranyloxy, tetrahydropyranylalkoxy, tetrahydropyranylamino, tetrahydrothiopyranylamino, tetrahydropyranyloxy, dioxohexahydrothiopyranylamino, thiazolylalkoxy and thiophenyl, with the subtituent on the substituted heterocyclic substituent being selected from the group consisting of alkyl, alkoxy, carboxyalkyl, hydroxy, tetrazolylmethoxy, alkylsulphonyl and alkoxycarbonylalkyl; or two adjacent groups $R^a$ to $R^d$ together form the remainder of a fused 1,4-dioxan, 1,3-dioxolan, 1-oxane or aryl ring, provided that not more than three of $R^a$ to $R^d$ are the same and $X^1$ is not substituted by carboxy or alkoxycarbonyl; and one of the symbols $G^1$ and $G^2$ is hydrogen and the other is hydrogen, alkyl, hydroxy, alkoxy, aroyl or a group COO—$R^e$ or OCO—$R^e$, where $R^e$ is alkyl or alkyl substituted by halogen, hydroxy, alkoxy, carboxy, alkylcarbonyloxycarbonyl, or arylcarbonyloxycarbonyl.

The subject invention also provides hydrates and solvates of the above compounds as well as physiologically usable salts of these compounds and their hydrates and solvates.

One preferred group of compounds are those where $R^a$ to $R^d$, each independent of each other, are each hydrogen, alkenyl, alkenylcarbonyloxyalkoxy, alkenyloxy, alkynyl, alkoxy, alkoxyalkenyl, alkoxyalkoxy, alkoxyalkyl, alkoxycarbonylalkoxy, alkoxycarbonylarylalkoxy, alkoxycarbonyloxy, alkyl, alkylcarbonylalkoxy, alkylcarbonyloxyalkoxy, alkylcarboxamidoalkoxy, alkylsulphanylalkoxy, aminoalkoxy, aryl, arylalkenyl, arylalkoxy, arylalkoxyalkoxy, arylalkyl, arylcarbonylalkoxy, arylcarboxamidoalkoxy, aryloxy, aryloxyalkoxy, carboxy, carboxyalkyl, carboxyalkoxy, carboxyarylalkoxy, carboxyaryloxy, carbamoylalkoxy, cycloalkyl, cycloalkoxy, cycloalkylalkoxy, cycloalkylamino, cycloalkylaminoalkyl, cycloalkylaminocarbonyloxy, cycloalkylcarbamoylalkoxy, dihydroxyalkoxy, halogen, haloalkenyl, haloalkoxy, haloalkyl, hydroxyalkoxy, hydroxyalkoxyalkoxy, hydroxyalkyl, hydroxycycloalkoxy, mono- or di-alkylaminoalkoxy, mono- or di-alkylaminoalkyl, mono- or di-alkylaminocarbonylalkoxy, or an unsubstituted or substituted heterocyclic substituent selected from the group consisting of morpholinylalkoxy, morpholinylalkyl, morpholinyloxoalkoxy, piperidinylalkoxy, piperidinyloxy, pyridinylaminoalkyl, alkylsulphonylpiperidinyloxy, furanylalkoxy, imidazolylalkyl, isothiazolyloxy, pyrrolidinyl, pyrrolidinylalkoxy, pyrrolidinylalkyl, pyrrolidinyloxy, pyrrolidinyloxoalkoxy, oxadiazolyl, tetrahydrofuranylalkoxy, tetrahydrofuranyloxy, tetrahydropyranylalkoxy, tetrahydropyranyloxy and thiazolylalkoxy, with the subtituent on the substituted heterocyclic substituent being selected from the group consisting of alkyl, alkoxy, tetrazolylmethoxy, alkylsulphonyl and alkoxycarbonylalkyl, or two adjacent groups $R^a$ to $R^d$ together form the remainder of a 1,4-dioxan, 1,3-dioxolan, 1-oxane or aryl ring.

A further preferred group of compounds are those where $R^a$ to $R^d$, each independent of each other, are each alkenyl, alkenyloxy, alkynyl, alkoxy, alkoxyalkenyl, alkoxyalkoxy, alkoxyalkyl, alkoxycarbonylarylalkoxy, alkyl, alkylcarbonylalkoxy, alkylsulphanylalkoxy, arylcarboxamidoalkoxy, carbamoylalkoxy, carboxyarylalkoxy, cycloalkoxy, cycloalkylalkoxy, cycloalkylaminocarbonyloxy, cycloalkylcarbamoylalkoxy, dihydroxyalkoxy, halogen, haloalkenyl, haloalkoxy, haloalkyl, hydroxyalkoxy, hydroxyalkoxyalkoxy, hydroxyalkyl, hydroxycycloalkoxy, mono- or di-alkylaminoalkoxy, or an unsubstituted or substituted heterocyclic substituent selected from the group consisting of piperidinyloxy, furanylalkoxy, isothiazolyloxy, morpholinylalkyl, pyridinylaminoalkyl, pyrrolidinylalkyl, pyrrolidinyloxy, tetrahydrofuranyloxy and tetrahydropyranyloxy, with the subtituent on the substituted heterocyclic substituent being selected from the group consisting of alkyl, alkoxy, tetrazolylmethoxy, alkylsulphonyl or alkoxycarbonylalkyl.

Another preferred group of compounds are those where $R^a$ to $R^d$, each independent of each other, are each hydrogen, alkenyl, alkynyl, alkoxy, alkyl, carbamoylalkoxy, cycloalkoxy, cycloalkylalkoxy, dihydroxyalkoxy, halogen, haloalkoxy, haloalkyl, hydroxyalkoxy, hydroxyalkyl, hydroxycycloalkoxy, mono- or di-alkylaminoalkoxy, or an unsubstituted or substituted heterocyclic substituent selected from the group consisting of morpholinylalkyl, piperidinyloxy, pyridinylaminoalkyl, pyrrolidinylalkyl, pyrrolidinyloxy and tetrahydropyranyloxy, with the subtituent on the substituted heterocyclic substituent being selected from the group consisting of alkyl, alkoxy, tetrazolylmethoxy, alkylsulphonyl, and alkoxycarbonylalkyl.

Yet another preferred group of compounds are those where $R^a$ to $R^d$, each independent of each other, are each hydrogen, alkenyl, alkynyl, alkoxy, alkyl, carbamoylalkoxy, halogen, hydroxyalkoxy, hydroxycycloalkoxy or mono- or di-alkylaminoalkoxy or an unsubstituted or substituted heterocyclic substituent selected from the group consisting of morpholinylalkyl, piperidinyloxy, pyridinylaminoalkyl, pyrrolidinylalkyl and tetrahydropyranyloxy, with the subtituent on the substituted heterocyclic substituent being selected from the group consisting of alkyl, alkoxy, tetrazolylmethoxy, alkylsulphonyl, and alkoxycarbonylalkyl.

Preferred groups for X are wherein $X^1$ is the group $C(R^a)$, $X^2$ is the group $C(R^b)$, $X^3$ is the group $C(R^c)$, and $X^4$ is the group $C(R^d)$. In such compounds, $R^a$ is favorably hydrogen, carbamoylalkoxy, hydroxyalkoxy, or halogen, especially hydrogen; $R^b$ is favorably hydrogen, alkenyl, alkynyl, alkoxy, or alkyl, especially alkoxy; $R^c$ is favorably hydrogen, alkoxy, mono- or di-alkylaminoalkoxy, or hydroxyalkoxy, especially hydrogen or alkoxy; and $R^d$ is favorably hydrogen, alkoxy, hydroxycycloalkoxy, mono- or di-alkylaminoalkoxy, or an unsubstituted or substituted heterocyclic substituent selected from the group of morpholinylalkyl, piperidinyloxy, pyridinylaminoalkyl, pyrrolidinylalkyl and tetrahydropyranyloxy, with the subtituent on the substituted heterocyclic substituent being alkyl or alkylsulphonyl.

It is also preferred that one of $G^1$ and $G^2$ is hydrogen and the other is hydrogen, alkyl, hydroxy, alkoxy, aroyl, or a group COO—$R^e$ or OCO—$R^e$, where $R^e$ is alkyl or alkyl substituted with halogen, hydroxy, alkoxy, carboxy, alkylcarbonyloxycarbonyl, or arylcarbonyloxycarbonyl. More preferred combinations of $G^1$ and $G^2$ are hydrogen and hydroxy, especially hydrogen and hydrogen. $R^1$ and E are favorably hydrogen.

The subject invention provides a preferred compounds of the formula:

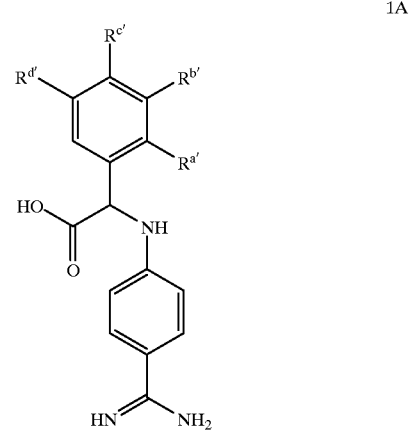

1A wherein, $R^{a'}$ is hydrogen, halogen, hydroxyalkoxy, or carbamoylalkoxy;

$R^{b'}$ is hydrogen, alkyl, alkoxy, hydroxycycloalkoxy, alkylpiperidinyloxy, alkylsulphonylpiperidinyloxy, tetrahydropyranyloxy, pyrrolidinylalkyl, alkenyl, or hydroxyalkoxy;

$R^{c'}$ is hydrogen, dialkylaminoalkoxy, hydroxyalkylalkoxy, hydroxyalkoxy, or alkoxy; and $R^{d'}$ is hydrogen, dialkylaminoalkoxy, alkoxy, alkynyl, pyrrolidinylalkyl, pyridinylaminoalkyl, or morpholinylalkyl.

This preferred group of compounds also includes hydrates and solvates thereof, and physiologically usable salts of the above mentioned compounds.

Rather than reciting every combination of $R^{a'}$, $R^{b'}$, $R^{c'}$, and $R^{d'}$, it is to be understood that all combinations of the recited substituents are possible to form compounds within the subject invention. For example, $R^{a'}$ can be hydrogen, halogen, for example flourine, hydroxyalkoxy, hydroxyethoxy, carbamoylalkoxy, or carbamoylmethoxy in combination with any grouping of $R^{b'}$, $R^{c'}$, and $R^{d'}$.

One preferred combination is where $R^{a'}$ is hydrogen, $R^{b'}$ is alkoxy, $R^{c'}$ is hydrogen, and $R^{d'}$ is alkoxy, for example (RS)-(4-carbamimidoyl-phenylamino)-(2-fluoro-3,5-dimethoxy-phenyl)-acetic acid or (RS)-(4-carbamimidoyl-phenylamino)-(3,5-diethoxy-2-fluoro-phenyl)-acetic acid.

Another preferred combination is where $R^{a'}$ is hydroxyalkoxy, $R^{b'}$ is hydrogen, $R^{c'}$ is alkoxy, and $R^{d'}$ is alkoxy, for example (RS)-(4-carbamimidoyl-phenylamino)-[4,5-diethoxy-2-(2-hydroxy-ethoxy)-phenyl]-acetic acid.

A further preferred combination is where $R^{a'}$ is carbamoylmethoxy, $R^{b'}$ is hydrogen, $R^{c'}$ is alkoxy, and $R^{d'}$ is alkoxy, for example (RS)-(4-carbamimidoyl-phenylamino)-(2-carbamoylmethoxy-4,5-diethoxy-phenyl)-acetic acid.

Preferred substituents for $R^{b'}$ include hydrogen, alkyl, alkoxy, hydroxycycloalkoxy, alkenyl, or hydroxyalkoxy, alkylpiperidinyloxy, alkylsulphonylpiperidinyloxy, or pyrrolidinylalkyl, and tetrahydropyranyloxy.

A preferred combination is where $R^{a'}$ is hydrogen, $R^{b'}$ is alkyl, $R^{c'}$ is hydrogen, and $R^{d'}$ is dialkylaminoalkoxy, for example (RS)-(4-carbamimidoyl-phenylamino)-[3-(3-dimethylamino-2,2-dimethyl-propoxy)-5-ethyl-phenyl]-acetic acid.

Yet another preferred combinaiton is where $R^{a'}$ is hydrogen, $R^{b'}$ is alkoxy, $R^{c'}$ is dialkylaminoalkoxy, and $R^{d'}$ is hydrogen, such as (RS)-(4-carbamimidoyl-phenylamino)-[4-(2-dimethylamino-ethoxy)-3-ethoxy-phenyl]-acetic acid.

Preferred combinations include: $R^{a'}$ is hydrogen, $R^{b'}$ is alkoxy, $R^{c'}$ is hydroxyalkoxy, and $R^{d'}$ is hydrogen, for example (RS)- and (SR)-(4-carbamimidoyl-phenylamino)-[3-ethoxy-4-[(RS)-2-hydroxy-1-methyl-ethoxy]-phenyl]-acetic acid; $R^{a'}$ is hydrogen, $R^{b'}$ is alkoxy, $R^{c'}$ is alkoxy, and $R^{d'}$ is hydrogen, for example (RS)-(4-carbamimidoyl-phenylamino)-(3-ethoxy-4-methoxy-phenyl)-acetic acid hydrochloride; $R^{a'}$ is hydrogen, $R^{b'}$ is alkoxy, $R^{c'}$ is hydrogen, and $R^{d'}$ is pyridinylaminoalkyl, for example (RS)-(4-carbamimidoyl-phenylamino)-[3-ethoxy-5-(pyridin-2-ylaminomethyl)-phenyl]-acetic acid; $R^{a'}$ is hydrogen, $R^{b'}$ is alkoxy, $R^{c'}$ is hydrogen, and $R^{d'}$ is morpholinylalkyl, for example (RS)-(4-carbamimidoyl-phenylamino)-(3-ethoxy-5-morpholin-4-yl-methyl-phenyl)-acetic acid; $R^{a'}$ is hydrogen, $R^{b'}$ is alkoxy, $R^{c'}$ is hydrogen, and $R^{d'}$ is alkoxy, for example (RS)-(4-carbamimidoyl-phenylamino)-3,5-diethoxy-phenyl)-acetic acid; and $R^{a'}$ is hydrogen, $R^{b'}$ is alkoxy, $R^{c'}$ is hydroxyalkoxy, and $R^{d'}$ is hydrogen, for example (RS)-(4-carbamimidoyl-phenylamino)-[3-ethoxy-4-(2-hydroxy-ethoxy)-phenyl]-acetic acid.

Another combination of $R^{a'}$, $R^{b'}$, $R^{c'}$, and $R^{d'}$ that forms useful compounds within the subject invention is where $R^{a'}$ is hydrogen, $R^{b'}$ is hydroxycycloalkoxy, $R^{c'}$ is hydrogen, and $R^{d'}$ is alkoxy, for example (RS)- and (SR)-(4-carbamimidoyl-phenylamino)-[3-ethoxy-5-[(1-RS,2RS)-2-hydroxy-cyclopentyloxy]-phenyl]-acetic acid and (RS)- and (SR)-(4-carbamimidoyl-phenylamino)-[3-ethoxy-5-[(1-RS,2RS)-2-hydroxy-cyclohexyloxy]-phenyl]-acetic acid.

Also preferred is where $R^{a'}$ is hydrogen, $R^{b'}$ is alkenyl, $R^{c'}$ is hydrogen, and $R^{d'}$ is pyrrolidinylalkyl, such as (RS)-(4-carbamimidoyl-phenylamino)-(3-pyrrolidin-1-ylmethyl-5-vinyl-phenyl)-acetic acid, and where $R^{a'}$ is hydrogen, $R^{b'}$ is hydroxyalkoxy, $R^{c'}$ is alkoxy, and $R^{d'}$ is alkoxy, such as (RS)-(4-carbamimidoyl-phenylamino)-[4,5-diethoxy-2-(3-hydroxy-propoxy)-phenyl]-acetic acid.

Yet other preferred combinations are where $R^{a'}$ is hydrogen, $R^{b'}$ is alkylpiperidinyloxy, $R^{c'}$ is hydrogen, and $R^{d'}$ is alkoxy, such as (RS)-(4-carbamimidoyl-phenylamino)-[3-ethoxy-5-(1-methyl-piperidin-4-yloxy)-phenyl]-acetic acid; where $R^{a'}$ is hydrogen, $R^{b'}$ is alkylsulphonylpiperidinyloxy, $R^{c'}$ is hydrogen, and $R^{d'}$ is alkoxy, such as (RS)-(4-carbamimidoyl-phenylamino)-[3-ethoxy-5-(1-methanesulphonyl-piperidin-4-yloxy)-phenyl]-acetic acid; and where $R^{a'}$ is hydrogen, $R^{b'}$ is pyrrolidinylalkyl, $R^{c'}$ is hydrogen, and $R^{d'}$ is alkynyl, such as (RS)-(4-carbamimidoyl-phenylamino)-(3-ethynyl-5-pyrrolidin-1-ylmethyl-phenyl)-acetic acid.

Other of the subject compounds include combinations where $R^{a'}$ is hydrogen, $R^{b'}$ is tetrahydropyranyloxy, $R^{c'}$ is hydrogen, and $R^{d'}$ is alkoxy, such as (4-carbamimidoyl-phenylamino)-[3-ethoxy-5-(tetrahydropyran-4-yloxy)-phenyl]-acetic acid.

Of course as mentioned above, $R^{c'}$ can be individually hydrogen, dialkylaminoalkoxy, hydroxyalkylalkoxy, hydroxyalkoxy, or alkoxy, and $R^{d'}$ can be individually hydrogen, dialkylaminoalkoxy, alkoxy, alkynyl, pyrrolidinylalkyl, pyridinylaminoalkyl, or morpholinylalkyl. Each and every combination is to be considered as if written out explicitly.

The subject invention also provides for phamaceutical compositions containing the subject compounds, for example in galenical administration form. Also provided are methods for making and using the subject compounds.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The invention is concerned with novel N-(4-carbamimidoyl-phenyl)-glycine derivatives of the formula:

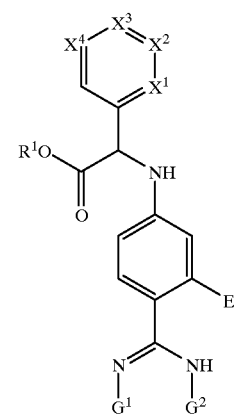

I wherein
  $R^1$ represents hydrogen or the residue of an ester group which is cleavable under physiological conditions;
  E represents hydrogen or hydroxy;
  three of the symbols $X^1$ to $X^4$ independently of one another represent a group $C(R^a)$, $C(R^b)$ or $C(R^c)$ and the fourth represents a group $C(R^d)$ or N;
  $R^a$ to $R^d$ each independently represent hydrogen, alkenyl, alkenylcarbonyloxyalkoxy, alkenyloxy, alkynyl, alkynyloxy, alkoxy, alkoxyalkenyl, alkoxyalkoxy, alkoxyalkyl, alkoxyalkyl(alkyl)aminoalkyl, alkoxyalkylcarboxamido, alkoxycarbonyl, alkoxycarbonylalkoxy, alkoxycarbonylalkyl, alkoxycarbonylalkylcarboxamido, alkoxycarbonylarylalkoxy, alkoxycarbonylaryloxy, alkoxycarbonylcarboxamido, alkyl, alkyl (alkylcarbonyl)amino, alkylcarbonyl, alkylcarbonylalkoxy, alkylcarbonyloxyalkoxy, alkylcarboxamido, alkylcarboxamidoalkoxy, alkylsulphanyl, alkylsulphanylalkoxy, alkylsulphinyl, alkylsulphonyl, alkylsulphonylamino, alkylsulphonylaminoalkoxy, alkylureidyl, alkylthioureidyl, amino, aminoalkoxy, aryl, arylalkenyl, arylalkynyl, arylalkoxy, arylalkoxyalkoxy, arylalkyl, arylalkylcarboxamido, arylcarbonylalkoxy, arylcarboxamido, arylcarboxamidoalkoxy, aryloxy, aryloxyalkoxy, arylsulphonylamino, arylsulphonylaminoalkoxy, carboxy, carboxyalkyl, carboxyalkylcarboxamido, carboxyalkoxy, carboxyarylalkoxy, carboxyaryloxy, carboxycarboxamido, carbamoylalkoxy, cycloalkyl, cycloalkoxy, cycloalkylalkoxy, cycloalkylamino, cycloalkylaminoalkyl, cycloalkylaminocarbonyloxy, cycloalkylcarbamoylalkoxy, cycloalkylcarboxamido, dihydroxyalkoxy, halogen, haloalkenyl, haloalkoxy, haloalkyl, hydroxy, hydroxyalkoxy, hydroxyalkoxyalkoxy, hydroxyalkyl, hydroxycycloalkoxy, hydroxycycloalkylamino, mono- or di-alkylamino, mono- or di-alkylaminoalkoxy, mono- or di-alkylaminoalkyl, mono- or di-alkylaminocarbonylalkoxy, 2,2,2-trifluoroacetylaminoalkoxy or a heterocyclic substituent selected from the group of azepanylcarbonylalkoxy, benzoimidazolyl, morpholinylalkoxy, morpholinylalkyl, morpholinyloxoalkoxy, piperidinylalkoxy, piperidinylamino, piperidinylaminoalkyl, piperidinyloxy, alkylsulphonylpiperidinyloxy, furanylalkoxy, 1,3-dioxo-1,3-dihydroisoindolylalkyl, imidazolyl, imidazolylalkyl, isothiazolyloxy, dihydroisoxazolyl, piperazinyl, piperazinylalkyl, pyridinylaminoalkyl, bis-pyridinylalkylamino, pyridinyloxy, pyrimidinylaminoalkylazepanylideneamino, pyrrolidinyl, pyrrolidinylalkoxy, pyrrolidinylalkyl, pyrrolidinyloxy, pyrrolidinyloxoalkoxy, oxopyrrolidinylalkoxy, oxadiazolyl, tetrahydrofuranylalkoxy, tetrahydrofuranyloxy, tetrahydropyranylalkoxy, tetrahydropyranylamino, tetrahydrothiopyranylamino, tetrahydropyranyloxy, dioxohexahydrothiopyranylamino, thiazolylalkoxy and thiophenyl, with the heterocyclic substituents being optionally substituted with alkyl, alkoxy, carboxyalkyl, hydroxy, tetrazolylmethoxy, alkylsulphonyl or alkoxycarbonylalkyl or two adjacent groups $R^a$ to $R^d$ together forming the remainder of a fused 1,4-dioxan, 1,3-dioxolan, 1-oxane or aryl ring, provided that not more than three of $R^a$ to $R^d$ have the same significance and $X^1$ is not substituted by carboxy or alkoxycarbonyl; and one of the symbols $G^1$ and $G^2$ represents hydrogen and the other represents hydrogen, alkyl, hydroxy, alkoxy, aroyl or a group COO—$R^e$ or OCO—$R^e$ and $R^e$ represents alkyl optionally substituted by halogen, hydroxy, alkoxy, carboxy, alkylcarbonyloxycarbonyl or arylcarbonyloxycarbonyl, as well as hydrates or solvates and physiologically usable salts thereof.

Further, the invention is concerned with a process for the manufacture of the above compounds, pharmaceutical preparations that contain such compounds as well as the use of these compounds for the production of pharmaceutical preparations.

Examples of physiologically usable salts of these compounds of formula I are salts with physiologically compatible mineral acids, such as hydrochloric acid, sulphuric acid, sulphurous acid or phosphoric acid; or with organic acids, such as methanesulphonic acid, p-toluenesulphonic acid, acetic acid, trifluoroacetic acid, citric acid, fumaric acid, maleic acid, tartaric acid, succinic acid or salicylic acid.

The compounds of formula I can be solvated, especially hydrated. The hydration can take place in the course of the manufacturing process or can occur gradually as a consequence of hygroscopic properties of an initially anhydrous compound of formula I.

The compounds of formula I contain at least one asymmetric C atom and can therefore exist as an enantiomeric mixture, diastereomeric mixture or as optically pure compounds.

In the scope of the present invention "alkyl", alone or in combination with other groups, such as in alkoxy, alkoxycarbonyl etc., denotes a straight-chain or branched hydrocarbon residue containing 1–6, preferably 1–4 carbon atoms, such as, methyl, ethyl, propyl, isopropyl and butyl.

The term "alkoxy" stands for the group alkyl-O— with alkyl as defined above, e.g. methoxy, ethoxy, n-propoxy, iso-propoxy, n-butoxy, iso-butoxy.

The term "alkenyl" stands for alone or in combination with other groups, a straight-chain or branched hydrocarbon residue containing an olefinic bond and up to 6, preferably up to 4 C-atoms.

The term "alkynyl" stands for alone or in combination with other groups, a straight-chain or branched hydrocarbon residue containing a triple bond and up to 6, preferably up to 4 C-atoms.

The term "cycloalkyl" stands for a cyclic alkyl group of three to six carbon atoms, e.g. cyclopropyl, cyclobutyl, cyclopentyl and cyclohexyl.

The term "cycloalkoxy" or "cycloalkyloxy" denotes a cycloalkyl group that is bonded via an oxy (—O—) group, such as e.g. cyclopentyloxy.

The term "aryl", alone or in combination, such as in aryloxy, aralkyl etc. denotes a carbocyclic, aromatic residue such as phenyl, naphthyl or indanyl, preferably phenyl and naphthyl, especially phenyl, which can be substituted, e.g. by halogen, such as bromine, fluorine or chlorine, alkoxy, such as methoxy, ethoxy or propoxy, alkylenedioxy, such as methylenedioxy, hydroxy, nitro, amino, mono- or di-alkyl-amino, phenyl, phenoxy, COOH or COO-alkyl, such as $COOCH_3$ or $COOC_2H_5$. Preferred substituents are alkoxy, halogen, preferably fluorine, alkyl, amino, nitro, dialkylamino and carboxy and especially alkoxy, halogen and alkyl. Examples of aralkyl groups are benzyl, phenethyl, mono- or dimethoxy-benzyl, aminobenzyl or nitrobenzyl, examples of aryloxy groups are phenoxy or methoxycarbonyl-phenoxy and examples of aralkyloxy groups are benzyloxy, methoxy-benzyloxy and phenethoxy.

The term "halogen" stands for fluorine, chlorine, bromine and iodine, preferably fluorine and chlorine.

The term "hydroxy" stands for the group —OH.

The term "carbonyl" stands for the group —C(O)—.

The term "carboxy" stands for the group —C(O)OH.

The term "carboxamido" stands for the group stands for —C(O)—NH—.

The term "carbamoyl" stands for the group $NH_2$—C(O)—.

The term "oxy" stands for the group —O—.

The term "amino" stands for the group —$NH_2$.

The term "sulphanyl" stands for the group —S—.

The term "sulphinyl" stands for the group —SO—.

The term "sulphonyl" stands for the group —$SO_2$—.

The term "ureidyl" stands for the group $NH_2$—C(O)—NH—.

The term "thioureidyl" stands for the group $NH_2$—C(S)—NH—.

Examples of haloalkyl are trifluoromethyl and pentafluoroethyl; examples of haloalkoxy are trifluoromethoxy and pentafluoroethoxy.

Examples of ester groups cleavable under physiological conditions denoted by $R^1$ are alkyl, especially methyl and ethyl; morpholinoethyl; tetrahydropyranyl; alkoxycarbonylalkyl, such as tert.-butoxycarbonylmethyl (pivoxyl); alkoxycarbonyloxyalkyl, such as 1-(ethoxycarbonyloxy) ethyl, hexyloxycarbonyloxyalkyl (hexetil) and 1-isopropyloxycarbonyloxy)ethyl (proxetil); alkylcarbonyloxyalkyl, such as 1-acetoxyethyl (axetil), 1-(pivaloyloxy)ethyl and 1-(cyclohexylacetoxy)ethyl. Especially preferred ester groups are methyl and ethyl, particularly ethyl.

The invention includes especially the aforementioned compounds in which three of the symbols $X^1$ to $X^4$ independently of one another represent a group $C(R^a)$, $C(R^b)$ or $C(R^c)$ and the fourth represents a group $C(R^d)$.

In a preferred embodiment the present invention embraces especially compounds as defined above in which $R^a$ to $R^d$ independently of one another represent hydrogen, alkenyl, alkenylcarbonyloxyalkoxy, alkenyloxy, alkynyl, alkoxy, alkoxyalkenyl, alkoxyalkoxy, alkoxyalkyl, alkoxycarbonylalkoxy, alkoxycarbonylarylalkoxy, alkoxycarbonylaryloxy, alkyl, alkylcarbonylalkoxy, alkylcarbonyloxyalkoxy, alkylcarboxamidoalkoxy, alkylsulphanylalkoxy, aminoalkoxy, aryl, arylalkenyl, arylalkoxy, arylalkoxyalkoxy, arylalkyl, arylcarbonylalkoxy, arylcarboxamidoalkoxy, aryloxy, aryloxyalkoxy, carboxy, carboxyalkyl, carboxyalkoxy, carboxyarylalkoxy, carboxyaryloxy, carbamoylalkoxy, cycloalkyl, cycloalkoxy, cycloalkylalkoxy, cycloalkylamino, cycloalkylaminoalkyl, cycloalkylaminocarbonyloxy, cycloalkylcarbamoylalkoxy, dihydroxyalkoxy, halogen, haloalkenyl, haloalkoxy, haloalkyl, hydroxyalkoxy, hydroxyalkoxyalkoxy, hydroxyalkyl, hydroxycycloalkoxy, mono- or di-alkylaminoalkoxy, mono- or di-alkylaminoalkyl, mono- or di-alkylaminocarbonylalkoxy or a heterocyclic substituent selected from the group of morpholinylalkoxy, morpholinylalkyl, morpholinyloxoalkoxy, piperidinylalkoxy, piperidinyloxy, pyridinylaminoalkyl, alkylsulphonylpiperidinyloxy, furanylalkoxy, imidazolylalkyl, isothiazolyloxy, pyrrolidinyl, pyrrolidinylalkoxy, pyrrolidinylalkyl, pyrrolidinyloxy, pyrrolidinyloxoalkoxy, oxadiazolyl, tetrahydrofuranylalkoxy, tetrahydrofuranyloxy, tetrahydropyranylalkoxy, tetrahydropyranyloxy and thiazolylalkoxy, with the heterocyclic substituents being optionally substituted with alkyl, alkoxy, tetrazolylmethoxy, alkylsulphonyl or alkoxycarbonylalkyl or two adjacent groups $R^a$ to $R^d$ together forming the remainder of a fused 1,4-dioxan, 1,3-dioxolan, 1-oxane or aryl ring.

Especially preferred are the compounds defined above in which $R^a$ to $R^d$ independently of one another represent hydrogen, alkenyl, alkenyloxy, alkynyl, alkoxy, alkoxyalkenyl, alkoxyalkoxy, alkoxyalkyl, alkoxycarbonylarylalkoxy, alkyl, alkylcarbonylalkoxy, alkylsulphanylalkoxy, arylcarboxamidoalkoxy, carbamoylalkoxy, carbonylarylalkoxy, cycloalkoxy, cycloalkylalkoxy, cycloalkylaminocarbonyloxy, cycloalkylcarbamoylalkoxy, dihydroxyalkoxy, halogen, haloalkenyl, haloalkoxy, haloalkyl, hydroxyalkoxy, hydroxyalkoxyalkoxy, hydroxyalkyl, hydroxycycloalkoxy, mono- or di-alkylaminoalkoxy or heterocyclic substituent selected from the group of piperidinyloxy, furanylalkoxy, isothiazolyloxy, morpholinylalkyl, pyridinylaminoalkyl, pyrrolidinylalkyl, pyrrolidinyloxy, tetrahydrofuranyloxy and tetrahydropyranyloxy, with the heterocyclic substituents being optionally substituted with alkyl, alkoxy, tetrazolylmethoxy, alkylsulphonyl or alkoxycarbonylalkyl.

Further preferred compounds are those in which $R^a$ to $R^d$ independently of one another represent hydrogen, alkenyl, alkenyloxy, alkynyl, alkoxy; alkoxyalkenyl, alkoxyalkoxy, alkoxyalkyl, alkyl, alkylcarbonylalkoxy, alkylsulphanylalkoxy, arylcarboxamidoalkoxy, alkoxycarbonylarylalkoxy, carbamoylalkoxy, carboxyarylalkoxy, cycloalkoxy, cycloalkylalkoxy, cycloalkylaminocarbonyloxy, cycloalkylcarbamoylalkoxy, dihydroxyalkoxy, halogen, haloalkenyl, haloalkoxy, haloalkyl, hydroxyalkoxy, hydroxyalkoxyalkoxy, hydroxyalkyl, hydroxycycloalkoxy, mono- or di-alkylaminoalkoxy or heterocyclic substituent selected from the group of piperidinyloxy, furanylalkoxy, isothiazolyloxy, morpholinylalkyl, pyridinylaminoalkyl, pyrrolidinylalkyl, pyrrolidinyloxy, tetrahydrofuranyloxy and tetrahydropyranyloxy, with the heterocyclic substituents being optionally substituted with alkyl, alkoxy, tetrazolylmethoxy, alkylsulphonyl or alkoxycarbonylalkyl.

Particularly preferred compounds are those in which $R^a$ bis $R^d$ independently of one another represent hydrogen, alkenyl, alkynyl, alkoxy, alkyl, carbamoylalkoxy, cycloalkoxy, cycloalkylalkoxy, dihydroxyalkoxy, halogen, haloalkoxy, haloalkyl, hydroxyalkoxy, hydroxyalkyl, hydroxycycloalkoxy, mono- or di-alkylaminoalkoxy or heterocyclic substituent selected from the group of morpholinylalkyl, piperidinyloxy, pyridinylaminoalkyl, pyrrolidinylalkyl, pyrrolidinyloxy and tetrahydropyranyloxy, with the heterocyclic substituents being optionally substituted with alkyl, alkoxy, tetrazolylmethoxy, alkylsulphonyl or alkoxycarbonylalkyl.

In a further preferred embodiment of the invention compounds are preferred in which $R^a$ bis $R^d$ independently of one another represent hydrogen, alkenyl, alkynyl, alkoxy, alkyl, carbamoylalkoxy, halogen, hydroxyalkoxy, hydroxycycloalkoxy, mono- or di-alkyl-aminoalkoxy or heterocyclic substituent selected from the group of morpholinylalkyl, piperidinyloxy, pyridinylaminoalkyl, pyrrolidinylalkyl and tetrahydropyranyloxy, with the heterocyclic substituents being optionally substituted with alkyl, alkoxy, tetrazolylmethoxy, alkylsulphonyl or alkoxycarbonylalkyl.

In a particular embodiment the invention relates to the aforementioned compounds in which $X^1$ represents the group $C(R^a)$, $X^2$ represents the group $C(R^b)$, $X^3$ represents the group $C(R^c)$ and $X^4$ represents the group $C(R^d)$.

The invention embraces especially compounds in accordance with the above definitions in which $R^a$ represents hydrogen, carbamoylalkoxy, hydroxyalkoxy or halogen, preferably hydrogen.

Furthermore, the invention also relates in particular to compounds in accordance with the above definitions in which $R^b$ represents hydrogen, alkenyl, alkynyl, alkoxy or alkyl, preferably alkoxy.

Moreover, the invention relates especially to compounds as defined above in which $R^c$ represents hydrogen, alkoxy, mono- or di-alkylaminoalkoxy or hydroxyalkoxy, particularly hydrogen or alkoxy.

In a further particular embodiment the invention embraces compounds in accordance with the above definitions in which R$^d$ represents hydrogen, alkoxy, hydroxycycloalkoxy, mono- or di-alkylaminoalkoxy or a heterocyclic substituent selected from the group of morpholinylalkyl, piperidinyloxy, pyridinylaminoalkyl, pyrrolidinylalkyl or tetrahydropyranyloxy, with the heterocyclic substituents being optionally substituted with alkyl or alkylsulphonyl.

Furthermore, the invention embraces especially compounds in accordance with the above definitions in which one of the symbols G$^1$ and G$^2$ represents hydrogen and the other represents hydrogen, alkyl, hydroxy, alkoxy, aroyl or a group COO—R$^e$ or OCO—R$^e$ and R$^e$ represents alkyl optionally substituted with halogen, hydroxy, alkoxy, carboxy, alkylcarbonyloxycarbonyl or arylcarbonyloxycarbonyl.

Preferred compounds in accordance with the above definitions are those in which one of the symbols G$^1$ and G$^2$ represents hydrogen or hydroxy and the other represents hydrogen. In a particular embodiment both symbols G$^1$ and G$^2$ represent hydrogen.

Furthermore, compounds in accordance with the above definitions in which R$^1$ represents hydrogen are preferred.

Preferred compounds in accordance with the above definitions are also those in which the symbol E represents hydrogen.

In a particular embodiment of the compounds described above there are preferred those in which not more than two of R$^a$ to R$^d$ are simultaneously hydrogen.

In a further embodiment the invention relates to the compounds described above in which X$^1$ represents the group C(R$^a$) and X$^2$, X$^3$ and X$^4$ independently of one another represent a group selected from the groups C(R$^d$), C(R$^b$) and C(R$^c$). Moreover, the invention relates to the compounds defined above in which X$^2$ represents the group C(R$^b$) and X$^1$, X$^3$ and X$^4$ independently of one another represent a group selected from the groups C(R$^d$), C(R$^a$) and C(R$^c$). The invention furthermore relates to the compounds described above in which X$^3$ represents the group C(R$^c$) and X$^1$, X$^2$ and X$^4$ independently of one another represent a group selected from the groups C(R$^d$), C(R$^b$) and C(R$^a$). Moreover, the invention relates to the compounds described above in which X$^4$ represents the group C(R$^d$) and X$^1$, X$^2$ and X$^3$ independently of one another represent a group selected from the groups C(R$^a$), C(R$^b$) and C(R$^c$).

In particular, preferred compounds are the compounds of formula I described in the Examples as individual compounds in the form of the free acids, their esters as well as hydrates or solvates and physiologically usable salts thereof.

Preferred individual compounds are those selected from the group consisting of:

a) (RS)-(4-carbamimidoyl-phenylamino)-[4-(2-dimethylamino-ethoxy)-3-ethoxy-phenyl]-acetic acid;
b) (RS)- and (SR)-(4-carbamimidoyl-phenylamino)-[3-ethoxy-5-[(1-RS,2RS)-2-hydroxy-cyclopentyloxy]-phenyl]-acetic acid;
c) (RS)-(4-carbamimidoyl-phenylamino)-(3,5-diethoxy-2-fluoro-phenyl)-acetic acid;
d) (RS)-(4-carbamimidoyl-phenylamino)-[3-ethoxy-5-[(1-methyl-piperidin-4-yloxy)-phenyl]-acetic acid;
e) (RS)- and (SR)-(4-carbamimidoyl-phenylamino)-[3-ethoxy-4-[(RS)-2-hydroxy-1-methyl-ethoxy]-phenyl]-acetic acid;
f) (RS)- and (SR)-(4-carbamimidoyl-phenylamino)-[3-ethoxy-5-[(1RS,2RS)-2-hydroxy-cyclohexyloxy]-phenyl]-acetic acid;
g) (RS)-(4-carbamimidoyl-phenylamino)-[3-ethoxy-5-(1-methanesulphonyl-piperidin-4-yloxy)-phenyl]-acetic acid;

h) (4-carbamimidoyl-phenylamino)-[3-ethoxy-5-(tetrahydropyran-4-yloxy)-phenyl]-acetic acid;
i) (RS)-(4-carbamimidoyl-phenylamino)-(3-ethynyl-5-pyrrolidin-1-ylmethyl-phenyl)-acetic acid;
j) (RS)-(4-carbamimidoyl-phenylamino)-(3-pyrrolidin-1-ylmethyl-5-vinyl-phenyl)-acetic acid;
k) (RS)-(4-carbamimidoyl-phenylamino)-(3-ethoxy-4-methoxy-phenyl)-acetic acid hydrochloride;
l) (RS)-(4-carbamimidoyl-phenylamino)-(2-fluoro-3,5-dimethoxy-phenyl)-acetic acid;
m) (RS)-(4-carbamimidoyl-phenylamino)-[3-ethoxy-5-(pyridin-2-ylaminomethyl)-phenyl]-acetic acid;
n) (RS)-(4-carbamimidoyl-phenylamino)-(3-ethoxy-5-morpholin-4-ylmethyl-phenyl)-acetic acid;
o) (RS)-(4-carbamimidoyl-phenylamino)-[3-ethoxy-4-(2-hydroxy-ethoxy)-phenyl]-acetic acid;
p) (RS)-(4-carbamimidoyl-phenylamino)-[4,5-diethoxy-2-(2-hydroxy-ethoxy)-phenyl]-acetic acid;
q) (RS)-(4-carbamimidoyl-phenylamino)-[3-(3-dimethylamino-2,2-dimethyl-propoxy)-5-ethyl-phenyl]-acetic acid;
r) (RS)-(4-carbamimidoyl-phenylamino)-[3-ethoxy-4-(2-hydroxy-ethoxy)-phenyl]-acetic acid;
s) (RS)-(4-carbamimidoyl-phenylamino)-[4,5-diethoxy-2-(3-hydroxy-propoxy)-phenyl]-acetic acid; and
t) (RS)-(4-carbamimidoyl-phenylamino)-(2-carbamoylmethoxy-4,5-diethoxy-phenyl)-acetic acid.

The compounds of formula I can be obtained by converting the nitrile group in a compound of formula:

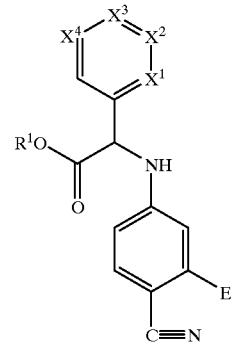

II wherein X$^1$, X$^2$, X$^3$, X$^4$, R$^1$ and E have the significance given above, into a carbamimidoyl group or into a N-hydroxy-carbamimidoyl group and, if desired, modifying a reactive group present in an obtained compound of formula I and, if desired, converting a compound of formula I obtained into a physiologically compatible salt or converting a salt of a compound of formula I into the free acid or base.

The conversion of the nitrile group in a compound of formula II into a carbamimidoyl group —C(NH)NH$_2$ or a N-hydroxy-carbamimidoyl group —C(NOH)NH$_2$ can be carried out according to methods known per se. For example, the conversion into a N-hydroxy-carbamimidoyl group can be performed by dissolving a compound of formula II in a solvent, such as DMF, ethanol or methanol, treating the solution with hydroxylamine or a salt of hydroxylamine with an inorganic acid, such as hydroxylamine hydrochloride, and thereafter with a base, such as diisopropylethylamine or triethylamine, sodium hydride or sodium methanolate, conveniently at a temperature up to 80° C.

The conversion of the nitrile group into a carbamimidoyl group can be carried out e.g. by treating a compound of formula II in a solvent, such as ethanol or methanol, or a solvent mixture, such as chloroform and methanol or chloroform and ethanol, with a dry stream of hydrogen chloride, conveniently at a temperature below 10° C., thereafter treating the reaction solution with a solvent, such as diethyl ether, and filtering off the precipitated iminoether. The thus-obtained material is treated in a solvent, such as methanol or ethanol, either with gaseous ammonia or an ammonium salt, such as ammonium chloride, conveniently at a temperature up to 80° C. Alternatively, the solution containing the iminoether can be evaporated and the residue can be treated with gaseous ammonia or an ammonium salt in methanol or ethanol. In an analogous manner, the iminoether can be converted into a N-hydroxy-carbamimidoyl compound of formula I with hydroxylamine or a salt thereof in the presence of a base.

As modifications of functional groups present in a compound of formula I there come into consideration especially the conversion of a N-hydroxy-carbamimidoyl group into a carbamimidoyl group, the esterification of a carboxy group, the saponification of an ester group and the cleavage of an ether group, such as an arylalkyl ether group, e.g. the benzyl ether group. All of these reactions can be carried out according to methods known per se.

For the conversion of a N-hydroxy-carbamimidoyl group into a carbamimidoyl group, an amidoxime of formula I can be hydrogenated in a solvent, such as ethanol, methanol, dioxan, THF or glacial acetic acid, or a solvent mixture, such as ethanol and glacial acetic acid, with hydrogen and a catalyst, such as palladium, platinum or nickel. In so doing, other reactive groups present in the compound of formula I and reactive towards the reducing agent can be modified. For example, in the case of hydrogenation with palladium a benzyloxy group $R^a$, $R^b$, $R^c$ or $R^d$ is converted into the hydroxy group.

By reacting a compound of formula I in which $G^1$ and $G^2$ represent hydrogen with a chloroformic acid ester of the formula $ClC(O)O$—$R^e$ in which $R^e$ has the significance set forth above and wherein a hydroxy or carboxy group is present in protected form, in a solvent, such as dichloromethane, dioxan or DMF, or a solvent mixture, such as dichloromethane and water or ethyl acetate and water, in the presence of an organic base, such as pyridine or triethylamine, or an inorganic base, such as sodium hydroxide, sodium carbonate or potassium hydrogen carbonate, there is obtained the corresponding compound of formula I in which $G^1$ and $G^2$ represent the group —C(O)O—$R^e$. Analogously, a compound of formula I in which $G^1$ and $G^2$ represent hydrogen can be converted with a p-nitrophenyl carbonate of the formula p-$NO_2C_6H_4OCOO$—$R^e$ into the corresponding compound of formula I in which one of $G^1$ and $G^2$ represents —COO—$R^e$. The reaction is carried out by treating the p-nitrophenyl carbonate in THF and DMF firstly with N,N-diisopropylethylamine and then with a compound of formula I in which $G^1$ and $G^2$ represent hydrogen.

By reacting a compound of formula I in which $G^1$ and $G^2$ represent hydrogen with an acyl chloride, such as an aroyl chloride, there is obtained the corresponding compound of formula I in which one of $G^1$ and $G^2$ represents hydrogen and the other represents acyl. The reaction is carried out by treating the acyl chloride in THF and DMF firstly with N,N-diisopropylethylamine and then with a compound of formula I in which $G^1$ and $G^2$ represent hydrogen.

Compounds of formula I in which $G^1$ or $G^2$ represents a group —COO—$R^e$ and $R^e$ represents alkyl substituted by alkylcarbonyloxy or aroyloxy can be manufactured according to methods known per se (Synthesis 1990, p. 1159–66; J.Med.Chem. 31, p. 318–22, 1988) by reacting the carbamimidoyl compound with a p-nitrophenyl-alkanoyloxy-ethyl carbonate.

By reacting a compound of formula I in which one of the residues $G^1$ and $G^2$ represents hydroxy and the other represents hydrogen with an acyl halide there can be obtained a compound of formula I in which one of the residues $G^1$ and $G^2$ represents —$OCOR^e$. The reaction is carried out by treating the acyl chloride in THF and DMF firstly with N,N-diisopropylethylamine and then with a compound of formula I in which $G^1$ and $G^2$ represent hydrogen.

The compounds of formula II can be prepared according to methods known per se, e.g. as described hereinafter and/or as described in the Examples or in analogy to these methods. For example, an aldehyde of formula:

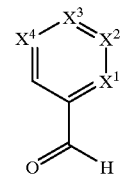

III in which $X^1$, $X^2$, $X^3$ and $X^4$ have the significances given above, can be reacted with a p-aminobenzonitrile of formula:

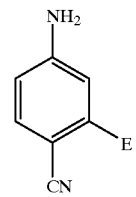

IV wherein E has the significance given above, and benzyl isonitrile and a primary alkanol such as methanol or ethanol, in the prescence of boron trifluoride etherate. Hydrolysis of the resulting iminoether with water yields a compound of formula II in which $R^1$ represents methyl or ethyl. By hydrolysis of the ester group $R^1$, e.g. by treatment with LiOH in tetrahydrofuran, there is obtained a compound of formula II in which $R^1$ represents hydrogen.

Further reactions for the preparaton f compounds of formula II:

By reaction of compounds of formula II in which one or more of $R^a$–$R^d$ represents alkylthio with an oxidizing agent such as e.g. meta-chlorperbenzoic acid or ozone in a suitable solvent such as acetone-water or methylene chloride there is obtained a compound of formula II in which the alkylthio group is converted into an alkylsulphinyl or alkylsulphonyl group;

represents alkoxy such as methoxy, isopropoxy or benzyloxy with a Lewis acid such as boron tribromide or boron trichloride in a suitable solvent such as methylene chloride or optionally by catalytic hydrogenation in e.g. ethyl acetate or ethanol there are obtained compounds of formula II in which the alkoxy group is converted into a hydroxy group;

represents hydroxy
- with an alkylating agent such as an alkyl bromide, alkyl iodide or alkyl mesylate in the presence of a base such as potassium carbonate or caesium carbonate in a solvent such as DMF or acetone or
- by a Mitsunobu reaction with an alkohol in the presence of DEAD and triphenylphosphine in a solvent such as THF or Dioxan or
- by reaction with an epoxide such as cyclopentene oxide in the presence of a base such as potassium carbonate, preferably at a temperature up to 150° C. there are obtained compounds of formula II in which the hydroxy group is converted into an alkoxy group;

represents hydroxy with an aryl- or heteroarylboronic acid such as phenylboronic acid or 3-pyridylboronic acid in the presence of copper acetate and a base such as Pyridine or triethylamine in a solvent such as methylene chloride there are obtained compounds of formula II in which the hydroxy group is converted into an aryloxy or heteroaryloxy group;

represents hydroxy with trifluoromethanesulphonic anhydride in the presence of a base such as pyridine or triethylamine and in a suitable solvent such as methylene chloride or THF and subsequent reaction with an aryl- or heteroarylboronic acid such as pyridineboronic acid or thiopheneboronic acid in the presence of a suitable catalyst such as tetrakis-(triphenylphosphine)-palladium in a solvent such as toluene, preferably at a temperature up to 100° C., there are obtained compounds of formula II in which the hydroxy group is converted into an aryl or heteroaryl group;

represents nitro by catalytic hydrogenation in the presence of e.g. a palladium-charcoal catalyst in a solvent such as ethanol or THF there are obtained compounds of formula II in which the nitro group is converted into an amino group;

represents amino with
- an alkylating agent such as an alkyl halide or alkyl mesylate in the presence of a base such as Hüinig's base or triethylamine in a solvent such as THF, preferably at an elevated temperature, or
- a carbonyl compound such as pyridinecarboxaldehyde or 1-methyl-4-piperidone in the presence of a reducing agent, such as e.g. sodium triacetoxyborhydride in a solvent such as ethyl acetate, or
- an epoxide such as e.g. cyclopentene oxide in the presence of a perchlorate salt such as lithium perchlorate in a solvent such as acetonitrile, preferably at an elevated temperature there are obtained compounds of formula II in which the amino group is converted into an alkylamino or dialkylamino group;

represents amino with an acid chloride such as cyclopentanecarboxylic acid chloride, phenylsulphonyl chloride or butylsulphamoyl chloride in the presence of a base such as triethylamine or Hüinig's base and in an inert solvent such as THF or methylene chloride there are obtained compounds of formula II in which the amino group is converted into an amide or sulphonamide or sulphamide group;

represents amino with an isocyanate such as e.g. butyl isocyanate in a suitable solvent such as THF there are obtained compounds of formula II in which the amino group is converted into a urea group;

represents halogen
- with an acetylene compound such as e.g. trimethylsilylacetylene in the presence of palladium acetate and triphenylphosphine in a solvent such as triethylamine in a Stille reaction with a stannane such as e.g. allyltributylstannane or tributylethynylstannane in the presence of a catalyst such as tetrakis-(triphenylphosphine)-palladium and in a suitable solvent such as dimethylacetamide, preferably at an elevated temperature, there are obtained compounds of formula II in which the halogen substituent is converted into an in allyl or alkynyl or vinyl group;

represents halogen in a Suzuki reaction with an aryl- or heteroarylboronic acid such as phenylboronic acid or 3-pyridylboronic acid in the presence of tetrakis-(triphenylphosphine)-palladium and a base such as e.g. potassium carbonate and in a solvent such as toluene or dioxan there are obtained compounds of formula II in which the halogen substituent is converted into an aryl or heteroaryl group;

represents halogen with a boronic acid ester such as bis(pinacolato)diboron in the presence of potassium acetate and bis-(triphenylphosphine)-palladium-(II) chlorid in a solvent such as dioxan and subsequent reaction with aryl or heteroaryl halides such as e.g. 3-bromopyridine in the presence of potassium carbonate and tetrakis-(triphenylphosphine)-palladium in a solvent such as toluene at an elevated temperature there are obtained compounds of formula II in which the halogen substituent is converted into an aryl or heteroaryl group;

represents alkenyl or alkynyl by catalytic hydrogenationin the presence of e.g. palladium-charcoal as the catalyst and in a solvent such as ethanol, ethanol-acetic acid or THF there are obtained compounds of formula II in which the akenyl or alkynyl group is reduced to an alkyl group;

represents vinyl in a 3+2 cycloaddition with e.g. nitroethane and di-tert-butyl dicarbonate in the presence of dimethylaminopyridine in a solvent such as acetonitrile there are obtained compounds of formula II in which the vinyl group is converted into a dihydroisoxazole group;

represents hydroxymethyl with methanesulphonyl chloride in the presence of a base such as triethylamine and in a solvent such as methylene chloride or THF and subsequent reaction with a suitable amine such as e.g. pyrrolidine or morpholine in a solvent such as THF there are obtained compounds of formula II in which the hydroxymethyl group is converted into a mono- or di-alkylaminomethyl group;

represents hydroxymethyl with an oxidizing agent such as oxalyl chloride and dimethyl sulphoxide in the presence of triethylamine and in a solvent such as methylene chloride, preferably at a low temperature, there are obtained compounds of formula II in which the hydroxymethyl group is converted into a formyl group;

represents formyl in a Wittig reaction with an alkyltriphenylphosphonium halide such as e.g. methyltriphenylphosphonium bromide in the presence of a base such as e.g. potassium carbonate in a solvent such as dioxan-water, preferably at an elevated temperature there are obtained compounds of formula II in which the formyl group is converted into an alkenyl group;

represents formyl with an amine such as e.g. pyrrolidine and a suitable reducing agent such as sodium cyanoborhydride in a solvent such as methanol at einem pH von 6, adjusted with e.g. acetic acid, there are obtained compounds of formula II in which the formyl group is converted into an alkylaminomethyl group;

represents formyl
- with a 1,2-diamine such as e.g. 1,2-phenylenediamine in the presence of an oxidizing agent such as DDQ in a solvent such as acetonitrile or
- mit glyoxal and ammonia in water-ethanol there are obtained compounds of formula II in which the formyl group is converted into an imidazolyl group;

represents benzyloxycarbonyl-alkoxy by catalytic hydrogenation in the presence of e.g. palladium-charcoal as the catalyst in a solvent such as ethanol-acetic acid there are obtained compounds of formula II in which the benzyloxycarbonyl-alkoxy group is converted into a carboxy-alkoxy group;

represents carboxy-alkoxy with an amine such as e.g. pyrrolidine or morpholine and a coupling reagent such as e.g. BOP in the presence of a base such as 4-ethylmorpholine and in a solvent such as DMF there are obtained compounds of formula II in which the carboxy-alkoxy group is converted into a carbamoyalkoxy.

Compounds of formula III are known per se. They can be obtained e.g. by reacting compounds of formula III in which one or more of $R^a$–$R^d$
- is a hydroxy group
  - with an alkylating agent such as e.g. benzyl bromide or ethyl bromide in the presence of a base such as potassium carbonate oder caesium carbonate in a suitable solvent such as DMF or acetone, preferably at an elevated temperature, or
  - in a Mitsunobu reaction with an alcohol in the presence of DEAD and triphenylphosphine in a solvent such as THF or Dioxan to give compounds of formula II in which the hydroxy group is substituted by an alkoxy group;
- is a formyl group in a Wittig reaction with an alkyltriphenylphosphonium halide such as e.g. methyl-triphenylphosphonium bromide in the presence of a base such as e.g. potassium carbonate in a solvent such as dioxan-water, preferably at an elevated emperature, to give compounds of formula II in which the formyl group is substituted by an alkenyl group.

Compounds of formula III in which one of the residues $R^a$–$R^d$ represents alkylthio or 1-hydroxyalkyl can also be obtained by reacting an aldehyde, protected e.g. as an acetal or aminal, with the residue $R^a$–$R^d$ in question being either hydrogen, bromine or iodine, with a strong base such as e.g. butyl-lithium in e.g. THF and subsequent reaction with disulphides such as e.g. dimethyl disulphide in a solvent such as THF or aldehydes such as e.g. acetaldehyde as well as subsequent deprotection of the aldehyde function with an aqueus acid.

Compounds of formula III can also be obtained by
- formylation of a suitably substituted aromatic according to conventional methods such as Vilsmeier reaction, reaction with titanium tertrachloride and dichloromethyl methy lether, reaction with chloroform-sodium hydroxide or with hexamethylenetetramine and acetic acid;
- oxidation of a benzyl alcohol according to known methods, e.g. by means of manganese dioxide;
- reaction of a toluene derivative N-bromosuccinimide in the presence of a radical initiator, e.g. AIBN, and subsequent reaction with 2-nitropropane in the presence of a base such as sodium ethylate.

Insofar as their preparation is not described in the Examples, the compounds of formulas III and IV can be prepared according to the methods set forth above or according to analogous methods.

The compounds of formula I, their solvates and salts inhibit the formation of coagulation factors Xa, IXa and thrombin induced by factor VIIa and tissue factor. These compounds consequently influence both platelet aggregation which is induced by these factors and plasmatic blood coagulation. They therefore inhibit the formation of thrombi and can be used for the control or prevention of diseases, such as thrombosis, apoplexy, cardiac infarction, inflammation and arteriosclerosis. Furthermore, these compounds have an effect on tumor cells and prevent metastases. They can therefore also be employed as antitumor agents.

Accordingly, the present invention also relates to a pharmaceutical preparation containing a compound as described above in a galenical administration form.

The invention likewise embraces compounds as described above for use as medicaments, especially as inhibitors of the formation of coagulation factors Xa, IXa and thrombin induced by factor VIIa and tissue factor, particularly as medicaments for the treatment or prevention of thromboses, apoplexy, cardiac infarction, inflammation and arteriosclerosis or as antitmour agents.

Moreover, the invention relates to the use of a compound as described above for the production of medicaments containing a compound as described above for the treatment or prevention of thromboses, apoplexy, cardiac infarction, inflammation and arteriosclerosis or of antitmour agents.

The inhibition of the amidolytic activity of factor VIIa/tissue factor complex by the compounds in accordance with the invention can be demonstrated with the aid of a chromogenic peptide substrate as described hereinafter.

The measurements were carried out on microtitre plates at room temperature. To this end, 100 $\mu$l of a solution of 26 nM of tissue factor, 9 nM of soluble factor VIIa and 8 mM of calcium chloride were added to 25 $\mu$l of a solution of the inhibitor in a buffer [pH 7.5, 100 mM, comprising 0.14M NaCl, 0.1M N-(2-hydroxyethyl)piperazine-N'-(2-ethanesulphonic acid) (HEPES), 0.5 mg/l of fatty-acid-free BSA (bovine serum albumin) and 0.05% $NaN_3$] in each well of the plate. After an incubation time of 15 minutes the reaction was started by the addition of 50 $\mu$l of chromogenic substrate Chromozym-tPA (3.5 mM, $MeSO_2$-D-Phe-Gly-Arg-paranitroanilide) and the hydrolysis of the substrate was followed spectrophotometrically on a kinetic microtitre plate reader over 10 minutes. Using the plot of the inhibition curves, the Ki values were determined according to the method described in Biochem. J. 55, 1953, 170–171. The results will be evident from the following Table (Ki in $\mu$M/l):

| Example | Ki |
| --- | --- |
| 4 e | 0.061 |
| 15 | 0.084 |
| 17 | 0.0385 |
| 26 e | 0.1144 |

The activity of the low molecular weight substances can, moreover, be characterized in the "prothrombin time" (PT) clotting test. The substances are prepared as a 10 mM solution in DMSO or DMSO/0.1M HCl (DHCl) and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 $\mu$l of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 μl of plasma/inhibitor mixture in the measurement container. The clotting reaction was initiated by the addition of 0.1 ml of Innovin® (recombinant human tissue factor combined with calcium buffer and synthetic phospholipids(Dade Behring®, Inc.). The time up to the fibrin cross-linking was determined photooptically from the ACL. The inhibitor concentration, which brought about a doubling of the PT clotting time, was determined by means of a graph.

The Ki value of the compounds of the present invention preferably amounts to about 0.1 to 500 nM, especially about 0.1 to 100 nM. The PT values preferably amount to about 0.1 to 10 μM, especially to about 0.1 to 5 μM.

As mentioned earlier, medicaments containing a compound of formula I, a solvate or a salt thereof also form an object of the present invention, as does a process for the production of such medicaments which comprises bringing one or more of such compounds, solvates or salts and, if desired, other therapeutically useful substances into a galenical administration form. These medicaments can be administered orally, e.g. in the form of dragees, hard and soft gelatine capsules, solutions, emulsions or suspensions, or rectally, for example in the form of suppositories, or as a spray. However, administration can also be carried out parenterally, e.g. in the form of injection solutions.

For the production of tablets, coated tablets, dragees and hard gelatine capsules, the active ingredient can be mixed with pharmaceutically inert, inorganic or organic excipients. Suitable excipients for tablets, coated tablets, dragees and hard gelatine capsules are, for example, lactose, maize starch or derivatives thereof, talc, stearic acid or its salts. Suitable excipients for soft gelatine capsules are, for example, vegetable oils, waxes, fats, semi-solid and liquid polyols; depending on the nature of the active ingredient no excipients are, however, usually required in the case of soft gelatine capsules. Suitable excipients for the production of solutions and syrups are e.g. water, polyols, sucrose, invert sugar and glucose; suitable excipients for injection solutions are e.g. water, alcohols, polyols; glycerol and vegetable oils, and suitable excipients for suppositories are natural and hardened oils, waxes, fats, semi-liquid or liquid polyols. In addition, the pharmaceutical preparations can also contain preservatives, solubilizers, stabilizers, wetting agents, emulsifiers, sweeteners, colorants, flavorants, salts for varying the osmotic pressure, buffers, coating agents or antioxidants.

The dosage of the active ingredient for the control or prevention of the illnesses mentioned above can vary within wide limits and will, of course, be adapted to the individual requirements in each particular case. In general, in the case of oral or parenteral, e.g. intravenous or subcutaneous, administration, a dose of about 0.1 to 20 mg/kg, preferably about 0.6 to 4 mg/kg, per day should be adequate for adults, although the upper limit which has just been mentioned may be exceeded or the dose may be lower when this is shown to be indicated.

The invention is illustrated in more detail by the following Examples.

EXAMPLES

Example 1

1.1

A solution of 1.19 g of 3,5-dimethoxybenzaldehyde and 0.7234 g of 4-aminobenzonitrile in 20 ml methanol was stirred at room temperature. After 1 hour 0.75 ml of benzyl isonitrile was added. The solution obtained was cooled to 0° C., then treated dropwise with 2.33 ml of boron trifluoride etherate in a manner such that the temperature did not exceed 10° C. The reaction mixture was stirred at room temperature for 1 hour, then concentrated under reduced pressure. The residue was taken up in 21 ml of methanol and 2.2 ml of water, the resulting solution was stirred at room temperature for 2 hours and then concentrated. The crude product was isolated by extraction and purified by chromatography on silica gel and yielded 1.66 g of methyl (RS)-(4-cyano-phenylamino)-(3,5-diethoxy-phenyl)-acetate as a brown foam.

1.2

22.9 ml of a 1N LiOH solution were added to a solution of the compound obtained in Example 1.1 in 25 ml of tetrahydrofuran. The reaction mixture was stirred at room temperature for 2 hours. The THF was distilled off, the residual aqueous solution was acidified with 1N HCl and extracted with ethyl acetate. The crude product was precipitated by treatment with a mixture of ethyl ether and cyclohexane. There were obtained 1.29 g of (RS)-(4-cyano-phenylamino)-(3,5-diethoxy-phenyl)-acetic acid as a solid.

1.3

2.61 g of hydroxylamine hydrochloride and 10.5 ml of triethylamine were added to a solution of 1.28 g of the compound obtained in Example 1.2 in 26 ml of ethanol. The solution was heated to reflux overnight and then concentrated. The residue was purified by chromatography on silica gel and yielded 0.74 g of (E)- and/or (Z)-(RS)-(3,5-diethoxy-phenyl)-[4-(N-hydroxycarbamimidoyl)-phenylamino]-acetic acid as a grey-white solid.

Example 2

In analogy to Example 1, 2.a
   from 4-ethoxy-3-methoxy-benzaldehyde, 4-aminobenzonitrile and benzyl isonitrile there was obtained methyl RS)-(4-cyano-phenylamino)-(4-ethoxy-3-methoxy-phenyl)-acetate, therefrom via (RS)-(4-cyano-phenylamino)-(4-ethoxy-3-methoxy-phenyl)-acetic acid there was obtained (E)- and/or (Z)-(RS)-(4-ethoxy-3-methoxy-phenyl)-[4-(N-hydroxycarbamimidoyl)-phenylamino]-acetic acid;

2.b
   from 4-benzyloxy-3-ethoxybenzaldehyde, 4-aminobenzonitrile and benzyl isonitrile there was obtained methyl (RS)-(4-benzyloxy-3-ethoxy-phenyl)-(4-cyano-phenylamino)-acetate, therefrom via (RS)-(4-benzyloxy-3-ethoxy-phenyl)-(4-cyano-phenylamino)-acetic acid there was obtained (E)- and/or (Z)-(RS)-(4-benzyloxy-3-ethoxy-phenyl)-[4-(N-hydroxycarbamimidoyl)-phenylamino]-acetic acid;

2.c
   from 3,5-dimethoxybenzaldehyde, 4-amino-2-hydroxybenzonitrile (prepared by hydrogenating 2-hydroxy-4-nitro-benzonitrile [W. Borsche, Ann. Chem. (1912) 390, 1] with Pd/C) and benzyl isonitrile there was obtained methyl (RS)-(4-cyano-3-hydroxy-phenylamino)-(3,5-dimethoxy-phenyl)-acetate, therefrom via (RS)-(4-cyano-3-hydroxy-phenylamino)-(3,5-dimethoxy-phenyl)-acetic acid there was obtained (E)- and/or (Z)-(RS)-(3,5-dimethoxy-phenyl)-[3-hydroxy-4-(N-hydroxycarbamimidoyl)-phenylamino]-acetic acid;

2.d
   from benzaldehyde, 4-aminobenzonitrile and benzyl isonitrile there was obtained (RS)-(4-cyano-3-hydroxyphenylamino)-(3,5-dimethoxy-phenyl)-acetic acid, therefrom via (RS)-(4-cyano-phenylamino)-phenyl-acetic acid there was obtained (E)- and/or (Z)-(RS)-[4-(N-hydroxycarbamimidoyl)-phenylamino]-phenyl-acetic acid;

2.e
from 4-benzyloxy-3-methoxybenzaldehyde, 4-aminobenzonitrile and benzyl isonitrile there was obtained methyl (RS)-(4-benzyloxy-3-methoxy-phenyl)-(4-cyano-phenylamino)-acetate, therefrom via (RS)-(4-benzyloxy-3-methoxy-phenyl)-(4-cyano-phenylamino)-acetic acid there was obtained (E)- and/or (Z)-(RS)-(4-benzyloxy-3-methoxy-phenyl)-[4-(N-hydroxycarbamimidoyl)-phenylamino]-acetic acid;

2.f
from methyl 4-(4-formyl-2-methoxy-phenoxy)-benzoate, 4-aminobenzonitrile and benzyl isonitrile there was obtained methyl (RS)-4-[4-[(4-cyano-phenylamino)-methoxycarbonyl-methyl]-2-methoxy-phenoxy]-benzoate, therefrom via (RS)-4-[4-[carboxy-(4-cyano-phenyl-amino)-methyl]-2-methoxy-phenoxy]-benzoic acid there was obtained (E)- and/or (Z)-(RS)-4-[4-[carboxy-[4-(N-hydroxycarbamimidoyl)-phenylamino]-methyl]-2-methoxy-phenoxy]-benzoic acid;

2.g
from 3,5-trifluoromethylbenzaldehyde, 4-aminobenzonitrile and benzyl isonitrile there was obtained methyl (RS)-(3,5-bis-trifluoromethyl-phenyl)-(4-cyano-phenylamino)-acetate, therefrom via (RS)-(3,5-bis-trifluoromethyl-phenyl)-(4-cyano-phenylamino)-acetic acid there was obtained (E)- and/or (Z)-(RS)-(3,5-bis-trifluoromethyl-phenyl)-[4-(N-hydroxycarbamimidoyl)-phenylamino]-acetic acid.

Example 3

A solution of 0.3 g of the compound obtained in Example 1.3. in 6 ml of ethanol, 3 ml of dimethylformamide (DMF), 5 ml of water and 5 ml of aceti acid was hydrogenated for 4 hours in the presence of a catalytic amount of einer catalytic amount of Raney-Ni. The reaction mixture was filtered. The crude product was purified by chromatography on silica gel and yielded 0.12 g of (RS)-(4-Carbamimidoyl-phenylamino)-3,5-diethoxy-phenyl)-acetic acid as a grey-white solid.

Example 4

In analogy to Example 3, 4.a
the compound obtained in Example 2.a was converted into (RS)-(4-carbamimidoyl-phenylamino)-(4-ethoxy-3-methoxy-phenyl)-acetic acid acetate (1:1);

4.b
the compound obtained in Example 2.b was converted into (RS)-(4-benzyloxy-3-ethoxy-phenyl)-(4-carbamimidoyl-phenylamino)-acetic acid acetate (1:1);

4.c
the compound obtained in Example 2.c was converted into (RS)-(4-carbamimidoyl-3-hydroxy-phenylamino)-(3,5-dimethoxy-phenyl)-acetic acid acetate (1:1);

4.d
the compound obtained in Example 2.d was converted into (RS)-(4-carbamimidoyl-phenylamino)-phenyl-acetic acid;

4.e
the compound obtained in Example 2.e was converted into (RS)-(4-benzyloxy-3-methoxy-phenyl)-(4-carbamimidoyl-phenylamino)-acetic acid;

4.f
the compound obtained in Example 2.f was converted into (RS)-4-[4-[(4-carbamimidoyl-phenylamino)-carboxy-methyl]-2-methoxy-phenoxy]-benzoic acid acetate (1:1); and 4.g
the compound obtained in Example 2.g was converted into (RS)-(3,5-bis-trifluoromethyl-phenyl)-(4-carbamimidoyl-phenylamino)-acetic acid.

Example 5

5.1
In analogy to Example 1.1, methyl 5-formyl-2,3-dimethoxy-benzoate (F. Y. Wu, D. L. b rink, J. Agric. Food Chem. (1977) 25 692) was reacted with 4-aminobenzonitrile and benzyl isonitrile to give methyl (RS)-5-[(4-cyano-phenylamino)-methoxycarbonyl-methyl]-2,3-dimethoxy-benzoate.

5.2
In analogy to Example 1.2, the compound obtained Example 5.1 was converted into methyl (E)- and/or (Z)-(RS)-5-[[4-(N-hydroxycarbamimidoyl)-phenylamino]-methoxycarbonylmethyl]-2,3-dimethoxy-benzoate.

5.3
In analogy to Example 3, the compound obtained in Example 5.2 was converted into methyl (RS)-5-[(4-carbamimidoyl-phenylamino)-methoxycarbonyl-methyl]-2,3-dimethoxy-benzoate acetate (1:1).

5.4
In analogy to Example 1.2, the compound obtained in Example 5.3 was converted into methyl (RS)-5-[(4-carbamimidoyl-phenylamino)-carboxy-methyl]-2,3-dimethoxy-benzoate.

Example 6

6.1
In analogy to Example 1.1, 3,5-dimethylbenzaldehyde was reacted with 4-aminobenzonitrile and benzyl isonitrile to give methyl (RS)-(4-cyano-phenylamino)-(3,5-dimethyl-phenyl)-acetate. In analogy to Example 1.2, this compound was converted into (RS)-(4-cyano-phenylamino)-(3,5-dimethyl-phenyl)-acetic acid.

6.2
A solution of 0.5 g of the compound obtained in Example 6.1 in 20 ml of $CHCl_3$/methanol (5:1) was cooled to 0° C. Then, a dry stream of HCl gas was conducted over the mixture for 20 minutes. The reaction mixture was held for 2 days at 4° C., then concentrated. The residue was dissolved in 200 ml of saturated methanolic ammonia solution, heated to reflux for 3 hours and then concentrated. The residue was crystallized from ethyl acetate and yielded 0.552 g of methyl (RS)-(4-carbamimidoyl-phenylamino)-(3,5-dimethyl-phenyl)-acetate hydrochloride (1:1) as a crystalline solid.

6.3
In analogy to Example 1.3, the compound obtained in Example 6.2 was converted into (RS)-(4-carbamimidoyl-phenylamino)-(3,5-dimethyl-phenyl)-acetic acid hydrochloride (1:1).

Example 7

In analogy to Example 6, 7.a
3,4-dimethoxybenzaldehyde was reacted with 4-aminobenzonitrile and benzyl isonitrile to give methyl (RS)-(4-cyano-phenylamino)-(3,4-dimethyl-phenyl)-acetate and this was converted via (RS)-(4-cyano-phenylamino)-(3,4-dimethyl-phenyl)-acetic acid and methyl (RS)-(4-carbamimidoyl-phenylamino)-(3,4-dimethyl-phenyl)-acetate hydrochloride (1:1) into (RS)-(4-carbamimidoyl-phenylamino)-(3,4-dimethyl-phenyl)-acetic acid hydrochloride (1:1);

7.b
3,4-diethoxybenzaldehyde was reacted with 4-aminobenzonitrile and benzyl isonitrile to give methyl (RS)-(4-cyano-phenylamino)-(3,4-diethoxy-phenyl)-acetate and this was converted via (RS)-(4-cyano-phenylamino)-(3,4-diethoxy-phenyl)-acetic acid and methyl (RS)-(4-carbamimidoyl-phenylamino)-(3,4-diethoxy-phenyl)-acetate hydrochloride (1:1) into (RS)-(4-carbamimidoyl-phenylamino)-(3,4-diethoxy-phenyl)-acetic acid;

7.c
3,4-dimethoxybenzaldehyde was reacted with 4-aminobenzonitrile and benzyl isonitrile to give methyl (RS)-(4-cyano-phenylamino)-(3,4-dimethoxy-phenyl)-acetate and this was converted via (RS)-(4-cyano-phenylamino)-(3,4-dimethoxy-phenyl)-acetic acid and methyl (RS)-(4-carbamimidoyl-phenylamino)-(3,4-dimethoxy-phenyl)-acetate hydrochloride (1:1) into (RS)-(4-carbamimidoyl-phenylamino)-(3,4-dimethoxy-phenyl)-acetic acid hydrochloride (1:1);

7.d
3,5-dimethoxybenzaldehyde was reacted with 4-aminobenzonitrile and benzyl isonitrile to give methyl (RS)-(4-cyano-phenylamino)-(3,5-dimethoxy-phenyl)-acetate and this was converted via (RS)-(4-cyano-phenylamino)-(3,5-dimethoxy-phenyl)-acetic acid and methyl (RS)-(4-carbamimidoyl-phenylamino)-(3,5-dimethoxy-phenyl)-acetate hydrochloride (1:1) into (RS)-(4-carbamimidoyl-phenylamino)-(3,5-dimethoxy-phenyl)-acetic acid hydrochloride (1:1);

7.e
3,5-dichlorobenzaldehyde was reacted with 4-aminobenzonitrile and benzyl isonitrile to give methyl (RS)-(4-cyano-phenylamino)-(3,5-dichloro-phenyl)-acetate and this was converted via (RS)-(4-cyano-phenylamino)-(3,5-dichloro-phenyl)-acetic acid and methyl (RS)-(4-carbamimidoyl-phenylamino)-(3,5-dichloro-phenyl)-acetate hydrochloride (1:1 into (RS)-(4-carbamimidoyl-phenylamino)-(3,5-dichloro-phenyl)-acetic acid hydrochloride (1:1);

7.f
4,5-dimethoxy-2-fluorobenzaldehyde was reacted with 4-aminobenzonitrile and benzyl isonitrile to give methyl (RS)-(4-cyano-phenylamino)-(2-fluoro-4,5-dimethoxy-phenyl)-acetate and this was converted via (RS)-(4-cyano-phenylamino)-(2-fluoro-4,5-dimethoxy-phenyl)-acetic acid and methyl (RS)-(4-carbamimidoyl-phenylamino)-(2-fluoro-4,5-dimethoxy-phenyl)-acetate hydrochloride (1:1) into (RS)-(4-carbamimidoyl-phenylamino)-(2-fluoro-4,5-dimethoxy-phenyl)-acetic acid hydrochloride (1:1);

7.g
3-ethoxy-4-methoxybenzaldehyde was reacted with 4-aminobenzonitrile and benzyl isonitrile to give methyl (RS)-(4-cyano-phenylamino)-(3-ethoxy-4-methoxy-phenyl)-acetate and this was converted via (RS)-(4-cyano-phenylamino)-(3-ethoxy-4-methoxy-phenyl)-acetic acid and methyl (RS)-(4-carbamimidoyl-phenylamino)-(3-ethoxy-4-methoxy-phenyl)-acetate hydrochloride (1:1) into (RS)-(4-carbamimidoyl-phenylamino)-(3-ethoxy-4-methoxy-phenyl)-acetic acid hydrochloride (1:1);

7.h
2,6-dimethoxypyridine-4-aldehyde (I. Kompis, W. Müller, E. Böhni, R. Then, M. Montavon Eur. J. Chem.-Chim.Ther. (1977) 12, 531) was reacted with 4-aminobenzonitrile and benzyl isonitrile to give methyl (RS)-(4-cyano-phenylamino)-(2,6-dimethoxy-pyridin-4-yl)-acetate and this was converted via (RS)-(4-cyano-phenylamino)-(2,6-dimethoxy-pyridin-4-yl)-acetic acid and methyl (RS)-(4-carbamimidoyl-phenylamino)-(2,6-dimethoxy-pyridin-4-yl)-acetate hydrochloride (1:1) into (RS)-(4-carbamimidoyl-phenylamino)-(2,6-dimethoxy-pyridin-4-yl)-acetic acid hydrochloride (1:1); and 7.i
3,5-dimethoxybenzaldehyde was reacted with 3-aminobenzonitrile and benzyl isonitrile to give methyl (RS)-(3-cyano-phenylamino)-(3,5-dimethoxy-phenyl)-acetate and this was converted via (RS)-(3-cyano-phenylamino)-(3,5-dimethoxy-phenyl)-acetic acid and methyl (RS)-(3-carbamimidoyl-phenylamino)-(3,5-dimethoxy-phenyl)-acetate hydrochloride (1:1) into (RS)-(3-carbamimidoyl-phenylamino)-(3,5-dimethoxy-phenyl)-acetic acid hydrochloride (1:1).

Example 8

8.1
In analogy to Example 1.1, 3-benzyloxy-5-methoxy-benzaldehyde was reacted with 4-aminobenzonitrile and benzyl isonitrile to give methyl (RS)-(3-benzyloxy-5-methoxy-phenyl)-(4-cyano-phenylamino)-acetate.

8.2
In analogy to Example 1.2, the compound obtained in Example 8.1 was converted into (RS)-(3-benzyloxy-5-methoxy-phenyl)-(4-cyano-phenylamino)-acetic acid.

8.3
In analogy to Example 1.2, the compound obtained in Example 8.2 was converted into methyl (RS)-(3-benzyloxy-5-methoxy-phenyl)-(4-carbamimidoyl-phenylamino)-acetate hydrochloride (1:1) and methyl (RS)-(4-carbamimidoyl-phenylamino)-(3-hydroxy-5-methoxy-phenyl)-acetate hydrochloride (1:1).

8.4
In analogy to Example 1.2, the first compound obtained in Example 8.3 was converted into (RS)-(3-benzyloxy-5-methoxy-phenyl)-(4-carbamimidoyl-phenylamino)-acetic acid hydrochloride (1:1) and the second compoud obtained in Example 8.3 was converted into (RS)-(4-carbamimidoyl-phenylamino)-(3-hydroxy-5-methoxy-phenyl)-acetic acid hydrochloride (1:1).

Example 9

In analogy to Example 8, 3-benzyloxy-5-methoxybenzaldehyde was reacted with 4-aminobenzonitrile and benzyl isonitrile to give methyl (RS)-(3-benzyloxy-5-methoxy-phenyl)-(4-cyano-phenylamino)-acetate. This compound was then converted into (RS)-(3-benzyloxy-5-ethoxy-phenyl)-(4-cyano-phenylamino)-acetic acid and this was converted via methyl (RS)-(3-benzyloxy-5-ethoxy-phenyl)-(4-carbamimidoyl-phenylamino)-acetate hydrochloride (1:1) into (RS)-(3-benzyloxy-5-ethoxy-phenyl)-(4-carbamimidoylphenylamino)-acetic acid hydrochloride (1:1) and via methyl (RS)-(4-carbamimidoyl-phenylamino)-(3-ethoxy-5-hydroxy-phenyl)-acetate hydrochloride (1:1) into (RS)-(4-carbamimidoyl-phenylamino)-(3-ethoxy-5-hydroxy-phenyl)-acetic acid hydrochloride (1:1).

Example 10

10.a

A solution of 0.5 g of (RS)-(4-cyano-phenylamino)-(3,4-diethoxy-phenyl)-acetic acid (Example 7.b) in 24 ml of $CHCl_3$/methanol (5:1) was cooled to 0° C. A stream of dry HCl gas was conducted over this. The reaction mixture was held at 4° C. for 1 day, then concentrated. The residue was taken up in $CH_2Cl_2$ and washed with saturated $NaHCO_3$ solution. The organic phase was dried over $Na_2SO_4$ and filtered. The filtrate was concentrated and the residue was dissolved in ethanol. The solution was treated with 1.02 g of hydroxylamine hydrochloride and 4.1 ml of triethylamine. The reaction mixture was heated at reflux for 3 hours. The crude product was extracted and crystallized from diethyl ether and yielded 0.27 g of methyl (E)- and/or (Z)-(RS)-(3,4-diethoxy-phenyl)-[4-(N-hydroxycarbamimidoyl)-phenylamino]-acetate as a crystalline solid.

10.b

In analogy to Example 17.a, methyl (RS)-(4-cyano-phenylamino)-(3,5-dimethoxy-phenyl)-acetic acetate (Example 7.d) was converted into (E)- and/or (Z)-(RS)-(3,5-dimethoxy-phenyl)-[4-(N-hydroxycarbamimidoyl)-phenylamino]-acetate hydrochloride (1:1).

Example 11

In analogy to Example 1.3, 11.a (RS)-(4-cyano-phenylamino)-(3,4-diethoxy-phenyl)-acetic acid (Example 7.b) was converted into (E)- and/or (Z)-(RS)-(3,4-diethoxy-phenyl)-[4-(N-hydroxycarbamimidoyl)-phenylamino]-acetic acid; and 11.b (RS)-(4-cyano-phenylamino)-(3,5-dimethoxy-phenyl)-acetic acid (see Example 7.d) was converted into (E)- and/or (Z)-(RS)-(3,5-dimethoxy-phenyl)-[4-(N-hydroxycarbamimidoyl)-phenylamino]-acetic acid.

Example 12

12.1

0.808 ml of ethyl bromoacetate and 1 g of potassium carbonate were added to a solution of 838 mg of 2-hydroxy-4,5-dimethylbenzaldehyde (J.Chem.Soc. (1953) 820) in 150 ml of acetone. The suspension obtained was heated to reflux overnight and then filtered. The filtrate was concentrated. The crude product was isolated by extraction and purified by chromatography on silica gel and yielded 952 mg of ethyl (2-formyl-4,5-dimethyl-phenoxy)-acetate as a pale yellow solid.

12.2.

In analogy to Example 1, the compound obtained in Example 12:1 was reacted with 4-aminobenzonitrile and benzyl isonitrile to give methyl (RS)-(4-cyano-phenylamino)-(2-ethoxycarbonylmethoxy-4,5-dimethyl-phenyl)-acetate. The product obtained was then converted via (RS)-(2-carboxymethoxy-4,5-dimethyl-phenyl)-(4-cyano-phenylamino)-acetic acid into (E)- and/or (Z)-(RS)-(2-carboxymethoxy-4,5-dimethyl-phenyl)-[4-(N-hydroxycarbamimidoyl)-phenylamino]-acetic acid.

Example 13

In analogy to Example 12.1, 2-hydroxy-3,5-dimethoxy-benzaldehyde (A. K. Sinhababu, R. T. Borchardt, J. Org. Chem. (1983), 48, 1941–1944) was converted into ethyl (2-formyl-4,6-dimethoxy-phenoxy)-acetate. In analogy to Example 1, the product obtained was reacted with 4-aminobenzonitrile to give methyl (RS)-(4-cyano-phenylamino)-(2-ethoxycarbonylmethoxy-3,5-dimethoxy-phenyl)-acetate. This compound was converted via (RS)-(2-carboxymethoxy-3,5-dimethoxy-phenyl)-(4-cyano-phenylamino)-acetic acid into (E)- and/or (Z)-(RS)-(2-carboxymethoxy-3,5-dimethoxy-phenyl)-[4-(N-hydroxycarbamimidoyl)-phenylamino]-acetic acid.

Example 14

In analogy to Example 3, the compound obtained in Example 12.2 was converted into (RS)-(4-carbamimidoyl-phenylamino)-(2-carboxymethoxy-4,5-dimethyl-phenyl)-acetic acid.

Example 15

In analogy to Example 3, the compound obtained in Example 13 was converted into (RS)-(4-carbamimidoyl-phenylamino)-(2-carboxymethoxy-3,5-dimethoxy-phenyl)-acetic acid.

Example 16

16.1

A suspension of 10.88 g of 2-benzyloxy-4,5-dimethoxy-benzaldehyde and 4.72 g of 4-aminobenzonitrile was stirred vigorously at room temperature. After one hour 5 ml of benzyl isonitrile were added. The reaction mixture was cooled to 0° C. Then, 15 ml of boron trifluoride etherate were added in a manner such that the temperature did not exceed 10° C. The brown solution obtained was stirred at 5° C. A precipitate began to form after 15 minutes. The mixture was then stirred for a further 3 hours at 5° C., the solid was filtered off and dried. There were obtained 19.1 g of methyl (E)- and/or (Z)-(RS)-N-benzyl-2-(2-benzyloxy-4,5-dimethoxy-phenyl)-2-(4-cyano-phenylamino)-acetimidate trifluoroborane complex as a grey-white crystalline solid.

16.2

A suspension of 13.1 g of the compound obtained in Example 16.1 in 1300 ml of methanol and 130 ml of water was heated to reflux for 1 hour. The solution obtained was concentrated under reduced pressure. After most of the methanol had been evaporated a precipitate began to form and this was filtered off and dried and yielded 9.6 g of methyl (RS)-(2-benzyloxy-4,5-dimethoxy-phenyl)-(4-cyano-phenylamino)-acetic acid.

16.3.

400 mg of palladium/carbon were added to a solution of 3.8 g of the compound obtained in Example 16.2 in 170 ml methanol and 17 ml of THF. The reaction mixture was hydrogenated for 5 hours, then filtered and concentrated under reduced pressure. The crude product was purified by chromatography on silica gel and yielded 1.5 g of methyl (RS)-(4-cyano-phenylamino)-(2-hydroxy-4,5-dimethoxy-phenyl)-acetate.

16.4

In analogy to Example 12.1, the compound obtained wurde die in Example 16.3. was converted into methyl (RS)-(4-cyano-phenylamino)-(4,5-dimethoxy-2-methoxycarbonylmethoxy-phenyl)-acetate.

16.5

In analogy to Example 1.2 and 1.3, the compound obtained in Example 16.4 was converted via (RS)-(2-carboxymethoxy-4,5-dimethoxy-phenyl)-(4-cyano-phenylamino)-acetic acid into (E)- and/or (Z)-(RS)-(2-carboxymethoxy-4,5-dimethoxy-phenyl)-[4-(N-hydroxycarbamimidoyl)-phenylamino]-acetic acid.

Example 17

In analogy to Example 3, the compound obtained in Example 16.5 was converted into (RS)-(4-carbamimidoyl-phenylamino)-(2-carboxymethoxy-4,5-dimethoxy-phenyl)-acetic acid.

Example 18

18.1

0.49 ml of methyl R-lactate, 1.26 g of triphenylphosphine and 0.76 mmol of diethyl azodicarboxylate were added to a solution of 1.06 g of the compound obtained in Example 16.3 in 14 ml THF. The reaction mixture was stirred at room temperature for one hour, then concentrated under reduced pressure. The residue was purified by chromatography on silica gel and yielded 0.91 g of a 1:1 mixture of methyl (S)-2-[2-[(R)- and -[(S)-( 4-cyano-phenylamino)-methoxycarbonyl-methyl]-4,5-dimethoxy-phenoxy]-propionate as a brown foam.

18.2

In analogy to Example 1.2, the compound obtained in Example 18.1 was converted into the two epimers (S)-2-[2-[(R)- or -[(S)-carboxy-(4-cyano-phenylamino)-methyl]-4,5-dimethoxy-phenoxy]-propionic acid and (S)-2-[2-[(S)- or -[(R)-carboxy-(4-cyano-phenylamino)-methyl]-4,5-dimethoxy-phenoxy]-propionic acid. The epimers were separated by chromatography on silica gel.

18.3

In analogy to Example 1.3, the first epimer from Example 18.2 was converted into (E)- and/or (Z)-(S)-2-[2-[(R)- or -[(S)-carboxy-[4-(N-hydroxycarbamimidoyl)-phenylamino]-methyl]-4,5-dimethoxy-phenoxy]-propionic acid and the second epimer from Example 18.2 was converted into (E)- and/or (Z)-(S)-2-[2-[(S)- or -[(R)-carboxy-[4-(N-hydroxycarbamimidoyl)-phenylamino]-methyl]-4,5-dimethoxy-phenoxy]-propionic acid.

Example 19

In analogy to Example 3, the first epimer from Example 18.3 was converted into (S)-2-[(S)- or -[(R)-2-[(4-carbamimidoyl-phenylamino)-carboxy-methyl]-4,5-dimethoxy-phenoxy]-propionic acid and the second epimer from Example 18.3 was converted into (S)-2-[(R)- or -[(S)-2-((4-carbamimidoyl-phenylamino)-carboxy-methyl]-4,5-dimethoxy-phenoxy]-propionic acid.

Example 20

20.1

In analogy to Example 1.1, 2-hydroxy-3,5-dimethylbenzaldehyde (G. Casiraghi, G. Casnati, J.Chem. Soc. 1862 (1980)), 4-aminobenzonitrile and benzyl isonitrile were reacted to give methyl (RS)-(4-cyano-phenylamino)-(2-hydroxy-3,5-dimethyl-phenyl)-acetate.

20.2

In analogy to Example 16.4–16.6, the compound obtained in Example 20.1 was coverted via methyl (RS)-(4-cyano-phenylamino)-(2-ethoxycarbonylmethoxy-4,5-dimethyl-phenyl)-acetate and (RS)-(2-carboxymethoxy-4,5-dimethyl-phenyl)-(4-cyano-phenylamino)-acetic acid into (E)- and/or (Z)-(RS)-(2-carboxymethoxy-3,5-dimethyl-phenyl)-[4-(N-hydroxycarbamimidoyl)-phenylamino]-acetic acid.

Example 21

In analogy to Example 3, the compound obtained in Example 20.2 was converted into (RS)-(4-carbamimidoyl-phenylamino)-(2-carboxymethoxy-3,5-dimethyl-phenyl)-acetic acid acetate (1:1).

Example 22

22.1

2.35 ml of diisopropylethylamine and 0.83 mmol of phenylacetyl chloride were added to a solution of 2.3 g of methyl (RS)-(2-amino-4-benzyloxy-5-methoxy-phenyl)-(4-cyano-phenylamino)-acetate (prepared by reacting 4-benzyloxy-5-methoxy-2-nitrobenzaldehyde with 4-aminobenzonitrile and benzyl isonitrile to give methyl (RS)-(4-benzyloxy-5-methoxy-2-nitro-phenyl)-(4-cyano-phenylamino)-acetate and hydrogenation of the nitro group with Pt/C) in 60 ml THF. The solution obtained was stirred for 3 hours at 50° C. and then at room temperature overnight and concentrated under reduced pressure. The residue was purified by chromatography on silica gel and yielded 2.05 g of methyl (RS)-(4-benzyloxy-5-methoxy-2-phenylacetylamino-phenyl)-(4-cyano-phenylamino)-acetate as a crystalline colorless solid.

22.2

In analogy to Example 1.2 and 1.3, the compound obtained in Example 22.1 was converted via (RS)-(4-benzyloxy-5-methoxy-2-phenylacetylamino-phenyl)-(4-cyano-phenylamino)-acetic acid into (E)- and/or (Z)-(RS)-(4-benzyloxy-5-methoxy-2-phenylacetylamino-phenyl)-[4-(N-hydroxycarbamimidoyl)-phenylamino]-acetic acid.

Example 23

In analogy to Example 22, methyl (RS)-(2-amino-4-benzyloxy-5-methoxy-phenyl)-(4-cyano-phenylamino)-acetate was reacted 23.a with acetyl chloride to give methyl (RS)-(2-acetylamino-4-benzyloxy-5-methoxy-phenyl)-(4-cyano-phenylamino)-acetate and this was converted via (RS)-(2-acetylamino-4-benzyloxy-5-methoxy-phenyl)-(4-cyano-phenylamino)-acetic acid into (E)- and/or (Z)-(RS)-(2-acetylamino-4-benzyloxy-5-methoxy-phenyl)-[4-(N-hydroxycarbamimidoyl)-phenylamino]-acetic acid;

23.b with methoxyacetyl chloride to give methyl (RS)-[4-benzyloxy-5-methoxy-2-(2-methoxy-acetylamino)-phenyl]-(4-cyano-phenylamino)-acetate and this was converted via (RS)-[4-benzyloxy-5-methoxy-2-(2-methoxy-acetylamino)-phenyl]-(4-cyano-phenylamino)-acetic acid into (E)- and/or (Z)-(RS)-[4-benzyloxy-5-methoxy-2-(2-methoxy-acetylamino)-phenyl]-[4-(N-hydroxycarbamimidoyl)-phenylamino]-acetic acid;

23.c with methanesulphonyl chloride to give methyl (RS)-[4-benzyloxy-2-(bis-methanesulphonylamino)-5-methoxy-phenyl]-(4-cyano-phenylamino)-acetate and this was converted via (RS)-(4-benzyloxy-2-methanesulphonylamino-5-methoxy-phenyl)-(4-cyano-phenylamino)-acetic acid to give (E)- and/or (Z)-(RS)-(4-benzyloxy-2-methanesulphonylamino-5-methoxy-phenyl)-[4-(N-hydroxycarbamimidoyl)-phenylamino]-acetic acid.

Example 24

In analogy to Example 3, 24.a the compound prepared in Example 22.2 was converted into (RS)-(4-benzyloxy-5-methoxy-2-phenylacetylamino-phenyl)-(4-carbamimidoyl-phenylamino)-acetic acid;

24.b the compound prepared in Example 23.a was converted into (RS)-(2-acetylamino-4-benzyloxy-5-methoxy-phenyl)-(4-carbamimidoyl-phenylamino)-acetic acid;

the compound prepared in Example 23.b was converted into [4-benzyloxy-5-methoxy-2-(2-methoxy-acetylamino)-phenyl]-(4-carbamimidoyl-phenylamino)-acetic acid; and 24.d the compound prepared in Example 23.c was converted into (RS)-(4-benzyloxy-2-methanesulphonylamino-5-methoxy-phenyl)-(4-carbamimidoyl-phenylamino)-acetic acid.

Example 25

25.1

In analogy to Example 18.1., the compound prepared in Example 16.3. was reacted with 2-benzyloxyethanol to give methyl (RS)-[2-(2-benzyloxy-ethoxy)-4,5-dimethoxy-phenyl]-(4-cyano-phenylamino)-acetate.

25.2

In analogy to Example 1.2 and 1.3, the compound prepared in Example 25.1. was converted via (RS)-[2-(2-benzyloxy-ethoxy)-4,5-dimethoxy-phenyl]-(4-cyano-phenylamino)-acetic acid into (E)- and/or (Z)-(RS)-[2-(2-benzyloxy-ethoxy)-4,5-dimethoxy-phenyl]-[4-(N-hydroxycarbamimidoyl)-phenylamino]-acetic acid.

Example 26

26.a

In analogy to Example 3, the compound prepared in Example 25.2. was converted into (RS)-[2-(2-benzyloxy-ethoxy)-4,5-dimethoxy-phenyl]-(4-carbamimidoyl-phenylamino)-acetic acid.

26.b 11 mg of palladium/carbon (10%) were added to a solution of 100 mg of the compound prepared in Example 25.2 in 5 ml of ethanol, 5 m of THF, 2 ml of water and 1 ml of acetic acid. The reaction mixture was hydrogenated overnight and then filtered. The filtrate was concentrated under reduced pressure. The residue was crystallized from methanol/acetone and yielded 30 mg of (RS)-(4-carbamimidoyl-phenylamino)-[2-(2-hydroxy-ethoxy)-4,5-dimethoxy-phenyl]-acetic acid as a colorless crystalline solid.

Example 27

27.1

6.2 ml of methyl acrylate, 25 ml of triethylamine, 270 mg of Pd(OAc)$_2$ and 1.5 g of tri-(o-tolyl)-phosphine were added to a solution of 14.7 g of 6-bromoveratraldehyde in 100 ml of dimethylacetamide. The reaction mixture was heated for 4 hours to 110° C., then left to cool to room temperature and poured into a mixture of ethyl acetate and water. The crude product was extracted and purified by chromatography on silica gel and yielded 10.8 g of methyl (E)-3-(2-formyl-4,5-dimethoxy-phenyl)-acrylate as a yellow solid.

27.2

1.1 g of Mg powder were added to a solution of 1.15 g of the compound obtained in Example 27.1 in 20 ml of methanol. The reaction mixture was stirred at room temperature for 2 hours, treated with 25 ml of 3N HCl and extracted with ethyl acetate. The crude product was purified by chromatography on silica gel and yielded 776 mg of methyl 3-(2-hydroxymethyl-4,5-dimethoxy-phenyl)-propionate as a yellow oil.

27.3

1.5 mg of MnO$_2$ were added to a solution of 812 mg of the compound obtained in Example 27.2 in 15 ml of 1,2-dichloroethane. The reaction mixture was stirred for 3 hours at 50° C., then filtered and concentrated. The residue was purified by chromatography on silica gel and yielded 671 mg of methyl 3-(2-formyl-4,5-dimethoxy-phenyl)-propionate as a colorless resin.

27.4

In analogy to Example 1.1, the compound obtained in Example 27.3 was reacted with 4-aminobenzonitrile and benzyl isonitrile to give methyl (RS)-3-[2-[(4-cyano-phenylamino)-methoxycarbonyl-methyl]-4,5-dimethoxy-phenyl]-propionate. In analogy to Example 1.2 and 1.3, the compound obtained was then converted via (RS)-3-t2-[carboxy-(4-cyano-phenylamino)-methyl]-4,5-dimethoxy-phenyl]-propionic acid into (E)- and/or (Z)-(RS)-3-[2-[carboxy-[4-(N-hydroxycarbamimidoyl)-phenylamino]-methyl]-4,5-dimethoxy-phenyl]-propionic acid.

Example 28

In analogy to Example 3, the compound obtained in Example 27.4 was converted into (RS)-3-[2-[(4-carbamimidoyl-phenylamino)-carboxy-methyl]-4,5-dimethoxy-phenyl]-propionic acid.

Example 29

29.1

In analogy to Example 27., 2-bromo-3,5-dimethoxy-benzaldehyde (J.Org.Chem. (1983), 48, 1941) was converted into methyl (E)-3-(2-formyl-4,6-dimethoxy-phenyl)-acrylate.

29.2

160 mg of palladium/carbon (10%) were added to a solution of 3.7 g of the compound obtained in Example 29.1 in 60 ml THF. The reaction mixture was hydrogenated for 5 hours, then filtered and concentrated. The residue was purified by chromatography on silica gel and yielded methyl 3-(2-hydroxymethyl-4,6-dimethoxy-phenyl)-propionate as a colorless oil.

29.3

In analogy to Example 27.3, the compound obtained in Example 29.2 was converted into methyl 3-(2-formyl-4,6-dimethoxy-phenyl)-propionate.

29.4

In analogy to Example 1.1, the compound obtained in Example 29.3 was reacted with 4-aminobenzonitrile and benzyl isonitrile to give methyl (RS)-3-[2-[(4-cyano-phenylamino)-methoxycarbonyl-methyl]-4,6-dimethoxy-phenyl]-propionate. In analogy to Example 1.2 and 1.3, this compound was then converted via (RS)-3-[2-[carboxy-(4-cyano-phenylamino)-methyl]-4,6-dimethoxy-phenyl]-propionic acid into (E)- and/or (Z)-(RS)-3-[2-[carboxy-[4-(N-hydroxycarbamimidoyl)-phenylamino]-methyl]-4,6-dimethoxy-phenyl]-propionic acid.

Example 30

In analogy to Example 3, the compound obtained in Example 29.4 was converted into (RS)-3-[2-[(4-carbamimidoyl-phenylamino)-carboxy-methyl]-4,6-dimethoxy-phenyl]-propionic acid.

Example 31

31.1

6.27 g of tert-butyl-dimethylsilyl chloride, 6.63 ml of triethylamine and 270 mg of imidazole were added to a solution of 10 g of diethyl 5-(hydroxymethyl)isophthalate in 100 ml of DMF. The reaction ixture was stirred at room temperature for 4 hours and worked up by extraction. The silylated crude product was dissolved in 150 ml of THF. The solution obtained was treated with 17.8 g of LiBH$_4$. The reaction mixture was stirred at 40° C. overnight. Then, saturated NH$_4$Cl solution was cautiously added at 0° C. The crude producty was isolated by extraction and purified by chromatography on silica gel and yielded 4.93 g of tert-butyl-(3,5-dimethoxy-benzyloxy)-dimethyl-silane and 5.31 g of ethyl 3-(tert-butyl-dimethyl-silanyloxymethyl)-5-hydroxymethyl-benzoate.

31.2

0.64 ml of oxalyl chloride was added at −60° C. to a solution of 0.76 ml of dimethyl sulphoxide in 10 ml of CH$_2$Cl$_2$. After 5 minutes 2 g of ethyl 3-(tert-butyl-dimethyl-silanyloxymethyl)-5-hydroxymethyl-benzoate (Example 31.1) in 20 ml of CH$_2$Cl$_2$ were addded over 5 minutes in a manner such that the temperature did not exceed −60° C. After 15 minutes 4.295 m triethylamine were added. The reaction mixture was left too warm to room temperature and was worked up by extraction and yielded 2.0 g of ethyl 3-(tert-butyl-dimethyl-silanyloxymethyl)-5-formyl-benzoate.

31.3

In analogy to Example 1, the compound obtained [in] Example 31.2 was reacted with 4-aminobenzonitrile and benzyl isonitrile to give ethyl (RS)-3-[(4-cyano-phenylamino)-methoxycarbonyl-methyl]-5-hydroxymethyl-benzoate. This compound was then converted via (RS)-3-[carboxy-(4-cyano-phenylamino)-methyl]-5-hydroxymethyl-benzoic acid into (E)- and/or (Z)-(RS)-3-[carboxy-[4-(N-hydroxycarbamimidoyl)-phenylamino]-methyl]-5-hydroxymethyl-benzoic acid.

Example 32

32.a

In analogy to Example 3, the compound obtained in Example 31.3 was converted into (RS)-3-[(4-carbamimidoyl-phenylamino)-carboxy-methyl]-5-hydroxymethyl-benzoic acid.

32.b 0.42 ml of thionyl chloride was added to a solution of 0.2 g of the compound obtained in Example 32.a. The reaction mixture was stirred at room temperature overnight and then conecentrated. The residue was treated with diethyl ether and yielded 0.157 g of methyl (RS)-3-[(4-carbamimidoyl-phenylamino)-methoxycarbonyl-methyl]-5-hydroxymethyl-benzoate hydrochloride (1:1).

Example 33

33.1

In analogy to Example 31.2, tert-butyl-(3,5-dimethoxy-benzyloxy)-dimethyl-silane (Example 31.1) was converted into 3,5-bis-(tert-butyl-dimethyl-silanyloxymethyl)-benzaldehyde.

33.2

In analogy to Example 1, the compound obtained in Example 33.1 was reacted with 4-aminobenzonitrile and benzyl isonitrile to give methyl (RS)-(3,5-bis-hydroxymethyl-phenyl)-(4-cyano-phenylamino)-acetate. This compound was converted via (RS)-(3,5-bis-hydroxymethyl-phenyl)-(4-cyano-phenylamino)-acetic acid into (E)- and/or (Z)-(RS)-(3,5-bis-hydroxymethyl-phenyl)-[4-(N-hydroxycarbamimidoyl)-phenylamino]-acetic acid.

Example 34

In analogy to Example 3, the compound obtained in Example 33.2 was converted into (RS)-(3,5-bis-hydroxymethyl-phenyl)-(4-carbamimidoyl-phenylamino)-acetic acid.

Example 35

The following compounds were prepared in analogy to Example 1:
a) (E)- and/or (Z)-(RS)-(3,4-Dipropoxy-phenyl)-[4-(N-hydroxycarbamimidoyl)-phenylamino]-acetic acid; MS: 402 (M+H$^+$);
   from 3,4-di-n-propoxy-benzaldehyde via methyl (RS)-(4-cyano-phenylamino)-(3,4-dipropoxy-phenyl)-acetate and (RS)-(4-cyano-phenylamino)-(3,4-dipropoxy-phenyl)-acetic acid;
b) (RS)-(3,4-diisopropoxy-phenyl)-[4-(N-hydroxycarbamimidoyl)-phenylamino]-acetic acid; MS: 402 (M+H$^+$);
   from 3,4-diisopropoxy-benzaldehyde via methyl (RS)-(4-cyano-phenylamino)-(3,4-diisopropoxy-phenyl)-acetate and (RS)-(4-cyano-phenylamino)-(3,4-diisopropoxy-phenyl)-acetic acid;
c) (RS)-(3,5-diisopropoxy-phenyl)-[4-(N-hydroxycarbamimidoyl)-phenylamino]-acetic acid; MS: 402 (M+H$^+$);
   from 3,5-diisopropoxy-benzaldehyde via methyl (RS)-(4-cyano-phenylamino)-(3,5-diisopropoxy-phenyl)-acetate and (RS)-(4-cyano-phenylamino)-(3,5-diisopropoxy-phenyl)-acetic acid;
d) (RS)-[4-(N-hydroxycarbamimidoyl)-phenylamino]-(4-methoxy-3-propoxy-phenyl)-acetic acid; MS: 372 (M+H$^+$);
   from 3-propoxy-4-methoxy-benzaldehyde via methyl (RS)-(4-cyano-phenylamino)-(4-methoxy-3-propoxy-phenyl)-acetate and (RS)-(4-cyano-phenylamino)-(4-methoxy-3-propoxy-phenyl)-acetic acid;
e) (RS)-[4-(N-hydroxycarbamimidoyl)-phenylamino]-(4-isopropoxy-3-methoxy-phenyl)-acetic acid; MS: 374 (M+H$^+$);
   from 4-isopropoxy-3-methoxy-benzaldehyde via methyl (RS)-(4-cyano-phenylamino)-(4-isopropoxy-3-methoxy-phenyl)-acetate and (RS)-(4-cyano-phenylamino)-(4-isopropoxy-3-methoxy-phenyl)-acetic acid;
f) (E)- and/or (Z)-(RS)-[4-(N-hydroxycarbamimidoyl)-phenylamino]-naphthalen-2-yl-acetic acid; MS: 336 (M+H$^+$);
   from 2-naphthaldehyde via methyl (RS)-(4-cyano-phenylamino)-naphthalen-2-yl-acetate and (RS)-(4-cyano-phenylamino)-naphthalen-2-yl-acetic acid.

Example 36

The following amidines were prepared in analogy to Example 3 from the amidoximes prepared in Example 35:
a) (RS)-(4-Carbamimidoyl-phenylamino)-(3,4-dipropoxy-phenyl)-acetic acid; MS: 386 (M+H$^+$);
b) (RS)-(4-carbamimidoyl-phenylamino)-(3,4-diisopropoxy-phenyl)-acetic acid; MS: 386 (M+H$^+$);
c) (RS)-(4-carbamimidoyl-phenylamino)-(3,5-diisopropoxy-phtnyl)-acetic acid; MS: 386 (M+H$^+$);
d) (RS)-(4-carbamimidoyl-phenylamino)-(4-methoxy-3-propoxy-phenyl)-acetic acid; MS: 358 (M+H$^+$);
e) (RS)-(4-carbamimidoyl-phenylamino)-(4-isopropoxy-3-methoxy-phenyl)-acetic acid; MS: 358 (M+H$^+$);
f) (RS)-(4-carbamimidoyl-phenylamino)-naphthalen-2-yl-acetic acid; MS: 320 (M+H$^+$).

Example 37 a) Methyl (RS)-[4-(N-hydroxycarbamimidoyl)-phenylamino]-(6-methoxy-naphthalen-2-yl)-acetate was obtained from 6-methoxy-2-naphthaldehyde via methyl (RS)-(4-cyano-phenylamino)-(6-methoxy-naphthalen-2-yl)-acetate in analogy to Example 1.3.

b) The methyl ester was hydrolyzed in analogy to Example 1.2 and yielded (E)- and/or (Z)-(RS)-[4-(N-hydroxycarbamimidoyl)-phenylamino]-(6-methoxy-naphthalen-2-yl)-acetic acid; MS: 366 (M+H$^+$)

Example 38

The amidoxime obtained in Example 37a was hydrolyzed in analogy to Example 3 and yielded (RS)-(4-carbamimidoyl-phenylamino)-(6-methoxy-naphthalen-2-yl)-acetic acid, MS: 350 (M+H$^+$).

Example 39

39.1

In analogy to Example 1.1, from 3-benzyloxybenzaldehyde and 4-aminobenzonitrile there was obtained methyl (RS)-(3-benzyloxy-phenyl)-(4-cyano-phenylamino)-acetate. MS: 373 (M+H)$^+$.

39.2

Hydrogen chloride was introduced into a solution of 2.01 g of methyl (RS)-(3-benzyloxy-phenyl)-(4-cyano-phenylamino)-acetate in 25 ml of methylene chloride and 5 ml of methanol at 0° C. during 75 min. The solution was held for 23 hrs. at 4° C. and thereafter evaporated in a vacuum. The residue was treated in 20 ml of methanol with 1.66 g of ammonium acetate and boiled at reflux for 3.5 hrs. The solution was evaporated in a vacuum and the residue was taken up in 95 ml of methylene chloride, 75 ml of water and 19 ml of saturated sodium carbonate solution, treated with 3.1 g of di-tert.-butyl dicarbonate and stirred vigorously for 3.5 hrs. at 20° C. After extraction and chromatography on silica gel there was obtained methyl (E)/Z)-(RS)-(3-benzyloxy-phenyl)-[4-(tert-butoxycarbonylamino-tert-butoxycarbonylimino-methyl)-phenylamino]-acetate as a yellow foam. MS: 590 (M+H)$^+$.

39.3

655 mg of methyl (E)/(Z)-(RS)-(3-benzyloxy-phenyl)-[4-(tert-butoxycarbonylamino-tert-butoxycarbonylimino-methyl)-phenylamino]-acetate were treated in 3 ml of methylene chloride with 3 ml of trifluoroacetic acid and left to stand for 50 min. at room temperature. The solution was evaporated in a vacuum and the residue was chromatographed on silica gel. There were obtained 440 mg of methyl (RS)-(3-benzyloxy-phenyl)-(4-carbamimidoyl-phenylamino)-acetate trifluoroacetate, m.p. 162° C., MS: 390 (M+H)$^+$.

39.4

In analogy to Example 70, from methyl (RS)-(3-benzyloxy-phenyl)-(4-carbamimidoyl-phenylamino)-acetate trifluoroacetate there was obtained (RS)-(3-benzyloxy-phenyl)-(4-carbamimidoyl-phenylamino)-acetic acid, m.p. 306° C., MS: 376 (M+H)$^+$.

Example 40

40.1

In analogy to Example 1.1, from 2-(ethoxycarbonylmethoxy)benzaldehyde, 4-aminobenzonitrile, toluene-4-sulphonyl methyl isocyanide and BF$_3$OEt$_2$ in ethanol there was obtained ethyl (RS)-(4-cyano-phenylamino)-(2-ethoxycarbonylmethoxy-phenyl)-acetate, m.p. 108° C., MS: 383 (M+H)$^+$.

40.2

Hydrogen chloride was introduced into a solution of 1.5 g of ethyl (RS)-(4-cyano-phenylamino)-(2-ethoxycarbonylmethoxy-phenyl)-acetate in 20 ml of chloroform and 4 ml of ethanol at 0° C. during one hour. After 6 hrs. room temperature the solution was evaporated and the residue was treated in 15 ml of ethanol with 1.2 g of ammonium acetate and boiled at reflux for 3.5 hrs. The reaction mixture was evaporated and the residue was treated in 35 ml of methylene chloride, 17 ml of water and 17 ml of saturated sodium bicarbonate solution with 916 mg of di-tert.-butyl dicarbonate and stirred vigorously for 2¼ hrs. at room temperature. After extraction and chromatography on silica gel there were obtained 1.7 g of ethyl (RS)-[4-(tert-butoxycarbonylamino-imino-methyl)-phenylamino]-(2-ethoxycarbonylmethoxy-phenyl)-acetate as a white foam. MS: 500 (M+H)$^+$.

40.3

499 mg of ethyl (RS)-[4-(tert-butoxycarbonylamino-imino-methyl)-phenylamino]-(2-ethoxycarbonylmethoxy-phenyl)-acetate were treated in 14 ml of THF with 2 ml of 1N LiOH, adjusted to pH 4 after 4 hrs. with 2 ml of 1N HCl and evaporated in a vacuum. From acetonitrile-water there were obtained 182 mg of (RS)-(4-carbamimidoyl-phenylamino)-(2-carboxymethoxy-phenyl)-acetic acid, m.p. 223° C., MS: 344 (M+H)$^+$.

Example 41

41.1

In analogy to Example 1.1, from 2,5-dimethoxybenzaldehyde and 4-aminobenzonitrile there was obtained methyl (RS)-(4-cyano-phenylamino)-(2,5-dimethoxy-phenyl)-acetate, MS: 327 (M+H)$^+$.

41.2

Analogously to Example 1.2 there was obtained therefrom (RS)-(4-cyano-phenylamino)-(2,5-dimethoxy-phenyl)-acetic acid, MS: 312 (M)$^+$.

41.3

This was converted analogously to Example 1.3 into (Z)-(RS)-(2,5-dimethoxy-phenyl)-[4-(N-hydroxycarbamimidoyl)-phenylamino]-acetic acid, MS: 346 (M+H)$^+$.

41.4

555 mg of (Z)-(RS)-(2,5-dimethoxy-phenyl)-[4-(N-hydroxycarbamimidoyl)-phenylamino]-acetic acid were stirred under hydrogen in 8 ml of acetic acid and 16 ml of water in the presence of Raney-nickel. After the addition 13 ml of acetic acid the solution was filtered clear and evaporated in a vacuum. The residue was triturated in water and then in methanol, filtered off under suction and dried. There were obtained 404 mg of (RS)-(4-carbamimidoyl-phenylamino)-(2,5-dimethoxy-phenyl)-acetic acid, m.p. 310° C., MS: 330 (M+H)$^+$.

Example 42

42.1

In analogy to Example 52.1, from 5-benzyloxy-2-hydroxy-benzaldehyde and ethyl bromoacetate there was obtained ethyl (4-benzyloxy-2-formyl-phenoxy)-acetate, m.p. 65° C., MS: 314 (M)$^+$.

42.2

From ethyl (4-benzyloxy-2-formyl-phenoxy)-acetate and 4-aminobenzonitrile there was obtained in ethanol analogously to Example 1.1 ethyl (RS)-(5-benzyloxy-2-ethoxycarbonylmethoxy-phenyl)-(4-cyano-phenylamino)-acetate as a yellow resin; MS: 489 (M+H)$^+$.

42.3

1.7 g of ethyl (RS)-(5-benzyloxy-2-ethoxycarbonylmethoxy-phenyl)-(4-cyano-phenylamino)-acetate, 1.13 ml of diethyl dithiophosphate and 4 ml of ethanol were heated for 2 hrs. to 60° C. The reaction mixture was diluted with ethyl acetate, washed with saturated sodium hydrogen carbonate solution, water and saturated sodium chloride solution, dried and evaporated in a vacuum. Chromatography on silica gel gave 1.6 g of ethyl (RS)-(5-benzyloxy-2-ethoxycarbonylmethoxy-phenyl)-(4-thiocarbamoyl-phenylamino)-acetate, m.p. 166° C., MS: 523 (M+H)$^+$.

42.4

1.6 g of ethyl (RS)-(5-benzyloxy-2-ethoxycarbonylmethoxy-phenyl)-(4-thiocarbamoyl-phenylamino)-acetate, 25 ml of acetone and 1.95 ml of methyl iodide were stirred for 3.5 hrs. at 40° C. The solution was evaporated and the residue was immediately dissolved in ethanol, treated with 0.18 ml of acetic acid and 720 mg of ammonium acetate and heated for 1.5 hrs. to 60° C. The reaction mixture was evaporated in a vacuum, treated in 27 ml of methylene chloride, 14 ml of water and 14 ml of saturated sodium hydrogen carbonate solution 740 mg of di-tert-butyl dicarbonate and stirred vigorously for 5 hrs. at room temperature. Extraction and chromatography on silica gel gave 1.4 g of ethyl (RS)-(5-benzyloxy-2-ethoxycarbonylmethoxy-phenyl)-[4-(tert-butoxycarbonylamino-imino-methyl)-phenylamino]-acetate as a white foam; MS: 606 (M+H)$^+$.

42.5

In analogy to Example 40.3 and neutralization of the mixture with acetic acid there was obtained from ethyl (RS)-(5-benzyloxy-2-ethoxycarbonylmethoxy-phenyl)-[4-(tert-butoxycarbonylamino-imino-methyl)-phenylamino]-acetate, after evaporation of the solvent in a vacuum, (RS)-(5-benzyloxy-2-hydroxycarbonylmethoxy-phenyl)-[4-(tert-butoxycarbonylamino-imino-methyl)-phenylamino]-acetic acid. This was dissolved in methylene chloride-TFA 1:1 and stirred for 1.5 hrs. at room temperature. The solution was evaporated, the residue in water was adjusted to pH 8 with ammonia and the solution was again evaporated. The (RS)-(5-benzyloxy-2-carboxymethoxy-phenyl)-(4-carbamimidoyl-phenylamino)-acetic acid crystallized from water and, for purification, was triturated several times in ethanol; m.p. 258° C., MS: 450 (M+H)$^+$.

Example 43

43.1

In analogy to Example 42.2, from ethyl (2-formyl-4-methoxy-phenoxy)-acetate and 4-aminobenzonitrile there was obtained ethyl (RS)-(4-cyano-phenylamino)-(2-ethoxycarbonylmethoxy-5-methoxy-phenyl)-acetate; MS: 413 (M+H)$^+$.

43.2

In a similar manner to that described in Example 40.2, from ethyl (RS)-(4-cyano-phenylamino)-(2-ethoxycarbonylmethoxy-5-methoxy-phenyl)-acetate there was obtained ethyl (RS)-[4-(tert-butoxy carbonylamino-imino-methyl)-phenylamino]-(2-ethoxycarbonylmethoxy-5-methoxy-phenyl)-acetate; MS: 530 (M+H)$^+$.

43.3

In analogy to Example 1.2 there was obtained therefrom (RS)-[4-(tert-butoxycarbonylamino-imino-methyl)-phenylamino]-(2-carboxymethoxy-5-methoxy-phenyl)-acetic acid.

43.4

356 mg of (RS)-[4-(tert-butoxy carbonylamino-imino-methyl)-phenylamino]-(2-carboxymethoxy-5-methoxy-phenyl)-acetic acid were stirred in 3.7 ml of methylene chloride and 3.7 ml of TFA for one hour. The reaction mixture was evaporated in a vacuum and the residue was chromatographed on silica gel with ethyl acetate-acetone-water-acetic acid (6:2:1:1). From ethyl acetate-acetone-water-acetic acid (12:2:1:1) there was obtained crystalline (RS)-(4-carbamimidoyl-phenylamino)-(2-carboxymethoxy-5-methoxy-phenyl)-acetic acid, m.p. 213° C. MS: 374 (M+H)$^+$.

Example 44

44.1

In analogy to Example 50.1, from 5-ethoxy-2-hydroxybenzaldehyde and ethyl bromoacetate there was obtained ethyl (4-ethoxy-2-formyl-phenoxy)-acetate. M.p. 61–62° C., MS: 252 (M)$^+$.

44.2

Analogously to Example 50.2, from ethyl (4-ethoxy-2-formyl-phenoxy)-acetate and 4-amino-benzonitrile with 2-morpholinoethyl isocyanide and BF$_3$OEt$_2$ in ethanol there was obtained ethyl (RS)-(4-cyano-phenylamino)-(5-ethoxy-2-ethoxycarbonylmethoxy-phenyl)-acetate, MS: 427 (M+H)$^+$.

44.3

In a similar manner to that described in Example 40.2, from ethyl (RS)-(4-cyano-phenylamino)-(5-ethoxy-2-ethoxycarbonylmethoxy-phenyl)-acetate there was obtained ethyl (RS)-[4-(tert-butoxy carbonylamino-imino-methyl)-phenylamino]-(5-ethoxy-2-ethoxycarbonylmethoxy-phenyl)-acetate. MS: 544 (M+H)$^+$.

44.4

617 mg of ethyl (RS)-[4-(tert-butoxycarbonylamino-imino-methyl)-phenylamino]-(5-ethoxy-2-ethoxycarbonylmethoxy-phenyl)-acetate were treated in 15.8 ml of THF with 2.26 ml of 1N LiOH and stirred for 3 hrs. at room temperature. The reaction mixture was adjusted to pH 7 with TFA and evaporated in a vacuum. The residue was dissolved in 4.5 ml of methylene chloride and 4.5 ml of TFA and, after 1 hr. evaporated in a vacuum. The residue was dissolved in water and again evaporated, then neutralized in MeOH with ammonia. The (RS)-(4-carbamimidoyl-phenylamino)-(2-carboxymethoxy-5-ethoxy-phenyl)-acetic acid crystallized from MeOH and was purified by trituration in ethyl acetate-acetone-water-acetic acid (12:2:1:1); m.p. 241° C., MS: 388 (M+H)$^+$.

Example 45

45.1

2.49 g of 5-ethoxy-2-hydroxy-benzaldehyde, 2.7 ml of ethyl 5-bromovalerate, 15 ml of DMSO, 3.1 g of K$_2$CO$_3$ and 75 mg of KI were stirred for 2.5 hrs. at 55° C. After working up and chromatography on silica gel there were obtained 4.7 g of ethyl 5-(4-ethoxy-2-formyl-phenoxy)-pentanoate. MS: 294 (M)$^+$.

45.2

In analogy to Example 40.1, from ethyl 5-(4-ethoxy-2-formyl-phenoxy)-pentanoate and 4-aminobenzonitrile there was prepared ethyl (RS)-5-{2-[(4-cyano-phenylamino)-ethoxy-carbonyl-methyl]-4-ethoxy-phenoxy}-pentanoate; m.p. 80–81° C. MS: 469 (M+H)$^+$.

45.3

In analogy to Example 40.2 there was obtained therefrom ethyl (RS)-5-(2-{[4-(tert-butoxy-carbonylamino-imino-methyl)-phenylamino]-ethoxycarbonylmethyl}-4-ethoxy-phenoxy)-pentanoate. MS: 586 (M+H)$^+$.

45.4

In a similar manner to that described in Example 44.4 there was obtained therefrom (RS)-5-{2-[(4-carbamimidoyl-phenylamino)-carboxy-methyl]-4-ethoxy-phenoxy}-pentanoic acid, m.p. 260° C. MS: 428 (M–H)$^-$.

Example 46

46.1

In analogy to Example 45.1, from 5-ethoxy-2-hydroxybenzaldehyde and 2-bromethyl methyl ether there was prepared 5-ethoxy-2-(2-methoxy-ethoxy)-benzaldehyde. MS: 224 (M)⁺.

46.2

In analogy to Example 1.1, from 5-ethoxy-2-(2-methoxy-ethoxy)-benzaldehyde, 4-amino-N-hydroxy-benzamidine, 2-morpholinoethyl isocyanide and BF₃OEt₂ in MeOH there was prepared methyl (E)/(Z)-(RS)-[5-ethoxy-2-(2-methoxy-ethoxy)-phenyl]-[4-(N-hydroxycarbamimidoyl)-phenylamino]-acetate. MS: 418 (M+H)⁺.

46.3

The methyl (E)/(Z)-(RS)-[5-ethoxy-2-(2-methoxy-ethoxy)-phenyl]-[4-(N-hydroxycarbamimidoyl)-phenylamino]-acetate was saponified in THF with 1N LiOH to give (E)/(Z)-(RS)-[5-ethoxy-2-(2-methoxy-ethoxy)-phenyl]-[4-(N-hydroxycarbamimidoyl)-phenylamino]-acetic acid. The reaction mixture was neutralized with acetic acid, the solution was evaporated and the crude product was used in 46.4.

46.4

In analogy to Example 50.5 there was obtained therefrom (RS)-(4-carbamimidoyl-phenylamino)-[5-ethoxy-2-(2-methoxy-ethoxy)-phenyl]-acetic acid. The crude product was triturated in water-MeOH 1:1 filtered off under suction and dried; m.p. 275° C., MS: 388 (M+H)⁺.

Example 47

47.1

Analogously to Example 52.1, from 5-ethoxy-2-hydroxybenzaldehyde and methyl 3-bromo-methylbenzoate there was prepared methyl 3-(4-ethoxy-2-formyl-phenoxymethyl)-benzoate; m.p. 67–69° C., MS: 314 (M)⁺.

47.2

Analogously to Example 52.2, from methyl 3-(4-ethoxy-2-formyl-phenoxymethyl)-benzoate and 4-aminobenzonitrile in MeOH there was obtained methyl (RS)-3-{2-[(4-cyano-phenylamino)-methoxycarbonyl-methyl]-4-ethoxy-phenoxymethyl}-benzoate. MS: 475 (M+H)⁺.

47.3

In analogy to Example 50.3, from methyl (RS)-3-{2-[(4-cyano-phenylamino)-methoxy-carbonyl-methyl]-4-ethoxy-phenoxymethyl}-benzoate there was obtained methyl (E)/(Z)-(RS)-3-(4-ethoxy-2-{[4-(N-hydroxycarbamimidoyl)-phenylamino]-methoxycarbonylmethyl}-phenoxymethyl)-benzoate. MS: 508 (M+H)⁺.

47.4

Analogously to Example 46.3, from methyl (E)/(Z)-(RS)-3-(4-ethoxy-2-{[4-(N-hydroxycarbamimidoyl)-phenylamino]-methoxycarbonylmethyl}-phenoxymethyl)-benzoate there was prepared (E)/(Z)-(RS)-3-(4-ethoxy-2-{[4-(N-hydroxycarbamimidoyl)-phenylamino]-carboxymethyl}-phenoxymethyl)-benzoic acid.

47.5

Analogously to Example 50.5 there was prepared therefrom (RS)-3-{2-[(4-carbamimidoyl-phenylamino)-carboxymethyl]-4-ethoxy-phenoxymethyl}-benzoic acid. The crude product was triturated in water and then in ethanol; m.p. 260° C., MS: 464 (M+H)⁺.

Example 48

48.1

In analogy to Example 45.1, from 5-ethoxy-2-hydroxybenzaldehyde and chloroacetamide there was prepared 2-(4-ethoxy-2-formyl-phenoxy)-acetamide, m.p. 127–129° C., MS: 223 (M)⁺.

48.2

In analogy to Example 1.1, from 2-(4-ethoxy-2-formyl-phenoxy)-acetamide, 4-amino-benzonitrile, 2-morpholinoethyl isocyanide and BF₃OEt₂ in methanol there was obtained methyl (RS)-(2-carbamoylmethoxy-5-ethoxy-phenyl)-(4-cyano-phenylamino)-acetate as a white foam; MS: 384 (M+H)⁺.

48.3

In analogy to Example 1.3, from methyl (RS)-(2-carbamoylmethoxy-5-ethoxy-phenyl)-(4-cyano-phenylamino)-acetate, hydroxylamine hydrochloride and triethylamine in methanol there was prepared methyl (Z)-(RS)-(2-carbamoylmethoxy-5-ethoxy-phenyl)-[4-(N-hydroxycarbamimidoyl)-phenylamino]-acetate, m.p. 175° C., MS: 417 (M+H)⁺.

48.4

305 mg of ethyl (Z)-(RS)-(2-carbamoylmethoxy-5-ethoxy-phenyl)-[4-(N-hydroxycarbamimidoyl)-phenylamino]-acetate were treated in 8 ml of methanol-acetic acid (1:1) with Raney-nickel and stirred under hydrogen. The reaction mixture was filtered, evaporated in a vacuum and, for purification, the residue was triturated in acetonitrile. There were obtained 265 mg of methyl (RS)-(4-carbamimidoyl-phenylamino)-(2-carbamoylmethoxy-5-ethoxy-phenyl)-acetate; m.p. 200° C. (dec.), MS: 401 (M+H)⁺.

48.5

The methyl (RS)-(4-carbamimidoyl-phenylamino)-(2-carbamoylmethoxy-5-ethoxy-phenyl)-acetate was saponified in THF with 1N LiOH to give (RS)-(4-carbamimidoyl-phenylamino)-(2-carbamoylmethoxy-5-ethoxy-phenyl)-acetic acid and purified by trituration in water and dilute ammonia; m.p. 266° C., MS: 387 (M+H)⁺.

Example 49

49.1

In analogy to Example 50.1, from 5-(benzyloxy)-2-hydroxybenzaldehyde there was prepared 5-benzyloxy-2-(2-hydroxy-ethoxy)-benzaldehyde, m.p. 83° C., MS: 272 (M)⁺.

49.2

In analogy to Example 1.1, from 5-benzyloxy-2-(2-hydroxy-ethoxy)-benzaldehyde, 4-amino-benzonitrile, 2-morpholinoethyl isocyanide and BF₃OEt₂ in methanol there was obtained methyl (RS)-[5-benzyloxy-2-(2-hydroxy-ethoxy)-phenyl]-(4-cyano-phenylamino)-acetate, MS: 433 (M+H)⁺.

49.3

Catalytic hydrogenation of methyl (RS)-[5-benzyloxy-2-(2-hydroxy-ethoxy)-phenyl]-(4-cyano-phenylamino)-acetate on Pd/C in ethyl acetate-ethanol gave methyl (RS)-(4-cyano-phenylamino)-[5-hydroxy-2-(2-hydroxy-ethoxy)-phenyl]-acetate, MS: 343 (M+H)⁺.

49.4

In analogy to Example 64.1, from methyl (RS)-(4-cyano-phenylamino)-[5-hydroxy-2-(2-hydroxy-ethoxy)-phenyl]-acetate and ethyl bromide in the presence of sodium iodide in DMF there was prepared methyl (RS)-(4-cyano-phenylamino)-[5-ethoxy-2-(2-hydroxy-ethoxy)-phenyl]-acetate; MS: 370 (M)⁺.

49.5

In analogy to Example 1.3, from methyl (RS)-(4-cyano-phenylamino)-[5-hydroxy-2-(2-hydroxy-ethoxy)-phenyl]-acetate, hydroxylamine hydrochloride and triethylamine in methanol there was prepared methyl (RS)-(E/Z)-[5-ethoxy-2-(2-hydroxy-ethoxy)-phenyl]-[4-(N-hydroxycarbamimidoyl)-phenylamino]-acetate, MS: 404 (M+H)⁺.

49.6

In analogy to Example 48.4, from methyl (RS)-(E/Z)-[5-ethoxy-2-(2-hydroxy-ethoxy)-phenyl]-[4-(N- hydroxycarbamimidoyl)-phenylamino]-acetate there was obtained methyl (RS)-(4-carbamimidoyl-phenylamino)-[5-ethoxy-2-(2-hydroxy-ethoxy)-phenyl]-acetate acetate; m.p. 183° C., MS: 388 (M+H)$^+$.

49.7

In analogy to Example 48.5, from methyl (RS)-(4-carbamimidoyl-phenylamino)-[5-ethoxy-2-(2-hydroxy-ethoxy)-phenyl]-acetate acetate there was prepared (RS)-(4-carbamimidoyl-phenylamino)-[5-ethoxy-2-(2-hydroxy-ethoxy)-phenyl]-acetic acid; m.p. 268° C., MS: 374 (M+H)$^+$.

Example 50

50.1

2.5 g of 2-hydroxy-4-methoxybenzaldehyde, 6.8 g of $K_2CO_3$, 3.3 ml of chloroethanol and 33 ml of DMSO were heated for 8 hrs. to 80° C. Extraction with ethyl acetate and chromatography on silica gel with methylene chloride-acetone gave 2.1 g of 2-(2-hydroxy-ethoxy)-4-methoxy-benzaldehyde, m.p. 94° C., MS: 196 (M)$^+$.

50.2

In analogy to Example 1.1, from 2-(2-hydroxy-ethoxy)-4-methoxy-benzaldehyde, 4-aminobenzonitrile 2-morpholinoethyl isocyanide and $BF_3OEt_2$ there was obtained methyl (RS)-(4-cyano-phenylamino)-[2-(2-hydroxy-ethoxy)-4-methoxy-phenyl]-acetate. MS: 357 (M+H)$^+$.

50.3

In analogy to Example 1.3, from methyl (RS)-(4-cyano-phenylamino)-[2-(2-hydroxy-ethoxy)-4-methoxy-phenyl]-acetate, hydroxylamine hydrochloride and triethylamine in methanol there was obtained methyl (Z)-(RS)-[4-(N-hydroxycarbamimidoyl)-phenylamino]-[2-(2-hydroxy-ethoxy)-4-methoxy-phenyl]-acetate. M.p. 92° C., MS: 390 (M+H)$^+$.

50.4

The methyl (Z)-(RS)-[4-(N-hydroxycarbamimidoyl)-phenylamino]-[2-(2-hydroxy-ethoxy)-4-methoxy-phenyl]-acetate was saponified in THF with 1N LiOH to give (Z)-(RS)-[4-(N-hydroxycarbamimidoyl)-phenylamino]-[2-(2-hydroxy-ethoxy)-4-methoxy-phenyl]-acetic acid.

50.5

Analogously to Example 3, there was obtained therefrom in acetic acid-water (2:1) (RS)-(4-carbamimidoyl-phenylamino)-[2-(2-hydroxy-ethoxy)-4-methoxy-phenyl]-acetic acid acetate (1:2). The crude product was chromatographed on silica gel 100 C18-reversed phase with water-methanol (19:1) to (4:1) and then purified by chromatography an silica gel with ethyl acetate-acetone-water-acetic acid (12:2:1:1) to (6:2:1:1) and trituration in acetonitrile, m.p. 205° C., MS: 360 (M+H)$^+$.

Example 51

51.1

In analogy to Example 50.1, from 4-benzyloxy-2-hydroxybenzaldehyde and 2-chloroethanol there was obtained 4-benzyloxy-2-(2-hydroxy-ethoxy)-benzaldehyde; m.p. 95° C., MS: 272 (M)$^+$.

51.2

In analogy to Example 1.1, from 4-benzyloxy-2-(2-hydroxy-ethoxy)-benzaldehyde, 4-aminobenzonitrile, 2-morpholinoethyl isocyanide and $BF_3OEt_2$ there was prepared methyl (RS)-[4-benzyloxy-2-(2-hydroxy-ethoxy)-phenyl]-(4-cyano-phenylamino)-acetate. MS: 432 (M)$^+$.

51.3

Analogously to Example 50.3, from methyl (RS)-[4-benzyloxy-2-(2-hydroxy-ethoxy)-phenyl]-(4-cyano-phenylamino)-acetate there was prepared methyl (RS)-(E)/(Z)-[4-benzyloxy-2-(2-hydroxy-ethoxy)-phenyl]-[4-(N-hydroxycarbamimidoyl)-phenylamino]-acetate; m.p. 90° C., MS: 466 (M+H)$^+$.

51.4

Analogously to Example 50.4, this was saponified in THF with 1N LiOH to give (RS)-(E)/(Z)-[4-benzyloxy-2-(2-hydroxy-ethoxy)-phenyl]-[4-(N-hydroxycarbamimidoyl)-phenylamino]-acetic acid.

51.5

Analogously to Example 50.5 there was obtained therefrom (RS)-[4-benzyloxy-2-(2-hydroxy-ethoxy)-phenyl]-(4-carbamimidoyl-phenylamino)-acetic acid. The crude product crystallized from water and was purified by trituration in MeOH. MS: 436 (Nl+H)$^+$.

Example 52

52.1

In analogy to Example 12.1 and addition of 3 mol % KI, from 2-hydroxy-4,5-dimethoxy-benzaldehyde and methyl 3-bromomethyl-benzoate there was obtained methyl 3-(2-formyl-4,5-dimethoxy-phenoxymethyl)-benzoate. M.p. 144° C., MS: 330 (M)$^+$.

52.2

In analogy to Example 1.1, from methyl 3-(2-formyl-4,5-dimethoxy-phenoxymethyl)-benzoate, 4-aminobenzonitrile, 2-morpholinoethyl isocyanide and $BF_3OEt_2$ there was obtained methyl (RS)-3-{2-[(4-cyano-phenylamino)-methoxycarbonyl-methyl]-4,5-dimethoxy-phenoxymethyl}-benzoate. MS: 513 (M+Na)$^+$.

52.3

In analogy to Example 1.3, from methyl (RS)-3-{2-[(4-cyano-phenylamino)-methoxycarbonyl-methyl]-4,5-dimethoxy-phenoxymethyl}-benzoate in methanol there was obtained methyl (Z)-(RS)-3-(2-{[4-(N-hydroxycarbamimidoyl)-phenylamino]-methoxycarbonylmethyl}-4,5-dimethoxy-phenoxymethyl)-benzoate, m.p. 173° C. MS: 524 (M+H)$^+$.

Example 53

53.1

In analogy to Example 18.1, from 5-ethyl-2,4-dihydroxy-benzaldehyde, ethanol, triphenylphosphine and diethyl azodicarboxylate there was prepared 4-ethoxy-5-ethyl-2-hydroxy-benzaldehyde; MS: 194 (M)$^+$.

53.2

In analogy to Example 45.1, from 4-ethoxy-5-ethyl-2-hydroxy-benzaldehyde and chloro-acetamide there was prepared 2-(5-ethoxy-4-ethyl-2-formyl-phenoxy)-acetamide; m.p. 163–164° C., MS: 251 (M)$^+$.

53.3

In analogy to Example 1.1, from 2-(5-ethoxy-4-ethyl-2-formyl-phenoxy)-acetamide, 4-aminobenzonitrile, 2-morpholinoethyl isocyanide and $BF_3OEt_2$ in methanol there was obtained methyl (RS)-(2-carbamoylmethoxy-4-ethoxy-5-ethyl-phenyl)-(4-cyano-phenylamino)-acetate; m.p. 150–152° C., MS: 412 (M+H)$^+$.

53.4

In analogy to Example 1.3, from methyl (RS)-(2-carbamoylmethoxy-4-ethoxy-5-ethyl-phenyl)-(4-cyano-phenylamino)-acetate, hydroxylamine hydrochloride and triethylamine in methanol there was prepared methyl (RS)-(E/Z)-(2-carbamoylmethoxy-4-ethoxy-5-ethyl-phenyl)-[4-(N-hydroxycarbamimidoyl)-phenylamino]-acetate, m.p. 130–133° C., MS: 445 (M+H)$^+$.

53.5

In analogy to Example 48.4, from methyl (RS)-(E/Z)-(2-carbamoylmethoxy-4-ethoxy-5-ethyl-phenyl)-[4-(N-hydroxycarbamimidoyl)-phenylamino]-acetate there was obtained methyl (RS)-(4-carbamimidoyl-phenylamino)-(2-carbamoylmethoxy-4-ethoxy-5-ethyl-phenyl)-acetate acetate; m.p. 230° C., MS: 429 (M+H)$^+$.

53.6

In analogy to Example 48.5, from methyl (RS)-(4-carbamimidoyl-phenylamino)-(2-carbamoylmethoxy-4-ethoxy-5-ethyl-phenyl)-acetate acetate there was prepared (RS)-(4-carbamimidoyl-phenylamino)-(2-carbamoylmethoxy-4-ethoxy-5-ethyl-phenyl)-acetic acid; m.p. 299° C., MS: 415 (M+H)$^+$.

Example 54

54.1

In analogy to Example 50.1, from 4-ethoxy-5-ethyl-2-hydroxy-benzaldehyde there was prepared 4-ethoxy-5-ethyl-2-(2-hydroxy-ethoxy)-benzaldehyde; MS: 238 (M)$^+$.

54.2

In analogy to Example 1.1, from 4-ethoxy-5-ethyl-2-(2-hydroxy-ethoxy)-benzaldehyde, 4-aminobenzonitrile, 2-morpholinoethyl isocyanide and BF$_3$OEt$_2$ in methanol there was obtained methyl (RS)-(4-cyano-phenylamino)-[4-ethoxy-5-ethyl-2-(2-hydroxy-ethoxy)-phenyl-acetate; MS: 399 (M+H)$^+$.

54.3

In analogy to Example 1.3, from methyl (RS)-(4-cyano-phenylamino)-[4-ethoxy-5-ethyl-2-(2-hydroxy-ethoxy)-phenyl]-acetate, hydroxylamine hydrochloride and triethylamine in methanol there was prepared methyl (RS)-(E/Z)-[4-ethoxy-5-ethyl-2-(2-hydroxy-ethoxy)-phenyl]-[4-(N-hydroxycarbamimidoyl)-phenylamino]-acetate; MS: 432 (M+H)$^+$.

54.4

In analogy to Example 48.4, from methyl (RS)-(E/Z)-[4-ethoxy-5-ethyl-2-(2-hydroxy-ethoxy)-phenyl]-[4-(N-hydroxycarbamimidoyl)-phenylamino]-acetate there was obtained methyl (RS)-(4-carbamimidoyl-phenylamino)-[4-ethoxy-5-ethyl-2-(2-hydroxy-ethoxy)-phenyl]-acetate acetate; m.p. 188° C., MS: 416 (M+H)$^+$.

54.5

In analogy to Example 48.5, from methyl (RS)-(4-carbamimidoyl-phenylamino)-[4-ethoxy-5-ethyl-2-(2-hydroxy-ethoxy)-phenyl]-acetate acetate there was prepared (RS)-(4-carbamimidoyl-phenylamino)-[4-ethoxy-5-ethyl-2-(2-hydroxy-ethoxy)-phenyl]-acetic acid; m.p. 271° C., MS: 402 (M+H)$^+$.

Example 55

55.1

In analogy to Example 52.1, from 4-ethoxy-5-ethyl-2-hydroxy-benzaldehyde and ethyl bromoacetate there was prepared ethyl (5-ethoxy-4-ethyl-2-formyl-phenoxy)-acetate; m.p. 99–101° C., MS: 280 (M)$^+$.

55.2

In analogy to Example 1.1, from ethyl (5-ethoxy-4-ethyl-2-formyl-phenoxy)-acetate, 4-amino-N-hydroxy-benzamidine, 2-morpholinoethyl isocyanide and BF$_3$OEt$_2$ in EtOH there was prepared ethyl (RS)-(E/Z)-(4-ethoxy-2-ethoxycarbonylmethoxy-5-ethyl-phenyl)-[4-(N-hydroxycarbamimidoyl)-phenylamino]-acetate, MS: 488 (M+H)$^+$.

55.3

In analogy to Example 48.4, from ethyl (RS)-(E/Z)-(4-ethoxy-2-ethoxycarbonylmethoxy-5-ethyl-phenyl)-[4-(N-hydroxycarbamimidoyl)-phenylamino]-acetate there was obtained ethyl (4-carbamimidoyl-phenylamino)-(4-ethoxy-2-ethoxycarbonylmethoxy-5-ethyl-phenyl)-acetate acetate, m.p. 195° C., MS: 472 (M+H)$^+$.

55.4

In analogy to Example 48.5, from ethyl (4-carbamimidoyl-phenylamino)-(4-ethoxy-2-ethoxycarbonylmethoxy-5-ethyl-phenyl)-acetate there was prepared (4-carbamimidoyl-phenylamino)-(2-carboxymethoxy-4-ethoxy-5-ethyl-phenyl)-acetic acid, which was purified by trituration in water, m.p. 252° C.

Example 56

56.1

In analogy to Example 52.1, from 2-hydroxy-5-methyl-3-propylbenzaldehyde and 2-chloroethanol there was obtained 2-(2-hydroxy-ethoxy)-5-methyl-3-propyl-benzaldehyde. MS: 222 (M)$^+$.

56.2

In analogy to Example 52.2, from 2-(2-hydroxy-ethoxy)-5-methyl-3-propyl-benzaldehyde and 4-aminobenzonitrile there was prepared methyl (RS)-(4-cyano-phenylamino)-[2-(2-hydroxy-ethoxy)-5-methyl-3-propyl-phenyl]-acetate, m.p. 137–139° C. MS: 382 (M)$^+$.

56.3

Analogously to Example 52.3, from methyl (RS)-(4-cyano-phenylamino)-[2-(2-hydroxy-ethoxy)-5-methyl-3-propyl-phenyl]-acetate there was prepared methyl (E)/(Z)-(RS)-[4-(N-hydroxycarbamimidoyl)-phenylamino]-[2-(2-hydroxy-ethoxy)-5-methyl-3-propyl-phenyl]-acetate. MS: 416 (M+H)$^+$.

56.4

Analogously to Example 52.4 this was saponified in THF with 1N LiOH to give (E)/(Z)-(RS)-[4-(N-hydroxycarbamimidoyl)-phenylamino]-[2-(2-hydroxy-ethoxy)-5-methyl-3-propyl-phenyl]-acetic acid.

56.5

Analogously to Example 52.5 there was obtained therefrom (RS)-(4-carbamimidoyl-phenylamino)-[2-(2-hydroxy-ethoxy)-5-methyl-3-propyl-phenyl]-acetic acid. The substance crystallized from water and was purified by trituration in ethanol; m.p. 240° C., MS: 386 (M+H)$^+$.

Example 57

57.1

In analogy to Example 52.1, from 3-allyl-5-methylsalicylaldehyde there was prepared 3-allyl-2-(2-hydroxy-ethoxy)-5-methyl-benzaldehyde. MS: 220 (M)$^+$.

57.2

In analogy to Example 52.2, from 3-allyl-2-(2-hydroxy-ethoxy)-5-methyl-benzaldehyde and 4-aminobenzonitrile there was prepared methyl (RS)-[3-allyl-2-(2-hydroxy-ethoxy)-5-methyl-phenyl]-(4-cyano-phenylamino)-acetate, m.p. 123° C., MS: 381 (M+H)$^+$.

57.3

A solution of methyl (RS)-[3-allyl-2-(2-hydroxy-ethoxy)-5-methyl-phenyl]-(4-cyano-phenylamino)-acetate in methylene chloride-MeOH 5:1 was saturated at 0° C. with hydrogen chloride and then left to stand for 1 day at room temperature. The solution was evaporated in a vacuum and the residue together with ammonium acetate in MeOH was boiled at reflux. After evaporation of the solution and chromatography on silica gel with methylene chloride-MeOH there was obtained methyl (RS)-[3-allyl-2-(2-hydroxy-ethoxy)-5-methyl-phenyl]-(4-carbamimidoyl-phenylamino)-acetate.

57.4

This was saponified in THF with 1N LiOH to give (RS)-[3-allyl-2-(2-hydroxy-ethoxy)-5-methyl-phenyl]-(4-carbamimidoyl-phenylamino)-acetic acid, m.p. 228° C. (from water), MS: 384 (M+H)$^+$.

Example 58

58.1

4.2 g of hexamethylenetetramine were cautiously added to 1.5 g of 2-methyl-4-propylphenol in 11 ml of trifluoroacetic acid and the mixture was heated for 5 hrs. to 120° C. After the addition of 11 ml of 1N hydrochloric acid the mixture was stirred for 1 hr. at 107° C. The mixture was cooled to room temperature, diluted with ethyl acetate and washed in sequence with water, dilute sodium hydrogen carbonate solution, water and sodium chloride solution. Evaporation of the solution and chromatography on silica gel with hexane-toluene gave 2-hydroxy-3-methyl-5-propyl-benzaldehyde. MS: 178 (M)$^+$.

58.2

In analogy to Example 52.1, from 2-hydroxy-3-methyl-5-propyl-benzaldehyde and 2-chloro-ethanol there was prepared 2-(2-hydroxy-ethoxy)-3-methyl-5-propyl-benzaldehyde. MS: 222 (M)$^+$.

58.3

In analogy to Example 52.2, from 2-(2-hydroxy-ethoxy)-3-methyl-5-propyl-benzaldehyde and 4-aminobenzonitrile there was prepared methyl (RS)-(4-cyano-phenylamino)-[2-(2-hydroxy-ethoxy)-3-methyl-5-propyl-phenyl]-acetate, m.p. 100° C., MS: 382 (M)$^+$.

58.4

In analogy to Example 57.3, from methyl (RS)-(4-cyano-phenylamino)-[2-(2-hydroxy-ethoxy)-3-methyl-5-propyl-phenyl]-acetate there was obtained methyl (RS)-(4-carbamimidoyl-phenylamino)-[2-(2-hydroxy-ethoxy)-3-methyl-5-propyl-phenyl]-acetate.

58.5

This was saponified in THF with 1N LiOH to give (RS)-(4-carbamimidoyl-phenylamino)-[2-(2-hydroxy-ethoxy)-3-methyl-5-propyl-phenyl]-acetic acid, m.p. 230° C. (from water), MS: 386 (M+H)$^+$.

Example 59

59.1

In analogy to Example 1.1, 3-nitrobenzaldehyde was reacted with 4-aminobenzonitrile and benzyl isonitrile to give methyl (RS)-(4-cyano-phenylamino)-(3-nitro-phenyl)-acetate.

59.2

600 mg of palladium-on-charcoal (10%) were added to a solution of 6.2 g of the nitro compound obtained in Example 59.1 in 150 ml of THF. The mixture was hydogenated for 5 hrs. under normal pressure. Then, the catalyst was filtered off. The crude product was purified by chromatography on silica gel.

59.3

In analogy to Example 22.1, the compound obtained in Example 54.2 was reacted with acetyl chloride to give methyl (RS)-(3-acetylamino-phenyl)-(4-cyano-phenylamino)-acetate.

59.4

In analogy to Example 1.2 and then 1.3, the compound described in Example 54.3 was converted via (RS)-(3-acetylamino-phenyl)-(4-cyano-phenylamino)-acetic acid into (E)- and/or (Z)-(RS)-(3-acetylamino-phenyl)-[4-(N-hydroxycarbamimidoyl)-phenylamino]-acetic acid.

Example 60

60.1

In analogy to Example 3, the compound described in Example 59.4 was converted into (RS)-(3-acetylamino-phenyl)-(4-carbamimidoyl-phenylamino)-acetic acid acetate (1:1).

Example 61

61.1

1.7 ml of diisopropylethylamine and 1.2 ml of methyl iodide were added to a solution of 2.8 g of the aniline described in Example 54.2 in 15 ml of THF. The reaction mixture was boiled at reflux overnight. The crude product was isolated by extraction. By chromatography on silica gel there was obtained 0.59 g of methyl (RS)-(4-cyano-phenylamino)-(3-methylamino-phenyl)-acetate as a yellow solid and 1.49 g of methyl (RS)-(4-cyano-phenylamino)-(3-dimethylamino-phenyl)-acetate as a white powder.

61.2

In analogy to Example 1.2 and then 1.3, the monomethylated compound from Example 61.1 was converted via (RS)-(4-cyano-phenylamino)-(3-methylamino-phenyl)-acetic acid into (E)- and/or (Z)-(RS)-[4-(N-hydroxycarbamimidoyl)-phenylamino]-(3-methylamino-phenyl)-aceic acid and the corresponding dimethylated compound was converted via (RS)-(4-cyano-phenylamino)-(3-dimethylamino-phenyl)-acetic acid into (E)- and/or (Z)-(RS)-(3-dimethylamino-phenyl)-[4-(N-hydroxycarbamimidoyl)-phenylamino]-acetic acid.

Example 62

In analogy to Example 61, from methyl (RS)-(3-amino-phenyl)-(4-cyano-phenylamino)-acetate and ethyl iodide there was obtained methyl (RS)-(4-cyano-phenylamino)-(3-diethylamino-phenyl)-acetate, which was subsequently converted via (RS)-(4-cyano-phenylamino)-(3-diethylamino-phenyl)-acetic acid into (RS)-(E)- and/or -(Z)-(3-diethylamino-phenyl)-[4-(N-hydroxycarbamimidoyl)-phenylamino]-acetic acid.

Example 63

In analogy to Example 3, 63.a
  from the monomethylated compound described in Example 61.2 there was obtained (RS)-(4-carbamimidoyl-phenylamino)-(3-methylamino-phenyl)-acetic acid hydrochloride (1:1);

63.b
  from the dimethylated compound described in Example 61.2 there was obtained (RS)-(4-carbamimidoyl-phenylamino)-(3-diethylamino-phenyl)-acetic acid hydrochloride (1:1);

63.c
  from the compound described in Example 62 there was obtained (RS)-(4-carbamimidoyl-phenylamino)-(3-diethylamino-phenyl)-acetic acid hydrochloride (1:1).

Example 64

64.1

2.76 ml of 2-bromoethanol and 5.40 g of potassium carbonate were added to a solution of 5 g of 3-ethoxy-4-hydroxybenzaldehyde in 150 ml of DMF. The reaction mixture was heated to 70° C. overnight and subsequently to 120° C. for a further 4 hrs. Then, the mixture was left to cool to room temperature, filtered and concentrated in a high vacuum. The crude product was isolated by extraction and purified by chromatography on silica gel. There were obtained 6.09 g of 3-ethoxy-4-(2-hydroxy-ethoxy)-benzaldehyde as a white solid.

64.2

In analogy to Example 1.1, from the aldehyde described in Exarmple 64.1, 4-aminobenzonitrile and benzyl isonitrile there was obtained methyl (RS)-(4-cyano-phenylamino)-[3-ethoxy-4-(2-hydroxy-ethoxy)-phenyl]-acetate.

64.3

Dry HCl gas was conducted during 20 min, through a solution, cooled to −10° C., of 926 mg of the compound obtained in Example 59.2 in 10 ml of $CHCl_3$/MeOH 3:1. The reaction mixture was left to stand at 4° C. overnight and was subsequently concentrated. The residue was dissolved in 5 ml of MeOH and treated with 5 ml of saturated methanolic ammonia. The solution was stirred for 3 hrs. at room temperature and then evaporated. The crude product was isolated by chromatography on silica gel. There were obtained 391 mg of methyl (RS)-(4-carbamimidoyl-phenylamino)-[3-ethoxy-4-(2-hydroxy-ethoxy)-phenylacetate hydrochloride(1:1) as a white lyophilisate.

Example 65

In analogy to Example 64, 65.a
from 3-ethoxy-4-hydroxybenzaldehyde and 1-chloro-2-dimethylaminoethane hydrochloride there was obtained 4-(2-dimethylamino-ethoxy)-3-ethoxy-benzaldehyde, which was subsequently converted by reaction with 4-aminobenzonitrile and benzyl isonitrile into methyl (RS)-(4-cyano-phenylamino)-[4-(2-dimethylamino-ethoxy)-3-ethoxy-phenyl]-acetate and then into methyl (RS)-(4-carbamimidoyl-phenylamino)-[4-(2-dimethylamino-ethoxy)-3-ethoxy-phenyl]-acetate hydrochloride (1:2);

65.b
from 3-hydroxy-4-isopropoxybenzaldehyde (prepared in 75% yield by monoalkylation of 3,4-dihydroxybenzaldehyde with isopropyl bromide and $K_2CO_3$ in DMF) and 2-bromoethanol there was obtained 3-(2-hydroxy-ethoxy)-4-isopropoxy-benzaldehyde, which was subsequently converted by reaction with 4-aminobenzonitrile and toluene-4-sulphonyl methylisocyanide into methyl (RS)-(4-cyano-phenylamino)-[3-(2-hydroxy-ethoxy)-4-isopropoxy-phenyl]-acetate and then into methyl (RS)-(4-carbainimidoyl-phenylamino)-[3-(2-hydroxy-ethoxy)-4-isopropoxy-phenyl]-acetate hydrochloride (1:1);

65.c
from 3-hydroxy-4-isopropoxybenzaldehyde and iodoacetamide there was obtained 2-(5-formyl-2-isopropoxy-phenoxy)-acetamide, which was subsequently converted by reaction with 4-aminobenzonitrile and toluene-4-sulphonylmethyl isocyanide into methyl (RS)-(3-carbamoylmethoxy-4-isopropoxy-phenyl)-(4-cyano-phenylamino)-acetate and then into methyl (RS)-(4-carbamimidoyl-phenylamino)-(3-carbamoylmethoxy-4-isopropoxy-phenyl)-acetate hydrochloride (1:1);

65.d
from 3,4-dihydroxybenzaldehyde and 1-bromobutane there was obtained 3,4,-dibutoxy-benzaldehyde, which was subsequently converted by reaction with 4-aminobenzonitrile and benzyl isonitrile into methyl (RS)-(4-cyano-phenylamino)-(3,4-dibutoxy-phenyl)-acetate and then into methyl (RS)-(4-carbamimidoyl-phenylamino)-(3,4-dibutoxy-phenyl)-acetate.

Example 66

66.1

In analogy to Example 59.1, from methyl (RS)-(4-cyano-phenylamino)-(3-ethoxy-4-hydroxy-phenyl)-acetate (Example 350.1) and 2-chloro-1-propanol there was obtained a mixture of methyl (RS)- and (SR)-(4-cyano-phenylamino)-[3-ethoxy-4-[(RS)-2-hydroxy-1-methyl-ethoxy]-phenyl]-acetate.

66.2

In analogy to Example 64.3, the compound described in Example 66.1 was converted into a mixture of methyl (RS)- and (SR)-(4-carbamimidoyl-phenylamino)-[3-ethoxy-4-[(RS)-2-hydroxy-1-methyl-ethoxy]-phenyl]-acetate hydrochloride (1:1).

Example 67

67.1

In analogy to Example 64.1, from 3-ethoxy-4-hydroxy-benzaldehyde and 1-chlor-2-methyl-2-propanol there was obtained 3-ethoxy-4-(2-hydroxy-2-methyl-propoxy)-benzaldehyde.

67.2

In analogy to Example 1.1, from the aldehyde obtained in Example 62.1, 4-amino-N-hydroxy-benzamidine and toluene-4-sulphonylmethyl isocyanide there was obtained ethyl (RS)-(E)- and/or -(Z)-[3-ethoxy-4-(2-hydroxy-2-methyl-propoxy)-phenyl]-[4-(N-hydroxycarbamimidoyl)-phenylamino]-acetate.

67.3

In analogy to Example 3, from the amidoxime obtained in Example 62.2 there was obtained ethyl (4-carbamimidoyl-phenylamino)-[3-ethoxy-4-(2-hydroxy-2-methyl-propoxy)-phenyl]-acetate.

Example 68

68.1

In analogy to Example 64.1, from 3-hydroxy-4-nitrobenzaldehyde and ethyl iodide there was obtained 3-ethoxy-4-nitro-benzaldehyde.

68.2

In analogy to Example 1, from the aldehyde obtained in Example 68.1, 4-aminobenzonitrile and toluene-4-sulphonylmethyl isocyanide there was obtained methyl (RS)-(4-cyano-phenylamino)-(3-ethoxy-4-nitro-phenyl)-acetate.

68.3

In analogy to Example 54.2, from the nitro comouund obtained in Example 68.2 there was obtained methyl (RS)-(4-amino-3-ethoxy-phenyl)-(4-cyano-phenylamino)-acetate.

68.4

In analogy to Example 61.1, from the aniline described in Example 68.3 and isopropyl bromide there was obtained methyl (RS)-(4-cyano-phenylamino)-(3-ethoxy-4-isopropylamino-phenyl)-acetate.

68.5

In analogy to Example 64.3, from the compound described in Example 68.4 there was obtained methyl (RS)-(4-carbamimidoyl-phenylamino)-(3-ethoxy-4-isopropylamino-phenyl)-acetate hydrochloride (1:1).

Example 69

In analogy to Example 68.4 and 68.5, 69.a
from methyl (RS)-(4-amino-3-ethoxy-phenyl)-(4-cyano-phenylamino)-acetate and ethyl iodide there was obtained methyl (RS)-(4-cyano-phenylamino)-(3-ethoxy-4-ethylamino-phenyl)-acetate, which was subsequently converted into methyl (RS)-(4-carbamimidoyl-phenylamino)-(3-ethoxy-4-ethylamino-phenyl)-acetate hydrochloride (1:1);

69.b
from methyl (RS)-(4-amino-3-ethoxy-phenyl)-(4-cyano-phenylamino)-acetate and ethyl iodide there was obtained methyl (RS)-(4-cyano-phenylamino)-(4-diethylamino-3-ethoxy-phenyl)-acetate, which was subsequently converted into methyl (RS)-(4-carbamimidoyl-phenylamino)-(4-diethylamino-3-ethoxy-phenyl)-acetate hydrochloride (1:1);

69.c
from methyl (RS)-(3-amino-4-ethoxy-phenyl)-(4-cyano-phenylamino)-acetate [prepared in analogy to Example 68.1-3 from 5-hydroxy-3-nitrobenzaldehyde and ethyl bromide via 4-ethoxy-3-nitro-benzaldehyde and methyl (RS)-(4-cyano-phenylamino)-(4-ethoxy-3-nitro-phenyl)-acetate] and methyliodid there was obtained methyl (RS)-(4-cyano-phenylamino)-(4-ethoxy-3-methylamino-phenyl)-acetate, which was subsequently converted into methyl (RS)-(4-carbamimidoyl-phenylamino)-(4-ethoxy-3-methylamino-phenyl)-acetate hydrochloride (1:1);

69.d
from methyl (RS)-(3-amino-4-ethoxy-phenyl)-(4-cyano-phenylamino)-acetate (educt from Example 64.c) and methyl iodide there was obtained methyl (RS)-(4-cyano-phenylamino)-(3-dimethylamino-4-ethoxy-phenyl)-acetate, which was subsequently converted into methyl (RS)-(4-carbamimidoyl-phenylamino)-(3-dimethylamino-4-ethoxy-phenyl)-acetate hydrochloride (1:2);

69.e
from methyl (RS)-(3-amino-4-ethoxy-phenyl)-(4-cyano-phenylamino)-acetate (educt from Example 64.c) and ethyl iodide there was obtained methyl (RS)-(4-cyano-phenylamino)-(4-ethoxy-3-ethylamino-phenyl)-acetate, which was subsequently converted into methyl (RS)-(4-carbamimidoyl-phenylamino)-(4-ethoxy-3-ethylamino-phenyl)-acetate hydrochloride (1:1);

69.f
from methyl (RS)-(3-amino-4-ethoxy-phenyl)-(4-cyano-phenylamino)-acetate (educt from Example 64.c) and ethyl iodide there was obtained methyl (RS)-(4-cyano-phenylamino)-(3-diethylamino-4-ethoxy-phenyl)-acetate, which was subsequently converted into methyl (RS)-(4-carbamimidoyl-phenylamino)-(3-diethylamino-4-ethoxy-phenyl)-acetate hydrochloride (1:1).

Example 70

70.1
In analogy to Example 64.1, 4-hydroxy-3-nitrobenzaldehyde was converted with methyl iodide into 3-nitro-p-anisaldehyde.

70.2
In analogy to Example 1.1, the aldehyde obtained in Example 70.1 was converted with 4-aminobenzonitrile and benzyl isonitrile into methyl (RS)-(4-cyano-phenylamino)-(4-methoxy-3-nitro-phenyl)-acetate.

70.3
In analogy to Example 59.2, from the nitro compound described in Example 70.2 there was obtained methyl (RS)-(3-amino-4-methoxy-phenyl)-(4-cyano-phenylamino)-acetate.

70.4
In analogy to Example 22.1, from the aniline described in Example 68.3 and acetyl chloride there was obtained methyl (RS)-(3-acetylamino-4-methoxy-phenyl)-(4-cyano-phenylamino)-acetate.

70.5
In analogy to Example 1.2, from the ester described in Example 70.4 there was obtained (RS)-(3-acetylamino-4-methoxy-phenyl)-(4-cyano-phenylamino)-acetic acid.

70.6
In analogy to Example 1.3, from the nitrile described in Example 70.5 there was obtained (E)- and/or (Z)-(RS)-(3-acetylamino-4-methoxy-phenyl)-[4-(N-hydroxycarbamimidoyl)-phenylamino]-acetic acid.

Example 71

71.a
In analogy to Example 70.2–6, from 4-methyl-3-nitrobenzaldehyde, 4-aminobenzonitrile and benzyl isonitrile there was obtained methyl (RS)-(4-cyano-phenylamino)-(4-methyl-3-nitro-phenyl)-acetate, which was subsequently subsequently converted into methyl (RS)-(3-amino-4-methyl-phenyl)-(4-cyano-phenylamino)-acetate. This was subsequently converted with acetyl chloride into methyl (RS)-(3-acetylamino-4-methyl-phenyl)-(4-cyano-phenylamino)-acetate and then via (RS)-(3-acetylamino-4-methyl-phenyl)-(4-cyano-phenylamino)-acetic acid into (E)- and/or (Z)-(RS)-(3-acetylamino-4-methyl-phenyl)-[4-(N-hydroxycarbamimidoyl)-phenylamino]-acetate.

71.b
In analogy to Example 70.4–6, from the methyl (RS)-(3-amino-4-methoxy-phenyl)-(4-cyano-phenylamino)-acetate described in Example 70.3, glutaric anhydride and Hünig's base in DMF there was obtained (RS)-4-{5-[(4-cyano-phenylamino)-methoxycarbonyl-methyl]-2-methoxy-phenylcarbamoyl}-butyric acid, which was subsequently converted via (RS)-4-{5-[carboxy-(4-cyano-phenylamino)-methyl]-2-methoxy-phenylcarbamoyl}-butyric acid into (RS)-(E)- and/or -(Z)-4-(5-{carboxy-[4-(N-hydroxycarbamimidoyl)-phenylamino]-methyl}-2-methoxy-phenylcarbamoyl)-butyric acid.

71.c
In analogy to Example 70.4–6, from the methyl (RS)-(3-amino-4-methoxy-phenyl)-(4-cyano-phenylamino)-acetate described in Example 70.3, succinic anhydride and Hünig's base there was obtained (RS)-N-{5-[(4-cyano-phenylamino)-methoxycarbonyl-methyl]-2-methoxy-phenyl}-succinamidic acid, which was subsequently converted via (RS)-N-{5-[carboxy-(4-cyano-phenylamino)-methyl]-2-methoxy-phenyl}-succinamidic acid into (RS)-(E)- and/or -(Z)-N-(5-{carboxy-[4-(N-hydroxycarbamimidoyl)-phenylamino]-methyl}-2-methoxy-phenyl)-succinamidic acid.

Example 72

72.1
In analogy to Example 22.1, the methyl (RS)-(4-cyano-phenylamino)-(4-ethoxy-3-ethyl-amino-phenyl)-acetate obtained as an intermediate in Example 69.e was converted with acetyl chloride into methyl (RS)-[3-(acetyl-ethyl-amino)-4-ethoxy-phenyl]-(4-cyano-phenylamino)-acetate.

72.2
In analogy to Example 64.3, the nitrile obtained in Example 72.1 was converted into (RS)-[3-(acetyl-ethyl-amino)-4-ethoxy-phenyl]-(4-carbamimidoyl-phenylamino)-acetic acid.

Example 73

73.1
In analogy to Example 22.1, the methyl (RS)-(4-cyano-phenylamino)-(3-ethoxy-4-hydroxy-phenyl)-acetate described in Example 350 was converted with trifluoromethanesulphonic anhydride in $CH_2Cl_2$ in the presence of triethylamine into methyl (RS)-(4-cyano-phenylamino)-(3-ethoxy-4-trifluoromethanesulphonyloxy-phenyl)-acetate.

73.2

118 mg of phenylboronic acid and 101 mg of potassium carbonate were added to a solution of 222 mg of the compound described in Example 72.1 in 5 ml of toluene. Argon was conducted through the reaction mixture for 15 min. Subsequently, the mixture was treated with 17 mg of tetrakis-(triphenyl)-palladium and and heated for 5 hrs. to 90° C. The crude product wurde isolated by extraction and purified by chromatography on silica gel. There were obtained 166 mg of methylc(RS)-(4-cyano-phenylamino)-(2-ethoxy-biphenyl-4-yl)-acetate as a white solid.

73.3

In analogy to Example 59.3, the nitrile obtained in Example 68.2 was converted into ethyl (RS)-(4-carbamimidoyl-phenylamino)-(2-ethyl-biphenyl-4-yl)-acetate hydrochloride (1:1).

Example 74

In analogy to Example 73, the ethyl (RS)-(4-cyano-phenylamino)-(3-ethyl-4-hydroxy-phenyl)-acetate described in Example 180 was converted into ethyl (RS)-(4-cyano-phenylamino)-(3-ethyl-4-trifluoromethanesulphonyloxy-phenyl)-acetate, which was subsequently converted via ethyl (RS)-(4-cyano-phenylamino)-(2-ethyl-biphenyl-4-yl)-acetate into ethyl (RS)-(4-carbamimidoyl-phenylamino)-(2-ethyl-biphenyl-4-yl)-acetate hydrochloride (1:1).

Example 75

A solution of 271 mg of the ester obtained in Example 64.3 in 5 ml of THF was cooled to 0° C. and treated with 3.5 ml of 1N LiOH. The mixture was stirred for 2 hrs., neutralized with 1N HCl and the THF was evaporated, with a colorless precipitate forming. This was filtered off and washed well with $H_2O$ and $Et_2O$. There were obtained 195 mg of (RS)-(4-carbamimidoyl-phenylamino)-[3-ethoxy-4-(2-hydroxy-ethoxy)-phenyl]-acetic acid as a white solid.

Example 76

In analogy to Example 75, 76.a
from the ester obtained in Example 65.a there was obtained (RS)-(4-carbamimidoyl-phenylamino)-[4-(2-dimethylamino-ethoxy)-3-ethoxy-phenyl]-acetic acid;

76.b
from the ester obtained in Example 65.b there was obtained (RS)-(4-carbamimidoyl-phenylamino)-[3-(2-hydroxy-ethoxy)-4-isopropoxy-phenyl]-acetic acid;

76.c
from the ester obtained in Example 60.c there were obtained (RS)-(4-carbamimidoyl-phenylamino)-(3-carbamoylmethoxy-4-isopropoxy-phenyl)-acetic acid and (RS)-(4-carbamimidoyl-phenylamino)-(3-carboxymethoxy-4-isopropoxy-phenyl)-acetic acid;

76.d
from the ester obtained in Example 65.d there was obtained (RS)-(4-carbamimidoyl-phenylamino)-(3,4-dibutoxy-phenyl)-acetic acid;

76.e
from the ester obtained in Example 61.2 there was obtained a mixture of (RS)- and (SR)-(4-carbamimidoyl-phenylamino)-[3-ethoxy-4-[(RS)-2-hydroxy-1-methyl-ethoxy]-phenyl]-acetic acid;

76.f
from the ester obtained in Example 67.3 there was obtained (RS)-(4-carbamimidoyl-phenylamino)-[3-ethoxy-4-(2-hydroxy-2-methyl-p ropoxy)-phenyl]-acetic acid;

76.g
from the ester obtained in Example 68.5 there was obtained (RS)-(4-carbamimidoyl-phenylamino)-(3-ethoxy-4-isopropylamino-phenyl)-acetic acid;

76.h
from the ester obtained in Example 69.a there was obtained (RS)-(4-carbamimidoyl-phenylamino)-(3-ethoxy-4-ethylamino-phenyl)-acetic acid;

76.i
from the ester obtained in Example 69.b there was obtained (RS)-(4-carbamimidoyl-phenylamino)-(4-diethylamino-3-ethoxy-phenyl)-acetic acid;

76.j
from the ester obtained in Example 69.c there was obtained methyl (RS)-(4-carbamimidoyl-phenylamino)-(4-ethoxy-3-methylamino-phenyl)-acetate hydrochloride (1:1);

76.k
from the ester obtained in Example 69.d there was obtained (RS)-(4-carbamimidoyl-phenylamino)-(3-dimethylamino-4-ethoxy-phenyl)-acetic acid;

76.l
from the ester obtained in Example 69.e there was obtained (RS)-(4-carbamimidoyl-phenylamino)-(4-ethoxy-3-ethylamino-phenyl)-acetic acid;

76.m
from the ester obtained in Example 69.f there was obtained (RS)-(4-carbamimidoyl-phenylamino)-(3-diethylamino-4-ethoxy-phenyl)-acetic acid;

76.n
from the ester obtained in Example 72.2 there was obtained (RS)-[3-(acetyl-ethyl-amino)-4-ethoxy-phenyl]-(4-carbamimidoyl-phenylamino)-acetic acid;

76.o
from the ester obtained in Example 73.3 there was obtained (RS)-(4-carbamimidoyl-phenylamino)-(2-ethoxy-biphenyl-4-yl)-acetic acid;

76.p
from the ester obtained in Example 74 there was obtained (RS)-(4-carbamimidoyl-phenylamino)-(2-ethyl-biphenyl-4-yl)-acetic acid.

Example 77

In analogy to Example 3, 77.a
from the amidoxime obtained in Example 70.6 there was obtained (RS)-(3-acetylamino-4-methoxy-phenyl)-(4-carbamimidoyl-phenylamino)-acetic acid;

77.b
from the amidoxime obtained in Example 71.a there was obtained (RS)-(3-acetylamino-4-methyl-phenyl)-(4-carbamimidoyl-phenylamino)-acetic acid;

77.c
from the amidoxime obtained in Example 71.b there was obtained (RS)-4-{5-[(4-carbamimidoyl-phenylamino)-carboxy-methyl]-2-methoxy-phenylcarbamoyl}-butyric acid hydrochloride (1:1);

72.d
from the amidoxime obtained in Example 71.c there was obtained (RS)-N-{5-[(4-carbamimidoylphenylamino)-carboxy-methyl]-2-methoxy-phenyl}-succinamidic acid hydrochloride (1:2).

Example 78

78.1

In analogy to Example 64. 1, from 3,5-dihydroxybenzaldehyde and ethyl iodide there was obtained 3-ethoxy-5-hydroxy-benzaldehyde.

78.2

In analogy to Example 18.1, from the phenol obtained in Example 78.1 and 2-benzyloxy-ethanol there was obtained 3-(2-benzyloxy-ethoxy)-5-ethoxy-benzaldehyde.

78.3

In analogy to Example 1.1, from the benzaldehyde obtained in Example 78.2, 4-aminobenzonitrile and benzyl isonitrile there was obtained methyl (RS)-[3-(2-benzyloxy-ethoxy)-5-ethoxy-phenyl]-(4-cyano-phenylamino)-acetate.

78.4

In analogy to Example 1.2, from the ester obtained in Example 78.3 there was obtained (RS)-[3-(2-benzyloxy-ethoxy)-5-ethoxy-phenyl]-(4-cyano-phenylamino)-acetic acid.

78.5

In analogy to Example 1.3, from ther nitrile obtained in Example 78.4 there was obtained (E)- and/or (Z)-(RS)-[3-(2-benzyloxy-ethoxy)-5-ethoxy-phenyl]-[4-(N-hydroxycarbamimidoyl)-phenylamino]-acetic acid.

Example 79

79.1

In analogy to Example 64.1, from the phenol obtained in Example 78.1 and ethyl bromo-acetate there was obtained ethyl (3-ethoxy-5-formyl-phenoxy)-acetate.

79.2

In analogy to Example 1.1, from the benzaldehyde obtained in Example 79.1, 4-aminobenzonitrile and benzyl isonitrile there was obtained ethyl (RS)-(4-cyano-phenylamino)-(3-ethoxy-5-ethoxycarbonylmethoxy-phenyl)-acetate.

79.3

In analogy to Example 1.2, from the ester obtained in Example 79.2 there was obtained (RS)-(3-carboxymethoxy-5-ethoxy-phenyl)-(4-cyano-phenylamino)-acetic acid.

79.4

In analogy to Example 1.3, from the nitrile obtained in Example 79.3 there was obtained (RS)-(3-carboxymethoxy-5-ethoxy-phenyl)-(4-cyano-phenylamino)-acetic acid.

Example 80

In analogy to Example 67, 80.a

From the phenol described in Example 78.1 and ethyl-4-bromobutyrate there was obtained ethyl 4-(3-ethoxy-5-formyl-phenoxy)-butyrate, which was subsequently converted with 4-amino-N-hydroxy-benzamidine and toluene-4-sulphonylmethyl isocyanide into ethyl (RS)-(E)- and/or -(Z)-4-(3-ethoxy-5-{ethoxycarbonyl-[4-(N-hydroxycarbamimidoyl)-phenylamino]-methyl}-phenoxy)-butyrate and then into ethyl (RS)-4-{3-[(4-carbamimidoyl-phenylamino)-ethoxycarbonylmethyl]-5-ethoxy-phenoxy}-butyrate acetate (1:1).

80.b

From 3,5-dihydroxybenzaldehyde and 1-bromobutane there was obtained 3,5-dibutoxy-benzaldehyde, which was subsequently converted with 4-amino-N-hydroxy-benzamidine and toluene-4-sulphonylmethyl isocyanide into methyl (3,5-dibutoxy-phenyl)-[4-(N-hydroxycarbamimidoyl)-phenylamino]-acetate and then into methyl (4-carbamimidoyl-phenylamino)-(3,5-dibutoxy-phenyl)-acetate; compound was reacted with acetic acid.

Example 81

81.1

A solution of dimethyl-5-iodisophthalate in 800 ml of THF was treated with with 22.2 g of $CaCl_2$. Then, 15.2 g of $NaBH_4$ were added portionwise. The mixture was stirred for one day at room temperature. Then, the mixture was acidified with 250 ml of 3N HCl and diluted with 2 l of $H_2O$. The crude product was isolated by extraction and purified by crystallization from THF/hexane. There were obtained 11.2 g of (3-hydroxymethyl-5-iodo-phenyl)-methanol as white crystals.

81.2

4.13 g of tetrakis-(triphenyl)-palladium were added to a solution, gassed with argon, of 4.72 g of the iodide described in Example 76.1 in 250 ml of toluene. Then, the mixture was gassed with CO heated to 70° C. 6.15 ml of tributyltin hydride were added using a spray pump within 6 hrs. The mixture was left to cool to room temperature and filtered. The solid was dissolved in methanol gelost and stirred with active charcoal. After filtration over Dicalite the product was crystallized out by the addition of MeOH. There was obtained 3,5-bis-hydroxymethyl-benzyldehyde as a light grey solid.

81.3

In analogy to Example 1.1, the benzaldehyde obtained in Example 76.2 was reacted with 4-aminobenzonitrile and benzyl isonitrile to give methyl (RS)-(3,5-bis-hydroxymethyl-phenyl)-(4-cyano-phenylamino)-acetate.

81.4

A solution of 1.82 ml of DMSO in 150 ml of $CH_2Cl_2$ was treated at −78° C. with 1.86 ml of oxalyl chloride. The mixture was srirred for 30 min. at −78° C. Then, 2.62 g of the compound described in Example 76.3 in 50 ml of $CH_2Cl_2$ were added dropwise. The mixture was stirred for a further 30 min. at −78° C. and then 17.88 ml of triethylamine were added dropwise thereto. The reaction mixture was stirred for a further 2 hrs. at −78° C. Then, it was left to warm to room temperature and evaporated. The residue was purified by chromatography on silica gel. There were obtained 2.34 g of methyl (RS)-(4-cyano-phenylamino)-(3,5-diformyl-phenyl)-acetate as a light yellow, solid foam.

81.5

A suspension of 425 mg of the dialdehyde described in Example 76.4, 456 mg of potassium carbonate and 943 mg of methyl-triphenylphosphonium bromide in 17 ml of dioxan with 1.5% $H_2O$ was heated for 16 hrs. to 110° C. The reaction mixture was concentrated. The crude product was isolated by chromatography on silica gel. There were obtained 293 mg of methyl (RS)-(4-cyano-phenylamino)-(3,5-divinyl-phenyl)-acetate as a light yellow solid.

81.6

In analogy to Example 29.2, from the compound obtained in Example 76.5 there was obtained methyl (RS)-(4-cyano-phenylamino)-(3,5-diethyl-phenyl)-acetate.

81.7

In analogy to Example 59.3, from the nitrile obtained in Example 76.6 there was obtained methyl (4-carbamimidoyl-phenylamino)-(3,5-diethyl-phenyl)-acetate.

Example 82

In analogy to Example 81.5–7, from the dialdehyde described in Example 81.4 and ethyl-triphenylphosphonium bromide there was obtained methyl (4-cyano-phenylamino)-

(3,5-dipropenyl-phenyl)-acetate, which was converted via methyl (RS)-(4-cyano-phenylamino)-(3,5-dipropyl-phenyl)-acetate into methyl (4-carbamimidoyl-phenylamino)-(3,5-dipropyl-phenyl)-acetate.

Example 83

In analogy to Example 64.3, the methyl (4-cyano-phenylamino)-(3,5-dipropenyl-phenyl)-acetate intermediate described in Example 82 was converted into methyl (RS)-(4-carbamimidoyl-phenylamino)-(3,5-dipropenyl-phenyl)-acetate hydrochloride (1:1) (configuration in E and Z).

Example 84

84.1

A solution of 130 mg of the aldehyde described in Example 81.2 in 10 ml of DMF was treated with 62 mg of NaH and stirred for 10 min. at room temperature. Then, 0.15 ml of methyl iodide was added and the mixture was stirred for one day at room temperature. The reaction mixture was evaporated. The crude product was purified by chromatography on silica gel. There were obtained 85 mg of 3,5-bis-methoxymethyl-benzaldehyde.

84.2

In analogy to Example 1.1, the benzaldehyde described in Example 84.1 was converted with 4-aminobenzonitrile and toluene-4-sulphonylmethyl isocyanide into methyl (RS)-(3,5-bis-methoxymethyl-phenyl)-(4-cyano-phenylamino)-acetate.

84.3

In analogy to Example 64.3, the nitrile obtained in Example 84.2 was converted into methyl (RS)-(3,5-bis-methoxymethyl-phenyl)-(4-carbamimidoyl-phenylamino)-acetate hydrochloride (1:1).

Example 85

85.1

A solution of 2.87 g of methyl (RS)-(4-cyano-phenylamino)-(3,5-diformyl-phenyl)-acetate in 20 ml of dioxan and 1.3 ml of DMF was treated with 3.18 g of methyltriphenylphosphonium bromid and 1.84 g of potassium carbonate. The suspension was heated for 3 days to 100° C. It was left to cool to room temperature, filtered and concentrated. The crude product was isolated by extraction isoliert and purified by chromatography on silica gel. There were obtained 1.31 g of methyl (RS)-(4-cyano-phenylamino)-(3-formyl-5-vinyl-phenyl)-acetate as a light yellow solid.

85.2

Eine suspension von 200 mg of the aldehyde described in Example 80.1 and 0.062 ml of pyrrolidine in 2 ml of MeOH was adjusted to pH 6 by the dropwise addition of acetic acid. Then, 46 mg of sodium cyanoborhydride were added and the mixture was stirred overnight at room temperature. It was acidified to pH 3 with 1N HCl and subsequently evaporated. The crude product was isolated by extraction and purified by chromatography on silica gel gereinigt. There were obtained 200 mg of methyl (RS)-(4-cyano-phenylamino)-(3-pyrrolidin-1-ylmethyl-5-vinyl-phenyl)-acetate as a colorless oil.

85.3

In analogy to Example 64.3, from the compound described in Example 85.2 there was obtained methyl (RS)-(4-carbamimidoyl-phenylamino)-(3-pyrrolidin-1-ylmethyl-5-vinyl-phenyl)-acetate hydrochloride (1:2).

Example 86

In analogy to Example 3, 86.1
the amidoxime described in Example 78.5 was converted into in (RS)-[3-(2-benzyloxy-ethoxy)-5-ethoxy-phenyl]-(4-carbamimidoyl-phenylamino)-acetic acid;

86.2
the amidoxime described in Example 79.4 was converted into (RS)-(4-carbamimidoyl-phenylamino)-(3-carboxymethoxy-5-ethoxy-phenyl)-acetic acid.

Example 87

In analogy to Example 16.3, 87.a
the compound obtained in Example 78.5 was converted into (RS)-(4-carbamimidoyl-phenylamino)-[3-ethoxy-5-(2-hydroxy-ethoxy)-phenyl]-acetic acid;

87.b
the compound described in Example 88.g was converted into (RS)-(4-carbamimidoyl-phenylamino)-(3-ethyl-5-pyrrolidin-1-ylmethyl-phenyl)-acetic acid acetic acid (1:1).

Example 88

In analogy to Example 75, 88.a
from the ester described in Example 80.a there was obtained (RS)-4-{3-[(4-carbamimidoyl-phenylamino)-carboxy-methyl]-5-ethoxy-phenoxy}-butyric acid;

88.b
from the ester described in Example 80.b there was obtained (RS)-(4-carbamimidoyl-phenylamino)-(3,5-dibutoxy-phenyl)-acetic acid;

88.c
from the ester described in Example 81.7 there was obtained (RS)-(4-carbamimidoyl-phenylamino)-(3,5-diethyl-phenyl)-acetic acid;

88.d
from the ester described in Example 82 there was obtained (RS)-(4-carbamimidoyl-phenylamino)-(3,5-dipropyl-phenyl)-acetic acid.

88.e
From the ester described in Example 83 there was obtained (4-carbamimidoyl-phenylamino)-(3,5-dipropenyl-phenyl)-acetic acid; compound with acetic acid.

88.f
From the ester described in Example 84.3 there was obtained (RS)-(3,5-bis-methoxymethyl-phenyl)-(4-carbamimidoyl-phenylamino)-acetic acid.

88.g
From the ester described in Example 85.3 there was obtained (RS)-(4-carbamimidoyl-phenylamino)-(3-pyrrolidin-1-ylmethyl-5-vinyl-phenyl)-acetic acid.

Example 89

89.1

114 g of hexamethylenetetramine were added to a solution of 20 g of 4-ethylphenol in 400 ml of AcOH. The reaction solution was stirred for 5 hrs. at 100° C. Then, 150 ml of $H_2O$ and 150 ml of 25% HCl solution were added. The mixture was stirred for 1 hr. at 100° C. Then, it was left to cool to room temperature. The crude product was isolated by extraction with diethyl ether and purified by chromatography on silica gel. There were obtained 8.6 g of 5-ethyl-2-hydroxy-benzaldehyde as a light yellow liquid.

89.2

In analogy to Example 64.1, the phenol obtained in Example 89.1 was converted with iodo-acetamide into 2-(4-ethyl-2-formyl-phenoxy)-acetamide.

89.3

In analogy to Example 1.1, the benzaldehyde described in Example 89.2 was converted with 4-aminobenzonitrile and benzyl isonitrile into ethyl (RS)-(2-carbamoylmethoxy-5-ethyl-phenyl)-(4-cyano-phenylamino)-acetate.

89.4

In analogy to Example 64.3, the nitrile described in Example 89.3 was converted into ethyl (RS)-(4- carbamimidoyl-phenylamino)-(2-carbamoylmethoxy-5-ethyl-phenyl)-acetate hydrochloride (1:1).

Example 90

90.a

In analogy to Example 90.2–4, from the aldehyde described in Example 89.1 and 1-chloro-2-dimethylaminoethane hydrochloride there was obtained 2-(2-dimethylamino-ethoxy)-5-ethyl-benzaldehyde, which was converted with 4-aminobenzonitrile and toluene-4-sulphonyl-methyl isocyanide into methyl (RS)-(4-cyano-phenylamino)-[2-(2-dimethylamino-ethoxy)-5-ethyl-phenyl]-actate and subsequently into methyl (RS)-(4-carbamimidoyl-phenylamino)-[2-(2-dimethylamino-ethoxy)-5-ethyl-phenyl]-acetate hydrochloride (1:1).

90.b

In analogy to Example 89, from 4-propylphenol there was obtained 2-hydroxy-5-propyl-benzaldehyde, which was converted by reaction with 2-bromoethanol into 2-(2-hydroxy-ethoxy)-5-propyl-benzaldehyde. This was converted with 4-aminobenzonitrile and benzyl isonitrile into methyl (RS)-(4-cyano-phenylamino)-[2-(2-hydroxy-ethoxy)-5-propyl-phenyl]-acetate and then into methyl (RS)-(4-carbamimidoyl-phenylamino)-[2-(2-hydroxy-ethoxy)-5-propyl-phenyl]-acetate acetate (1:1).

90.c

In analogy to Example 89.2–4, from the 2-hydroxy-5-propyl-benzaldehyde intermediate described in Example 89.b and iodoacetamide there was obtained 2-(2-formyl-4-propyl-phenoxy)-acetamide, which was converted with 4-aminobenzonitrile and toluene-4-sulphonylmethyl isocyanide into methyl (RS)-(2-carbamoylmethoxy-5-propyl-phenyl)-(4-cyano-phenylamino)-acetate and then into methyl (RS)-(4-carbamimidoyl-phenylamino)-(2-carbamoylmethoxy-5-propyl-phenyl)-acetate hydrochloride (1:1).

90.d

In analogy to Example 89, from 4-(2-hydroxy-ethyl)-phenol there was obtained 5-(2-hydroxyethyl)salicylaldehydw, which was converted by reaction with 2-bromoethanol into 2-(2-hydroxy-ethoxy)-5-(2-hydroxy-ethyl)-benzaldehyde. This was converted with 4-aminobenzonitrile and benzyl isonitrile into ethyl (RS)-(4-cyano-phenylamino)-[2-(2-hydroxy-ethoxy)-5-(2-hydroxy-ethyl)-phenyl]-acetate and then into ethyl (RS)-(4-carbamimidoyl-phenylamino)-[2-(2-hydroxy-ethoxy)-5-(2-hydroxy-ethyl)-phenyl]-acetate hydrochloride (1:1).

90.e

In analogy to Example 89, from 4-isopropylphenol there was obtained 5-isopropyl-salicylaldehyde, which was converted by reaction with 2-bromoethanol into 2-(2-hydroxy-ethoxy)-5-isopropyl-benzaldehyde. This was converted with 4-aminobenzonitrile and benzyl isonitrile into methyl (RS)-(4-cyano-phenylamino)-[2-(2-hydroxy-ethoxy)-5-isopropyl-phenyl]-acetate and then into methyl (RS)-(4-carbamimidoyl-phenylamino)-[2-(2-hydroxy-ethoxy)-5-isopropyl-phenyl]-acetate.

Example 91

91.1

21 ml of $CHCl_3$ were added dropwise within 30 minutes to a suspension, heated to 55° C., of 20 g of 4-hydroxypropiophenone in 95 ml of 28% NaOH. The yellow suspension was heated for 1.5 hrs. to 55° C. Then, a further 5 ml of $CHCl_3$ were added dropwise. After a further 5 hours at 60° C. the mixture was left to cool to room temperature and poured into 70 ml of concentrated hydrochloric acid and 200 ml of water. A yellow precipitate formed and was filtered off. The crude product remaining was isolated from the filtrate by extraction. Solid and extract were combined and purified by chromatography on silica gel. There were obtained 2.24 g of 2-hydroxy-5-propionyl-benzaldehyde as a greenish solid.

91.2

In analogy to Example 89.2–4, from the phenol described in Example 91.1 and 2-bromo-ethanol there was obtained 2-(2-hydroxy-ethoxy)-5-propionyl-benzaldehyde. This was converted with 4-aminobenzonitrile and toluene-4-sulphonylmethyl isocyanide into methyl (RS)-(4-cyano-phenylamino)-[2-(2-hydroxy-ethoxy)-5-propionyl-phenyl]-acetate and subsequently into methyl (RS)-(4-carbamimidoyl-phenylamino)-[2-(2-hydroxy-ethoxy)-5-propionyl-phenyl]-acetate hydrochloride (1:1).

Example 92

92.1

In analogy to Example 64.1, the phenol described in Example 89.1 was converted with N-(2-bromoethyl)-phthalimide into 2-[2-(1,3-dioxo-1,3-dihydro-isoindol-2-yl)-ethoxy]-5-ethyl-benzaldehyde.

92.2

In analogy to Example 1.1, the benzaldehyde obtained in Example 92.1 was converted with 4-aminobenzonitrile and benzyl isonitrile into methyl (RS)-(4-cyano-phenylamino)-{2-[2-(1,3-dioxo-1,3-dihydro-isoindol-2-yl)-ethoxy]-4,5-dimethoxy-phenyl}-acetate.

92.3

0.82 ml of hydrazine hydrate was added to a solution of 2.73 g of the phthalimide described in Example 92.2 in 20 ml of MeOH and 20 ml of $CHCl_3$. The reaction mixture was stirred for one day at room temperature and then treated with 10 ml of acetic acid in 20 ml of MeOH. The mixture was stirred Man liess overnight at room temperature. Subsequently, the precipitated hydrazine acetate was filtered off. The filtrate was evaporated. The crude product was isolated by chromatography on silica gel. There were obtained 1.48 g of methyl (RS)-[2-(2-amino-ethoxy)-5-ethyl-phenyl]-(4-cyano-phenylamino)-acetate acetate (1:1) as a white lyophilizate.

92.4

In analogy to Example 59.3, the nitrile obtained in Example 92.3 was converted into methyl (RS)-[2-(2-amino-ethoxy)-5-ethyl-phenyl]-(4-carbamimidoyl-phenylamino)-acetate hydrochloride (1:3).

Example 93

In analogy to Example 64.3, the nitrile obtained in Example 92.2 was converted into methyl (RS)-(4-carbamimidoyl-phenylamino)-{2-[2-(1,3-dioxo-1,3-dihydro-isoindol-2-yl)-ethoxy]-5-ethyl-phenyl}-acetate hydrochloride (1:1).

Example 94

94.1

In analogy to Example 22. 1, the amine obtained in Example 92.3 was converted with acetyl chloride into methyl (RS)-[2-(2-acetylamino-ethoxy)-5-ethyl-phenyl]-(4-cyano-phenylamino)-acetate.

94.2

In analogy to Example 64.3, the nitrile obtained in Example 94.1 was converted into methyl (RS)-[2-(2-acetylamino-ethoxy)-5-ethyl-phenyl]-(4-carbamimidoyl-phenylamino)-acetate hydrochloride (1:1).

Example 95

In analogy to Example 94, 95.a

From the amine obtained in Example 92.3 and trifluoroacetic anhydride there was obtained methyl (RS)-(4-cyanophenylamino)-{5-ethyl-2-[2-(2,2,2-trifluoro-acetylamino)-ethoxy]-phenyl}-acetate, which was subsequently converted into methyl (RS)-(4-carbamimidoyl-phenylamino)-{5-ethyl-2-[2-(2,2,2-trifluoro-acetylamino)-ethoxy]-phenyl}-acetate hydrochloride (1:1).

95.b

From the amine obtained in Example 92.3 and methanesulphonyl chloride there was obtained methyl (RS)-(4-cyano-phenylamino)-[5-ethyl-2-(2-methanesulphonylamino-ethoxy)-phenyl]-acetate, which was subsequently converted into methyl (RS)-(4-carbamimidoyl-phenylamino)-[5-ethyl-2-(2-methanesulphonylamino-ethoxy)-phenyl]-acetate hydrochloride (1:1).

95.c

From the amine obtained in Example 92.3 and phenylsulphonyl chloride there was obtained methyl (RS)-[2-(2-benzenesulphonylamino-ethoxy)-5-ethyl-phenyl]-(4-cyanophenylamino)-acetate, which was subsequently converted into methyl (RS)-[2-(2-benzene-sulphonylamino-ethoxy)-5-ethyl-phenyl]-(4-carbamimidoyl-phenylamino)-acetate hydrochloride (1:1).

Example 96

In analogy to Example 75, 96.a
from the ester obtained in Example 89.4 there was obtained (RS)-(4-carbamimidoyl-phenylamino)-(2-carbamoylmethoxy-5-ethyl-phenyl)-acetic acid;

96.b
from the ester obtained in Example 89.a there was obtained (RS)-(4-carbamimidoyl-phenylamino)-[2-(2-dimethylamino-ethoxy)-5-ethyl-phenyl]-acetic acid;

96.c
from the ester obtained in Example 90.b there was obtained (RS)-(4-carbamimidoyl-phenylamino)-[2-(2-hydroxy-ethoxy)-5-propyl-phenyl]-acetic acid;

96.d
from the ester obtained in Example 90.c there was obtained (RS)-(4-carbamimidoyl-phenylamino)-(2-carbamoylmethoxy-5-propyl-phenyl)-acetic acid;

96.e
from the ester obtained in Example 90.d there was obtained (RS)-(4-carbamimidoyl-phenylamino)-[2-(2-hydroxy-ethoxy)-5-(2-hydroxy-ethyl)-phenyl]-acetic acid;

96.f
from the ester obtained in Example 90.e there was obtained (RS)-(4-carbamimidoyl-phenylamino)-[2-(2-hydroxy-ethoxy)-5-isopropyl-phenyl]-acetic acid;

96.g
from the ester obtained in Example 92.4 there was obtained (RS)-[2-(2-amino-ethoxy)-5-ethyl-phenyl]-(4-carbamimidoyl-phenylamino)-acetic acid acetate (1:1);

96.h
from the ester obtained in Example 92 there was obtained (RS)-N-(2-{2-[(4-carbamimidoyl-phenylamino)-carboxy-methyl]-4-ethyl-phenoxy}-ethyl)-phthalamidic acid;

96.i
from the ester obtained in Example 94.2 there was obtained (RS)-[2-(2-acetylamino-ethoxy)-5-ethyl-phenyl]-(4-carbamimidoyl-phenylamino)-acetic acid;

96.j
from the ester obtained in Example 95.a there was obtained (RS)-(4-carbamimidoyl-phenylamino)-{5-ethyl-2-[2-(2,2,2-trifluoro-acetylamino)-ethoxy]-phenyl}-acetic acid;

96.k
from the ester obtained in Example 95.b there was obtained (RS)-(4-carbamimidoyl-phenylamino)-[5-ethyl-2-(2-methanesulphonylamino-ethoxy)-phenyl]-acetic acid;

96.l
from the ester obtained in Example 95.c there was obtained (RS)-[2-(2-benzenesulphonylamino-ethoxy)-5-ethyl-phenyl]-(4-carbamimidoyl-phenylamino)-acetic acid;

96.m
from the ester obtained in Example 91.2 there was obtained methyl (RS)-(4-carbamimidoyl-phenylamino)-[2-(2-hydroxy-ethoxy)-5-propionyl-phenyl]-acetate hydrochloride (1:1).

Example 97

14 mg of NaBH$_4$ were added to a solution of the ketone described in Example 96.m in 5 ml of EtOH, 5 ml of H$_2$O and 5 ml of DMF. The reaction solution was stirred overnight at room temperature and subsequently concentrated completely. The residue was taken up in H$_2$O, with a white precipitate forming. This was filtered off. There were obtained 82 mg of a mixture of (RS)- and (SR)-(4-carbamimidoyl-phenylamino)-[2-(2-hydroxy-ethoxy)-5-[(RS)-1-hydroxy-propyl]-phenyl]-acetic acid a white solid.

Example 98

98.1

In analogy to Example 1.1, 4,5-dimethoxy-2-methylbenzaldehyde was converted with 4-aminobenzonitrile and toluene-4-sulphonylmethyl isocyanide into methyl (RS)-(4-cyano-phenylamino)-(4,5-dimethoxy-2-methyl-phenyl)-acetate, which was subsequently converted in analogy to Example 64.3 into methyl (RS)-(4-carbamimidoyl-phenylamino)-(4,5-dimethoxy-2-methyl-phenyl)-acetate hydrochloride (1:1).

98.2

In analogy to Example 98.1, 2,5-dimethyl-4-methoxybenzaldehyde was converted with 4-aminobenzonitrile and toluene-4-sulphonylmethyl isocyanide into methyl (RS)-(4-cyano-phenylamino)-(4-methoxy-2,5-dimethyl-phenyl)-acetate, which was subsequently converted into methyl (RS)-(4-carbamimidoyl-phenylamino)-(4-methoxy-2,5-dimethyl-phenyl)-acetate acetate (1:1).

Example 99

99.1

In analogy to Example 64.1, 4,5-diethoxy-2-hydroxybenzaldehyde (prepared by Bayer-Villiger oxidation of 3,4-dimethoxybenzaldehyde with meta-chloroperbenzoic acid in MeOH, subsequent hydrolysis of the formylphenol ester formed with KOH in MeOH to 3,4-diethoxy-phenol and subsequent Gattermann formylation with zinc cyanide, KCl and HCl in diethyl ether) was converted with 2-bromoethanol into 4,5-diethoxy-2-(2-hydroxy-ethoxy)-benzaldehyde.

99.2

In analogy to Example 1.1, from the benzaldehyde obtained in Example 99.1, 4-amino-N-hydroxy-benzamidine and benzyl isonitrile there was obtained ethyl (E)- and/or (Z)-(RS)-[4,5-diethoxy-2-(2-hydroxy-ethoxy)-phenyl]-[4-(N-hydroxycarbamimidoyl)-phenylamino]-acetate.

99.3

In analogy to Example 3, from the amidoxime obtained in Example 99.2 there was obtained ethyl (RS)-(4-carbamimidoyl-phenylamino)-[4,5-diethoxy-2-(2-hydroxy-ethoxy)-phenyl]-acetate acetate (1:1).

Example 100

In analogy to Example 99, 100.a

From 4,5-diethoxy-2-hydroxy-benzaldehyde and 3-bromo-1-propanol there was obtained 4,5-diethoxy-2-(3-hydroxy-propoxy)-benzaldehyde, which was converted with 4-amino-N-hydroxy-benzamidine and benzyl isonitrile into ethyl (RS)-(E)- and/or -(Z)-[4,5-diethoxy-2-(3-hydroxy-propoxy)-phenyl]-[4-(N-hydroxycarbamimidoyl)-phenylamino]-acetate and subsequently into ethyl (RS)-(4-carbamimidoyl-phenylamino)-[4,5-diethoxy-2-(3-hydroxy-propoxy)-phenyl]-acetate acetate (1:1).

100.b

From 4,5-diethoxy-2-hydroxy-benzaldehyde and ethyl bromoacetate there was obtained ethyl (4,5-diethoxy-2-formyl-phenoxy)-acetate, which was converted with 4-amino-N-hydroxy-benzamidine and benzyl isonitrile into ethyl (RS)-(E)- and/or -(Z)-(4,5-diethoxy-2-ethoxy-carbonylmethoxy-phenyl)-[4-(N-hydroxycarbamimidoyl)-phenylamino]-acetate and subsequently into ethyl (RS)-(4-carbamimidoyl-phenylamino)-(4,5-diethoxy-2-ethoxy-carbonylmethoxy-phenyl)-acetate acetate (1:1).

100.c

From 4,5-diethoxy-2-hydroxy-benzaldehyde and ethyl 2-bromoisobutyrate there was obtained ethyl 2-(4,5-diethoxy-2-formyl-phenoxy)-2-methyl-propionate, which was converted with 4-amino-N-hydroxy-benzamidine and benzyl isonitrile into ethyl (RS)-(E)- and/or (Z)-2-(4,5-diethoxy-2-{[4-(N-hydroxycarbamimidoyl)-phenylamino]-methoxycarbonylmethyl}-phenoxy)-2-methyl-propionate and subsequently into ethyl (RS)-2-{2-[(4-carbamimidoyl-phenylamino)-methoxycarbonyl-methyl]-4,5-diethoxy-phenoxy}-2-methyl-propionate.

100.d

From 4,5-diethoxy-2-hydroxy-benzaldehyde and iodoacetamide there was obtained 2-(4,5-diethoxy-2-formyl-phenoxy)-acetamide, which was converted with 4-amino-N-hydroxy-benzamidine and benzyl isonitrile into ethyl (2-carbamoylmethoxy-4,5-diethoxy-phenyl)-[4-(N-hydroxycarbamimidoyl)-phenylamino]-acetate and subsequently into ethyl (RS)-(4-carbamimidoyl-phenylamino)-(2-carbamoylmethoxy-4,5-diethoxy-phenyl)-acetate hydrochloride (1:1).

Example 101

101.1

In analogy to Example 16.1–2, from 6-bromoveratraldehyde, 4-aminobenzonitrile and benzyl isonitrile there was obtained methyl (RS)-(2-bromo-4,5-dimethoxy-phenyl)-(4-cyano-phenylamino)-acetate.

101.2

In analogy to Example 64.3, from the nitrile obtained in Example 101.1 there was obtained methyl (RS)-(2-bromo-4,5-dimethoxy-phenyl)-(4-carbamimidoyl-phenylamino)-acetate hydrochloride (1:1).

Example 102

102.1

A solution of 0.91 mg of the bromide described in Example 101.1 in 20 ml of 1,2-dimethoxyethane was treated with 0.32 g of 3-thiopheneboronic acid and 0.76 mg of CsF.

Argon was conducted through this suspension for 30 min. Then, 87 mg of tetrakis-(triphenylphosphine)-palladium were added. The reaction mixture was boiled overnight at reflux. The crude product was subsequently isolated by extraction and purified by chromatography on silica gel. There were obtained 241 mg of methyl (RS)-(4-cyano-phenylamino)-(4,5-dimethoxy-2-thiophen-3-yl-phenyl)-acetate as a grey solid.

102.2

In analogy to Example 64.3, from the compound described in Example 101.1 there was obtained methyl (RS)-(4-carbamimidoyl-phenylamino)-(4,5-dimethoxy-2-thiophen-3-yl-phenyl)-acetate acetate (1:1).

Example 103

103.1

4.70 g of diboronpinacol ester and 3.63 g of potassium acetate were added to a solution of 5 g of the bromide described in Example 101.1 in 100 ml of dioxan. Argon was conducted through the reaction mixture for 15 minutes. Subsequently, 0.52 g of bis(triphenyl-phosphine)-palladium (II) chloride was added. The reaction mixture was heated overnight to 80° C., then filtriert and evaporated. The crude product was isolated by chromatography on silica gel. There were obtained 3.89 g of methyl (RS)-(4-cyano-phenylamino)-[4,5-dimethoxy-2-(4,4,5,5-tetramethyl-[1,3,2]dioxaborolan-2-yl)-phenyl]-acetate as a pink foam.

103.2

In analogy to Example 73.2, from the boronic acid ester described in Example 102.1 1 there was obtained methyl (RS)-(4-cyano-phenylamino)-(4,5-dimethoxy-2-pyridin-3-yl-phenyl)-acetate.

103.3

In analogy to Example 64.3, from compound obtained in Example 103.2 1 there was obtained methyl (RS)-(4-carbamimidoyl-phenylamino)-(4,5-dimethoxy-2-pyridin-3-yl-phenyl)-acetate hydrochloride (1:1).

Example 104

104.a

In analogy to Example 102, from the bromide described in Example 101.1 and phenylboronic acid 1 there was obtained methyl (RS)-(4-cyano-phenylamino)-(4,5-dimethoxy-biphenyl-2-yl)-acetate, which was subsequently converted into methyl (RS)-(4-carbamimidoyl-phenylamino)-(4,5-dimethoxy-biphenyl-2-yl)-acetate hydrochloride (1:1).

104.b

In analogy to Example 73.2–3 from the bromide described in Example 101.1 and 2-thiopheneboronic acid 1 there was obtained methyl (RS)-(4-cyano-phenylamino)-(4,5-dimethoxy-2-thiophen-2-yl-phenyl)-acetate, which was subsequently converted into (RS)-(4-carbamimidoyl-phenylamino)-(4.5-dimethoxy-2-thiophen-2-yl-phenyl)-acetic acid methylester acetate (1:1).

Example 105

In analogy to Example 75, 105.a

From the ester described in Example 98.1 there was obtained (RS)-(4-carbamimidoyl-phenylamino)-(4,5-dimethoxy-2-methyl-phenyl)-acetic acid.

105.b

From the ester described in Example 98.2 there was obtained (RS)-(4-carbamimidoyl-phenylamino)-(4-methoxy-2,5-dimethyl-phenyl)-acetic acid.

105.c

From the ester described in Example 99.3 there was obtained (RS)-(4-carbamimidoyl-phenylamino)-[4,5-diethoxy-2-(2-hydroxy-ethoxy)-phenyl]-acetic acid.

105.d

From the ester described in Example 100.a there was obtained (RS)-(4-carbamimidoyl-phenylamino)-[4,5-diethoxy-2-(3-hydroxy-propoxy)-phenyl]-acetic acid.

105.e

From the ester described in Example 100.b there was obtained (RS)-(4-carbamimidoyl-phenylamino)-(2-carboxymethoxy-4,5-diethoxy-phenyl)-acetic acid.

105.f

From the ester described in Example 100.c there was obtained (RS)-2-{2-[(4-carbamimidoyl-phenylamino)-carboxy-methyl]-4,5-diethoxy-phenoxy}-2-methyl-propionsäure.

105.g

From the ester described in Example 100.d there was obtained (RS)-(4-carbamimidoyl-phenylamino)-(2-carbamoylmethoxy-4,5-diethoxy-phenyl)-acetic acid.

105.h

From the ester described in Example 101.2 there was obtained (RS)-(2-bromo-4,5-dimethoxy-phenyl)-(4-carbamimidoyl-phenylamino)-acetic acid.

105.i

From the ester described in Example 102.2 there was obtained (RS)-(4-carbamimidoyl-phenylamino)-(4,5-dirnethoxy-2-thiophen-2-yl-phenyl)-acetic acid.

105.j

From the ester described in Example 104.a there was obtained (RS)-(4-carbamimidoyl-phenylamino)-(4,5-dimethoxy-biphenyl-2-yl)-acetic acid.

105.k

From the ester described in Example 104.b there was obtained (RS)-(4-carbamimidoyl-phenylamino)-(4,5-dimethoxy-2-thiophen-3-yl-phenyl)-acetic acid.

105.l

From the ester described in Example 104.3 there was obtained (RS)-(4-carbamimidoyl-phenylamino)-(4,5-dimethoxy-2-pyridin-3-yl-phenyl)-acetic acid.

Example 106

106.1

In analogy to Example 102.1, from the bromide described in Example 103.1 and 2-furanboronic acid there was obtained (RS)-(4-cyano-phenylamino)-(2-furan-2-yl-4,5-dimethoxy-phenyl)-acetic acid.

106.2

In analogy to Example 1.2, from the compound described in Example 106.1 there was obtained (RS)-(4-cyano-phenylamino)-(2-furan-2-yl-4,5-dimethoxy-phenyl)-acetic acid.

106.3

In analogy to Example 1.3, from the compound described in Example 106.2 there was obtained (2-furan-2-yl-4,5-dimethoxy-phenyl)-[4-(N-hydroxycarbamimidoyl)-phenylamino]-acetic acid.

106.4

In analogy to Example 3, from the amidoxime obtained in Example 106.3 there was obtained (RS)-(4-carbamimidoyl-phenylamino)-(2-furan-2-yl-4,5-dimethoxy-phenyl)-acetic acid.

Example 107

107.1

2.13 ml of fuming nitric acid were added within 30 minutes to a solution, cooled to −30° C. of 10 g of 3,4-diethoxybenzaldehyde in 185 ml of 1,2-dichloroethane. Subsequently, the reaction mixture was left to warm to 0° C. and was poured on to ice. The product was isolated by extraction. There were obtained 12.06 g of 4,5-diethoxy-2-nitro-benzaldehyde.

107.2

In analogy to Example 1.1 from the benzaldehyde obtained in Example 107.1, 4-aminobenzonitrile and benzyl isonitrile there was obtained methyl (RS)-(4-cyano-phenylamino)-(4,5-diethoxy-2-nitro-phenyl)-acetate.

107.3

In analogy to Example 59.2, by reduction of the nitro compound obtained in Example 107.2 with platinum-on-charcoal there was obtained methyl (RS)-(2-amino-4,5-diethoxy-phenyl)-(4-cyano-phenylamino)-acetate.

107.4

In analogy to Example 22.1, from the aniline obtained in Example 107.3 and glutaric anhydride there was obtained (RS)-4-{2-[carboxy-(4-cyano-phenylamino)-methyl]-4,5-diethoxy-phenylcarbamoyl}-butyric acid.

107.5

In analogy to Example 1.3, from the compound obtained in Example 107.4 there was obtained (RS)-4-(2-{carboxy-[4-(N-hydroxycarbamimidoyl)-phenylamino]-methyl}-4,5-diethoxy-phenylcarbamoyl)-butyric acid.

107.6

In analogy to Example 3, from the amidoxime onbtained in Example 107.5 there was obtained 4-{2-[(4-carbamimidoyl-phenylamino)-carboxy-methyl]-4,5-diethoxy-phenylcarbamoyl}-butyric acid (compound with acetic acid).

Example 108

108.1

In analogy to Example 22.1, from the aniline described in Example 107.3 and monomethyl oxalyl chloride there was obtained (RS)-(4-cyano-phenylamino)-[4,5-diethoxy-2-(oxalyl-amino)-phenyl]-acetic acid.

108.2

In analogy to Example 64.3, from compound obtained in Example 107.1 there was obtained methyl (RS)-(4-carbamimidoyl-phenylamino)-[4,5-diethoxy-2-(methoxyoxalyl-amino)-phenyl]-acetate hydrochloride (1:1).

108.3

In analogy to Example 1.2, from the ester obtained in Example 107.2 there was obtained (RS)-(4-carbamimidoyl-phenylamino)-[4,5-diethoxy-2-(oxalyl-amino)-phenyl]-acetic acid.

Example 109

109.1

A solution, cooled to 0° C., of 6.81 g of 3,4-dimethylbenzyl alcohol and 11.62 ml of N,N,N',N'-tetramethyl-ethylenediamine in 150 ml of pentane was treated with 62.5 ml of n-butyllithium solution (1.6M in hexane). The reaction mixture was boiled at reflux for 11 hrs. Then, 12.69 g of iodine in 50 ml of THF were added dropwise at −30° C. The mixture was stirred for 15 min. at −30° C. and then left to warm to room temperature. The reaction mixture was added to 100 ml of 10% sulphuric acid. The crude product was isolated by extraction and purified by chromatography on silica gel. There were obtained 2.95 g of (2-iodo-4,5-dimethyl-phenyl)-methanol as a light yellow solid.

109.2

In analogy to Example 27.1, from the iodide obtained in Example 109.1 and methyl acrylate there was obtained methyl (E)-3-(2-hydroxymethyl-4,5-dimethyl-phenyl)-acrylate.

109.3

In analogy to Example 27.2, from the compound described in Example 109.2 there was obtained methyl 3-(2-hydroxymethyl-4,5-dimethyl-phenyl)-propionate.

109.4

In analogy to Example 27.3 from the compound described in Example 109.3 there was obtained methyl 3-(2-formyl-4,5-dimethyl-phenyl)-propionate.

109.5

In analogy to Example 1, from the benzaldehyde obtained in Example 109.4, 4-aminobenzonitrile and benzyl isonitrile there was obtained methyl (RS)-3-[2-[(4-cyano-phenylamino)-methoxycarbonyl-methyl]-4,5-dimethyl-phenyl]-propionate, which was converted via (RS)-3-[2-[carboxy-(4-cyano-phenylamino)-methyl]-4,5-dimethyl-phenyl]-propionic acid into (E)- and/or (Z)-(RS)-3-[2-[carboxy-[4-(N-hydroxycarbamimidoyl)-phenylamino]-methyl]-4,5-dimethyl-phenyl]-propionic acid.

109.6

In analogy to Example 3, from the amidoxime obtained in Example 109.5 there was obtained (RS)-3-{2-[(4-carbamimidoyl-phenylamino)-carboxy-methyl]-4,5-dimethyl-phenyl}-propionic acid.

Example 110

110.1

In analogy to Example 64.1, 3.75 g of the phenol described in Example 89.1 were alkylated with cis,trans-crotyl bromide. The crude intermediate, 2-but-2-enyloxy-5-ethyl-benzaldehyde, was isolated by extraction, subsequently heated one day to 200° C. and then distilled in a bulb-tube oven. There were obtained 3.39 g of (RS)-5-ethyl-2-hydroxy-3-(1-methyl-allyl)-benzaldehyde as a yellow liquid.

110.2

In analogy to Example 64.1, the phenol described in Example 110.1 was converted with 2-bromoethanol into (RS)-5-ethyl-2-(2-hydroxy-ethoxy)-3-(1-methyl-allyl)-benzaldehyde.

110.3

In analogy to Example 1.1, the benzaldehyde described in Example 110.2 was converted with 4-amino-N-hydroxy-benzamidine and benzyl isonitrile into ethyl [5-ethyl-2-(2-hydroxy-ethoxy)-3-(1-methyl-allyl)-phenyl]-[4-(N-hydroxycarbamimidoyl)-phenylamino]-acetate.

110.3.4

In analogy to Example 3, the amidoxime obtained in Example 110.3 was converted into a mixture of ethyl (RS)- and (SR)-[(RS)-3-sec-butyl-5-ethyl-2-(2-hydroxy-ethoxy)-phenyl]-(4-carbamimidoyl-phenylamino)-acetate.

Example 111

In analogy to Example 110, the phenol described in Example 87.b was converted by alkylation with cis,trans-crotyl bromide and subsequent heating to 200° C. into (RS)-2-hydroxy-3-(1-methyl-allyl)-5-propyl-benzaldehyde. This phenol was converted with 2-bromoethanol into (RS)-2-(2-hydroxy-ethoxy)-3-(1-methyl-allyl)-5-propyl-benzaldehyde. The thus-obtained benzaldehyde was converted with 4-amino-N-hydroxy-benzamidine and benzyl isonitrile into ethyl [4-(N-hydroxycarbamimidoyl)-phenylamino]-[2-(2-hydroxy-ethoxy)-3-(1-methyl-allyl)-5-propyl-phenyl]-acetate, which was subsequently converted into a mixture of ethyl (RS)- and (SR)-[(RS)-3-sec-butyl-2-(2-hydroxy-ethoxy)-5-propyl-phenyl]-(4-carbamimidoyl-phenylamino)-acetate acetate (1:1).

Example 112

112.1

In analogy to Example 1.1, the benzaldehyde obtained in Example 110.2 was converted with 4-aminobenzonitrile and benzyl isonitrile into a mixture of ethyl (RS)- and (SR)-(4-cyano-phenylamino)-[5-ethyl-2-(2-hydroxy-ethoxy)-3-[(RS)-1-methyl-allyl]-phenyl]-acetate.

112.2

In analogy to Example 59.3, thenitrile obtained in Example 112.1 was converted into a mixture of ethyl (RS)- and (SR)-(4-carbamimidoyl-phenylamino)-[5-ethyl-2-(2-hydroxy-ethoxy)-3-[(RS)-1-methyl-allyl]-phenyl]-acetate hydrochloride (1:1).

Example 113

113.1

In analogy to Example 89.1, from methyl 5-methoxy-salicylate there was obtained methyl 3-formyl-2-hydroxy-5-methoxy-benzoate.

113.2

In analogy to Example 64.1, from the phenol obtained in Example 113.1 and 2-bromoethanol there was obtained 7-methoxy-5-oxo-2,3-dihydro-5H-benzo[e][1,4]dioxepine-9-carbaldehyde.

113.3

In analogy to Example 1.1, from the benzaldehyde obtained in Example 113.2, 4-amino-N-hydroxy-benzamidine and benzyl isonitrile there was obtained methyl (RS)-3-[(4-cyano-phenylamino)-methoxycarbonyl-methyl]-2-(2-hydroxy-ethoxy)-5-methoxy-benzoate.

Example 114

114.1

8.41 ml of bromine in 100 ml of CHCl$_3$ were added dropwise within 2 hrs. to a solution, cooled to 0° C., of 20 g of 4-ethylphenol in 200 ml of CHCl$_3$ and 100 ml of MeOH. The reaction mixture was left to warm to room temperature and was concentrated. The product was isolated by extraction. There were obtained 33.14 g of 2-bromo-4-ethyl-phenol as a light brown oil.

114.2

In analogy to Example 89.1, from the phenol described in Example 114.1 there was obtained 3-bromo-5-ethyl-2-hydroxy-benzaldehyde.

114.3

In analogy to Example 59.1 from the phenol described in Example 114.2 and 2-bromoethanol there was obtained 3-bromo-5-ethyl-2-(2-hydroxy-ethoxy)-benzaldehyde.

114.4

In analogy to Example 1.1 from the benzaldehyde obtained in Example 114.3, 4-aminobenzonitrile and benzyl isonitrile there was obtained methyl (RS)-[3-bromo-5-ethyl-2-(2-hydroxy-ethoxy)-phenyl]-(4-cyano-phenylamino)-acetate.

114.5

In analogy to Example 69.3, from the nitrile obtained in Example 114.4 there was obtained methyl (RS)-[3-bromo-5-ethyl-2-(2-hydroxy-ethoxy)-phenyl]-(4-carbamimidoyl-phenylamino)-acetate hydrochloride (1:1).

Example 115

115.1

In analogy to Example 73.1, from the bromide described in Example 110.4 and phenylboronic acid there was obtained (4-cyano-phenyl)-5-[ethyl-2-(2-hydroxy-ethoxy)-biphenyl-3-yl]-acetic acid.

115.2

In analogy to Example 64.3, from the compound described in Example 115.1 there was obtained methyl (RS)-(4-carbamimidoyl-phenylamino)-[5-ethyl-2-(2-hydroxy-ethoxy)-biphenyl-3-yl]-acetate hydrochloride (1:1).

Example 116

In analogy to Example 75, 116.a
from the ester described in Example 110.4 there was obtained a mixture of (RS)- and (SR)-[(RS)-3-sec-butyl-5-ethyl-2-(2-hydroxy-ethoxy)-phenyl]-(4-carbamimidoyl-phenylamino)-acetic acid;

116.b
from the ester described in Example 111 there was obtained a mixture of (RS)- and (SR)-[(RS)-3-sec-butyl-2-(2-hydroxy-ethoxy)-5-propyl-phenyl]-(4-carbamimidoyl-phenylamino)-acetic acid;

116.c
from the ester described in Example 112.2 there was obtained a mixture of (RS)- and (SR)-(4-carbamimidoyl-phenylamino)-[5-ethyl-2-(2-hydroxy-ethoxy)-3-[(RS)-1-methyl-allyl]-phenyl]-acetic acid;

116.d
from the ester described in Example 113.4 there were obtained (RS)-(4-carbamimidoyl-phenylamino)-(7-methoxy-5-oxo-2,3-dihydro-5H-benzo [e][1,4] dioxepin-9-yl)-acetic acid and (RS)-3-[(4-carbamimidoyl-phenylamino)-carboxy-methyl]-2-(2-hydroxy-ethoxy)-5-methoxy-benzoic acid;

116.e
from the ester described in Example 114.5 there was obtained (RS)-[3-bromo-5-ethyl-2-(2-hydroxy-ethoxy)-phenyl]-(4-carbamimidoyl-phenylamino)-acetic acid;

116.f
from the ester described in Example 115.2 there was obtained (RS)-(4-carbamimidoyl-phenylamino)-[5-ethyl-2-(2-hydroxy-ethoxy)-biphenyl-3-yl]-acetic acid.

Example 117

Analogously to the procedure described in Example 64.1, but using the following hydroxy-aldehydes and alkylating agents, there were prepared aldehydes which were converted into the corresponding amidoximes analogously to Example 1:

117.a
From 3-ethoxy-4-hydroxybenzaldehyde with 2-bromopropane there was obtained 3-ethoxy-4-isopropoxybenzaldehyde and therefrom via the intermediates methyl (RS)-(4-cyano-phenylamino)-(3-ethoxy-4-isopropoxy-phenyl)-acetate and (RS)-(4-cyano-phenylamino)-(3-ethoxy-4-isopropoxy-phenyl)-acetic acid there was obtained (E)- and/or (Z)-(RS)-(3-ethoxy-4-isopropoxy-phenyl)-[4-(N-hydroxycarbamimidoyl)-phenylamino]-acetic acid;

117.b
from 3-allyl-4-hydroxybenzaldehyde with 2-bromopropane there was obtained 3-allyl-4-isopropoxybenzaldehyde and therefrom via the intermediates methyl (RS)-(3-allyl-4-isopropoxy-phenyl)-(4-cyano-phenylamino)-acetate and (RS)-(3-allyl-4-isopropoxy-phenyl)-(4-cyano-phenylamino)-acetic acid there was obtained (E)- and/or (Z)-(RS)-(3-allyl-4-isopropoxy-phenyl)-[4-(N-hydroxycarbamimidoyl)-phenylamino]-acetic acid;

117.c
from 3-ethoxy-4-hydroxybenzaldehyde with bromocyclopropane there was obtained 3-ethoxy-4-cyclopropoxybenzaldehyde and therefrom via the intermediates methyl (RS)-(4-cyano-phenylamino)-(4-cyclopropoxy-3-ethoxy-phenyl)-acetate and (RS)-(4-cyano-phenylamino)-(4-cyclopropoxy-3-ethoxy-phenyl)-acetic acid there was obtained (RS)-(4-cyclopropoxy-3-ethoxy-phenyl)-[4-(N-hydroxycarbamimidoyl)-phenylamino]-acetic acid.

Example 118

Analogously to Example 3, the products obtained in Example 113 were converted into the corresponding amidines:

118.a
The product of Example 117.a was converted into (RS)-(4-carbamimidoyl-phenylamino)-(3-ethoxy-4-isopropoxy-phenyl)-acetic acid;

118.b
the product of Example 117.b was converted into (RS)-(4-carbamimidoyl-phenylamino)-(4-isopropoxy-3-propyl-phenyl)-acetic acid;

118.c
the product of Example 117.c was converted into (RS)-(4-carbamimidoyl-phenylamino)-(4-cyclopropoxy-3-ethoxy-phenyl)-acetic acid.

Example 119

119.1
3-Allyl-4-hydroxybenzaldehyde was converted with benzyl bromide analogously to the procedure described in Example 64.1 into 3-allyl-4-benzyloxybenzaldehyde.

119.2.
Analogously to the procedure described in Example 1.1, using 3-allyl-4-benzyloxy-benzaldehyde in place of 3,5-dimethoxybenzaldehyde, there was prepared methyl (RS)-(3-allyl-4-benzyloxy-phenyl)-(4-cyano-phenylamino)-acetate.

119.3.
The product from Example 119.2. was converted analogously to the procedure described in Example 6.2 into the amidine ester methyl (RS)-(3-allyl-4-benzyloxy-phenyl)-(4-carbamimidoyl-phenylamino)-acetate.

Example 120

The ester from Example 119.3. was hydrolyzed according to the procedure described in Example 75 to (RS)-(3-allyl-4-benzyloxy-phenyl)-(4-carbamimidoyl-phenylamino)-acetic acid.

Example 121

121.1.
Analogously to the procedure described in Example 64.1, from 3,5-dihydroxy-benzaldehyde and 1.3 equivalents of 2-bromopropane by reaction for 4 hours at 60° C. there was prepared 3-hydroxy-5-isopropoxy-benzaldehyde. This thus-obtained material was converted with 1.5 equivalents of ethyl bromide according to the same procedure into 3-ethoxy-5-isopropoxy-benzaldehyde.

121.2.
A solution of 1.2 g of 3-ethoxy-5-isopropoxybenzaldehyde (Example 117.1.) in 35 ml of methanol was treated with 0.87 g of 4-amino-N-hydroxybenzamidine and srirred for 1 hour at room temperature. Then, 0.70 ml of benzyl isonitrile were added. The solution obtained was cooled to 0° C. and then treated dropwise with 2.45 ml of boron trifluoride etherate in a manner such that the temperature did not exceed 10° C. The reaction mixture was stirred for 1 hour at room temperature and then concentrated under reduced pressure. The residue was taken up in 21 ml of methanol and 2.1 ml of water, the solution obtained was stirred for 1 hour at room temperature and then concentrated. The crude product was isolated by extraction and purified by chromatography on silica gel and yielded 0.44 g of yellowish, crystalline methyl (E)- and/or (Z)-(RS)-(3-ethoxy-5-isopropoxy-phenyl)-[4-(N-hydroxycarbamimidoyl)-phenylamino]-acetate.

Example 122

Analogously to the procedure described in Example 75, the ester obtained according to Example 121.2. was saponified to (E)- and/or (Z)-(RS)-(3-ethoxy-5-isopropoxy-phenyl)-[4-(N-hydroxycarbamimidoyl)-phenylamino]-acetic acid.

Example 123

Analogously to Example 3, the product from Example 122 was converted into (RS)-(4-carbamimidoyl-phenylamino)-(3-ethoxy-5-isopropoxy-phenyl)-acetic acid.

Example 124

124.1.

7.3 g of methyl (RS)-(3-benzyloxy-5-ethoxy-phenyl)-(4-cyano-phenylamino)-acetate were dissolved in 146 ml of ethanol and 146 ml of acetic acid, treated with 0.7 g of palladium-charcoal catalyst and at hydrogenated room temperature. After filtering off the catalyst the filtrate was concentrated and the residue was chromatographed with hexane-ethyl acetate (3:1) on silica gel. There were thus obtained 5.1 g of colorless methyl (RS)-(4-cyano-phenylamino)-(3-ethoxy-5-hydroxy-phenyl)-acetate.

124.2

Analogously to the procedure described in Example 18, but using the phenol obtained in Example 124.1 and 4-morpholino-ethanol in place of methyl lactate, there was prepared methyl (RS)-(4-cyano-phenylamino)-[3-ethoxy-5-(2-morpholin-4-yl-ethoxy)-phenyl]-acetate.

124.3

Analogously to the procedure described in Example 6.2., the material obtained in Example 124.1 was converted into methyl (4-carbamimidoyl-phenylamino)-[3-ethoxy-5-(2-morpholin-4-yl-ethoxy)-phenyl]-acetate hydrochloride (1:1).

Example 125

According to the procedure described in Example 75, the ester obtained in Example 124.3 was hydrolyzed to (RS)-(4-carbamimidoyl-phenylamino)-[3-ethoxy-5-(2-morpholin-4-yl-ethoxy)-phenyl]-acetic acid.

Example 126

126.1

Analogously to the procedure described in Example 18, but using the phenol obtained in Example 125.1 and tert-butyl 4-hydroxy-1-piperidinecarboxylate in place of methyl lactate, there was prepared tert-butyl (RS)-4-{3-(4-cyano-phenylamino)-methoxycarbonyl-methyl]-5-ethoxy-phenoxy}-piperidine-1-carboxylate.

126.2

1.5 g of the material obtained in Example 126.1 was stirred at 0° C. with 13 ml of 2 molar hydrochloric acid in ethyl acetate for 1.5 hours. The reaction mixture was evaporated and there was thus isolated 1.0 g of methyl (RS)-(4-cyano-phenylamino)-[3-ethoxy-5-(piperidin-4-yloxy)-phenyl]-acetate hydrochloride.

126.3

0.93 g of the amine obtained in Example 126.2 was dissolved in 15 ml of tetrahydrofuran and treated with 0.78 ml of N-ethyldiisopropylamine. Then, 0.19 ml of methane-sulphonyl chloride was sprayed in at 0° C. and the reaction mixture was stirred for 1.5 hours at 0° C. The reaction mixture was poured into ice-cold 2 molar hydrochloric acid and extracted with ethyl acetate. After evaporation of the organic phase and chromatography of the residue with ethyl acetate-hexane (1:1) on silica gel there was isolated 0.45 g of methyl (RS)-(4-cyano-phenylamino)-[3-ethoxy-5-(1-methanesulfonyl-piperidin-4-yloxy)-phenyl]-acetate.

126.4.

The material obtained in Example 126.3. was converted analogously to the procedure described in Example 6.2 into methyl (RS)-(4-carbamimidoyl-phenylamino)-[3-ethoxy-5-(1-methanesulphonyl-piperidin-4-yloxy)-phenyl]-acetate hydrochloride.

Example 127

Analogously to Example 197, but using the phenol obtained in Example 124.1, there was obtained, via a mixture of ethyl (RS)- and (SR)-(4-cyano-phenylamino)-[3-ethoxy-5-[(1RS,2RS)-2-hydroxy-cyclopentyloxy]-phenyl]-acetate, a mixture of ethyl (RS)- and (SR)-(4-carbamimidoyl-phenylamino)-[3-ethoxy-5-[(1RS,2RS)-2-hydroxy-cyclopentyloxy]-phenyl]-acetate hydrochloride.

Example 128

Analogously to the procedure described in Example 127, but using cyclohexene oxide in place of cyclopentene oxide, there was prepared, via a mixture of ethyl (RS)- and (SR)-(4-cyano-phenylamino)-[3-ethoxy-5-[(1RS,2RS)-2-hydroxy-cyclohexyloxy]-phenyl]-acetate, a mixture of ethyl (RS)- and (SR)-(4-carbamimidoyl-phenylamino)-[3-ethoxy-5-[(1RS, 2RS)-2-hydroxy-cyclohexyloxy]-phenyl]-acetate hydrochloride.

Example 129

Analogously to the procedure described in Example 206, but using the phenol obtained in Example 124.1, via methyl (RS)-(4-cyano-phenylamino)-[3-ethoxy-5-(4-trityloxy-cyclohexyloxy)-phenyl]-acetate there was prepared methyl (RS)-(4-carbamimidoyl-phenylamino)-[3-ethoxy-5-(4-hydroxy-cyclohexyloxy)-phenyl]-acetate.

Example 130

Analogously to the procedure described in Example 200.2 and 200.3, but using the phenol obtained in Example 124.1, via methyl (RS)-(4-cyano-phenylamino)-(3-ethoxy-5-isobutoxy-phenyl)-acetate there was prepared methyl (RS)-(4-carbamimidoyl-phenylamino)-(3-ethoxy-5-isobutoxy-phenyl)-acetate hydrochloride.

Example 131

Analogously to the procedure described in Example 75, the products of Examples 126.4., 127.2, 128 and 129 were hydrolyzed to the corresponding acids:

131.1.

From the product of Example 126.4. there was obtained (RS)-(4-carbamimidoyl-phenylamino)-[3-ethoxy-5-(1-methanesulphonyl-piperidin-4-yloxy)-phenyl]-acetic acid;

131.2.

From the product of Example 127.2. there was obtained a mixture of (RS)- and (SR)-(4-carbamimidoylphenylamino)-[3-ethoxy-5-[(1RS,2RS)-2-hydroxy-cyclopentyloxy]-phenyl]-acetic acid.

131.3.

From the product of Example 128 there was obtained a mixture of (RS)- and (SR)-(4-carbamimidoyl-phenylamino)-[3-ethoxy-5-[(1RS,2RS)-2-hydroxy-cyclohexyloxy]-phenyl]-acetic acid.

131.4

From the product of Example 129 there was obtained (RS)-(4-carbamimidoyl-phenylamino)-[3-ethoxy-5-(4-hydroxy-cyclohexyloxy)-phenyl]-acetic acid.

131.5

From the product of Example 130 there was obtained (RS)-(4-carbamimidoyl-phenylamino)-(3-ethoxy-5-isobutoxy-phenyl)-acetic acid.

Example 132

In analogy to Example 64.1, from the aldehyde described in Example 89.1 and ethyl bromo-acetate there was obtained ethyl (4-ethyl-2-formyl-phenoxy)-acetate, therefrom according to the procedure described in Example 1 there was obtained methyl (RS)-(4-cyano-phenylamino)-(2-ethoxycarbonylmethoxy-5-ethyl-phenyl)-acetate, therefrom there was obtained (RS)-(2-carboxymethoxy-5-ethyl-phenyl)-(4-cyano-phenylamino)-acetic acid and therefrom there was finally obtained (E)- and/or (Z)-(RS)-(2-carboxymethoxy-5-ethyl-phenyl)-[4-(N-hydroxycarbamimidoyl)-phenylamino]-acetic acid.

Example 133

Analogously to Example 3, the product obtained in Example 132 was converted into (RS)-(4-carbamimidoyl-phenylamino)-(2-carboxymethoxy-5-ethyl-phenyl)-acetic acid.

Example 134

134.1.

In analogy to Example 64.1 from the aldehyde described in Example 89.1 and benzyl bromide there was obtained 2-benzyloxy-5-ethyl-benzaldehyde.

134.2.

The aldehyde from Example 134.1 was converted analogously to Example 1.1 with 4-aminobenzonitrile and toluene-4-sulphonylmethyl isocyanide into methyl (RS)-(2-benzyloxy-5-ethyl-phenyl)-(4-cyano-phenylamino)-acetate.

134.3.

Analogously to the procedure described in Example 124.1, the product of Example 134.2 was hydrogenated to methyl (RS)-(4-cyano-phenylamino)-(5-ethyl-2-hydroxy-phenyl)-acetate.

134.4.

Analogously to Example 59.1, the phenol obtained in Example 134.3 was converted with 2-bromo-ethyl methyl ether into methyl (RS)-(4-cyano-phenylamino)-[5-ethyl-2-(2-methoxy-ethoxy)-phenyl]-acetate.

134.5.

Analogously to the procedure described in Example 6.2, the material obtained in Example 134.4 was converted into methyl (RS)-(4-carbamimidoyl-phenylamino)-[5-ethyl-2-(2-methoxy-ethoxy)-phenyl]-acetate hydrochloride (1:1).

Example 135

In analogy to Example 89.2–4, from the aldehyde described in Example 89.1 and 2-bromo-ethanol there was obtained 5-ethyl-2-(2-hydroxy-ethoxy)-benzaldehyde, which was converted with 4-aminobenzonitrile and toluene-4-sulphonylmethyl isocyanide into methyl (RS)-(4-cyano-phenylamino)-[5-ethyl-2-(2-hydroxy-ethoxy)-phenyl]-acetate and then into methyl (RS)-(4-carbamimidoyl-phenylamino)-[5-ethyl-2-(2-hydroxy-ethoxy)-phenyl]-acetate hydrochloride (1:1).

Example 136

Analogously to the procedure described in Example 18, but using the phenol obtained in Example 134.3 and 4-morpholino-ethanol in place of methyl lactate there was prepared methyl (RS)-(4-cyano-phenylamino)-[5-ethyl-2-(2-morpholin-4-yl-ethoxy)-phenyl]-acetate, which was converted according to the procedure described in Example 64.3 into methyl (RS)-(4-carbamimidoyl-phenylamino)-[5-ethyl-2-(2-morpholin-4-yl-ethoxy)-phenyl]-acetate hydrochloride (1:1).

Example 137

According to the procedure described in Example 75, the esters obtained in Examples 134.5, 135 and 136 were hydrolyzed to the following acids:

137.a

From the product of Example 134.5 there was obtained (RS)-(4-carbamimidoyl-phenylamino)-[5-ethyl-2-(2-methoxy-ethoxy)-phenyl]-acetic acid.

137.b

From the product of Example 135 there was obtained (RS)-(4-carbamimidoyl-phenylamino)-[5-ethyl-2-(2-hydroxy-ethoxy)-phenyl]-acetic acid.

137.c rom the product of Example 136 there was obtained (RS)-(4-carbamimidoyl-phenylamino)-[5-ethyl-2-(2-morpholin-4-yl-ethoxy)-phenyl]-acetic acid.

Example 138

138.1.

In analogy to Example 69.1, from 2-allyl-4-benzyloxyphenol and ethyl bromide there was obtained 2-allyl-4-benzyloxy-1-ethoxy-benzene.

138.2.

Analogously to the procedure described in Example 124.1, the product from Example 138.1. was hydrogenated to 4-ethoxy-3-propyl-phenol.

138.3.

According to the procedure described in Example 94.1, the product from Example 138.2. was converted into 5-ethoxy-2-hydroxy-4-propyl-benzaldehyde.

138.4.

In analogy to Example 64.1, from the product of Example 138.3 there was obtained 5-ethoxy-2-(2-hydroxy-ethoxy)-4-propyl-benzaldehyde.

138.5

Analogously to Example 1, from the aldehyde of Example 138.4. via the intermediates methyl (RS)-(4-cyano-phenylamino)-[5-ethoxy-2-(2-hydroxy-ethoxy)-4-propyl-phenyl]-acetate and methyl (RS)-(4-cyano-phenylamino)-[5-ethoxy-2-(2-hydroxy-ethoxy)-4-propyl-phenyl]-acetic acid there was prepared (RS)-[5-ethoxy-2-(2-hydroxy-ethoxy)-4-propyl-phenyl]-[4-(N-hydroxycarbamimidoyl)-phenylamino]-acetic acid.

Example 139

Analogously to Example 3, the product obtained in Example 138.5 was converted into (RS)-(4-carbamimidoyl-phenylamino)-[5-ethoxy-2-(2-hydroxy-ethoxy)-4-propyl-phenyl]-acetic acid.

Example 140

140.1.

Analogously to the procedure described in Example 140.1–3., 2-benzyloxy-2-(2-methyl-allyl)-phenol was converted via the intermediates 1-benzyloxy-4-ethoxy-3-(2-methyl-allyl)-benzene and 4-ethoxy-3-isobutyl-phenol into 5-ethoxy-2-hydroxy-4-isobutyl-benzaldehyde.

140.2.

In analogy to Example 64.1., from the product of Example 140.1. and benzyl bromide there was obtained 2-benzyloxy-5-ethoxy-4-isobutyl-benzaldehyde.

140.3.

Analogously to Example 1.1., the aldehyde from Example 140.2 was converted into methyl (RS)-(RS)-(2-benzyloxy-5-ethoxy-4-isobutyl-phenyl)-(4-cyano-phenylamino)-acetate.

140.4.

Analogously to the procedure described in Example 124.1., but using ethanol/THF in place of ethanol/acetic acid as the solvent, the product of Example 140.3 was hydrogenated to methyl (RS)-(4-cyano-phenylamino)-(5-ethoxy-2-hydroxy-4-isobutyl-phenyl)-acetate.

140.5.

According to the procedure described in Example 18, from the product of Example 140.4. and 2-(benzyloxy)ethanol there was prepared methyl (RS)-[2-(2-benzyloxy-ethoxy)-5-ethoxy-4-isobutyl-phenyl]-(4-cyano-phenylamino)-acetate.

140.6

Analogously to Example 64.3., the product of Example 140.5. was converted into methyl (RS)-[2-(2-benzyloxy-ethoxy)-5-ethoxy-4-isobutyl-phenyl]-(4-carbamimidoyl-phenylamino)-acetate hydrochloride (1:1).

140.7.

Analogously to Example 140.4. the product obtained in Example 140.6. was hydrogenated to methyl (RS)-(4-carbamimidoyl-phenylamino)-[5-ethoxy-2-(2-hydroxy-ethoxy)-4-isobutyl-phenyl]-acetate hydrochloride (1:1).

Example 141

The ester from Example 140.6. was hydrolyzed according to the procedure described in Example 75 to methyl (RS)-(4-carbamimidoyl-phenylamino)-[5-ethoxy-2-(2-hydroxy-ethoxy)-4-isobutyl-phenyl]-acetic acid hydrochloride (1:1).

Example 142

142.1.

Analogously to the procedure described in Example 124.1., but using ethyl acetate in place of ethanol/acetic acid as the solvent, 2-allyl-4-ethyl-phenol was hydrogenated to 4-ethyl-2-propyl-phenol.

142.2.

According to the procedure described in Example 94.1, the product from Example 142.1. was converted into 5-ethyl-2-hydroxy-3-propyl-benzaldehyde.

142.3.

Analogously to Example 132, but starting from the aldehyde prepared according to Example 142.2., via the intermediates ethyl (4-ethyl-2-formyl-6-propyl-phenoxy)-acetate, methyl (RS)-(4-cyano-phenylamino)-(2-ethoxycarbonylmethoxy-5-ethyl-3-propyl-phenyl)-acetate and (RS)-(2-carboxymethoxy-5-ethyl-3-propyl-phenyl)-(4-cyano-phenylamino)-acetic acid there was prepared (E)- and/or (Z)-(RS)-(2-carboxymethoxy-5-ethyl-3-propyl-phenyl)-[4-(N-hydroxycarbamimidoyl)-phenylamino]-acetic acid.

Example 143

Analogously to Example 142.3, the aldehyde prepared according to Example 142.2. was converted, using benzyl bromide in place of the bromoacetate and via the intermediates 2-benzyloxy-5-ethyl-3-propyl-benzaldehyde, methyl (RS)-(2-benzyloxy-5-ethyl-3-propyl-phenyl)-(4-cyano-phenylamino)-acetate and (RS)-(2-benzyloxy-5-ethyl-3-propyl-phenyl)-(4-cyano-phenylamino)-acetic acid, into (E)- and/or (Z)-(RS)-(2-benzyloxy-5-ethyl-3-propyl-phenyl)-[4-(N-hydroxycarbamimidoyl)-phenylamino]-acetic acid.

Example 144

Analogously to Example 3, the following amidoximes were converted into the corresponding amidines:

144.a

The product from Example 142.4 was converted into (RS)-(4-carbamimidoyl-phenylamino)-(2-carboxymethoxy-5-ethyl-3-propyl-phenyl)-acetic acid;

144.b

The product from Example 143 was converted into (RS)-(4-carbamimidoyl-phenylamino)-(5-ethyl-2-hydroxy-3-propyl-phenyl)-acetic acid.

Example 145

145.1

25 g of 2-(2-methyl-2-propenyl)-4-ethyl-phenol were stirred for 48 hours at 195° C. After chromatography of the reaction mixture with hexane-ethyl acetate (19:1) on silica gel there were obtained 22.9 g of oily 2-(2-methyl-2-propenyl)-4-ethyl-phenol.

145.2

According to the procedure described in Example 94.1, the product from Example 145.1. was formylated to 5-ethyl-2-hydroxy-3-(2-methyl-allyl)-benzaldehyde.

145.3

In analogy to Example 89.2–4, from the aldehyde described in Example 145.2 and 2-bromo-ethyl methyl ether there was obtained 5-ethyl-2-(2-methoxy-ethoxy)-3-(2-methyl-allyl)-benzaldehyde, which was converted with 4-aminobenzonitrile and toluene-4-sulphonylmethyl isocyanide into methyl (RS)-(4-cyano-phenylamino)-[5-ethyl-2-(2-methoxy-ethoxy)-3-(2-methyl-allyl)-phenyl]-acetate and then into methyl (RS)-(4-carbamimidoyl-phenylamino)-[5-ethyl-2-(2-methoxy-ethoxy)-3-(2-methyl-allyl)-phenyl]-acetate hydrochloride (1:1).

Example 146

In analogy to Example 134.1–5, from 5-ethyl-2-hydroxy-3-(2-propenyl)-benzaldehyde and benzyl bromide there was obtained 3-allyl-2-benzyloxy-5-ethyl-benzaldehyde, therefrom there was obtained methyl (RS)-(3-allyl-2-benzyloxy-5-ethyl-phenyl)-(4-cyano-phenylamino)-acetate and then there was obtained methyl (RS)-(4-cyano-phenylamino)-(5-ethyl-2-hydroxy-3-propyl-phenyl)-acetate, which was converted with 2-(benzyloxy)ethanol into methyl (RS)-[2-(2-benzyloxy-ethoxy)-5-ethyl-3-propyl-phenyl]-(4-cyano-phenylamino)-acetate and finally into methyl (RS)-[2-(2-benzyloxy-ethoxy)-5-ethyl-3-propyl-phenyl]-(4-carbamimidoyl-phenylamino)-acetate hydrochloride (1:1).

Example 147

Analogously to the procedure described in Example 124.1, but using ethyl acetate/THF in place of ethanol/acetic acid as the solvent, the product from Example 136. was hydrogenated to methyl (RS)-(4-carbamimidoyl-phenylamino)-[5-ethyl-2-(2-hydroxy-ethoxy)-3-propyl-phenyl]-acetate hydrochloride (1:1).

Example 148

According to the procedure described in Example 146, from the aldehyde of Example 145.2. there was obtained 2-benzyloxy-5-ethyl-3-(2-methyl-allyl)-benzaldehyde, therefrom there was obtained methyl (RS)-[2-benzyloxy-5-ethyl-3-(2-methyl-allyl)-phenyl]-(4-cyano-phenylamino)-acetate, therefrom there was obtained methyl (RS)-(4-cyano-phenylamino)-(5-ethyl-2-hydroxy-3-isobutyl-phenyl)-acetate, then there was obtained methyl (RS)-[2-(2-benzyloxy-ethoxy)-5-ethyl-3-isobutyl-phenyl]-(4-cyano-phenylamino)-acetate and finally there was obtained methyl (RS)-[2-(2-benzyloxy-ethoxy)-5-ethyl-3-isobutyl-phenyl]-(4-carbamimidoyl-phenylamino)-acetate hydrochloride (1:1).

Example 149

The esters from the following Examples were hydrolyzed to the corresponding acids according to the procedure described in Example 75:

149.a

The product from Example 145.3. was converted into (RS)-(4-carbamimidoyl-phenylamino)-[5-ethyl-2-(2-methoxy-ethoxy)-3-(2-methyl-allyl)-phenyl]-acetic acid;

149.b the product from Example 147 was converted into (RS)-(4-carbamimidoyl-phenylamino)-[5-ethyl-2-(2-hydroxy-ethoxy)-3-propyl-phenyl]-acetic acid;

149.c the product from Example 148 was converted into (RS)-[2-(2-benzyloxy-ethoxy)-5-ethyl-3-isobutyl-phenyl]-(4-carbamimidoyl-phenylamino)-acetic acid hydrochloride (1:1).

Example 150

The acids from the following Examples were hydrogenated to the corresponding products according to the procedure described in 124.1:

150.a

The material from Example 149.a was converted into (RS)-(4-carbamimidoyl-phenylamino)-[5-ethyl-3-isobutyl-2-(2-methoxy-ethoxy)-phenyl]-acetic acid;

150.b the material from Example 149.c was converted into (RS)-(4-carbamimidoyl-phenylamino)-[5-ethyl-2-(2-hydroxy-ethoxy)-3-isobutyl-phenyl]-acetic acid.

Example 151

151.1.

Analogously to the procedure described in Example 12.1, but using benzyl bromoacetate in place of ethyl bromoacetate, methyl (RS)-(4-cyano-phenylamino)-(5-ethyl-2-hydroxy-3-propyl-phenyl)-acetate (prepared in Example 146) was converted into methyl (RS)-(2-benzyloxycarbonylmethoxy-5-ethyl-3-propyl-phenyl)-(4-cyano-phenylamino)-acetate.

151.2.

The product from Example 141.1. was hydrogenated according to the procedure described in 124.1, but using ethyl acetate/THF in place of ethanol/acetic acid as the solvent, to methyl (RS)-(2-carboxymethoxy-5-ethyl-3-propyl-phenyl)-(4-cyano-phenylamino)-acetate.

151.3.

A solution of 0.8 g of the product obtained in Example 151.2. in 8 ml of DMF was treated with 0.86 g of BOP, 0.3 ml of 4-ethylmorpholine and 0.19 ml of pyrrolidine and stirred overnight at room temperature. The reaction mixture was evaporated and the residue was taken up in ethyl acetate and extracted once with 5% potassium hydrogen sulphate-10% potassium sulphate solution and twice with water. Die organic phase was dried and evaporated, and the residue was chromatographed with hexane-ethyl acetate (1: 1). There was thus obtained 0.58 g of beige methyl (RS)-(4-cyano-phenylamino)-[5-ethyl-2-(2-oxo-2-pyrrolidin-1-yl-ethoxy)-3-propyl-phenyl]-acetate.

151.4.

In analogy to Example 64.3, from the product of Example 151.3 there was obtained methyl (RS)-(4-carbamimidoyl-phenylamino)-[5-ethyl-2-(2-oxo-2-pyrrolidin-1-yl-ethoxy)-3-propyl-phenyl]-acetate hydrochloride (1:1).

Example 152

The following products were prepared analogously to the procedure described in Example 151.3–4, but using the following bases in place of pyrrolidine:

152.a

Methyl (RS)-(4-carbamimidoyl-phenylamino)-[5-ethyl-2-(2-morpholin-4-yl-2-oxo-ethoxy)-3-propyl-phenyl]-acetate hydrochloride (1:1) was prepared using morpholine via the intermediate methyl (RS)-(4-cyano-phenylamino)-[5-ethyl-2-(2-morpholin-4-yl-2-oxo-ethoxy)-3-propyl-phenyl]-acetate;

152.b

Methyl (RS)-[2-(2-azepan-1-yl-2-oxo-ethoxy)-5-ethyl-3-propyl-phenyl]-(4-carbamimidoyl-phenylamino)-acetate hydrochloride (1:1) was prepared using hexamethylene-imine via the intermediate methyl (RS)-[2-(2-azepan-1-yl-2-oxo-ethoxy)-5-ethyl-3-propyl-phenyl]-(4-cyano-phenylamino)-acetate;

152.c

Methyl (RS)-(4-carbamimidoyl-phenylamino)-(2-cyclopropylcarbamoylmethoxy-5-ethyl-3-propyl-phenyl)-acetate hydrochloride (1:1) was prepared using cyclopropylamine via the intermediate methyl (RS)-(4-cyano-phenylamino)-(2-cyclopropylcarbamoylmethoxy-5-ethyl-3-propyl-phenyl)-acetate.

Example 153

The esters from the following Examples were hydrolyzed to the corresponding acids according to the procedure described in Example 75:

153.a

The product from Example 151.4. was converted into (RS)-(4-carbamimidoyl-phenylamino)-[5-ethyl-2-(2-oxo-2-pyrrolidin-1-yl-ethoxy)-3-propyl-phenyl]-acetic acid;

153.b the product from Example 152.a was converted into (RS)-(4-carbamimidoyl-phenylamino)-[5-ethyl-2-(2-morpholin-4-yl-2-oxo-ethoxy)-3-propyl-phenyl]-acetic acid;

153.c the product from Example 152.b was converted into (RS)-[2-(2-azepan-1-yl-2-oxo-ethoxy)-5-ethyl-3-propyl-phenyl]-(4-carbamimidoyl-phenylamino)-acetic acid;

153.d the product from Example 152.c was converted into (RS)-(4-carbamimidoyl-phenylamino)-(2-cyclopropylcarbamoylmethoxy-5-ethyl-3-propyl-phenyl)-acetic acid.

Example 154

Racemates can be resolved into the individual isomers by chromatography with heptane-ethanol (83:17) and with the addition of 0.4% TFA on a column with a chiral carrier material (Chiralpak AD).

154.a

From (RS)-(4-carbamimidoyl-phenylamino)-(3,4-diethoxy-phenyl)-acetic acid there were obtained (R)-(4-carbamimidoyl-phenylamino)-(3,4-diethoxy-phenyl)-acetic acid and (S)-(4-carbamimidoyl-phenylamino)-(3,4-diethoxy-phenyl)-acetic acid.

154.b

From (RS)-(4-carbamimidoyl-phenylamino)-[3-ethoxy-5-(tetrahydro-pyran-4-yloxy)-phenyl-acetic acid there were obtained (R)-(4-carbamimidoyl-phenylamino)-[3-ethoxy-5-(tetrahydro-pyran-4-yloxy)-phenyl]-acetic acid and (S)-(4-carbamimidoyl-phenylamino)-[3-ethoxy-5-(tetrahydro-pyran-4-yloxy)-phenyl]-acetic acid.

154.c

From (RS)-(4-carbamimidoyl-phenylamino)-(2-carboxymethoxy-5-ethoxy-phenyl)-acetic acid there were obtained (S)-(4-carbamimidoyl-phenylamino)-(2-carboxymethoxy-5-ethoxy-phenyl)-acetic acid and (R)-(4-carbamimidoyl-phenylamino)-(2-carboxymethoxy-5-ethoxy-phenyl)-acetic acid.

Example 155

155.1

In analogy to Example 22.1, 5.00 g of the methyl (RS)-(4-cyano-phenylamino)-(3-ethoxy-5-hydroxy-phenyl)-acetate described in Example 124.1 were reacted with 3.29 ml of trifluoro-methanesulphonic anhydride in $CH_2Cl_2$ in the presence of 5.34 ml of triethylamine. There were obtained 6.19 g of methyl (RS)-(4-cyano-phenylamino)-(3-ethoxy-5-trifluoromethanesulphonyloxy-phenyl)-acetate as a pale yellow solid. MS: 457 ([M–H]$^-$)

155.2

In analogy to Example 73.2, the compound methyl (RS)-(4-cyano-phenylamino)-(3-ethoxy-5-trifluoromethanesulphonyloxy-phenyl)-acetate described in Example 155.1 was converted by reaction with phenylboronic acid into methyl (RS)-(4-cyano-phenylamino)-(5-ethoxy-biphenyl-3-yl)-acetate. MS: 386 ([M]$^+$).

Analogously to Example 6.2, the compound methyl (RS)-(4-cyano-phenylamino)-(5-ethoxy-biphenyl-3-yl)-acetate described in Example 155.1 was converted into methyl (RS)-(4-carbamimidoyl-phenylamino)-(5-ethoxy-biphenyl-3-yl)-acetate (acetic acid salt); MS: 404 ([M+H]$^+$)

ANALOGOUS EXAMPLES 155.a

Analogously to Example 155, from methyl (RS)-(4-cyano-phenylamino)-(3-ethoxy-5-hydroxy-phenyl)-acetate via methyl (RS)-(4-cyano-phenylamino)-(3-ethoxy-5-trifluoromethanesulphonyloxy-phenyl)-acetate by reaction with 3-aminophenylboronic acid there was obtained the compound methyl (RS)-(3'-amino-5-ethoxy-biphenyl-3-yl)-(4-cyano-phenylamino)-acetate, which was converted into methyl (RS)-(3'-amino-5-ethoxy-biphenyl-3-yl)-(4-carbamimidoyl-phenylamino)-acetate hydrochloride; MS: 419 ([M+H]$^+$).

155.b

Analogously to Example 145, from methyl (RS)-(4-cyano-phenylamino)-(3-ethoxy-5-hydroxy-phenyl)-acetate via methyl (RS)-(4-cyano-phenylamino)-(3-ethoxy-5-trifluoromethanesulphonyloxy-phenyl)-acetate by reaction with thiophene-2-boronic acid there was obtained the compound methyl (RS)-(4-cyano-phenylamino)-(3-ethoxy-5-thiophen-2-yl-phenyl)-acetate, which was converted into methyl (RS)-(4-carbamimidoyl-phenylamino)-(3-ethoxy-5-thiophen-2-yl-phenyl)-acetate hydrochloride.

155.c

Analogously to Example 155, from the ethyl (RS)-(4-cyano-phenylamino)-(3-hydroxy-5-methyl-phenyl)-acetate described in Example 156.1 there was prepared ethyl (RS)-(4-cyano-phenylamino)-(3-methyl-5-trifluoromethanesulphonyloxy-phenyl)-acetate, which was converted by reaction with 4-N,N-dimethylaminophenylboronic acid into ethyl (RS)-(4-cyano-phenylamino)-(4'-dimethylamino-5-methyl-biphenyl-3-yl)-acetate and finally into ethyl (RS)-(4-carbamimidoyl-phenylamino)-(4'-dimethylamino-5-methyl-biphenyl-3-yl)-acetate.

155.d

Analogously to Example 155, from the ethyl (RS)-(4-cyano-phenylamino)-(3-hydroxy-5-methyl-phenyl)-acetate described in Example 156. there was prepared ethyl (RS)-(4-cyano-phenylamino)-(3-methyl-5-trifluoromethanesulphonyloxy-phenyl)-acetate, which was converted by reaction with 3-N,N-dimethylaminophenylboronic acid into ethyl (RS)-(4-cyano-phenylamino)-(3'-dimethylamino-5-methyl-biphenyl-3-yl)-acetate and finally into ethyl (RS)-(4-carbamimidoyl-phenylamino)-(3'-dimethylamino-5-methyl-biphenyl-3-yl)-acetate hydrochloride.

155.e

Analogously to Example 155, from the ethyl (RS)-(4-cyano-phenylamino)-(3-hydroxy-5-methyl-phenyl)-acetate described in Example 181.1 there was prepared ethyl (RS)-(4-cyano-phenylamino)-(3-methyl-5-trifluoromethanesulphonyloxy-phenyl)-acetate, which was converted by reaction with 3-aminophenylboronic acid into ethyl (RS)-(3'-amino-5-methyl-biphenyl-3-yl)-(4-cyano-phenylamino)-acetate and finally into ethyl (RS)-(3'-amino-5-methyl-biphenyl-3-yl)-(4-carbamimidoyl-phenylamino)-acetate (compound with acetic acid); MS 403 ([M+H]$^+$).

Example 156

156.1

A solution of 5.00 g of 1-bromo-3,5-dimethylbenzene in $CCl_4$ was treated with 20.20 g of N-bromosuccinimide and 0.655 g of dibenzoyl peroxide and boiled at reflux for 5 hrs. Then, the mixture was left to cool to room temperature, the resulting succinimide was filtered off and the solvent was removed in a vacuum. By column chromatography (cyclohexane/ethyl acetate) there were isolated 3.87 g of 1-bromo-3-bromomethyl-5-dibromomethyl-benzene, which was suspended in water and boiled at reflux together with 1.74 g of calcium carbonate, 2.73 g of sodium acetate and 0.58 g of tetrabutylammonium bromide for 15 hrs. Then, the mixture was left to cool to room temperature, filtered and the filtrate was acidified with dil. HCl to pH 2. The crude product obtained by extraction with $CH_2Cl_2$ was purified by column chromatography (cyclohexane/ethyl acetate). There was obtained 0.80 g of 3-bromo-5-hydroxymethyl-benzaldehyde; MS: 214/216 ([M]$^+$).

156.2

Analogously to Example 27.2, by reaction of the 3-bromo-5-hydroxymethyl-benzaldehyde described in Example 156.1 with 4-aminobenzonitrile and benzyl isonitrile there was obained ethyl (3-bromo-5-hydroxymethyl-phenyl)-(4-cyano-phenylamino)-acetate.

156.3

403 mg of the ethyl (RS)-(3-bromo-5-hydroxymethyl-phenyl)-(4-cyano-phenylamino)-acetate described in Example 156.2 were suspended in 3.1 ml of triethylamine and 4 mg of triphenylphosphine were added. Argon was conducted through the reaction mixture for 30 min. Then, 7 mg of palladium(II) acetate and 0.22 ml of trimethylsilylacetylene were added and the mixture was heated for 26 hrs. to 80° C. Then, the mixture was left to cool to room temperature and the crude product was isolated by extraction arid purified by column chromatography (n-hexane/ethyl acetate). There were obtained 398 mg of ethyl (RS)-(4-cyano-phenylamino)-(3-hydroxymethyl-5-trimethylsilanylethynyl-phenyl)-acetate as a brown oil; MS: 406 ([M]$^+$).

156.4

398 mg of the ethyl (RS)-(4-cyano-phenylamino)-(3-hydroxymethyl-5-trimethylsilanyl-phenyl)-acetate described in Example 156.3 were dissolved in 6 ml of $CH_2Cl_2$ g and 0.41 ml of triethylamine followed by 0.1 ml of methanesulphonyl chloride were added dropwise at 0° C. The mixture was stirred overnight and an intermediate was then isolated by extraction. This was taken up in 5 ml of THF and stirred together with 0.41 ml of triethylamine and 0.32 ml of pyrrolidine. By repeat extraction there was obtained a crude product, which was purified by column chromatography (cyclohexan/ethyl acetate). There were obtained 130 mg of ethyl (RS)-(4-cyano-phenylamino)-(3-pyrrolidin-1-ylmethyl-5-trimethylsilanyl-phenyl)-acetate as a light brown solid; MS: 460 ([M]$^+$).

156.5

130 mg of the ethyl (RS)-(4-cyano-phenylamino)-(3-pyrrolidin-1-ylmethyl-5-trimethyl-silanylethynyl-phenyl)-acetate described in Example 156.4 were dissolved in 2 ml of THF and treated at 0° C. with 0.43 ml of a 1 molar solution of tetrabutylammonium fluoride in THF. After 5 hrs. at 0° C. water was added to the reaction mixture and an intermediate was extracted with ethyl acetate. This intermediate was treated at 0° C. in 5 ml of MeOH with 31 mg of sodium cyanoborohydride. Then, the pH was adjusted to 6 with methanolic HCl and the reaction mixture was stirred overnight at room temperature. The reaction mixture was then made basic with methanolic $KHCO_3$ and, after removal of the solvent in a vacuum, the residue was purified by column chromatography ($CH_2Cl_2$/methanol). There were obtained 27 mg of ethyl (RS)-(4-cyano-phenylamino)-(3-ethynyl-5-pyrrolidin-1-ylmethyl-phenyl)-acetate as a light yellow solid; MS: 374 ([M+H]$^+$).

156.6

The ethyl (RS)-(4-cyano-phenylamino)-(3-ethynyl-5-pyrrolidin-1-ylmethyl-phenyl)-acetate described in Example 156.5 was converted in analogy to Examples 6.2 and 1.2 into (RS)-(4-carbamimidoyl-phenylamino)-(3-ethynyl-5-pyrrolidin-1-ylmethyl-phenyl)-acetic acid; MS: 377 ([M+H]$^+$).

Example 157

In analogy to Example 1.2, the methyl (RS)-(4-carbamimidoyl-phenylamino)-(5-ethoxy-biphenyl-3-yl)-acetate (compound with acetic acid) described in Example 155 was converted into (RS)-(4-carbamimidoyl-phenylamino)-(5-ethoxy-biphenyl-3-yl)-acetic acid; MS: 390 ([M+H]$^+$).

ANALOGOUS EXAMPLES 157.a

Analogously, the methyl (RS)-(3'-amino-5-ethoxy-biphenyl-3-yl)-(4-carbamimidoyl-phenylamino)-acetate hydrochloride described in Example 145.a was converted into (RS)-(4-carbamimidoyl-phenylamino)-(3-ethoxy-5-thiophen-2-yl-phenyl)-acetic acid; MS: 405 ([M+H]$^+$).

157.b

Analogously, the methyl (RS)-(4-carbamimidoyl-phenylamino)-(3-ethoxy-5-thiophen-2-yl-phenyl)-acetate hydrochloride described in Example 155.b was converted into (RS)-(4-carbamimidoyl-phenylamino)-(4'-dimethylamino-5-methyl-biphenyl-3-yl)-acetic acid; MS: 396 ([M+H]$^+$).

157.c

Analogously, the ethyl (RS)-(4-carbamimidoyl-phenylamino)-(4'-dimethylamino-5-methyl-biphenyl-3-yl)-acetate hydrochloride described in Example 155.c was converted into (RS)-(4-carbamimidoyl-phenylamino)-(4'-dimethylamino-5-methyl-biphenyl-3-yl)-acetic acid; MS: 404 ([M+H]$^+$).

157.d

Analogously, the ethyl (RS)-(4-carbamimidoyl-phenylamino)-(3'-dimethylamino-5-methyl-biphenyl-3-yl)-acetate hydrochloride described in Example 145.d was converted into (RS)-(4-carbamimidoyl-phenylamino)-(3'-dimethylamino-5-methyl-biphenyl-3-yl)-acetic acid; MS: 404 ([M+H]$^+$).

157.e

Analogously, the ethyl (RS)-(3'-amino-5-methyl-biphenyl-3-yl)-(4-carbamimidoyl-phenylamino)-acetate (compound with acetic acid) described in Example 155.e was converted into (RS)-(3'-amino-5-methyl-biphenyl-3-yl)-(4-carbamimidoyl-phenylamino)-acetic acid; MS: 375 ([M+H]$^+$).

Example 158

158.1

Analogously to Example 12.1, 4-bromo-2-hydroxy-5-methoxy-benzaldehyde (CAS 63272-66-2) was converted by reaction with bromoethanol into 4-bromo-2-(2-hydroxyethoxy)-5-methoxy-benzaldehyde; MS: 274/276 ([M]$^+$).

158.2

In analogy to Example 27.2, the 4-bromo-2-(2-hydroxyethoxy)-5-methoxy-benzaldehyde prepared in Example 158.1 was converted by reaction with 4-aminobenzonitrile and benzyl isonitrile into methyl (RS)-[4-bromo-2-(2-hydroxy-ethoxy)-5-methoxy-phenyl]-(4-cyano-phenylamino)-acetate; MS: 434/436 ([M]$^+$).

158.3

The methyl (RS)-[4-bromo-2-(2-hydroxy-ethoxy)-5-methoxy-phenyl]-(4-cyano-phenylamino)-acetate described in Example 158.2 was converted analogously to Example 68.2 by reaction with 3-aminophenylboronic acid into methyl (RS)-[3'-amino-5-(2-hydroxy-ethoxy)-2-methoxy-biphenyl-4-yl]-(4-cyano-phenylamino)-acetate; MS: 448 ([M+H]$^+$).

158.4

In analogy to Example 6.2, the methyl (RS)-[3'-amino-5-(2-hydroxy-ethoxy)-2-methoxy-biphenyl-4-yl]-(4-cyano-phenylamino)-acetate described in Example 158.3 was converted into methyl (RS)-[3'-amino-5-(2-hydroxy-ethoxy)-2-methoxy-biphenyl-4-yl]-(4-carbamimidoyl-phenylamino)-acetate (compound with acetic acid); MS: 456 ([M+H]$^+$).

Example 159

Analogously to Example 1.2, the methyl (RS)-[3'-amino-5-(2-hydroxy-ethoxy)-2-methoxy-biphenyl-4-yl]-(4-carbamimidoyl-phenylamino)-acetate (compound with acetic acid) described in Example 158 was converted into (RS)-[3'-amino-5-(2-hydroxy-ethoxy)-2-methoxy-biphenyl-4-yl]-(4-carbamimidoyl-phenylamino)-acetic acid; MS: 451 ([M+H]$^+$).

Example 160

160.1

3.6 g of 2-bromo-4,5-dimethoxybenzaldehyde and 3.22 g of 2,2-dimethyl-1,3-propanediol were dissolved in 200 ml of toluene and boiled at reflux in the presence of 0.8 g of p-toluene-sulphonic acid for 3 hrs. Then, the reaction mixture was left to cool to room temperature and was washed with $NaHCO_3$ solution, water and saturated NaCl solution. Subsequently, the solvent was removed in a vacuum and there were obtained 5.1 g of 2-(2-bromo-4,5-dimethoxy-phenyl)-5,5-dimethyl-[1,3]dioxan as yellow-green needles.

160.2

1.0 g of the 2-(2-bromo-4,5-dimethoxy-phenyl)-5,5-dimethyl-[1,3]dioxan described in Example 150.1 were dissolved in 10 ml of 1-methyl-2-pyrrolidone and treated with 0.54 g of CuCN. The reaction mixture was boiled at reflux for 3 hrs. and, after cooling, the crude product was obtained by extraction. Purification was effected by column chromatography (n-hexane/ethyl acetate), with 0.83 g of 2-(5,5-dimethyl-[1,3]dioxan-2-yl)-4,5-dimethoxy-benzonitrile being obtained as a pale yellow oil.

160.3

In analogy to Example 1.3, from 2.77 g of 2-(5,5-dimethyl-[1,3]dioxan-2-yl)-4,5-dimethoxy-benzonitrile by reaction with $H_2NOH$ HCl there were obtained 1.47 g of (E)- and/or (Z)-2-(5,5-dimethyl-[1,3]dioxan-2-yl)-N-hydroxy-4,5-dimethoxy-benzamidine as a greenish resin; MS: 293 ([M−OH]⁻)

160.4

A mixture of 1.34 g of (E)- and/or (Z)-2-(5,5-dimethyl-[1,3]dioxan-2-yl)-N-hydroxy-4,5-dimethoxy-benzamidine, 1.20 ml of DBU and 0.61 ml of acetic anhydride in 50 ml of DMF was stirred for 1 hr. at room temperature and subsequently for 2 hrs. at 80° C. Subsequently, the DMF was removed in a vacuum and the residue was taken up in ethyl acetate. The ethyl acetate phase was washed with water and saturated NaCl solution and, after removal of the solvent, the residue was purified by column chromatography ($CH_2Cl_2$/ethyl acetate). There were obtained 0.43 g of 3-[2-(5,5-dimethyl-[1,3]dioxan-2-yl)-4,5-dimethoxy-phenyl]-5-methyl-[1,2,4]oxadiazole as a white solid; MS: 334 ([M]⁺).

160.5

2.0 g of 3-[2-(5,5-dimethyl-[1,3]dioxan-2-yl)-4,5-dimethoxy-phenyl]-5-methyl-[1,2,4]-oxadiazole were stirred in 100 ml of acetone in the presence of 10 ml of concentrated HCl for 3 hrs. at room temperature. Then, the pH of the reaction mixture was adjusted to 7 with saturated $NaHCO_3$ solution, the acetone was removed in a vacuum and the mixture was extracted with ethyl acetate. After removal of the solvent the residue was purified by column chromatography ($CH_2Cl_2$/ethyl acetate) and there were obtained 1.12 g of 4,5-dimethoxy-2-(5-methyl-[1,2,4]oxadiazol-3-yl)-benzaldehyde as a white solid; MS: 248 ([M]⁺).

160.6

In analogy to Example 27.2, from 141 mg of the 4,5-dimethoxy-2-(5-methyl-[1,2,4]oxadiazol-3-yl)-benzaldehyde described in Example 150.5 there were obtained 56 mg of methyl (RS)-(4-cyano-phenylamino)-[4,5-dimethoxy-2-(5-methyl-[1,2,4]oxadiazol-3-yl)-phenyl]-acetate as a yellow foam; MS: 409 ([M+H]⁺).

160.7

Analogously to Example 6.2, from the methyl (RS)-(4-cyano-phenylamino)-[4,5-dimethoxy-2-(5-methyl-[1,2,4] oxadiazol-3-yl)-phenyl]-acetate described in Example 150.6 there was obtained methyl (RS)-(4-carbamimidoyl-phenylamino)-[4,5-dimethoxy-2-(5-methyl-[1,2,4]-oxadiazol-3-yl)-phenyl]-acetate (compound with acetic acid); MS: 426 ([M+H]⁺).

Example 161

Analogously to Example 1.2, the methyl (RS)-(4-carbamimidoyl-phenylamino)-[4,5-dimethoxy-2-(5-methyl-[1,2,4]oxadiazol-3-yl)-phenyl]-acetate described in Example 160 was converted into (RS)-(4-carbamimidoyl-phenylamino)-[4,5-dimethoxy-2-(5-methyl-[1,2,4] oxadiazol-3-yl)-phenyl]-acetic acid; MS: 412 ([M+H]⁺).

Example 162

162.1

3-Methylsulphanylbenzaldehyde was obtained from 2-(3-bromophenyl)-1,3-dioxolan with n-butyllithium, dimethyl disulphide and subsequent treatment with 1M HCl (*J. Med. Chem.* 1998, 41, 373).

162.2

In analogy to Example 1.1, the 3-methylsulphanyl-benzaldehyde obtained in Example 162.1 was converted with 4-aminobenzonitrile and benzyl isonitrile in EtOH into ethyl (RS)-(4-cyano-phenylamino)-(3-methylsulphanyl-phenyl)-acetate; MS: 344 ([M+NH_4]⁺).

162.3

In analogy to Example 6.2, the ethyl (RS)-(4-cyano-phenylamino)-(3-methylsulphanyl-phenyl)-acetate obtained in Example 162.2 was converted into ethyl (RS)-(4-carbamimidoyl-phenylamino)-(3-methylsulphanyl-phenyl)-acetate hydrochloride (1:1); MS: 344 ([M+H]⁺).

Example 163

163.1

In analogy to Example 162.1, 3-ethylsulphanylbenzaldehyde was obtained from 2-(3-bromo-phenyl)-1,3-dioxolan with n-butyllithium, diethyl disulphide and subsequent treatment with 1M HCl; MS: 166 ([M]⁺).

163.2

In analogy to Example 1.1, the 3-ethylsulphanylbenzaldehyde obtained in Example 163.1 was converted with 4-aminobenzonitrile and benzyl isonitrile in EtOH into ethyl (RS)-(4-cyano-phenylamino)-(3-ethylsulphanyl-phenyl)-acetate; MS: 340 ([M]⁺).

163.3

In analogy to Example 6.2, the ethyl (RS)-(4-cyano-phenylamino)-(3-ethylsulphanyl-phenyl)-acetate obtained in Example 163.2 was converted into ethyl (RS)-(4-carbamimidoyl-phenylamino)-(3-ethylsulphanyl-phenyl)-acetate hydrochloride (1:1); MS: 358 ([M+H]⁺).

Example 164

164.1

Ethyl (RS)-(4-carbamimidoyl-phenylamino)-(3-ethylsulphanyl-phenyl)-acetate hydrochloride (1:1) described in Example 163.3 (150 mg, 0.381 mmol) was dissolved in acetone (3 ml). Water (1.5 ml) was added and the mixture was cooled to 0° C. Ozone (261 mg, 0.404 mmol) was added and the mixture was stirred for 40 min. at 0° C. The reaction mixture was concentrated and the product was purified by column chromatography ($SiO_2$, $CH_2Cl_2 \Longrightarrow CH_2Cl_2$/MeOH 4:1). There were obtained 91 mg (56%) g of ethyl (RS)-(4-carbamimidoyl-phenylamino)-(3-ethanesulphonyl-phenyl)-acetate hydrochloride (1:1) as a yellowish foam.

Example 165

165.1

In analogy to Example 164.1, from the ethyl (RS)-(4-carbamimidoyl-phenylamino)-(3-ethylsulphanyl-phenyl) acetate hydrochloride (1:1) described in Example 163.3 with ozone (0.53 equivalents) there was obtained a mixture of ethyl (RS)- and (SR)-(4-carbamimidoyl-phenylamino)-[(RS)-3-ethanesulphinyl-phenyl]-acetate hydrochloride (1:1).

Example 166

166.a

In analogy to Example 75, the ethyl (RS)-(4-carbamimidoyl-phenylamino)-(3-methylsulphanyl-phenyl)-acetate hydrochloride (1:1) obtained in Example 162.3 was converted into (RS)-(4-carbamimidoyl-phenylamino)-(3-methylsulphanyl-phenyl)-acetic acid; MS: 316 ([M+H]$^+$).

166.b

In analogy to Example 75, the ethyl (RS)-(4-carbamimidoyl-phenylamino)-(3-ethylsulphanyl-phenyl)-acetate hydrochloride (1:1) obtained in Example 163.3 was converted into (RS)-(4-carbamimidoyl-phenylamino)-(3-ethylsulphanyl-phenyl)-acetic acid; MS: 330 ([M+H]$^+$).

166.c

In analogy to Example 75, the ethyl (RS)-(4-carbamimidoyl-phenylamino)-(3-ethane-sulphonyl-phenyl)-acetate hydrochloride (1:1) obtained in Example 164.1 was converted into (RS)-(4-carbamimidoyl-phenylamino)-(3-ethanesulphonyl-phenyl)-acetic acid; MS: 362 ([M+H]$^+$).

166.d

In analogy to Example 75, the mixture of ethyl (RS)- and (SR)-(4-carbamimidoyl-phenylamino)-[(RS)-3-ethanesulphinyl-phenyl]-acetate hydrochloride (1:1) obtained in Example 165.1 was converted into a mixture of (RS)- and (SR)-(4-carbamimidoyl-phenylamino)-[(RS)-3-ethanesulphinyl-phenyl]-acetic acid; MS: 346 ([M+H]$^+$).

Example 167

167.1

A solution of anisaldehyde (13.6 g of, 100 mmol) and N,N'-diisopropylethylenediamine (14.4 g, 100 mmol) in toluene (100 ml) was heated for 10 h. under reflux on a water separator. Thereafter, the mixture was concentrated and dried under a high vacuum. A portion of the protected aldehyde obtained (5.46 g, 20.8 mmol) was dissolved in dry diethyl ether (50 ml). N,N,N',N'-Tetramethylethylenediamine (3.5 ml, 41.7 mmol) was added and the mixture was cooled to –78° C. A 1.6M solution of n-BuLi in hexane (26.1 ml, 41.7 mmol) was added slowly at –78° C. After 30 min. the mixture was left to warm to room temperature. After 1 h. the mixture was again cooled to –78° C. and dimethyl disulphide (3.71 ml, 41.7 mmol) was added. The mixture was left to warm slowly to room temperature. After 1 h. at room temperature water was added and the mixture was extracted three times with diethyl ether. The organic phase was concentrated. The residue was stirred for 2 h. with 10% HCl and subsequently extracted with diethyl ether. Die organic phase was dried and filtered, and the filtrate was concentrated. The residue was purified by chromatography (SiO$_2$, hexane/CH$_2$Cl$_2$ 1:1). 2.99 g of 4-methoxy-3-methylsulphanyl-benzaldehyde were obtained as a yellowish solid.

167.2

In analogy to Example 1.1, the 4-methoxy-3-methylsulphanyl-benzaldehyde obtained in Example 157.1 was converted with 4-aminobenzonitrile and benzyl isonitrile in EtOH into ethyl (RS)-(4-cyano-phenylamino)-(4-methoxy-3-methylsulphanyl-phenyl)-acetate; MS: 379 ([M+Na]$^+$).

167.3

In analogy to Example 6.2, the ethyl (RS)-(4-cyano-phenylamino)-(4-methoxy-3-methylsulphanyl-phenyl)-acetate obtained in Example 167.2 was converted into ethyl (RS)-(4-carbamimidoyl-phenylamino)-(4-methoxy-3-methylsulphanyl-phenyl)-acetate hydrochloride (1:1); MS: 374 ([M+H]$^+$).

Example 168

168.1

A 1M solution of BBr$_3$ in CH$_2$Cl$_2$ (4.5 ml, 4.5 mmol) was added at –78° C. to a solution of the ethyl (RS)-(4-cyano-phenylamino)-(4-methoxy-3-methylsulphanyl-phenyl)-acetate (320 mg, 0.899 mmol) obtained in Example 167.2 in CH$_2$Cl$_2$ (10 ml). The mixture was stirred at –78° C. for 5 min., at 0° C. for 30 min. and at room temperature for 2 h. Ice-water was added and the mixture was stirred for 10 min. The mixture was extracted with CH$_2$Cl$_2$. The organic phase was dried, filtered and concentrated. The residue was purified by chromatography (SiO$_2$, hexane/EtOAc 2:1). Ethyl (RS)-(4-cyano-phenylamino)-(4-hydroxy-3-methylsulphanyl-phenyl)-acetate was obtained as a colorless oil (198 mg, 64%); MS: 343 ([M+H]$^+$).

168.2

A suspension of the ethyl (RS)-(4-cyano-phenylamino)-(4-hydroxy-3-methylsulphanyl-phenyl)-acetate (198 mg, 0.58 mmol) described in Example 168.1, Cs$_2$CO$_3$ (227 mg, 0.64 mmol) and isopropyl iodide (58 μl, 0.58 mmol) in acetone (3 ml) was heated under reflux for 4 h. Water was added and the mixture was extracted with CH$_2$Cl$_2$. Die organic phase was dried, filtered and concentrated. The residue was purified by chromatography (SiO$_2$, hexane/EtOAc 2:1). Ethyl (RS)-(4-cyano-phenylamino)-(4-isopropoxy-3-methylsulphanyl-phenyl)-acetate (140 mg, 63%) was obtained as a colorless oil; MS: 443 ([M+OAc]$^+$).

168.3

In analogy to Example 6.2, the ethyl (RS)-(4-cyano-phenylamino)-(4-isopropoxy-3-methylsulphanyl-phenyl)-acetate obtained in Example 168.2 was converted into ethyl (RS)-(4-carbamimidoyl-phenylamino)-(4-isopropoxy-3-methylsulphanyl-phenyl)-acetate hydrochloride (1:1); MS: 402 ([M+H]$^+$).

Example 169

169.1

In analogy to Example 168.2, the ethyl (RS)-(4-cyano-phenylamino)-(4-hydroxy-3-methylsulphanyl-phenyl)-acetate obtained in Example 168.1 was converted with ethyl iodide and Cs$_2$CO$_3$ in acetone into ethyl (RS)-(4-cyano-phenylamino)-(4-ethoxy-3-methylsulphanyl-phenyl)-acetate.

169.2

In analogy to Example 6.2, the ethyl (RS)-(4-cyano-phenylamino)-(4-ethoxy-3-methylsulphanyl-phenyl)-acetate obtained in Example 169.1 was converted into ethyl (RS)-(4-carbamimidoyl-phenylamino)-(4-ethoxy-3-methylsulphanyl-phenyl)-acetate hydrochloride (1:1); MS: 388 ([M+H]$^+$).

Example 170

170.1

In analogy to Example 168.2, the ethyl (RS)-(4-cyano-phenylamino)-(4-hydroxy-3-methylsulphanyl-phenyl)-acetate obtained in Example 168.1 was converted with 2-methyl-3-iodo-propane and Cs$_2$CO$_3$ in acetone into ethyl (RS)-(4-cyano-phenylamino)-(4-isobutoxy-3-methylsulphanyl-phenyl)-acetate.

170.2

In analogy to Example 6.2, the ethyl (RS)-(4-cyano-phenylamino)-(4-isobutoxy-3-methylsulphanyl-phenyl)-acetate obtained in Example 170.1 was converted into ethyl (RS)-(4-carbamimidoyl-phenylamino)-(4-isobutoxy-3-methylsulphanyl-phenyl)-acetate hydrochloride (1:1); MS: 416 ([M+H]$^+$).

Example 171

171.1

In analogy to Example 168.2, the ethyl (RS)-(4-cyano-phenylamino)-(4-hydroxy-3-methylsulphanyl-phenyl)- acetate obtained in Example 168.1 was converted with ethyl bromoacetate and $Cs_2CO_3$ in acetone into ethyl (RS)-(4-cyano-phenylamino)-(4-ethoxycarbonylmethoxy-3-methylsulphanyl-phenyl)-acetate.

171.2

In analogy to Example 6.2, the ethyl (RS)-(4-cyano-phenylamino)-(4-ethoxycarbonylmethoxy-3-methylsulphanyl-phenyl)-acetate obtained in Example 171.1 was converted into ethyl (RS)-(4-carbamimidoyl-phenylamino)-(4-ethoxycarbonylmethoxy-3-methylsulphanyl-phenyl)-acetate hydrochloride (1:1); MS: 446 ([M+H]$^+$).

Example 172

172.1

In analogy to Example 168.2, the ethyl (RS)-(4-cyano-phenylamino)-(4-hydroxy-3-methylsulphanyl-phenyl)-acetate obtained in Example 168.1 was converted with iodoacetamide and $Cs_2CO_3$ in acetone into ethyl (RS)-(4-cyano-phenylamino)-(4-carbamoylmethoxy-3-methylsulphanyl-phenyl)-acetate; MS: 417 ([M+NH$_4$]$^+$).

172.2

In analogy to Example 6.2, the ethyl (RS)-(4-cyano-phenylamino)-(4-carbamoylmethoxy-3-methylsulphanyl-phenyl)-acetate obtained in Example 162.1 was converted into ethyl (RS)-(4-carbamimidoyl-phenylamino)-(4-carbamoylmethoxy-3-methylsulphanyl-phenyl)-acetate hydrochloride (1:1); MS: 417 ([M+H]$^+$).

Example 173

173.1

In analogy to Example 167.1, anisaldehyde was reacted with N,N'-diisopropylethylenediamine and subsequently with N,N,N',N'-tetramethylethylenediamine/n-BuLi and diethyl disulphide. After deprotection with 10% HCl and chromatography there was obtained 3-ethylsulphanyl-4-methoxy-benzaldehyde as a yellow oil; MS: 196 ([M]$^+$).

173.2

In analogy to Example 1.1, the 3-ethylsulphanyl-4-methoxy-benzaldehyde obtained in Example 173.1 was converted with 4-aminobenzonitrile and benzyl isonitrile in EtOH into ethyl (RS)-(4-cyano-phenylamino)-(3-ethylsulphanyl-4-methoxy-phenyl)-acetate; MS: 393 ([M+Na]$^+$).

173.3

In analogy to Example 6.2, the ethyl (RS)-(4-cyano-phenylamino)-(3-ethylsulphanyl-4-methoxy-phenyl)-acetate obtained in Example 173.2 was converted into ethyl (RS)-(4-carbamimidoyl-phenylamino)-(3-ethylsulphanyl-4-methoxy-phenyl)-acetate hydrochloride (1:1); MS: 388 ([M+H]$^+$).

Example 174

174.1

In analogy to Example 168.1, the ethyl (RS)-(4-cyano-phenylamino)-(3-ethylsulphanyl-4-methoxy-phenyl)-acetate obtained in Example 173.2 was converted with BBr$_3$ in $CH_2Cl_2$ into ethyl (RS)-(4-cyano-phenylamino)-(3-ethylsulphanyl-4-hydroxy-phenyl)-acetate; MS: 357 ([M+H]$^+$).

174.2

In analogy to Example 168.2, the ethyl (RS)-(4-cyano-phenylamino)-(3-ethylsulphanyl-4-hydroxy-phenyl)-acetate obtained in Example 174.1 was converted with isopropyl iodide and $Cs_2CO_3$ in acetone into ethyl (RS)-(4-cyano-phenylamino)-(3-ethylsulphanyl-4-isopropoxy-phenyl)-acetate; MS: 421 ([M+Na]$^+$).

174.3

In analogy to Example 6.2, the ethyl (RS)-(4-cyano-phenylamino)-(3-ethylsulphanyl-4-isopropoxy-phenyl)-acetate obtained in Example 164.2 was converted into ethyl (RS)-(4-carbamimidoyl-phenylamino)-(3-ethylsulphanyl-4-isopropoxy-phenyl)-acetate hydrochloride (1:1); MS: 416 ([M+H]$^+$).

Example 175

175.1

In analogy to Example 167.1, anisaldehyde was reacted with N,N'-diisopropylethylenediamine and subsequently with N,N,N',N'-tetramethylethylenediamine/n-BuLi and acetaldehyde. After deprotection with 10% HCl and chromatography (RS)-3-(1-hydroxy-ethyl)-4-methoxy-benzaldehyde was obtained as a yellowish oil; MS: 180 ([M]$^+$).

175.2

In analogy to Example 1.1, the (RS)-3-(1-hydroxy-ethyl)-4-methoxy-benzaldehyde obtained in Example 175.1 was converted with 4-aminobenzonitrile and benzyl isonitrile in EtOH into a mixture of ethyl (RS)- and (SR)-(4-cyano-phenylamino)-[3-[(RS)-1-hydroxy-ethyl]-4-methoxy-phenyl]-acetate; MS: 405 ([M+Na]$^+$).

175.3

In analogy to Example 6.2, the mixture of ethyl (RS)- and (SR)-(4-cyano-phenylamino)-[3-[(RS)-1-hydroxy-ethyl]-4-methoxy-phenyl]-acetate obtained in Example 165.2 was converted into a mixture of ethyl (RS)- and (SR)-(4-carbamimidoyl-phenylamino)-[3-[(RS)-1-ethoxy-ethyl]-4-methoxy-phenyl]-acetate hydrochloride (1:1); MS: 400 ([M+H]$^+$).

Example 176

176.1

In analogy to Example 178.1, 4-bromo-1-isopropoxy-2-isopropyl-benzene (obtained from 2-isopropylphenol by alkylation with isopropyl iodide/$K_2CO_3$ and subsequent bromination with KBr/MCPBA) was converted with n-BuLi and DMF into 4-isopropoxy-3-isopropyl-benzaldehyde; MS: 206 ([M]$^+$).

176.2

In analogy to Example 1.1, the 4-isopropoxy-3-isopropyl-benzaldehyde obtained in Example 176.1 was converted with 4-aminobenzonitrile and benzyl isonitrile in EtOH into ethyl (RS)-(4-cyano-phenylarnino)-(4-isopropoxy-3-isopropyl-phenyl)-acetate; MS: 403 ([M+Na]$^+$).

176.3

In analogy to Example 6.2, the ethyl (RS)-(4-cyano-phenylamino)-(4-isopropoxy-3-isopropyl-phenyl)-acetate converted into ethyl (RS)-(4-carbamimidoyl-phenylamino)-(4-isopropoxy-3-isopropyl-phenyl)-acetate hydrochloride (1:1).

Example 177

177.1

In analogy to Example 168.1, the ethyl (RS)-(4-cyano-phenylamino)-(4-isopropoxy-3-isopropyl-phenyl)-acetate obtained in Example 176.2 was converted with BBr$_3$ in $CH_2Cl_2$ into ethyl (RS)-(4-cyano-phenylamino)-(4-hydroxy-3-isopropyl-phenyl)-acetate.

177.2

In analogy to Example 168.2, the ethyl (RS)-(4-cyano-phenylamino)-(4-hydroxy-3-isopropyl-phenyl)-acetate obtained in Example 177.1 was converted with iodoacetamide and $Cs_2CO_3$ in acetone into ethyl (RS)-(4-carbamoylmethoxy-3-isopropyl-phenyl)-(4-cyano-phenylamino)-acetate; MS: 413 ([M+NH$_4$]$^+$).

177.3

In analogy to Example 6.2, the ethyl (RS)-(4-carbamoylmethoxy-3-isopropyl-phenyl)-(4-cyano-phenylamino)-acetate obtained in Example 177.2 was converted into ethyl (RS)-(4-carbamimidoyl-phenylamino)-(4-carbamoylmethoxy-3-isopropyl-phenyl)-acetate hydrochloride (1:1).

Example 178

178.1

A solution of 4-bromo-2-ethyl-1-methoxybenzene (*J. Chem. Soc., Perkin Trans.* 1, 1987, 1423; 2.13 g, 9.9 mmol) in THF (30 ml) was cooled to −78° C. A 1.6M solution of n-BuLi in hexane (7.42 ml, 11.9 mmol) was added slowly and the mixture was stirred for 1.5 h. at −78° C. The mixture was warmed slowly to −10° C. and subsequently again cooled to −78° C. DMF (2.29 ml, 29.7 mmol) was added slowly and the mixture was stirred for 1 h. at −78° C. and for 1 h. at 0° C. The reaction mixture was poured into ice-cold 3M HCl and extracted with diethyl ether. The organic phase was dried and filtered, and the filtrate was concentrated. The residue was purified by chromatography ($SiO_2$, hexane/EtOAc 8:1=>2:1). There were obtained 690 mg (42%) of 3-ethyl-4-methoxy-benzaldehyde as a yellowish liquid.

178.2

In analogy to Example 1.1, the 3-ethyl-4-methoxy-benzaldehyde obtained in Example 178.1 was converted with 4-aminobenzonitrile and benzyl isonitrile in EtOH into ethyl (RS)-(4-cyano-phenylamino)-(3-ethyl-4-methoxy-phenyl)-acetate; MS: 337 ([M−H]⁻).

178.3

In analogy to Example 6.2, the ethyl (RS)-(4-cyano-phenylamino)-(3-ethyl-4-methoxy-phenyl)-acetate obtained in Example 178.2 was converted into ethyl (RS)-(4-carbamimidoyl-phenylamino)-(3-ethyl-4-methoxy-phenyl)-acetate hydrochloride (1:1).

Example 179

179.1

$TiCl_4$ (45.6 g, 238 mmol) was added slowly to a solution of 2-ethylphenol (15 g, 119 mmol) in $CH_2Cl_2$ (150 ml) was at 0° C. The mixture was warmed to room temperature and dichloromethyl methyl ether (18.3 ml, 200 mmol) was added (strong HCl evolution). The mixture was stirred for 4 h. at room temperature, subsequently cooled to 0° C. and 1M HCl (119 ml, 119 mmol) was added dropwise. The mixture was stirred for 10 min. and subsequently extracted with diethyl ether. The organic phase was washed with saturated $NaHCO_3$ solution and with NaCl solution, dried, filtered and concentrated. The residue was purified by chromatography ($SiO_2$, $CH_2Cl_2$=>$CH_2Cl_2$/MeOH 9:1). 3-Ethyl-4-hydroxy-benzaldehyde was obtained as a brown oil (7.97 g, 45%).

179.2

A mixture of the 3-ethyl-4-hydroxy-benzaldehyde (7.8 g, 51.9 mmol) obtained in Example 179.1, $K_2CO_3$ (10.8 g, 78 mmol) and isopropyl iodide (7.86 ml, 78 mmol) was heated in DMF (65 ml) for 3 h. to 80° C. and subsequently stirred for 12 h. at room temperature. The mixture was poured into ice-cold 0.5M HCl and extracted with diethyl ether. The organic phase was washed with NaCl solution, dried, filtered and concentrated. The residue was purified by chromatography ($SiO_2$, hexane/EtOAc 4:1). 3-Ethyl-4-isopropoxy-benzaldehyde was obtained as an orange oil (6.12 g, 61%); MS: 192 ([M]⁺).

179.3

In analogy to Example 1.1, the 3-ethyl-4-isopropoxy-benzaldehyde obtained in Example 179.2 was converted with 4-aminobenzonitrile and benzyl isonitrile in EtOH into ethyl (RS)-(4-cyano-phenylamino)-(3-ethyl-4-isopropoxy-phenyl)-acetate; MS: 389 ([M+Na]⁺).

179.4

In analogy to Example 6.2, the ethyl (RS)-(4-cyano-phenylamino)-(3-ethyl-4-isopropoxy-phenyl)-acetate obtained in Example 179.3 was converted into ethyl (RS)-(4-carbamimidoyl-phenylamino)-(3-ethyl-4-isopropoxy-phenyl)-acetate hydrochloride (1:1); MS: 384 ([M+H]⁺).

Example 180

180.1

In analogy to Example 168.1, the ethyl (RS)-(4-cyano-phenylamino)-(3-ethyl-4-isopropoxy-phenyl)-acetate obtained in Example 179.3 was converted with $BBr_3$ in $CH_2Cl_2$ into ethyl (RS)-(4-cyano-phenylamino)-(3-ethyl-4-hydroxy-phenyl)-acetate; MS: 325 ([M+H]⁺).

180.2

In analogy to Example 168.2, the ethyl (RS)-(4-cyano-phenylamino)-(3-ethyl-4-hydroxy-phenyl)-acetate obtained in Example 180.1 was converted with iodoacetamide and $Cs_2CO_3$ in acetone into ethyl (RS)-(4-carbamoylmethoxy-3-ethyl-phenyl)-(4-cyano-phenylamino)-acetate; MS: 380 ([M−H]⁻).

180.3

In analogy to Example 6.2, the ethyl (RS)-(4-carbamoylmethoxy-3-ethyl-phenyl)-(4-cyano-phenylamino)-acetate obtained in Example 180.2 was converted into ethyl (RS)-(4-carbamimidoyl-phenylamino)-(4-carbamoylmethoxy-3-ethyl-phenyl)-acetate hydrochloride (1:1); MS: 399 ([M+H]⁺).

Example 181

181.1

In analogy to Example 168.2, the ethyl (RS)-(4-cyano-phenylamino)-(3-ethyl-4-hydroxy-phenyl)-acetate obtained in Example 180.1 was converted with propyl iodide and $Cs_2CO_3$ in acetone into ethyl (RS)-(4-cyano-phenylamino)-(3-ethyl-4-propoxy-phenyl)-acetate; MS: 366 ([M]⁺).

181.2

In analogy to Example 6.2, the ethyl (RS)-(4-cyano-phenylamino)-(3-ethyl-4-propoxy-phenyl)-acetate obtained in Example 171.1 was converted into ethyl (RS)-(4-carbamimidoyl-phenylamino)-(3-ethyl-4-propoxy-phenyl)-acetate hydrochloride (1:1); MS: 384 ([M+H]⁺).

Example 182

182.1

A suspension of the ethyl (RS)-(4-cyano-phenylamino)-(3-ethyl-4-hydroxy-phenyl)-acetate described in Example 180.1 (328 mg, 1.01 mmol) and $K_2CO_3$ (89 mg, 0.25 mmol) in cyclopentene oxide (0.896 ml, 10.1 mmol) and EtOH (0.5 ml) was heated under reflux for 9 h. The reaction mixture was concentrated and dried in a high vacuum. The residue was purified by chromatography ($SiO_2$, hexane/EtOAc 1:1). A mixture of ethyl (RS)- and (SR)-(4-cyano-phenylamino)-[3-ethyl-4-[(RS,2RS)-2-hydroxy-cyclopentyloxy]-phenyl]-acetate (226 mg, 55%) was obtained as a colorless foam; MS: 407 ([M−H]⁻).

182.2

In analogy to Example 6.2, the mixture of ethyl (RS)- and (SR)-(4-cyano-phenylamino)-[3-ethyl-4-[(RS,2RS)-2-hydroxy-cyclopentyloxy]-phenyl]-acetate obtained in Example 182.1 was converted into a mixture of ethyl (RS)- and (SR)-(4-carbamimidoyl-phenylamino)-[3-ethyl-4-[(1RS,2RS)-2-hydroxy-cyclopentyloxy]-phenyl]-acetate hydrochloride (1:1); MS: 426 ([M+H]⁺).

Example 183

183.1

A solution of the ethyl (RS)-(4-cyano-phenylamino)-(3-ethyl-4-hydroxy-phenyl)-acetate (400 mg, 1.23 mmol)

described in Example 180.1, ethylene carbonate (110 mg, 1.23 mmol) and tetrabutylammonium bromide (264 mg, 1.23 mmol) in DMF (0.6 ml) was heated to 155° C. for 6 h. The reaction mixture was concentrated and the residue was purified by chromatography (SiO$_2$, hexane/EtOAc 9:1). Ethyl (RS)-(4-cyano-phenylamino)-[3-ethyl-4-(2-hydroxy-ethoxy)-phenyl]-acetate (111 mg, 24%) was obtained as a yellow oil.

183.2

In analogy to Example 6.2, the ethyl (RS)-(4-cyano-phenylamino)-[3-ethyl-4-(2-hydroxy-ethoxy)-phenyl]-acetate obtained in Example 183.1 was converted into ethyl (RS)-(4-carbamimidoyl-phenylamino)-[3-ethyl-4-(2-hydroxyethoxy)-phenyl]-acetate hydrochloride (1:1).

Example 184

184.1

In analogy to Example 18.1, the ethyl (RS)-(4-cyano-phenylamino)-(3-ethyl-4-hydroxy-phenyl)-acetate obtained in Example 180.1 was converted with N-(2hydroxyethyl)-pyrrolidine, diethyl azodicarboxylate and triphenylphosphine in THF into ethyl (RS)-(4-cyano-phenylamino)-3-ethyl-4-(2-pyrrolidin-1-yl-ethoxy)-phenyl]-acetate.

184.2

In analogy to Example 6.2, the ethyl (RS)-(4-cyano-phenylamino)-[3-ethyl-4-(2-pyrrolidin-1-yl-ethoxy)-phenyl]-acetate obtained in Example 184.1 was converted into ethyl (RS)-(4-carbamimidoyl-phenylamino)-[3-ethyl-4-(2-pyrrolidin-1-yl-ethoxy)-phenyl]-acetate hydrochloride (1:1); MS: 439 ([M+H]$^+$).

Example 185

185.1

3-Ethyl-4-nitro-benzaldehyde was obtained from 4-nitrobenzaldehyde by protection with ethylene glycol, reaction with ethylmagnesium chloride and DDQ and subsequent deprotection with HCl (*J. Organomet. Chem.* 1993, 447, 1); MS: 179 ([M]$^+$).

185.2

In analogy to Example 1.1, the 3-ethyl-4-nitro-benzaldehyde obtained in Example 185.1 was converted with 4-aminobenzonitrile and benzyl isonitrile in EtOH into ethyl (RS)-(4-cyano-phenylamino)-(3-ethyl-4-nitro-phenyl)-acetate; MS: 354 ([M+H]$^+$).

185.3

In analogy to Example 6.2, the ethyl (RS)-(4-cyano-phenylamino)-(3-ethyl-4-nitro-phenyl)-acetate obtained in Example 185.2 was converted into ethyl (RS)-(4-carbamimidoyl-phenylamino)-(3-ethyl-4-nitro-phenyl)-acetate hydrochloride (1:1); MS: 371 ([M+H]$^+$).

Example 186

186.1

In analogy to Example 59.2, the ethyl (RS)-(4-cyano-phenylamino)-(3-ethyl-4-nitro-phenyl)-acetate obtained in Example 185.2 was converted with H$_2$ in THF/EtOH (1:1) under the catalytic activity of Pd/C into ethyl (RS)-(4-amino-3-ethyl-phenyl)-(4-cyano-phenylamino)-acetate; MS: 322 ([M–H]$^-$)

186.2

In analogy to Example 61.1, the ethyl (RS)-(4-amino-3-ethyl-phenyl)-(4-cyano-phenylamino)-acetate obtained in Example 186.1 was converted with ethyl iodide and diisopropyl-ethylamine in THF into ethyl (RS)-(4-cyano-phenylamino)-(3-ethyl-4-ethylamino-phenyl)-acetate; MS: 352 ([M+H]$^+$).

186.3

In analogy to Example 6.2, the ethyl (RS)-(4-cyano-phenylamino)-(3-ethyl-4-ethylamino-phenyl)-acetate obtained in Example 186.2 was converted into ethyl (RS)-(4-carbamimidoyl-phenylamino)-(3-ethyl-4-ethylamino-phenyl)-acetate hydrochloride (1:1); MS: 369 ([M+H]$^+$).

Example 187

187.1

In analogy to Example 61.1, the ethyl (RS)-(4-amino-3-ethyl-phenyl)-(4-cyano-phenylamino)-acetate obtained in Example 186.1 was converted with isopropyl iodide and diisopropylethylamine in THF into ethyl (RS)-(4-cyano-phenylamino)-(3-ethyl-4-isopropylamino-phenyl)-acetate MS: 366 ([M+H]$^+$).

187.2

In analogy to Example 6.2, the ethyl (RS)-(4-cyano-phenylamino)-(3-ethyl-4-isopropylamino-phenyl)-acetate obtained in Example 187.1 was converted into ethyl (RS)-(4-carbamimidoyl-phenylamino)-(3-ethyl-4-isopropylamino-phenyl)-acetate hydrochloride (1:1); MS: 383 ([M+H]$^+$).

Example 188

188.1

A solution of isopropyl isocyanate (130 mg, 1.55 mmol) in THF (2 ml) was added to a solution of the ethyl (RS)-(4-amino-3-ethyl-phenyl)-(4-cyano-phenylamino)-acetate (500 mg, 1.55 mmol) described in Example 186.1 in THF (10 ml). The mixture was stirred overnight at room temperature. Thereafter, further isopropyl isocyanate (260 mg, 3.1 mmol) was added and the mixture was stirred overnight at 50° C. The reaction mixture was concentrated. The residue was suspended in CH$_2$Cl$_2$/MeOH (98:2) and the colorless solid was filtered off. The solid was washed with EtOH and dried under a high vacuum. Ethyl (RS)-(4-cyano-phenylamino)-[3-ethyl-4-(3-isopropylureido)-phenyl]-acetate (395 mg, 62%) was obtained as a colorless solid; MS: 409 ([M+H]$^+$)

188.2

In analogy to Example 6.2, the ethyl (RS)-(4-cyano-phenylamino)-[3-ethyl-4-(3-isopropylureido)-phenyl]-acetate obtained in Example 188.1 was converted into ethyl (RS)-(4-carbamimidoyl-phenylamino)-[3-ethyl-4-(isopropylureido)-phenyl]-acetate hydrochloride (1:1), Example 189

189.a

In analogy to Example 75, the ethyl (RS)-(4-carbamimidoyl-phenylamino)-(4-methoxy-3-methylsulphanyl-phenyl)-acetate hydrochloride (1:1) obtained in Example 167.3 was converted into (RS)-(4-carbamimidoyl-phenylamino)-(4-methoxy-3-methylsulphanyl-phenyl)-acetic acid; MS: 346 ([M+H]$^+$).

189.b

In analogy to Example 75, the ethyl (RS)-(4-carbamimidoyl-phenylamino)-(4-isopropoxy-3-methylsulphanyl-phenyl)-acetate hydrochloride (1:1) obtained in Example 168.3 was converted into (RS)-(4-carbamimidoyl-phenylamino)-(4-isopropoxy-3-methylsulphanyl-phenyl)-acetic acid; MS: 374 ([M+H]$^+$).

189.c

In analogy to Example 75, the ethyl (RS)-(4-carbamimidoyl-phenylamino)-(4-ethoxy-3-methylsulphanyl-phenyl)-acetate hydrochloride (1:1) obtained in Example 169.2 was converted into (RS)-(4-carbamimidoyl-phenylamino)-(4-ethoxy-3-methylsulphanyl-phenyl)-acetic acid; MS: 360 ([M+H]$^+$).

189.d

In analogy to Example 75, the ethyl (RS)-(4-carbamimidoyl-phenylamino)-(4-isobutoxy-3- methylsulphanyl-phenyl)-acetate hydrochloride (1:1) obtained in Example 170.2 was converted into (RS)-(4-carbamimidoyl-phenylamino)-(4-isobutoxy-3-methylsulphanyl-phenyl)-acetic acid; MS: 388 ([M+H]$^+$).

189.e

In analogy to Example 75, the ethyl (RS)-(4-carbamimidoyl-phenylamino)-(4-ethoxy-carbonylmethoxy-3-methylsulphanyl-phenyl)-acetate hydrochloride (1:1) obtained in Example 171.2 was converted into (RS)-(4-carbamimidoyl-phenylamino)-(4-carboxy-methoxy-3-methylsulphanyl-phenyl)-acetic acid; MS: 390 ([M+H]$^+$).

189.f

In analogy to Example 75, the ethyl (RS)-(4-carbamimidoyl-phenylamino)-(4-carbamoylmethoxy-3-methylsulphanyl-phenyl)-acetate hydrochloride (1:1) obtained in Example 172.2 was converted into (RS)-(4-carbamimidoyl-phenylamino)-(4-carbamoylmethoxy-3-methylsulphanyl-phenyl)-acetic acid; MS: 389 ([M+H]$^+$).

189.g

In analogy to Example 75, the ethyl (RS)-(4-carbamimidoyl-phenylamino)-(3-ethylsulphanyl-4-methoxy-phenyl)-acetate hydrochloride (1:1) obtained in Example 173.3 was converted into (RS)-(4-carbamimidoyl-phenylamino)-(3-ethylsulphanyl-4-methoxy-phenyl)-acetic acid; MS: 360 ([M+H]$^+$).

189.h

In analogy to Example 75, the ethyl (RS)-(4-carbamimidoyl-phenylamino)-(3-ethylsulphanyl-4-isopropoxy-phenyl)-acetate hydrochloride (1:1) obtained in Example 174.3 was converted into (RS)-(4-carbamimidoyl-phenylamino)-(3-ethylsulphanyl-4-isopropoxy-phenyl)-acetic acid; MS: 388 ([M+H]$^+$).

189.j

In analogy to Example 75, the mixture of ethyl (RS)- and (SR)-(4-carbamimidoyl-phenylamino)-[3-[(RS)-1-ethoxy-ethyl]-4-methoxy-phenyl]-acetate hydrochloride (1:1) obtained in Example 175.3 was converted into a mixture of (RS)- and (SR)-(4-carbamimidoyl-phenylamino)-[3-[(RS)-1-ethoxy-ethyl]-4-methoxy-phenyl]-acetic acid; MS: 372 ([M+H]$^+$).

189.k

In analogy to Example 75, the ethyl (RS)-(4-carbamimidoyl-phenylamino)-(4-isopropoxy-3-isopropyl-phenyl)-acetate hydrochloride (1:1) obtained in Example 176.3 was converted into (RS)-(4-carbamimidoyl-phenylamino)-(4-isopropoxy-3-isopropyl-phenyl)-acetic acid; MS: 370 ([M+H]$^+$)

189.l

In analogy to Example 75, the ethyl (RS)-(4-carbamimidoyl-phenylamino)-(4-carbamoylmethoxy-3-isopropyl-phenyl)-acetate hydrochloride (1:1) obtained in Example 177.3 was converted into (RS)-(4-carbamimidoyl-phenylamino)-(4-carbamoylmethoxy-3-isopropyl-phenyl)-acetic acid; MS: 385 ([M+H]$^+$).

189.m

In analogy to Example 75, the ethyl (RS)-(4-carbamimidoyl-phenylamino)-(3-ethyl-4-methoxy-phenyl)-acetate hydrochloride (1:1) obtained in Example 178.3 was converted into (RS)-(4-carbamimidoyl-phenylamino)-(3-ethyl-4-methoxy-phenyl)-acetic acid; MS: 328 ([M+H]$^+$).

189.n

In analogy to Example 75, the ethyl (RS)-(4-carbamimidoyl-phenylamino)-(3-ethyl-4-isopropoxy-phenyl)-acetate hydrochloride (1:1) obtained in Example 179.4 was converted into (RS)-(4-carbamimidoyl-phenylamino)-(3-ethyl-4-isopropoxy-phenyl)-acetic acid; MS: 354 ([M+H]$^+$)

189.o

In analogy to Example 75, the ethyl (RS)-(4-carbamimidoyl-phenylamino)-(4-carbamoylmethoxy-3-ethyl-phenyl)-acetate hydrochloride (1:1) obtained in Example 180.3 was converted into (RS)-(4-carbamimidoyl-phenylamino)-(4-carbamoylmethoxy-3-ethyl-phenyl)-acetate; MS: 371 ([M+H]$^+$).

189.p

In analogy to Example 75, the ethyl (RS)-(4-carbamimidoyl-phenylamino)-(3-ethyl-4-propoxy-phenyl)-acetate hydrochloride (1:1) obtained in Example 181.2 was converted into (RS)-(4-carbamimidoyl-phenylamino)-(3-ethyl-4-propoxy-phenyl)-acetic acid; MS: 356 ([M+H]$^+$).

189.q

In analogy to Example 75, the mixture of ethyl (RS)- and (SR)-(4-carbamimidoyl-phenylamino)-[3-ethyl-4-[(1RS,2RS)-2-hydroxy-cyclopentyloxy]-phenyl]-acetate hydrochloride (1:1) obtained in Example 182.2 was converted into a mixture of (RS)- and (SR)-4-carbamimidoyl-phenylamino)-[3-ethyl-4-[(1RS,2RS)-2-hydroxy-cyclopentyloxy)-phenyl]-acetic acid; MS: 398 ([M+H]$^+$).

189.r

In analogy to Example 75, the ethyl (RS)-(4-carbamimidoyl-phenylamino)-[3-ethyl-4-(2-hydroxyethoxy)-phenyl]-acetate hydrochloride (1:1) obtained in Example 183.2 was converted into (RS)-(4-carbamimidoyl-phenylamino)-[3-ethyl-4-(2-hydroxyethoxy)-phenyl]-acetic acid; MS: 358 ([M+H]$^+$).

189.s

In analogy to Example 75, the ethyl (RS)-(4-carbamimidoyl-phenylamino)-[3-ethyl-4-(2-pyrrolidin-1-yl-ethoxy)-phenyl]-acetate hydrochloride (1:1) obtained in Example 184.2 was converted into (RS)-(4-carbamimidoyl-phenylamino)-[3-ethyl-4-(2-pyrrolidin-1-yl-ethoxy)-phenyl]-acetic acid converted; MS: 411 ([M+H]$^+$).

189.t

In analogy to Example 75, the ethyl (RS)-(4-carbamimidoyl-phenylamino)-(3-ethyl-4-ethylamino-phenyl)-acetate hydrochloride (1:1) obtained in Example 186.3 was converted into (RS)-(4-carbamimidoyl-phenylamino)-(3-ethyl-4-ethylamino-phenyl)-acetic acid; MS: 341 ([M+H]$^+$)

189.u

In analogy to Example 75, the ethyl (RS)-(4-carbamimidoyl-phenylamino)-(3-ethyl-4-isopropylamino-phenyl)-acetate hydrochloride (1:1) obtained in Example 187.2 was converted into (RS)-(4-carbamimidoyl-phenylamino)-(3-ethyl-4-isopropylamino-phenyl)-acetic acid; MS: 355 ([M+H]$^+$).

189.v

In analogy to Example 75, the ethyl (RS)-(4-carbamimidoyl-phenylamino)-[3-ethyl-4-(isopropylureido)-phenyl]-acetate hydrochloride (1:1) obtained in Example 188.2 was converted into (RS)-(4-carbamimidoyl-phenylamino)-[3-ethyl-4-(3-isopropyl-ureido)-phenyl]-acetic acid converted; MS: 398 ([M+H]$^+$).

Example 190

190.1

A suspension of 3,5-dimethylanisole (13.60 g, 100 mmol), N-bromosuccinimide (18.35 g, 100 mmol) and 2,2'-azobis(2-methylpropionitrile) in CCl$_4$ was heated under reflux for 1 h. The succinimide was filtered off, the filtrate was concentrated and the residue was chromatographed (SiO$_2$, CH$_2$Cl$_2$/hexane 1:4). There were obtained 14.61 g (68%) of 1-bromomethyl-3-methoxy-5-methyl-benzene.

2-Nitropropane (6.77 ml, 71.3 mmol) and subsequently 1-bromomethyl-3-methoxy-5-methyl-benzene (14.6 g, 67.9 mmol) were added to a solution of NaOEt (4.72 g, 67.9 mmol) in EtOH (60 ml). The mixture was heated for 1.5 h. to 65° C. After cooling the colorless precipitate of filtered off and the filtrate was concentrated. The product was purified by chromatography (SiO$_2$, CH$_2$Cl$_2$/hexane 1:2). There were obtained 7.87 g (77%) of 3-methoxy-5-methyl-benzaldehyde as a colorless liquid.

190.2

In analogy to Example 1.1, the 3-methoxy-5-methyl-benzaldehyde obtained in Example 190.1 was converted with 4-aminobenzonitrile and benzyl isonitrile in EtOH into ethyl (RS)-(4-cyano-phenylamino)-(3-methoxy-5-methyl-phenyl)-acetate; MS: 324 ([M]$^+$).

190.3

In analogy to Example 6.2, the ethyl (RS)-(4-cyano-phenylamino)-(3-methoxy-5-methyl-phenyl)-acetate obtained in Example 180.2 was converted into ethyl (RS)-(4-carbamimidoyl-phenylamino)-(3-methoxy-5-methyl-phenyl)-acetate hydrochloride (1:1); MS: 342 ([M+H]$^+$).

Example 191

191.1

In analogy to Example 168.1, the ethyl (RS)-(4-cyano-phenylamino)-(3-methoxy-5-methyl-phenyl)-acetate obtained in Example 190.2 was converted into ethyl (RS)-(4-cyano-phenylamino)-(3-hydroxy-5-methyl-phenyl)-acetate; MS: 310 ([M+H]$^+$).

191.2

In analogy to Example 168.2, the ethyl (RS)-(4-cyano-phenylamino)-(3-hydroxy-5-methyl-phenyl)-acetate obtained in Example 191.1 was converted with isopropyl iodide and Cs$_2$CO$_3$ in acetone into ethyl (RS)-(4-cyano-phenylamino)-(3-isopropoxy-5-methyl-phenyl)-acetate; MS: 353 ([M+H]$^+$).

191.3

In analogy to Example 6.2, the ethyl (RS)-(4-cyano-phenylamino)-(3-isopropoxy-5-methyl-phenyl)-acetate obtained in Example 191.2 was converted into ethyl (RS)-(4-carbamimidoyl-phenylamino)-(3-isopropoxy-5-methyl-phenyl)-acetate hydrochloride (1:1); MS: 370 ([M+H]$^+$).

Example 192

192.1

In analogy to Example 168.2, the ethyl (RS)-(4-cyano-phenylamino)-(3-hydroxy-5-methyl-phenyl)-acetate obtained in Example 191.1 was converted with iodoacetamide and Cs$_2$CO$_3$ in acetone into (RS)-(3-carbamoylmethoxy-5-methyl-phenyl)-(4-cyano-phenylamino)-acetate; MS: 366 ([M–H]$^-$).

192.2

In analogy to Example 6.2, the ethyl (RS)-(3-carbamoylmethoxy-5-methyl-phenyl)-(4-cyano-phenylamino)-acetate obtained in Example 192.1 was converted into ethyl (RS)-(4-carbamimidoyl-phenylamino)-(3-carbamoylmethoxy-5-methyl-phenyl)-acetate hydrochloride (1:1); MS: 385 ([M+H]$^+$).

Example 193

193.1

In analogy to Example 168.2, the ethyl (RS)-(4-cyano-phenylamino)-(3-hydroxy-5-methyl-phenyl)-acetate obtained in Example 191.1 was converted with ethyl iodide and Cs$_2$CO$_3$ in acetone into ethyl (RS)-(4-cyano-phenylamino)-(3-ethoxy-5-methyl-phenyl)-acetate; MS: 339 (1M+H]$^+$).

193.2

In analogy to Example 6.2, the ethyl (RS)-(4-cyano-phenylamino)-(3-ethoxy-5-methyl-phenyl)-acetate obtained in Example 193.1 was converted into ethyl (RS)-(4-carbamimidoyl-phenylamino)-(3-ethoxy-5-methyl-phenyl)-acetate hydrochloride (1:1); MS: 356 ([M+H]$^+$).

Example 194

194.1

In analogy to Example 18.1, the ethyl (RS)-(4-cyano-phenylamino)-(3-hydroxy-5-methyl-phenyl)-acetate obtained in Example 191.1 was converted with N-(2-hydroxyethyl)-pyrrolidine, diethyl azodicarboxylate and triphenylphosphine in THF into ethyl (RS)-(4-cyano-phenylamino)-[3-methyl-5-(2-pyrrolidin-1-yl-ethoxy)-phenyl]-acetate; MS: 408 ([M+H]$^+$).

194.2

In analogy to Example 6.2, the ethyl (RS)-(4-cyano-phenylamino)-[3-methyl-5-(2-pyrrolidin-1-yl-ethoxy)-phenyl]-acetate obtained in Example 194.1 was converted into ethyl (RS)-(carbamimidoyl-phenylamino)-[3-methyl-5-(2-pyrrolidin-1-yl-ethoxy)-phenyl]-acetate hydrochloride (1:1).

Example 195

195.1

In analogy to Example 18.1, the ethyl (RS)-(4-cyano-phenylamino)-(3-hydroxy-5-methyl-phenyl)-acetate obtained in Example 191.1 was converted with cyclopentanol, diethyl azodicarboxylate and triphenylphosphine in THF into ethyl (RS)-(4-cyano-phenylamino)-(3-cyclopentyloxy-5-methyl-phenyl)-acetate; MS: 379 ([M+H]$^+$).

195.2

In analogy to Example 6.2, the ethyl (RS)-(4-cyano-phenylamino)-(3-cyclopentyloxy-5-methyl-phenyl)-acetate obtained in Example 195.1 was converted into ethyl (RS)-(4-carbamimidoyl-phenylamino)-(3-cyclopentyloxy-5-methyl-phenyl)-acetate hydrochloride (1:1); MS: 396 ([M+H]$^+$).

Example 196

196.1

In analogy to Example 18.1, the ethyl (RS)-(4-cyano-phenylamino)-(3-hydroxy-5-methyl-phenyl)-acetate obtained in Example 191.1 was converted with 4-hydroxy-N-methylpiperidine, diethyl azodicarboxylate and triphenylphosphine in THF into ethyl (RS)-(4-cyano-phenylamino)-[3-methyl-5-(1-methyl-piperidin-4-yloxy)-phenyl]-acetate; MS: 408 ([M+H]$^+$).

196.2

In analogy to Example 6.2, the ethyl (RS)-(4-cyano-phenylamino)-[3-methyl-5-(1-methyl-piperidin-4-yloxy)-phenyl]-acetate obtained in Example 196.1 was converted into ethyl (RS)-(4-carbamimidoyl-phenylamino)-[3-methyl-5-(1-methyl-piperidin-4-yloxy)-phenyl]-acetate hydrochloride (1:1); MS: 425 ([M+H]$^+$).

Example 197

197.1

In analogy to Example 182.1, the ethyl (RS)-(4-cyano-phenylamino)-(3-hydroxy-5-methyl-phenyl)-acetate obtained in Example 191.1 was converted with cyclopentene oxide and K$_2$CO$_3$ in EtOH into a mixture of ethyl (RS)- and (SR)-(4-cyano-phenylamino)-[3-[(1RS,2RS)-2-hydroxy-cyclopentyloxy]-5-methyl-phenyl]-acetate; MS: 393 ([M–H]$^-$).

197.2

In analogy to Example 6.2, the mixture of ethyl (RS)- and (SR)-(4-cyano-phenylamino)-[3-[(1RS,2RS)-2-hydroxy-cyclopentyloxy]-5-methyl-phenyl]-acetate obtained in Example 197.1 was converted into a mixture of ethyl (RS)- and (SR)-(4-carbamimidoyl-phenylamino)-[3-[(1RS,2RS)-2-hydroxy-cyclopentyloxy]-5-methyl-phenyl]-acetate hydrochloride (1:1); MS: 412 ([M+H]+).

Example 198

198.1
In analogy to Example 190.1, 3,5-dimethylanisole was converted into 5-methoxy-benzene-1,3-dicarbaldehyde.
198.2
A mixture of the 5-methoxy-benzene-1,3-dicarbaldehyde (3.68 g, 22.4 mmol) obtained in Example 198.1, methyltriphenylphosphonium bromide (8.17 g, 22.4 mmol), $K_2CO_3$ (3.10 g, 22.4 mmol), water (0.68 ml) and dioxan (51 ml) was heated for 2 h. to 90° C. The reaction mixture was concentrated and the product was purified by chromatography ($SiO_2$, hexane/$CH_2Cl_2$ 4:1). There were obtained 1.74 g (48%) of 3-methoxy-5-vinyl-benzaldehyde as a colorless oil; MS: 162 ([M]+).
198.3
In analogy to Example 1.1, the 3-methoxy-5-vinyl-benzaldehyde obtained in Example 198.2 was converted with 4-aminobenzonitrile and benzyl isonitrile in EtOH into ethyl (RS)-(4-cyano-phenylamino)-(3-methoxy-5-vinyl-phenyl)-acetate; MS: 336 ([M]+).
188.4
In analogy to Example 6.2, the ethyl (RS)-(4-cyano-phenylamino)-(3-methoxy-5-vinyl-phenyl)-acetate obtained in Example 198.3 was converted into ethyl (RS)-(4-carbamimidoyl-phenylamino)-(3-methoxy-5-vinyl-phenyl)-acetate hydrochloride (1:1); MS: 354 ([M+H]+).

Example 199

199.1
Pd-C (10%, 236 mg, 0.22 mmol) was added a solution of the ethyl (RS)-(4-cyano-phenylamino)-(3-methoxy-5-vinyl-phenyl)-acetate (1.495 g, 4.44 mmol) obtained in Example 198.3 in EtOH (40 ml) and THF (4 ml) and the mixture was hydrogenated for 1 h. at room temperature. The reaction mixture was filtered, the filtrate was concentrated and the residue was purified by filtration over $SiO_2$ (eluent: AcOEt/hexane 1:1). There were obtained 1.5 g (99%) of ethyl (RS)-(4-cyano-phenylamino)-(3-ethyl-5-methoxy-phenyl)-acetate as a beige solid; MS: 338 ([M]+).
199.2
In analogy to Example 6.2, the ethyl (RS)-(4-cyano-phenylamino)-(3-ethyl-5-methoxy-phenyl)-acetate obtained in Example 199.1 was converted into ethyl (RS)-(4-carbamimidoyl-phenylamino)-(3-ethyl-5-methoxy-phenyl)-acetate hydrochloride (1:1); MS: 356 ([M+H]+).

Example 200

200.1
In analogy to Example 168.1, the ethyl (RS)-(4-cyano-phenylamino)-(3-ethyl-5-methoxy-phenyl)-acetate obtained in Example 199.1 was converted into ethyl (RS)-(4-cyano-phenylamino)-(3-ethyl-5-hydroxy-phenyl)-acetate; MS: 325 ([M+H]+).
200.2
In analogy to Example 168.2, the ethyl (RS)-(4-cyano-phenylamino)-(3-ethyl-5-hydroxy-phenyl)-acetate obtained in Example 200.1 was converted with 2-methyl-3-iodopropane and $Cs_2CO_3$ in acetone into ethyl (RS)-(4-cyano-phenylamino)-(3-ethyl-5-isobutoxy-phenyl)-acetate; MS: 381 ([M+H]+).
200.3
In analogy to Example 6.2, the ethyl (RS)-(4-cyano-phenylamino)-(3-ethyl-5-isobutoxy-phenyl)-acetate obtained in Example 200.2 was converted into ethyl (RS)-(4-carbamimidoyl-phenylamino)-(3-ethyl-5-isobutoxy-phenyl)-acetate hydrochloride (1:1); MS: 398 ([M+H]+).

Example 201

201.1
In analogy to Example 18.1, the ethyl (RS)-(4-cyano-phenylamino)-(3-ethyl-5-hydroxy-phenyl)-acetate obtained in Example 200.1 was converted with 4-hydroxy-N-methyl-piperidine, diethyl azodicarboxylate and triphenylphosphine in THF into ethyl (RS)-(4-cyano-phenylamino)-[3-ethyl-5-(1-methyl-piperidin-4-yloxy)-phenyl]-acetate; MS: 422 ([M+H]+).
201.2
In analogy to Example 6.2, the ethyl (RS)-(4-cyano-phenylamino)-[3-ethyl-5-(1-methyl-piperidin-4-yloxy)-phenyl]-acetate obtained in Example 201.1 was converted into ethyl (RS)-(4-carbamimidoyl-phenylamino)-[3-ethyl-5-(1-methyl-piperidin-4-yloxy)-phenyl]-acetate hydrochloride (1:1); MS: 439 ([M+H]+).

Example 202

202.1
In analogy to Example 18.1, the ethyl (RS)-(4-cyano-phenylamino)-(3-ethyl-5-hydroxy-phenyl)-acetate obtained in Example 200.1 was converted with N-(2-hydroxyethyl)-pyrrolidine, diethyl azodicarboxylate and triphenylphosphine in THF into ethyl (RS)-(4-cyano-phenylamino)-[3-ethyl-5-(2-pyrrolidin-1-yl-ethoxy)-phenyl]-acetate; MS: 422 ([M+H]+).
202.2
In analogy to Example 6.2, the ethyl (RS)-(4-cyano-phenylamino)-[3-ethyl-5-(2-pyrrolidin-1-yl-ethoxy)-phenyl]-acetate obtained in Example 202.1 was converted into ethyl (RS)-(4-carbamimidoyl-phenylamino)-[3-ethyl-5-(2-pyrrolidin-1-yl-ethoxy)-phenyl]-acetate hydrochloride (1:1); MS: 439 ([M+H]+).

Example 203

203.1
In analogy to Example 18.1, the ethyl (RS)-(4-cyano-phenylamino)-(3-ethyl-5-hydroxy-phenyl)-acetate obtained in Example 200.1 was converted with tetrahydro-2H-pyran-4-ol, diethyl azodicarboxylate and triphenylphosphine in THF into ethyl (RS)-(4-cyano-phenylamino)-[3-ethyl-5-(tetrahydro-pyran-4-yloxy)-phenyl]-acetate; MS: 409 ([M+H]+).
203.2
In analogy to Example 6.2, the ethyl (RS)-(4-cyano-phenylamino)-[3-ethyl-5-(tetrahydro-pyran-4-yloxy)-phenyl]-acetate obtained in Example 203.1 was converted into ethyl (RS)-(4-carbamimidoyl-phenylamino)-[3-ethyl-5-(tetrahydro-pyran-4-yloxy)-phenyl]-acetate hydrochloride (1:1); MS: 426 ([M+H]+).

Example 204

204.1
In analogy to Example 18.1, the ethyl (RS)-(4-cyano-phenylamino)-(3-ethyl-5-hydroxy-phenyl)-acetate obtained in Example 200.1 was converted with tetrahydrofurfuryl alcohol, diethyl azodicarboxylate and triphenylphosphine in THF into a mixture of ethyl (RS)- and (SR)-(4-cyano-phenylamino)-[3-ethyl-5-[(RS)-tetrahydro-furan-2-ylmethoxy]-phenyl]-acetate; MS: 408 ([M]+).
204.2
In analogy to Example 6.2, the mixture of ethyl (RS)- and (SR)-(4-cyano-phenylamino)-[3-ethyl-5-[(RS)-tetrahydro-furan-2-ylmethoxy]-phenyl]-acetate obtained in Example 204.1 was converted into a mixture of ethyl (RS)- and (SR)-(4-carbamimidoyl-phenylamino)-[3-ethyl-5-[(RS)-tetrahydro-furan-2-ylmethoxy]-phenyl]-acetate hydrochloride (1:1); MS: 426 ([M+H]$^+$).

Example 205

205.1
In analogy to Example 18.1, the ethyl (RS)-(4-cyano-phenylamino)-(3-ethyl-5-hydroxy-phenyl)-acetate obtained in Example 200.1 was converted with cyclopentanol, diethyl azodicarboxylate and triphenylphosphine in THF into ethyl (RS)-(4-cyano-phenylamino)-(3-cyclopentyloxy-5-ethyl-phenyl)-acetate; MS: 392 ([M]$^+$).

205.2
In analogy to Example 6.2, the ethyl (RS)-(4-cyano-phenylamino)-(3-cyclopentyloxy-5-ethyl-phenyl)-acetate obtained in Example 205.1 was converted into ethyl (RS)-(4-carbamimidoyl-phenylamino)-(3-cyclopentyloxy-5-ethyl-phenyl)-acetate hydrochloride (1:1); MS: 410 ([M+H]$^+$).

Example 206

206.1
In analogy to Example 18.1, the ethyl (RS)-(4-cyano-phenylamino)-(3-ethyl-5-hydroxy-phenyl)-acetate obtained in Example 200.1 was converted with trans-4-trityloxy-cyclohexanol (*Synth. Commun.* 1994, 24, 2399), diethyl azodicarboxylate and triphenylphosphine in THF into ethyl (RS)-(4-cyano-phenylamino)-[3-ethyl-5-(4-trityloxy-cyclohexyloxy)-phenyl]-acetate; MS: 687 ([M+Na]$^+$).

206.2
In analogy to Example 6.2 the ethyl (RS)-(4-cyano-phenylamino)-[3-ethyl-5-(4-trityloxy-cyclohexyloxy)-phenyl]-acetate obtained in Example 206.1 was converted into ethyl (RS)-(4-carbamimidoyl-phenylamino)-[3-ethyl-5-(4-hydroxy-cyclohexyloxy)-phenyl]-acetate hydrochloride (1:1); MS: 440 ([M+H]$^+$).

Example 207

207.1
In analogy to Example 18.1, the ethyl (RS)-(4-cyano-phenylamino)-(3-ethyl-5-hydroxy-phenyl)-acetate obtained in Example 200.1 was converted with tert-butyl-4-hydroxy-1-piperidinecarboxylate, diethyl azodicarboxylate and triphenylphosphine in THF into tert-butyl (RS)-4-{3-[(4-cyano-phenylamino)-ethoxycarbonylmethyl]-5-ethyl-phenoxy}-piperidine-1-carboxylate; MS: 508 ([M+H]$^+$).

207.2
In analogy to Example 6.2, the tert-butyl (RS)-4-{3-[(4-cyano-phenylamino)-ethoxycarbonylmethyl]-5-ethyl-phenoxy}-piperidine-1-carboxylate obtained in Example 207.1 was converted into ethyl (RS)-(4-carbamimidoyl-phenylamino)-[3-ethyl-5-(piperidin-4-yloxy)-phenyl]-acetate hydrochloride (1:1); MS: 425 ([M+H]$^+$).

Example 208

208.1
In analogy to Example 18.1, the ethyl (RS)-(4-cyano-phenylamino)-(3-ethyl-5-hydroxy-phenyl)-acetate obtained in Example 200.1 was converted with 3-dimethylamino-2,2-dimethyl-1-propanol, diethyl azodicarboxylate and triphenylphosphine in THF into ethyl (RS)-(4-cyano-phenylamino)-[3-(3-dimethylamino-2,2-dimethyl-propoxy)-5-ethyl-phenyl]-acetate; MS: 438 ([M+H]$^+$).

208.2
In analogy to Example 6.2, the ethyl (RS)-(4-cyano-phenylamino)-[3-(3-dimethylamino-2,2-dimethyl-propoxy)-5-ethyl-phenyl]-acetate obtained in Example 208.1 was converted into ethyl (RS)-(4-carbamimidoyl-phenylamino)-[3-(3-dimethylamino-2,2-dimethyl-propoxy)-5-ethyl-phenyl]-acetate; MS: 456 ([M+H]$^+$).

Example 209

209.1
Trifluoroacetic acid (1.67 ml, 21.7 mmol) was added dropwise at 0° C. to a solution of the tert-butyl (RS)-4-{3-[(4-cyano-phenylamino)-ethoxycarbonylmethyl]-5-ethyl-phenoxy}-piperidin-1-carboxylate (1.1 g, 2.17 mmol) obtained in Example 197.1 in CH$_2$Cl$_2$ (30 ml). The mixture was warmed slowly (2.5 h.) to room temperature and then poured into a mixture of saturated NaHCO$_3$ solution and ice. The mixture was extracted with CH$_2$Cl$_2$. The organic phase was dried and filtered, and the filtrate was concentrated. The amine obtained was reacted further without additional purification.

209.2
Methanesulphonyl chloride (71 mg, 0.61 mmol) was added slowly at 0° C. to a solution of the amine (250 mg, 0.51 mmol) obtained in Example 209.1 and N-ethyldiisopropylamine (81 mg, 0.61 mmol) in THF (3.5 ml). The mixture was stirred for 1.5 h. at 0° C. and for 1.5 h. at room temperature. The reaction mixture was concentrated and the residue was purified by chromatography (SiO$_2$, CH$_2$Cl$_2$→CH$_2$Cl$_2$/MeOH 95:5). There were obtained 201 mg (81%) of ethyl (RS)-(4-cyano-phenylamino)-[3-ethyl-5-(1-methanesulphonyl-piperidin-4-yloxy)-phenyl]-acetate as a beige foam; MS: 486 ([M+H]$^+$).

209.3
In analogy to Example 6.2, the ethyl (RS)-(4-cyano-phenylamino)-[3-ethyl-5-(1-methanesulphonyl-piperidin-4-yloxy)-phenyl]-acetate obtained in Example 209.2 was converted into ethyl (RS)-(4-carbamimidoyl-phenylamino)-[3-ethyl-5-(1-methanesulphonyl-piperidin-4-yloxy)-phenyl]-acetate hydrochloride (1:1); MS: 503 ([M+H]$^+$).

Example 210

210.1
Ethyl bromoacetate (104 mg, 0.61 mmol) was added slowly at 0° C. to a solution of the amine (250 mg, 0.51 mmol) obtained in Example 210.1 and N-ethyldiisopropylamine (81 mg, 0.61 mmol) in THF (3.5 ml). The mixture was stirred for 1 h. at 0° C. and for 3 h. at room temperature. The reaction mixture was concentrated and the residue was purified by chromatography (SiO$_2$, CH$_2$Cl$_2$→CH$_2$Cl$_2$/MeOH 95:5). There were obtained 176 mg, (69%) of ethyl (RS)-(4-cyano-phenylamino)-[3-(1-ethoxycarbonylmethyl-piperidin-4-yloxy)-5-ethyl-phenyl]-acetate as a yellow oil; MS: 494 ([M+H]$^+$).

210.2
In analogy to Example 6.2, the ethyl (RS)-(4-cyano-phenylamino)-[3-(1-ethoxycarbonylmethyl-piperidin-4-yloxy)-5-ethyl-phenyl]-acetate obtained in Example 210.1 was converted into ethyl (RS)-(4-carbamimidoyl-phenylamino)-[3-(1-ethoxycarbonylmethyl-piperidin-4-yloxy)-5-ethyl-phenyl]-acetate hydrochloride (1:1); MS: 511 ([M+H]$^+$).

Example 211

211.1
In analogy to Example 182.1, the ethyl (RS)-(4-cyano-phenylamino)-(3-ethyl-5-hydroxy-phenyl)-acetate obtained in Example 200.1 was converted with cyclopentene oxide and K$_2$CO$_3$ in EtOH into a mixture of ethyl (RS)- and (SR)-(4-cyano-phenylamino)-[3-ethyl-5-[(1RS,2RS)-2-hydroxy-cyclopentyloxy]-phenyl]-acetate; MS: 409 ([M+H]$^+$).

211.2

In analogy to Example 6.2, the mixture of ethyl (RS)- and (SR)-(4-cyano-phenylamino)-[3-ethyl-5-[(1RS,2RS)-2-hydroxy-cyclopentyloxyl-phenyl]-acetate obtained in Example 211.1 was converted into a mixture of ethyl (RS)- and (SR)-(4-carbamimidoyl-phenylamino)-[3-ethyl-5-[(1RS,2RS)-2-hydroxy-cyclopentyloxy]-phenyl]-acetate hydrochloride (1:1); MS: 426 ([M+H]$^+$).

Example 212

212.1

Copper(II) acetate (223 mg, 1.20 mmol), phenylboronic acid (164 mg, 1.32 mmol) and molecular sieve 4 Å were added to a solution of the ethyl (RS)-(4-cyano-phenylamino)-(3-ethyl-5-hydroxy-phenyl)-acetate (390 mg, 1.20 mmol) obtained in Example 200.1 in $CH_2Cl_2$ (12 ml). Pyridine (476 mg, 6.01 mmol) was added dropwise and the mixture was stirred for 60 h. under an atmosphere of air. The reaction mixture was concentrated and the residue was purified by chromatography ($SiO_2$, $CH_2Cl_2$). There were obtained 391 mg (81%) of ethyl (RS)-(4-cyano-phenylamino)-(3-ethyl-5-phenoxy-phenyl)-acetate as beige crystals; MS: 401 ([M+H]$^+$).

212.2

In analogy to Example 6.2, the ethyl (RS)-(4-cyano-phenylamino)-(3-ethyl-5-phenoxy-phenyl)-acetate obtained in Example 212.1 was converted into ethyl (RS)-(4-carbamimidoyl-phenylamino)-(3-ethyl-5-phenoxy-phenyl)-acetate hydrochloride (1:1); MS: 418 ([M+H]$^+$).

Example 213

213.1

In analogy to Example 212.1, the ethyl (RS)-(4-cyano-phenylamino)-(3-ethyl-5-hydroxy-phenyl)-acetate obtained in Example 200.1 was converted by reaction with 3-pyridylboronic acid into ethyl (RS)-(4-cyano-phenylamino)-[3-ethyl-5-(pyridin-3-yloxy)-phenyl]-acetate.

213.2

In analogy to Example 6.2, the ethyl (RS)-(4-cyano-phenylamino)-[3-ethyl-5-(pyridin-3-yloxy)-phenyl]-acetate obtained in Example 213.1 was converted into ethyl (RS)-(4-carbamimidoyl-phenylamino)-[3-ethyl-5-(pyridin-3-yloxy)-phenyl]-acetate hydrochloride (1:1).

Example 214

214.1

In analogy to Example 198.2, the 5-methoxy-benzene-1,3-dicarbaldehyde obtained in Example 198.1 was converted with ethyl-triphenylphosphonium bromide into 3-methoxy-5-propenyl-benzaldehyde.

214.2

In analogy to Example 1.1, the 3-methoxy-5-propenyl-benzaldehyde obtained in Example 214.1 was converted with 4-aminobenzonitrile and benzyl isonitrile in EtOH into ethyl (RS)-(E/Z)-(4-cyano-phenylamino)-(3-methoxy-5-propenyl-phenyl)-acetate.

214.3

In analogy to Example 199.1, the ethyl (RS)-(E/Z)-(4-cyano-phenylamino)-(3-methoxy-5-propenyl-phenyl)-acetate obtained in Example 214.2 was converted into ethyl (RS)-(4-cyano-phenylamino)-(3-methoxy-5-propyl-phenyl)-acetate; MS: 353 ([M+H]$^+$).

214.4

In analogy to Example 6.2, the ethyl (RS)-(4-cyano-phenylamino)-(3-methoxy-5-propyl-phenyl)-acetate obtained in Example 214.3 was converted into ethyl (RS)-(4-carbamimidoyl-phenylamino)-(3-ethoxy-5-propyl-phenyl)-acetate hydrochloride (1:1); MS: 370 ([M+H]$^+$).

Example 215

215.1

In analogy to Example 168.1, the ethyl (RS)-(4-cyano-phenylamino)-(3-methoxy-5-propyl-phenyl)-acetate obtained in Example 214.3 was converted into ethyl (RS)-(4-cyano-phenylamino)-(3-hydroxy-5-propyl-phenyl)-acetate.

215.2

In analogy to Example 168.2, the ethyl (RS)-(4-cyano-phenylamino)-(3-hydroxy-5-propyl-phenyl)-acetate obtained in Example 215.1 was converted with ethyl iodide and $Cs_2CO_3$ in acetone into ethyl (RS)-(4-cyano-phenylamino)-(3-ethoxy-5-propyl-phenyl)-acetate; MS: 366 ([M]$^+$).

215.3

In analogy to Example 6.2, the ethyl (RS)-(4-cyano-phenylamino)-(3-ethoxy-5-propyl-phenyl)-acetate obtained in Example 215.2 was converted into ethyl (RS)-(4-carbamimidoyl-phenylamino)-(3-ethoxy-5-propyl-phenyl)-acetate hydrochoride (1:1); MS: 384 (M+H]$^+$).

Example 216

216.1

In analogy to Example 190.1, 5-nitro-m-xylene was converted into 3-methyl-5-nitro-benzaldehyde; MS: 165 ([M]$^+$).

216.2

In analogy to Example 1.1, the 3-methyl-5-nitro-benzaldehyde obtained in Example 216.1 was converted with 4-aminobenzonitrile and benzyl isonitrile in EtOH into ethyl (RS)-(4-cyano-phenylamino)-(3-methyl-5-nitro-phenyl)-acetate; MS: 340 ([M+H]$^+$).

216.3

In analogy to Example 59.2, the ethyl (RS)-(4-cyano-phenylamino)-(3-methyl-5-nitro-phenyl)-acetate obtained in Example 216.2 was converted with $H_2$ in EtOH under the catalytic activity of Pd/C into ethyl (RS)-(3-amino-5-methyl-phenyl)-(4-cyano-phenylamino)-acetate; MS: 309 ([M]$^+$).

216.4

In analogy to Example 61.1, the ethyl (RS)-(3-amino-5-methyl-phenyl)-(4-cyano-phenylamino)-acetate obtained in Example 216.3 was converted with ethyl iodide and diisopropyl-ethylamine in THF into ethyl (RS)-(4-cyano-phenylamino)-(3-ethylamino-5-methyl-phenyl)-acetate; MS: 338 ([M+H]$^+$).

216.5

In analogy to Example 6.2, the ethyl (RS)-(4-cyano-phenylamino)-(3-ethylamino-5-methyl-phenyl)-acetate obtained in Example 216.4 was converted into ethyl (RS)-(4-carbamimidoyl-phenylamino)-(3-ethylamino-5-methyl-phenyl)-acetate hydrochloride (1:1); MS: 355 ([M+H]$^+$).

Example 217

217.1

In analogy to Example 61.1) the ethyl (RS)-(3-amino-5-methyl-phenyl)-(4-cyano-phenylamino)-acetate obtained in Example 216.3 was converted with ethyl iodide and diisopropyl-ethylamine in THF into ethyl (RS)-(4-cyano-phenylamino)-(3-diethylamino-5-methyl-phenyl)-acetate; MS: 366 ([M+H]$^+$).

217.2

In analogy to Example 6.2, the ethyl (RS)-(4-cyano-phenylamino)-(3-diethylamino-5-methyl-phenyl)-acetate obtained in Example 217.1 was converted into ethyl (RS)-(4-carbamimidoyl-phenylamino)-(3-diethylamino-5-methyl-phenyl)-acetate hydrochloride (1:1); MS: 383 ([M+H]$^+$).

Example 218

218.1

In analogy to Example 61.1, the ethyl (RS)-(3-amino-5-methyl-phenyl)-(4-cyano-phenylamino)-acetate obtained in Example 216.3 was converted with cyclopentyl bromide and diisopropylethylamine in THF into ethyl (RS)-(4-cyano-phenylamino)-(3-cyclopentylamino-5-methyl-phenyl)-acetate; MS: 378 ([M+H]$^+$).

218.2

In analogy to Example 6.2, the ethyl (RS)-(4-cyano-phenylamino)-(3-cyclopentylamino-5-methyl-phenyl)-acetate obtained in Example 218.1 was converted into ethyl (RS)-(4-carbamimidoyl-phenylamino)-(3-cyclopentylamino-5-methyl-phenyl)-acetate hydrochloride (1:1); MS: 395 ([M+H]$^+$).

Example 219

219.1

In analogy to Example 61.1, the ethyl (RS)-(3-amino-5-methyl-phenyl)-(4-cyano-phenylamino)-acetate obtained in Example 216.3 was converted with 1,4-dibromobutane and diisopropylethylamine in THF into ethyl (RS)-(4-cyano-phenylamino)-(3-methyl-5-pyrrolidin-1-yl-phenyl)-acetate; MS: 363 ([M]$^+$).

219.2

In analogy to Example 6.2, the ethyl (RS)-(4-cyano-phenylamino)-(3-methyl-5-pyrrolidin-1-yl-phenyl)-acetate obtained in Example 219.1 was converted into ethyl (RS)-(4-carbamimidoyl-phenylamino)-(3-methyl-5-pyrrolidin-1-yl-phenyl)-acetate hydrochloride (1:1); MS: 381 ([M+H]$^+$).

Example 220

220.1

In analogy to Example 188.1, the ethyl (RS)-(3-amino-5-methyl-phenyl)-(4-cyano-phenylamino)-acetate obtained in Example 216.3 was converted with n-butyl isocyanate in THF into ethyl (RS)-[3-(3-butyl-ureido)-5-methyl-phenyl]-(4-cyano-phenylamino)-acetate; MS: 409 ([M+H]$^+$).

220.2

In analogy to Example 6.2, the ethyl (RS)-[3-(3-butyl-ureido)-5-methyl-phenyl]-(4-cyano-phenylamino)-acetate obtained in Example 211.1 was converted into ethyl (RS)-[3-(3-butyl-ureido)-5-methyl-phenyl]-(4-carbamimidoyl-phenylamino)-acetate hydrochloride (1:1); MS: 426 ([M+H]$^+$).

Example 221

221.1

A solution of the ethyl (RS)-(3-amino-5-methyl-phenyl)-(4-cyano-phenylamino)-acetate (500 mg, 1.62 mmol) obtained in Example 216.3, cyclopentene oxide (136 mg, 1.62 mmol) and LiClO$_4$ (172 mg, 1.62 mmol) in acetonitrile (1.5 ml) was stirred for 70 h. at room temperature. Thereafter, the mixture was heated for 24 h. to 60° C. Subsequently, further cyclopentene oxide (136 mg, 1.62 mmol) and LiClO$_4$ (172 mg, 1.62 mmol) were added and the mixture was stirred for 1 h. at 60° C. After cooling water was added and the mixture was extracted with diethyl ether. The organic phase was dried, filtered and concentrated and the residue was purified by chromatography (SiO$_2$, CH$_2$Cl$_2$/MeOH 98:2). There were obtained 272 mg, (43%) of a mixture of ethyl (RS)- and (SR)-(4-cyano-phenylamino)-[3-[(1RS,2RS)-2-hydroxy-cyclopentylamino]-5-methyl-phenyl]-acetate as a yellowish solid; MS: 394 ([M+H]$^+$).

221.2

In analogy to Example 6.2, the mixture of ethyl (RS)- and (SR)-(4-cyano-phenylamino)-[3-[(1RS,2RS)-2-hydroxy-cyclopentylamino]-5-methyl-phenyl]-acetate obtained in Example 221.1 was converted into a mixture of ethyl (RS)- and (SR)-(4-cyano-phenylamino)-[3-[(1RS,2RS)-2-hydroxy-cyclopentylamino]-5-methyl-phenyl]-acetate hydrochloride (1:1); MS: 411 ([M+H]$^+$).

Example 222

222.1

A solution of the ethyl (RS)-(3-amino-5-methyl-phenyl)-(4-cyano-phenylamino)-acetate (475 mg, 1.54 mmol) obtained in Example 216.3, 2-chloropyrimidine (400 mg, 3.38 mmol), diisopropylethylamine (317 μl, 1.85 mmol) and 1,8-diazabicyclo[5.4.0]undec-7-ene (276 μl, 1.85 mmol) in THF (4 ml) was heated under reflux for 2 h. The reaction mixture was concentrated and the residue was purified by chromatography (SiO2, hexane/EtOAc 1:1→EtOAc). There were obtained 193 mg (23%) of ethyl (RS)-(4-cyano-phenylamino)-(3-methyl-5-{1-[3-(pyrimidin-2-ylamino)-propyl]-azepan-2-ylideneamino}-phenyl)-acetate as yellowish foam; MS: 540 ([M+H]$^+$).

222.2

In analogy to Example 6.2, the ethyl (RS)-(4-cyano-phenylamino)-(3-methyl-5-{1-[3-(pyrimidin-2-ylamino)-propyl]-azepan-2-ylideneamino}-phenyl)-acetate obtained in Example 222.1 was converted into ethyl (RS)-(4-carbamimidoyl-phenylamino)-(3-methyl-5-1-[3-(pyrimidin-2-ylamino)-propyl]-azepan-2-ylidenamino}-phenyl)-acetate hydrochloride (1:1); MS: 557 ([M+H]$^+$).

Example 223

223.1

Isophthalaldehyde was converted with HNO$_3$/H$_2$SO$_4$ and ammonium sulphate into 5-nitro-benzene-1,3-dicarbaldehyde (*InorganicChem.* 1998, 37, 2134).

223.2

In analogy to Example 198.2, the 5-nitro-benzene-1,3-dicarbaldehyd obtained in Example 223.1 was converted with methyl-triphenylphosphonium bromide into 3-nitro-5-vinyl-benzaldehyde; MS: 177 ([M]$^+$)

223.3

In analogy to Example 1.1, the 3-nitro-5-vinyl-benzaldehyde obtained in Example 223.2 was converted with 4-aminobenzonitrile and benzyl isonitrile in EtOH into ethyl (RS)-(4-cyano-phenylamino)-(3-nitro-5-vinyl-phenyl)-acetate; MS: 351 ([M]$^+$).

223.4

In analogy to Example 59.2, the ethyl (RS)-(4-cyano-phenylamino)-(3-nitro-5-vinyl-phenyl)-acetate obtained in Example 223.3 was converted with H$_2$ in EtOH under the catalytic activity of Pd/C into ethyl (RS)-(3-amino-5-ethyl-phenyl)-(4-cyano-phenylamino)-acetate; MS: 323 ([M]$^+$).

223.5

In analogy to Example 61.1, the ethyl (RS)-(3-amino-5-ethyl-phenyl)-(4-cyano-phenylamino)-acetate obtained in Example 223.4 was converted with 1,4-dibromobutane and diisopropylethylamine in THF into ethyl (RS)-(4-cyano-phenylamino)-(3-ethyl-5-pyrrolidin-1-yl-phenyl)-acetate; MS: 378 ([M+H]$^+$).

223.6

In analogy to Example 6.2, the ethyl (RS)-(4-cyano-phenylamino)-(3-ethyl-5-pyrrolidin-1-yl-phenyl)-acetate obtained in Example 223.5 was converted into ethyl (RS)-(4-carbamimidoyl-phenylamino)-(3-ethyl-5-pyrrolidin-1-yl-phenyl)-acetate hydrochloride (1:1); MS: 395 ([M+H]$^+$).

Example 224

224.1

A mixture of the ethyl (RS)-(3-amino-5-ethyl-phenyl)-(4-cyano-phenylamino)-acetate (500 mg, 1.55 mmol) obtained in Example 223.4, bis-(2-chloroethylamine) hydrochloride (276 mg, 1.55 mmol) and chlorobenzene (5 ml) was heated under reflux for 18 h. The reaction mixture was concentrated and the residue was purified by chromatography (SiO$_2$, CH$_2$Cl$_2$/MeOH 9:1). There were obtained 385 mg (63%) of ethyl (RS)-(4-cyano-phenylamino)-(3-ethyl-5-piperazin-1-yl-phenyl)-acetate as a brownish solid; MS: 393 ([M+H]$^+$).

224.2

In analogy to Example 6.2, the ethyl (RS)-(4-cyano-phenylamino)-(3-ethyl-5-piperazin-1-yl-phenyl)-acetate obtained in Example 224.1 was converted into ethyl (RS)-(4-carbamimidoyl-phenylamino)-(3-ethyl-5-piperazin-1-yl-phenyl)-acetate hydrochloride (1:1); MS: 410 ([M+H]$^+$).

Example 225

225.1

Cyclopentanecarbonyl chloride (0.104 ml, 0.85 mmol) was added dropwise at 0° C. to a solution of the ethyl (RS)-(3-amino-5-ethyl-phenyl)-(4-cyano-phenylamino)-acetate (250 mg, 0.772 mmol) obtained in Example 223.4 and diisopropylethylamine (0.146 ml, 0.85 mmol) in CH$_2$Cl$_2$ (5 ml). The reaction mixture was warmed slowly (2 h.) to room temperature. A saturated aqueous solution of KHSO$_4$ was added and the mixture was extracted with EtOAc. The organic phase was washed with H$_2$O, dried and filtered, and the filtrate was concentrated. The residue was purified by chromatography (SiO$_2$, hexane→hexane/EtOAc 2:1). There were obtained 215 mg (66%) of ethyl (RS)-(4-cyano-phenylamino)-[3-(cyclopentanecarbonyl-amino)-5-ethyl-phenyl]-acetate as a colorless foam; MS: 418 ([M−H]$^-$).

225.2

In analogy to Example 6.2, the ethyl (RS)-(4-cyano-phenylamino)-[3-(cyclopentanecarbonyl-amino)-5-ethyl-phenyl]-acetate obtained in Example 225.1 was converted into ethyl (RS)-(4-carbamimidoyl-phenylamino)-[3-(cyclopentanecarbonyl-amino)-5-ethyl-phenyl]-acetate hydrochloride; MS: 437 ([M+H]$^+$).

Example 226

226.1

In analogy to Example 225.1, the ethyl (RS)-(3-amino-5-ethyl-phenyl)-(4-cyano-phenylamino)-acetate obtained in Example 223.4 was converted with benzenesulphonyl chloride and diisopropylethylamine in CH$_2$Cl$_2$ into ethyl (RS)-(4-cyano-phernylamino)-(3-benzene-sulphonylamino-5-ethyl-phenyl)-acetate.

226.2

In analogy to Example 6.2, the ethyl (RS)-(4-cyano-phenylamino)-(3-benzenesulphonylamino-5-ethyl-phenyl)-acetate obtained in Example 226.1 was converted into ethyl (RS)-(4-carbamimidoyl-phenylamino)-(3-benzenesulphonylamino-5-ethyl-phenyl)-acetate hydrochloride (1:1); MS: 481 ([M+H]$^+$).

Example 227

227.1

In analogy to Example 225.1, the ethyl (RS)-(3-amino-5-ethyl-phenyl)-(4-cyano-phenylamino)-acetate obtained in Example 223.4 was converted with butylsulphamoyl chloride and diisopropylethylamine in CH$_2$Cl$_2$ into ethyl (RS)-(4-cyano-phenylamino)-(3-butyl-sulphamoyl-amino-5-ethyl-phenyl)-acetate.

227.2

In analogy to Example 6.2, the ethyl (RS)-(4-cyano-phenylamino)-(3-butylsulphamoyl-amino-5-ethyl-phenyl)-acetate obtained in Example 227.1 was converted into ethyl (RS)-(4-carbamimidoyl-phenylamino)-(3-butylsulphamoyl-amino-5-ethyl-phenyl)-acetate hydrochloride (1:1); MS: 476 ([M+H]$^+$).

Example 228

228.1

Na$_2$SO$_4$ (1.09 g, 7.7 mmol) was added to a solution of the ethyl (RS)-(3-amino-5-ethyl-phenyl)-(4-cyano-phenylamino)-acetate (250 mg, 0.77 mmol) obtained in Example 223.4 and 1-methyl-4-piperidone (174 mg, 1.54 mmol) in acetic acid (5 ml) and the mixture was stirred for 15 min. at room temperature. The mixture was subsequently cooled to 0° C. and NaHB(OAc)$_3$ (489 mg, 2.31 mmol) was slowly added portionwise. After 30 min. a saturated solution of NaHCO$_3$ was added and the mixture was extracted with EtOAc. The organic phase was dried and filtered, and the filtrate was concentrated. The residue was purified by chromatography (SiO$_2$, CH$_2$Cl$_2$/MeOH 9:1). There were obtained 287 mg (89%) of ethyl (RS)-(4-cyano-phenylamino)-[3-ethyl-5-(1-methyl-piperidin-4-ylamino)-phenyl]-acetate as a yellowish solid; MS: 421 ([M+H]$^+$).

228.2

In analogy to Example 6.2, the ethyl (RS)-(4-cyano-phenylamino)-[3-ethyl-5-(1-methyl-piperidin-4-ylamino)-phenyl]-acetate obtained in Example 228.1 was converted into ethyl (RS)-(4-carbamimidoyl-phenylamino)-[3-ethyl-5-(1-methyl-piperidin-4-ylamino)-phenyl]-acetate hydrochloride (1:1).

Example 229

229.1

In analogy to Example 228.1, the ethyl (RS)-(3-amino-5-ethyl-phenyl)-(4-cyano-phenylamino)-acetate obtained in Example 223.4 was converted with 3-pyridinecarboxaldehyde and NaHB(OAc)$_3$ in AcOH into ethyl (RS)-(4-cyano-phenylamino)-{3-ethyl-5-[(pyridin-3-ylmethyl)-amino]-phenyl}-acetate; MS: 415 ([M+H]$^+$).

229.2

In analogy to Example 6.2, the ethyl (RS)-(4-cyano-phenylamino)-{3-ethyl-5-[(pyridin-3-ylmethyl)-amino]-phenyl}-acetate obtained in Example 229.1 was converted into ethyl (RS)-(4-carbamimidoyl-phenylamino)-{3-ethyl-5-[(pyridin-3-ylmethyl)-amino]-phenyl }-acetate hydrochloride (1:1); MS: 432 ([M+H]$^+$).

Example 230

230.1

In analogy to Example 228.1, the ethyl (RS)-(3-amino-5-ethyl-phenyl)-(4-cyano-phenylamino)-acetate obtained in Example 223.4 was converted with 3-pyridinecarboxaldehyde and NaHB(OAc)$_3$ in AcOH into ethyl (RS)-[3-(bis-pyridin-3-ylmethyl-amino)-5-ethyl-phenyl]-(4-cyano-phenylamino)-acetate; MS: 506 ([M+H]$^+$).

230.2

In analogy to Example 6.2, the ethyl (RS)-[3-(bis-pyridin-3-ylmethyl-amino)-5-ethyl-phenyl]-(4-cyano-phenylamino)-acetate obtained in Example 230.1 was converted into ethyl (RS)-[3-(bis-pyridin-3-ylmethyl-amino)-5-ethyl-phenyl]-(4-carbamimidoyl-phenylamino)-acetate hydrochloride (1:1); MS: 523 ([M+H]$^+$).

Example 231

231.1

In analogy to Example 228.1, the ethyl (RS)-(3-amino-5-ethyl-phenyl)-(4-cyano-phenylamino)-acetate obtained in Example 223.4 was converted with tetrahydo-4H-pyran-4-one and NaHB(OAc)$_3$ in AcOH into ethyl (RS)-(4-cyano-phenylamino)-[3-ethyl-5-(tetrahydro-pyran-4-ylamino)-phenyl]-acetate; MS: 408 ([M+H]$^+$).

231.2

In analogy to Example 6.2, the ethyl (RS)-(4-cyano-phenylamino)-[3-ethyl-5-(tetrahydro-pyran-4-ylamino)- phenyl]-acetate obtained in Example 231.1 was converted into ethyl (RS)-(4-carbamimidoyl-phenylamino)-[3-ethyl-5-(tetrahydro-pyran-4-ylamino)-phenyl]-acetate hydrochloride (1:1); MS: 425 ([M+H]$^+$).

Example 232

232.1

In analogy to Example 228.1 the ethyl (RS)-(3-amino-5-ethyl-phenyl)-(4-cyano-phenylamino)-acetate obtained in Example 223.4 was converted with tetrahydo-4H-thiopyran-4-one and NaHB(OAc)$_3$ in AcOH into ethyl (RS)-(4-cyano-phenylamino)-[3-ethyl-5-(tetrahydro-thiopyran-4-ylamino)-phenyl]-acetate; MS: 424 ([M+H]$^+$).

232.2

In analogy to Example 6.2, the ethyl (RS)-(4-cyano-phenylamino)-[3-ethyl-5-(tetrahydro-thiopyran-4-ylamino)-phenyl]-acetate obtained in Example 232.1 was converted into ethyl (RS)-(4-carbamimidoyl-phenylamino)-[3-ethyl-5-(tetrahydro-thiopyran-4-ylamino)-phenyl]-acetate hydrochloride (1:1); MS: 441 ([M+H]$^+$).

Example 233

233.1

In analogy to Example 164.1, the ethyl (RS)-(4-cyano-phenylamino)-[3-ethyl-5-(tetrahydro-thiopyran-4-ylamino)-phenyl]-acetate obtained in Example 232.1 was converted with ozone in acetone/H$_2$O into ethyl (RS)-(4-cyano-phenylamino)-[3-(1,1-dioxo-hexahydro-thiopyran-4-ylamino)-5-ethyl-phenyl]-acetate; MS: 456 ([M+H]$^+$).

233.2

In analogy to Example 6.2 the ethyl (RS)-(4-cyano-phenylamino)-[3-(1,1-dioxo-hexahydro-thiopyran-4-ylamino)-5-ethyl-phenyl]-acetate obtained in Example 223.1 was converted into ethyl (RS)-(4-carbamimidoyl-phenylamino)-[3-(1,1-dioxo-hexahydro-thiopyran-4-ylamino)-5-ethyl-phenyl]-acetate hydrochloride (1:1); MS: 473 ([M+H]$^+$).

Example 234

234.1

MnO$_2$ (8.37 g, 96.3 mmol) was added to a solution of (3-ethoxy-5-hydroxymethyl-phenyl)-methanol (17.55 g, 96.3 mmol) in CH$_2$Cl$_2$ (175 ml) and the mixture was stirred for 64 h. at room temperature. Thereafter, further MnO$_2$ (8.37 g, 96.3 mmol) was added and the mixture was stirred for 6 h. The mixture was filtered over Celite and the filtrate was concentrated. The product was purified by chromatography. There were obtained 8.32 g (48%) of 3-ethoxy-5-hydroxymethyl-benzaldehyde as a colorless oil.

234.2

In analogy to Example 1.1, the 3-ethoxy-5-hydroxymethyl-benzaldehyde obtained in Example 234.1 was converted with 4-aminobenzonitrile and benzyl isonitrile in EtOH into ethyl (RS)-(4-cyano-phenylamino)-(3-ethoxy-5-hydroxymethyl-phenyl)-acetate; MS: 355 ([[M+H]$^+$).

234.3

Methanesulphonyl chloride was added slowly at 0° C. to a solution of the ethyl (RS)-(4-cyano-phenylamino)-(3-ethoxy-5-hydroxymethyl-phenyl)-acetate (200 mg, 0.564 mmol) obtained in Example 234.2 and N-ethyldiisopropylamine (88 mg, 0.68 mmol) in THF (3 ml). The mixture was stirred for 1.5 h. at 0° C. and for 1.5 h. at room temperature. The mixture was poured into ice-water/1M HCl and extracted with EtOAc. The organic phase was washed with H$_2$O, dried and filtered, and the filtrate was concentrated. There were obtained 232 mg of ethyl (RS)-(4-cyano-phenylamino)-(3-ethoxy-5-methanesulphonyloxymethyl-phenyl)-acetate as a yellow oil, which was used for the next reaction without additional purification.

234.4

N-Ethyldiisopropylamine (132 mg, 1.02 mmol) and pyrrolidine (145 mg, 2.04 mmol) were added to a solution of the ethyl (RS)-(4-cyano-phenylamino)-(3-ethoxy-5-methanesulphonyl-oxymethyl-phenyl)-acetate (221 mg, 0.511 mmol) obtained in Example 234.3 in THF (2 ml) and the mixture was stirred for 1 h. at room temperature. The reaction mixture was concentrated and the residue was purified by chromatography (SiO$_2$, CH$_2$Cl$_2$/MeOH 99:1). There were obtained 153 mg (73%) of ethyl (RS)-(4-cyano-phenylamino)-(3-ethoxy-5-pyrrolidin-1-ylmethyl-phenyl)-acetate as a yellowish foam; MS: 408 ([M+H]$^+$).

234.5

In analogy to Example 6.2, the ethyl (RS)-(4-cyano-phenylamino)-(3-ethoxy-5-pyrrolidin-1-ylmethyl-phenyl)-acetate obtained in Example 234.4 was converted into ethyl (RS)-(4-carbamimidoyl-phenylamino)-(3-ethoxy-5-pyrrolidin-1-ylmethyl-phenyl)-acetate hydrochloride (1:1).

Example 235

235.1

In analogy to Example 234.4, the ethyl (RS)-(4-cyano-phenylamino)-(3-ethoxy-5-methanesulphonyloxymethyl-phenyl)-acetate obtained in Example 234.3 was converted with cyclo-butylamine and N-ethyldiisopropylamine in THF into ethyl (RS)-(4-cyano-phenylamino)-(3-cyclobutylaminomethyl-5-ethoxy-phenyl)-acetate; MS: 408 ([M+H]$^-$).

235.2

In analogy to Example 6.2, the ethyl (RS)-(4-cyano-phenylamino)-(3-cyclobutylaminomethyl-5-ethoxy-phenyl)-acetate obtained in Example 235.1 was converted into ethyl (RS)-(4-carbamimidoyl-phenylamino)-(3-cyclobutylaminomethyl-5-ethoxy-phenyl)-acetate.

Example 236

236.1

In analogy to Example 234.4, the ethyl (RS)-(4-cyano-phenylamino)-(3-ethoxy-5-methanesulphonyloxymethyl-phenyl)-acetate obtained in Example 234.3 was converted with morpholine and N-ethyldiisopropylamine in THF into ethyl (RS)-(4-cyano-phenylamino)-(3-ethoxy-5-morpholin-4-ylmethyl-phenyl)-acetate; MS: 424 ([M+H]$^+$).

236.2

In analogy to Example 6.2, the ethyl (RS)-(4-cyano-phenylamino)-(3-ethoxy-5-morpholin-4-ylmethyl-phenyl)-acetate obtained in Example 236.1 was converted into ethyl (RS)-(4-carbamimidoyl-phenylamino)-(3-ethoxy-5-morpholin-4-ylmethyl-phenyl)-acetate hydrochloride; MS: 441 ([M+H]$^+$).

Example 237

237.1

In analogy to Example 234.4, the ethyl (RS)-(4-cyano-phenylamino)-(3-ethoxy-5-methanesulphonyloxymethyl-phenyl)-acetate obtained in Example 234.3 was converted with iso-propylamine and N-ethyldiisopropylamine in THF into ethyl (RS)-(4-cyano-phenylamino)-[3-ethoxy-5-(isopropylamino-methyl)-phenyl]-acetate; MS: 396 ([M+H]$^+$).

237.2

In analogy to Example 6.2, the ethyl (RS)-(4-cyano-phenylamino)-[3-ethoxy-5-(isopropylamino-methyl)-phenyl]-acetate obtained in Example 237.1 was converted into ethyl (RS)-(4-carbamimidoyl-phenylamino)-[3-ethoxy- 5-(isopropylamino-methyl)-phenyl]-acetate hydrochloride (1:1); MS: 413 ([M+H]$^+$).

Example 238

238.1

In analogy to Example 234.4, the ethyl (RS)-(4-cyano-phenylamino)-(3-ethoxy-5-methanesulphonyloxymethyl-phenyl)-acetate obtained in Example 234.3 was converted with 2-amino-pyridine and N-ethyldiisopropylamine in THF into ethyl (RS)-(4-cyano-phenylamino)-[3-ethoxy-5-(pyridin-2-ylaminomethyl)-phenyl]-acetate; MS: 431 ([M+H]$^+$).

238.2

In analogy to Example 6.2, the ethyl (RS)-(4-cyano-phenylamino)-[3-ethoxy-5-(pyridin-2-ylaminomethyl)-phenyl]-acetate obtained in Example 238.1 was converted into ethyl (RS)-(4-carbamimidoyl-phenylamino)-[3-ethoxy-5-(pyridin-2-ylaminomethyl)-phenyl]-acetate hydrochloride (1:1).

Example 239

239.1

In analogy to Example 234.4, the ethyl (RS)-(4-cyano-phenylamino)-(3-ethoxy-5-methanesulphonyloxymethyl-phenyl)-acetate obtained in Example 234.3 was converted with imidazole and N-ethyldiisopropylamine in THF into ethyl (RS)-(4-cyano-phenylamino)-(3-ethoxy-5-imidazol-1-ylmethyl-phenyl)-acetate; MS: 405 ([M+H]$^+$).

239.2

In analogy to Example 6.2, the ethyl (RS)-(4-cyano-phenylamino)-(3-ethoxy-5-imidazol-1-ylmethyl-phenyl)-acetate obtained in Example 239.1 was converted into ethyl (RS)-(4-carbamimidoyl-phenylamino)-(3-ethoxy-5-imidazol-1-ylmethyl-phenyl)-acetate hydrochloride (1:1); MS: 422 ([M+H]$^+$).

Example 240

240.1

In analogy to Example 234.4 the ethyl (RS)-(4-cyano-phenylamino)-(3-ethoxy-5-methanesulphonyloxymethyl-phenyl)-acetate obtained in Example 234.3 was converted with N-(2-methoxyethyl)-methylamine and N-ethyldiisopropylamine in THF into ethyl (RS)-(4-cyano-phenylamino)-(3-ethoxy-5-{[(2-methoxy-ethyl)-methyl-amino]-methyl}-phenyl)-acetate; MS: 426 ([M+H]$^+$).

240.2

In analogy to Example 6.2, the ethyl (RS)-(4-cyano-phenylamino)-(3-ethoxy-5-{[(2-methoxy-ethyl)-methyl-amino]-methyl}-phenyl)-acetate obtained in Example 240.1 was converted into ethyl (RS)-(4-carbamimidoyl-phenylamino)-(3-ethoxy-5-{[(2-methoxy-ethyl)-methyl-amino]-methyl}-phenyl)-acetate hydrochloride (1:1); MS: 443 ([M+H]$^+$).

Example 241

241.1

In analogy to Example 234.4, the ethyl (RS)-(4-cyano-phenylamino)-(3-ethoxy-5-methanesulphonyloxymethyl-phenyl)-acetate obtained in Example 234.3 was converted with diethyl-amine and N-ethyldiisopropylamine in THF into ethyl (RS)-(4-cyano-phenylamino)-(3-diethylaminomethyl-5-ethoxy-phenyl)-acetate; MS: 410 ([M+H]$^+$).

241.2

In analogy to Example 6.2, the ethyl (RS)-(4-cyano-phenylamino)-(3-diethylaminomethyl-5-ethoxy-phenyl)-acetate obtained in Example 241.1 was converted into ethyl (RS)-(4-carbamimidoyl-phenylamino)-(3-diethylaminomethyl-5-ethoxy-phenyl)-acetic acetate hydrochloride (1:1); MS: 428 ([M+H]$^+$).

Example 242

242.1

In analogy to Example 234.4, the ethyl (RS)-(4-cyano-phenylamino)-(3-ethoxy-5-methanesulphonyloxymethyl-phenyl)-acetate obtained in Example 234.3 was converted with N-methylpiperazine and N-ethyldiisopropylamine in THF into ethyl (RS)-(4-cyano-phenylamino)-[3-ethoxy-5-(4-methyl-piperazin-1-ylmethyl)-phenyl]-acetate; MS: 437 ([M+H]$^+$).

242.2

In analogy to Example 6.2, the ethyl (RS)-(4-cyano-phenylamino)-[3-ethoxy-5-(4-methyl-piperazin-1-ylmethyl)-phenyl]-acetate obtained in Example 242.1 was converted into ethyl (RS)-(4-carbamimidoyl-phenylamino)-[3-ethoxy-5-(4-methyl-piperazin-1-ylmethyl)-phenyl]-acetate hydrochloride (1:1); MS: 455 ([M+H]$^+$).

Example 243

243.1

In analogy to Example 234.4, the ethyl (RS)-(4-cyano-phenylamino)-(3-ethoxy-5-methanesulphonyloxymethyl-phenyl)-acetate obtained in Example 234.3 was converted with cyclo-pentylamine and N-ethyldiisopropylamine in THF into ethyl (RS)-(4-cyano-phenylamino)-(3-cyclopentylaminomethyl-5-ethoxy-phenyl)-acetate; MS: 422 ([M+H]$^+$).

243.1

In analogy to Example 6.2, the ethyl (RS)-(4-cyano-phenylamino)-(3-cyclopentylaminomethyl-5-ethoxy-phenyl)-acetate obtained in Example 243.1 was converted into ethyl (RS)-(4-carbamimidoyl-phenylamino)-(3-cyclopentylaminomethyl-5-ethoxy-phenyl)-acetate hydrochloride (1:1); MS: 439 ([M+H]$^+$).

Example 244

244.1

In analogy to Example 75.4, the ethyl (RS)-(4-cyano-phenylamino)-(3-ethoxy-5-hydroxy-methyl-phenyl)-acetate obtained in Example 234.2 was converted with DMSO, oxalyl chloride and triethylamine into ethyl (RS)-(4-cyano-phenylamino)-(3-ethoxy-5-formyl-phenyl)-acetate; MS: 352 ([M]$^+$).

244.2

A solution of 2,3-dichloro-5,6-dicyano-1,4-benzoquinone in acetonitrile (1.5 ml) was added dropwise very slowly (2 h.) to a solution of the ethyl (RS)-(4-cyano-phenylamino)-(3-ethoxy-5-formyl-phenyl)-acetate (460 mg, 1.305 mmol) obtained in Example 244.1 and 1,2-phenylenediamine in acetonitrile (2 ml). The reaction mixture was stirred for 4 h. at room temperature. Water/saturated Na$_2$CO$_3$ solution (1:1) was added and the mixture was extracted with CH$_2$Cl$_2$. The organic phase was washed with H$_2$O, dried, filtered and concentrated. The residue was purified by chromatography (SiO$_2$, hexane/EtOAc 3:2). There were obtained 173 mg (30%) of ethyl (RS)-[3-(1H-benzoimidazol-2-yl)-5-ethoxy-phenyl]-(4-cyano-phenylamino)-acetate as a colorless solid; MS: 441 ([M+H]$^+$).

244.3

In analogy to Example 6.2, the ethyl (RS)-[3-(1H-benzoimidazol-2-yl)-5-ethoxy-phenyl]-(4-cyano-phenylamino)-acetate obtained in Example 244.2 was converted into ethyl (RS)-[3-(1H-benzoimidazol-2-yl)-5-ethoxy-phenyl]-(4-carbamimidoyl-phenylamino)-acetate hydrochloride (1:1); MS: 458 ([M+H]$^+$).

Example 245

245.1

Firstly a 2M solution of $NH_3$ in EtOH (2.9 ml, 5.75, mmol) and then a 8.8M solution of glyoxal in $H_2O$ (0.32 ml, 2.79 mmol) were added to a suspension of the ethyl (RS)-(4-cyano-phenylamino)-(3-ethoxy-5-formyl-phenyl)-acetate (406 mg, 1.15 mmol) obtained in Example 244.1 in EtOH (1 ml) at −10° C. The mixture was stirred for 1 h. at room temperature. Thereafter, additional 2M $NH_3$ in EtOH (2.9 ml, 5.75, mmol) and 8.8M glyoxal in $H_2O$ (0.32 ml, 2.79 mmol) were added and the mixture was stirred for 2 h. at room temperature. $H_2O$ was added and the mixture was extracted with EtOAc. The organic phase was dried, filtered and concentrated. The residue was purified by chromatography ($SiO_2$, hexane/EtOAc 1:1). There were obtained 179 mg, (40%) of ethyl (RS)-(4-cyano-phenylamino)-[3-ethoxy-5-(1H-imidazol-2-yl)-phenyl]-acetate as a colorless solid; MS: 391 ([M+H]$^+$).

245.2

In analogy to Example 6.2, the ethyl (RS)-(4-cyano-phenylamino)-[3-ethoxy-5-(1H-imidazol-2-yl)-phenyl]-acetate obtained in Example 235.1 was converted into ethyl (RS)-(4-carbamimidoyl-phenylamino)-[3-ethoxy-5-(1H-imidazol-2-yl)-phenyl]-acetate hydrochloride (1:1); MS: 408 ([M+H]$^+$).

Example 246

246.1

In analogy to Example 198.2, 5-ethoxybenzene-1,3-dicarbaldehyde was converted with methyl-triphenylphosphonium bromide into 3-ethoxy-5-vinyl-benzaldehyde.

246.2

In analogy to Example 1.1, the converted 3-ethoxy-5-vinyl-benzaldehyde obtained in Example 246.1 was converted with 4-aminobenzonitrile and benzyl isonitrile in EtOH into ethyl (RS)-(4-cyano-phenylamino)-(3-ethoxy-5-vinyl-phenyl)-acetate; MS: 350 ([M]$^+$).

246.3

4-Dimethylaminopyridine (11 mg, 0.085 mmol) and thereafter slowly nitroethane (66 mg, 0.856 mmol) were added at 0° C. to a solution of the ethyl (RS)-(4-cyano-phenylamino)-(3-ethoxy-5-vinyl-phenyl)-acetate (300 mg, 0.856 mmol) obtained in Example 246.2 and di-t-butyl dicarbonate (280 mg, 1.28 mmol) in acetonitrile (6 ml). The mixture was stirred for 22 h. at room temperature. Thereafter, additional di-t-butyl dicarbonate (224 mg, 1.03 mmol) and nitroethane (33 mg, 0.43 mmol) were added and the mixture was stirred overnight at room temperature. Thereafter, additional 4-dimethylaminopyridin (11 mg, 0.085 mmol) was added and the mixture was stirred for 6 h. at room temperature. The reaction mixture was concentrated and the residue was purified by chromatography (SiO2, hexane/EtOAc 2:1→EtOAc). There were obtained 200 mg (46%) of a mixture of ethyl (RS)- and (SR)-[tert-butoxycarbonyl-(4-cyano-phenyl)-amino]-[3-ethoxy-5-[(RS)-3-methyl-4,5-dihydro-isoxazol-5-yl]-phenyl]-acetate as a yellowish foam; MS: 508 ([M+H]$^+$).

246.4

In analogy to Example 6.2, the mixture of ethyl (RS)- and (SR)-[tert-butoxycarbonyl-(4-cyano-phenyl)-amino]-[3-ethoxy-5-[(RS)-3-methyl-4,5-dihydro-isoxazol-5-yl]-phenyl]-acetate obtained in Example 246.3 was converted into a mixture of ethyl (RS)- and (SR)-(4-carbamimidoyl-phenylamino)-[3-ethoxy-5-[(RS)-3-methyl-4,5-dihydro-isoxazol-5-yl]-phenyl]-acetate hydrochloride (1:1); MS: 425 ([M+H]$^+$).

Example 247

247.1

A solution of the ethyl (RS)-(4-cyano-phenylamino)-(3-ethoxy-5-vinyl-phenyl)-acetate (300 mg, 0.856 mmol) obtained in Example 236.2 in acetonitrile (2 ml) was slowly added dropwise at −30° C. to a solution of nitrosyl tetrafluoroborate (112 mg, 0.942 mmol) in acetonitrile (3 ml). The mixture was stirred for 2 h. at 0° C. and for 1.5 h. at room temperature. The reaction mixture was concentrated and the residue was purified by chromatography ($SiO_2$, $CH_2Cl_2 \rightarrow CH_2Cl_2$/MeOH 4:1). There were obtained 135 mg (38%) of ethyl (RS)-(4-cyano-phenylamino)-[3-ethoxy-5-(3-hydroxy-2-methyl-3H-imidazol-4-yl)-phenyl]-acetate as a yellowish foam; MS: 421 ([M+H]$^+$).

247.2

In analogy to Example 6.2, the ethyl (RS)-(4-cyano-phenylamino)-[3-ethoxy-5-(3-hydroxy-2-methyl-3H-imidazol-4-yl)-phenyl]-acetate obtained in Example 237.1 was converted into ethyl (RS)-(4-carbamimidoyl-phenylamino)-[3-ethoxy-5-(3-hydroxy-2-methyl-3H-imidazol-4-yl)-phenyl]-acetate hydrochloride (1:1); MS: 438 ([M+H]$^+$).

Example 248

248.1

A 20% solution of $TiCl_3$ in $H_2O$ was added dropwise at 0° C. to a solution of the ethyl (RS)-(4-cyano-phenylamino)-[3-ethoxy-5-(3-hydroxy-2-methyl-3H-imidazol-4-yl)-phenyl]-acetate (355 mg, 0.844 mmol) obtained in Example 247.1 in MeOH (4.2 ml). The mixture was stirred for 3 h. at room temperature, subsequently poured into $NaHCO_3$ solution/ice-water and extracted with $CH_2Cl_2$. The organic phase was dried, filtered and concentrated. The residue was purified by chromatography ($SiO_2$, $CH_2Cl_2 \rightarrow CH_2Cl_2$/MeOH 95:5). There were obtained 50 mg (15%) of ethyl (RS)-(4-cyano-phenylamino)-[3-ethoxy-5-(2-methyl-3H-imidazol-4-yl)-phenyl]-acetate as a yellowish solid; MS: 405 ([M+H]$^+$).

248.2

In analogy to Example 6.2, the ethyl (RS)-(4-cyano-phenylamino)-[3-ethoxy-5-(2-methyl-3H-imidazol-4-yl)-phenyl]-acetate obtained in Example 248.1 was converted into ethyl (RS)-(4-carbamimidoyl-phenylamino)-[3-ethoxy-5-(2-methyl-3H-imidazol-4-yl)-phenyl]-acetate hydrochloride (1:1); MS: 422 ([M+H]$^+$).

Example 249

249.a

In analogy to Example 75, the ethyl (RS)-(4-carbamimidoyl-phenylamino)-(3-methoxy-5-methyl-phenyl)-acetate hydrochloride (1:1) obtained in Example 190.3 was converted into (RS)-(4-carbamimidoyl-phenylamino)-(3-methoxy-5-methyl-phenyl)-acetic acid; MS: 314 ([M+H]$^+$).

249.b

In analogy to Example 70, the ethyl (RS)-(4-carbamimidoyl-phenylamino)-(3-isopropoxy-5-methyl-phenyl)-acetate hydrochloride (1:1) obtained in Example 181.3 was converted into (RS)-(4-carbamimidoyl-phenylamino)-(3-isopropoxy-5-methyl-phenyl)-acetic acid; MS: 342 ([M+H]$^+$).

249.c

In analogy to Example 75, the ethyl (RS)-(4-carbamimidoyl-phenylamino)-(3-carbamoylmethoxy-5-methyl-phenyl)-acetate hydrochloride (1:1) obtained in Example 192.2 was converted into (RS)-(4-carbamimidoyl-phenylamino)-(3-carbamoylmethoxy-5-methyl-phenyl)-acetic acid; MS: 357 ([M+H]$^+$).

249.d

In analogy to Example 75, the ethyl (RS)-(4-carbamimidoyl-phenylamino)-(3-ethoxy-5-methyl-phenyl)- acetate hydrochloride (1:1) obtained in Example 193.2 was converted into (RS)-(4-carbamimidoyl-phenylamino)-(3-ethoxy-5-methyl-phenyl)-acetic acid; MS: 326 ([M–H]$^-$).

249.e

In analogy to Example 75, the ethyl (RS)-(carbamimidoyl-phenylamino)-[3-methyl-5-(2-pyrrolidin-1-yl-ethoxy)-phenyl]-acetate hydrochloride (1:1) obtained in Example 194.2 was converted into (RS)-(4-carbamimidoyl-phenylamino)-[3-methyl-5-(2-pyrrolidin-1-yl-ethoxy)-phenyl]-acetic acid; MS: 397 ([M+H]$^+$).

249.f

In analogy to Example 75, the ethyl (RS)-(4-carbamimidoyl-phenylamino)-(3-cyclopentyloxy-5-methyl-phenyl)-acetate hydrochloride (1:1) obtained in Example 195.2 was converted into (RS)-(4-carbamimidoyl-phenylamino)-(3-cyclopentyloxy-5-methyl-phenyl)-acetic acid; MS: 368 ([M+H]$^+$).

249.g

In analogy to Example 75, the ethyl (RS)-(4-carbamimidoyl-phenylamino)-[3-methyl-5-(1-methyl-piperidin-4-yloxy)-phenyl]-acetate hydrochloride (1:1) obtained in Example 196.2 was converted into (RS)-(4-carbamimidoyl-phenylamino)-[3-methyl-5-(1-methyl-piperidin-4-yloxy)-phenyl]-acetic acid; MS: 397 ([M+H]$^+$).

249.h

In analogy to Example 75, the mixture of ethyl (RS)- and (SR)-(4-carbamimidoyl-phenylamino)-[3-[(1RS,2RS)-2-hydroxy-cyclopentyloxy]-5-methyl-phenyl]-acetate hydrochloride (1:1) obtained in Example 197.2 was converted into a mixture of (RS)- and (SR)-(4-carbamimidoyl-phenylamino)-[3-[(1RS,2RS)-2-hydroxy-cyclopentyloxy]-5-methyl-phenyl]-acetic acid; MS: 382 (IM–H]$^-$).

249.j

In analogy to Example 75, the ethyl (RS)-(4-carbamimidoyl-phenylamino)-(3-methoxy-5-vinyl-phenyl)-acetate hydrochloride (1:1) obtained in Example 198.4 was converted into (RS)-(4-carbamimidoyl-phenylamino)-(3-methoxy-5-vinyl-phenyl)-acetic acid; MS: 326 ([M+H]$^+$).

249.k

In analogy to Example 75, the ethyl (RS)-(4-carbamimidoyl-phenylamino)-(3-ethyl-5-methoxy-phenyl)-acetate hydrochloride (1:1) obtained in Example 199.2 was converted into (RS)-(4-carbamimidoyl-phenylamino)-(3-ethyl-5-methoxy-phenyl)-acetic acid; MS: 328 ([M+H]$^+$).

249.l

In analogy to Example 75, the ethyl (RS)-(4-carbamimidoyl-phenylamino)-(3-ethyl-5-isobutoxy-phenyl)-acetate hydrochloride (1:1) obtained in Example 200.3 was converted into (RS)-(4-carbamimidoyl-phenylamino)-(3-ethyl-5-isobutoxy-phenyl)-acetic acid; MS: 370 ([M+H]$^+$).

249.m

In analogy to Example 70, the ethyl (RS)-(4-carbamimidoyl-phenylamino)-[3-ethyl-5-(1-methyl-piperidin-4-yloxy)-phenyl]-acetate hydrochloride (1:1) obtained in Example 201.2 was converted into (RS)-(4-carbamimidoyl-phenylamino)-[3-ethyl-5-(1-methyl-piperidin-4-yloxy)-phenyl]-acetic acid; MS: 409 ([M+H]$^+$).

249.n

In analogy to Example 75, the ethyl (RS)-(4-carbamimidoyl-phenylamino)-[3-ethyl-5-(2-pyrrolidin-1-yl-ethoxy)-phenyl]-acetate hydrochloride (1:1) obtained in Example 202.2 was converted into (RS)-(4-carbamimidoyl-phenylamino)-[3-ethyl-5-(2-pyrrolidin-1-yl-ethoxy)-phenyl]-acetic acid; MS: 411 ([M+H]$^+$).

249.o

In analogy to Example 70, the ethyl (RS)-(4-carbamimidoyl-phenylamino)-[3-ethyl-5-(tetrahydro-pyran-4-yloxy)-phenyl]-acetate hydrochloride (1:1) obtained in Example 203.2 was converted into (RS)-(4-carbamimidoyl-phenylamino)-[3-ethyl-5-(tetrahydro-pyran-4-yloxy)-phenyl]-acetic acid; MS: 398 ([M+H]$^+$).

249.p

In analogy to Example 75, the mixture of ethyl (RS)- and (SR)-(4-carbamimidoyl-phenylamino)-[3-ethyl-5-[(RS)-tetrahydro-furan-2-ylmethoxy]-phenyl]-acetate hydrochloride (1:1) obtained in Example 204.2 was converted into (4-carbamimidoyl-phenylamino)-[3-ethyl-5-(tetrahydro-furan-2-ylmethoxy]-phenyl]-acetic acid; MS: 398 ([M+H]$^+$).

249.q

In analogy to Example 70, the ethyl (RS)-(4-carbamimidoyl-phenylamino)-(3-cyclopentyloxy-5-ethyl-phenyl)-acetate hydrochloride (1:1) obtained in Example 205.2 was converted into (RS)-(4-carbamimidoyl-phenylamino)-(3-cyclopentyloxy-5-ethyl-phenyl)-acetic acid; MS: 382 ([M+H]$^+$).

249.r

In analogy to Example 75, the ethyl (RS)-(4-carbamimidoyl-phenylamino)-[3-ethyl-5-(4-hydroxy-cyclohexyloxy)-phenyl]-acetate hydrochloride (1:1) obtained in Example 206.2 was converted into (4-carbamimidoyl-phenylamino)-[3-ethyl-5-(4-hydroxy-cyclohexyloxy)-phenyl]-acetic acid; MS: 412 ([M+H]$^+$).

249.s

In analogy to Example 70, the ethyl (RS)-(4-carbamimidoyl-phenylamino)-[3-ethyl-5-(piperidin-4-yloxy)-phenyl]-acetate hydrochloride (1:1) obtained in Example 207.2 was converted into (RS)-(4-carbamimidoyl-phenylamino)-[3-ethyl-5-(piperidin-4-yloxy)-phenyl]-acetic acid; MS: 397 ([M+H]$^+$).

249.t

In analogy to Example 75, the ethyl (RS)-(4-carbamimidoyl-phenylamino)-[3-(3-dimethylamino-2,2-dimethyl-propoxy)-5-ethyl-phenyl]-acetate obtained in Example 208.2 was converted into (RS)-(4-carbamimidoyl-phenylamino)-[3-(3-dimethylamino-2,2-dimethyl-propoxy)-5-ethyl-phenyl]-acetic acid; MS: 427 ([M+H]$^+$).

249.u

In analogy to Example 75, the ethyl (RS)-(4-carbamimidoyl-phenylamino)-[3-ethyl-5-(1-methanesulphonyl-piperidin-4-yloxy)-phenyl]-acetate hydrochloride (1:1) obtained in Example 209.3 was converted into (RS)-(4-carbamimidoyl-phenylamino)-[3-ethyl-5-(1-methanesulphonyl-piperidin-4-yloxy)-phenyl]-acetic acid; MS: 475, ([M+H]$^+$).

249.v

In analogy to Example 75, the ethyl (RS)-(4-carbamimidoyl-phenylamino)-[3-(1-ethoxy-carbonylmethyl-piperidin-4-yloxy)-5-ethyl-phenyl]-acetate hydrochloride (1:1) obtained in Example 210.2 was converted into (RS)-(4-carbamimidoyl-phenylamino)-[3-(1-carboxymethyl-piperidin-4-yloxy)-5-ethyl-phenyl]-acetic acid; MS: 455 ([M+H]$^+$).

249.w

In analogy to Example 75, the mixture of ethyl (RS)- and (SR)-(4-carbamimidoyl-phenylamino)-[3-ethyl-5-[(1RS,2RS)-2-hydroxy-cyclopentyloxy]-phenyl]-acetate hydrochloride (1:1) obtained in Example 211.2 was converted into a mixture of (RS)- and (SR)-(4-carbamimidoyl-phenylamino)-[3-ethyl-5-[(1RS,2RS)-2-hydroxy-cyclopentyloxy]-phenyl]-acetic acid; MS: 398 ([M+H]$^+$).

249.x

In analogy to Example 75, the ethyl (RS)-(4-carbamimidoyl-phenylamino)-(3-ethyl-5-phenoxy-phenyl)- acetate hydrochloride (1:1) obtained in Example 212.2 was converted into (RS)-(4-carbamimidoyl-phenylamino)-(3-ethyl-5-phenoxy-phenyl)-acetic acid; MS: 390 ([M+H]$^+$).

249.y

In analogy to Example 75, the ethyl (RS)-(4-carbamimidoyl-phenylamino)-[3-ethyl-5-(pyridin-3-yloxy)-phenyl]-acetate hydrochloride (1: 1) obtained in Example 213.2 was converted into (RS)-(4-carbamimidoyl-phenylamino)-[3-ethyl-5-(pyridin-3-yloxy)-phenyl]-acetic acid; MS: 391 ([M+H]$^+$).

249.z

In analogy to Example 75, the ethyl (RS)-(4-carbamimidoyl-phenylamino)-(3-ethoxy-5-propyl-phenyl)-acetate hydrochloride (1:1) obtained in Example 214.4 was converted into (RS)-(4-carbamimidoyl-phenylamino)-(3-methoxy-propyl-phenyl)-acetic acid; MS: 342 ([M+H]$^+$).

249.aa

In analogy to Example 75, the ethyl (RS)-(4-carbamimidoyl-phenylamino)-(3-ethoxy-5-propyl-phenyl)-acetate hydrochloride (1:1) obtained in Example 215.3 was converted into (RS)-(4-carbamimidoyl-phenylamino)-(3-ethoxy-5-propyl-phenyl)-acetic acid; MS: 356 ([M+H]$^+$).

249.ab

In analogy to Example 75, the ethyl (RS)-(4-carbamimidoyl-phenylamino)-(3-ethylamino-5-methyl-phenyl)-acetate hydrochloride (1:1) obtained in Example 216.5 was converted into (RS)-(4-carbamimidoyl-phenylamino)-(3-ethylamino-5-methyl-phenyl)-acetic acid; MS: 327 ([M+H]$^+$).

249.ac

In analogy to Example 75, the ethyl (RS)-(4-carbamimidoyl-phenylamino)-(3-diethylamino-5-methyl-phenyl)-acetate hydrochloride (1:1) obtained in Example 217.2 was converted into (RS)-(4-carbamimidoyl-phenylamino)-(3-diethylamino-5-methyl-phenyl)-acetic acid; MS: 355 ([M+H]$^+$).

249.ad

In analogy to Example 75, the ethyl (RS)-(4-carbamimidoyl-phenylamino)-(3-cyclopentylamino-5-methyl-phenyl)-acetate hydrochloride (1:1) obtained in Example 218.2 was converted into (RS)-(4-carbamimidoyl-phenylamino)-(3-cyclopentylamino-5-methyl-phenyl)-acetic acid; MS: 367 ([M+H]$^+$).

249.ae

In analogy to Example 75, the ethyl (RS)-(4-carbamimidoyl-phenylamino)-(3-methyl-5-pyrrolidin-1-yl-phenyl)-acetate hydrochloride (1:1) obtained in Example 219.2 was converted into (RS)-(4-carbamimidoyl-phenylamino)-(3-methyl-5-pyrrolidin-1-yl-phenyl)-acetic acid; MS: 353 ([M+H]$^+$).

249.af

In analogy to Example 75, the ethyl (RS)-[3-(3-butyl-ureido)-5-methyl-phenyl]-(4-carbamimidoyl-phenylamino)-acetate hydrochloride (1:1) obtained in Example 220.2 was converted into (RS)-[3-(3-butyl-ureido)-5-methyl-phenyl]-(4-carbamimidoyl-phenylamino)-acetic acid; MS: 398 ([M+H]$^+$).

249.ag

In analogy to Example 75, the mixture of ethyl (RS)- and (SR)-(4-cyano-phenylamino)-[3-[(1RS,2RS)-2-hydroxy-cyclopentylamino]-5-methyl-phenyl]-acetate hydrochloride (1:1) obtained in Example 221.2 was converted into (4-carbamimidoyl-phenylamino)-[3-(2-hydroxy-cyclopentylamino)-5-methyl-phenyl]-acetic acid; MS: 383 ([M+H]$^+$).

249.ah

In analogy to Example 75, the ethyl (RS)-(4-carbamimidoyl-phenylamino)-(3-methyl-5-{1-[3-(pyrimidin-2-ylamino)-propyl]-azepan-2-ylideneamino}-phenyl)-acetate hydrochloride (1:1) obtained in Example 222.2 was converted into (RS)-(4-carbamimidoyl-phenylamino)-(3-methyl-5-{1-[3-(pyrimidin-2-ylamino)-propyl]-azepan-2-ylideneamino}-phenyl)-acetic acid; MS: 529 ([M+H]$^+$).

249.aj

In analogy to Example 75, the ethyl (RS)-(4-carbamimidoyl-phenylamino)-(3-ethyl-5-pyrrolidin-1-yl-phenyl)-acetate hydrochloride (1:1) obtained in Example 223.6 was converted into (RS)-(4-carbamimidoyl-phenylamino)-(3-ethyl-5-pyrrolidin-1-yl-phenyl)-acetic acid; MS: 367 ([M+H]$^+$)

249.ak

In analogy to Example 75, the ethyl (RS)-(4-carbamimidoyl-phenylamino)-(3-ethyl-5-piperazin-1-yl-phenyl)-acetate hydrochloride (1:1) obtained in Example 224.2 was converted into (RS)-(RS)-(4-carbamimidoyl-phenylamino)-(3-ethyl-5-piperazin-1-yl-phenyl)-acetic acid; MS: 382 ([M+H]$^+$).

249.al

In analogy to Example 75, the ethyl (RS)-(4-carbamimidoyl-phenylamino)-[3-(cyclopentanecarbonyl-amino)-5-ethyl-phenyl]-acetate hydrochloride obtained in Example 225.2 was converted into (RS)-(4-carbamimidoyl-phenylamino)-[3-(cyclopentanecarbonyl-amino)-5-ethyl-phenyl]-acetic acid; MS: 409 ([M+H]$^+$).

249.am

In analogy to Example 75, the ethyl (RS)-(4-carbamimidoyl-phenylamino)-(3-benzene-sulphonylamino-5-ethyl-phenyl)-acetate hydrochloride (1:1) obtained in Example 226.2 was converted into (RS)-(3-benzenesulphonylamino-5-ethyl-phenyl)-(4-carbamimidoyl-phenylamino)-acetic acid; MS: 453 ([M+H]$^+$).

249.an

In analogy to Example 75, the ethyl (RS)-(4-carbamimidoyl-phenylamino)-(3-butylsulphamoyl-amino-5-ethyl-phenyl)-acetate hydrochloride (1:1) obtained in Example 227.2 was converted into (RS)-(4-carbamimidoyl-phenylamino)-(3-butylsulphamoyl-amino-5-ethyl-phenyl)-acetic acid; MS: 448 ([M+H]$^+$).

249.ao

In analogy to Example 75, the ethyl (RS)-(4-carbamimidoyl-phenylamino)-[3-ethyl-5-(1-methyl-piperidin-4-ylamino)-phenyl]-acetate hydrochloride (1:1) obtained in Example 228.2 was converted into (RS)-(4-carbamimidoyl-phenylamino)-[3-ethyl-5-(1-methyl-piperidin-4-ylamino)-phenyl]-acetic acid; MS: 410.6 ([M+H]$^+$).

249.ap

In analogy to Example 75, the ethyl (RS)-(4-carbamimidoyl-phenylamino)-{3-ethyl-5-[(pyridin-3-ylmethyl)-amino]-phenyl}-acetate hydrochloride (1:1) obtained in Example 229.2 was converted into (RS)-(4-carbamimidoyl-phenylamino)-{3-ethyl-5-[(pyridin-3-ylmethyl)-amino]-phenyl}-acetic acid; MS: 404 ([M+H]$^+$).

249.aq

In analogy to Example 75, the ethyl (RS)-[3-(bis-pyridin-3-ylmethyl-amino)-5-ethyl-phenyl]-(4-carbamimidoyl-phenylamino)-acetate hydrochloride (1:1) obtained in Example 230.2 was converted into (RS)-[3-(bis-pyridin-3-ylmethyl-amino)-5-ethyl-phenyl]-(4-carbamimidoyl-phenylamino)-acetic acid; MS: 495 ([M+H]$^+$).

249.ar

In analogy to Example 75, the ethyl (RS)-(4-carbamimidoyl-phenylamino)-[3-ethyl-5-(tetrahydro-pyran- 4-ylamino)-phenyl]-acetate hydrochloride (1:1) obtained in Example 231.2 was converted into (RS)-(4-carbamimidoyl-phenylamino)-[3-ethyl-5-(tetrahydro-pyran-4-ylamino)-phenyl]-acetic acid; MS: 397 ([M+H]$^+$).

249.as

In analogy to Example 75, the ethyl (RS)-(4-carbamimidoyl-phenylamino)-[3-ethyl-5-(tetrahydro-thiopyran-4-ylamino)-phenyl]-acetate hydrochloride (1:1) obtained in Example 232.2 was converted into (RS)-(4-carbamimidoyl-phenylamino)-[3-ethyl-5-(tetrahydro-thiopyran-4-ylamino)-phenyl]-acetic acid; MS: 413 ([M+H]$^+$).

249.at

In analogy to Example 75, the ethyl (RS)-(4-carbamimidoyl-phenylamino)-[3-(1,1-dioxo-hexahydro-11 6-thiopyran-4-ylamino)-5-ethyl-phenyl]-acetate hydrochloride (1:1) obtained in Example 233.2 was converted into (RS)-(4-carbamimidoyl-phenylamino)-[3-(1,1-dioxo-hexahydro-11 6-thiopyran-4-ylamino)-5-ethyl-phenyl]-acetic acid; MS: 445 ([M+H]$^+$).

249.au

In analogy to Example 75, the ethyl (RS)-(4-carbamimidoyl-phenylamino)-(3-ethoxy-5-pyrrolidin-1-ylmethyl-phenyl)-acetate hydrochloride (1:1) obtained in Example 234.5 was converted into (RS)-(4-carbamimidoyl-phenylamino)-(3-ethoxy-5-pyrrolidin-1-ylmethyl-phenyl)-acetic acid; MS: 397 ([M+H]$^+$)

249.av

In analogy to Example 75, the ethyl (RS)-(4-carbamimidoyl-phenylamino)-(3-cyclobutylaminomethyl-5-ethoxy-phenyl)-acetate hydrochloride obtained in Example 235.2 was converted into (RS)-(4-carbamimidoyl-phenylamino)-(3-cyclobutylaminomethyl-5-ethoxy-phenyl)-acetic acid; MS: 397 ([M+H]$^+$), 249.aw In analogy to Example 75, the ethyl (RS)-(4-carbamimidoyl-phenylamino)-(3-ethoxy-5-morpholin-4-ylmethyl-phenyl)-acetate hydrochloride obtained in Example 236.2 was converted into (RS)-(4-carbamimidoyl-phenylamino)-(3-ethoxy-5-morpholin-4-ylmethyl-phenyl)-acetic acid; MS: 413 ([M+H]$^+$).

249.ax

In analogy to Example 75, the ethyl (RS)-(4-carbamimidoyl-phenylamino)-[3-ethoxy-5-(isopropylamino-methyl)-phenyl]-acetate hydrochloride (1:1) obtained in Example 237.2 was converted into (RS)-(4-carbamimidoyl-phenylamino)-[3-ethoxy-5-(isopropylamino-methyl)-phenyl]-acetic acid; MS: 385 ([M+H]$^+$).

249.ay

In analogy to Example 75, the ethyl (RS)-(4-carbamimidoyl-phenylamino)-[3-ethoxy-5-(pyridin-2-ylaminomethyl)-phenyl]-acetate hydrochloride (1:1) obtained in Example 238.2 was converted into (RS)-(4-carbamimidoyl-phenylamino)-[3-ethoxy-5-(pyridin-2-ylaminomethyl)-phenyl]-acetic acid; MS: 420 ([M+H]$^+$).

249.az

In analogy to Example 75, the ethyl (RS)-(4-carbamimidoyl-phenylamino)-(3-ethoxy-5-imidazol-1-ylmethyl-phenyl)-acetate hydrochloride (1:1) obtained in Example 239.2 was converted into (RS)-(4-carbamimidoyl-phenylamino)-(3-ethoxy-5-imidazol-1-ylmethyl-phenyl)-acetic acid; MS: 394 ([M+H]$^+$).

249.ba

In analogy to Example 75, the ethyl (RS)-(4-carbamimidoyl-phenylamino)-(3-ethoxy-5-{[(2-methoxy-ethyl)-methyl-amino]-methyl}-phenyl)-acetate hydrochloride (1:1) obtained in Example 240.2 was converted into (RS)-(4-carbamimidoyl-phenylamino)-(3-ethoxy-5-{[(2-methoxy-ethyl)-methyl-amino]-methyl}-phenyl)-acetic acid; MS: 415 ([M+H]$^+$).

249.bb

In analogy to Example 75, the ethyl (RS)-(4-carbamimidoyl-phenylamino)-(3-diethylaminomethyl-5-ethoxy-phenyl)-acetate hydrochloride (1:1) obtained in Example 241.2 was converted into (RS)-(4-carbamimidoyl-phenylamino)-(3-diethylaminomethyl-5-ethoxy-phenyl)-acetic acid; MS: 399 ([M+H]$^+$).

249.bc

In analogy to Example 75, the ethyl (RS)-(4-carbamimidoyl-phenylamino)-[3-ethoxy-5-(4-methyl-piperazin-1-ylmethyl)-phenyl]-acetate hydrochloride (1:1) obtained in Example 242.2 was converted into (RS)-(4-carbamimidoyl-phenylamino)-[3-ethoxy-5-(4-methyl-piperazin-1-ylmethyl)-phenyl]-acetic acid; MS: 426 ([M+H]$^+$).

249.bd

In analogy to Example 75, the ethyl (RS)-(4-carbamimidoyl-phenylamino)-(3-cyclopentylaminomethyl-5-ethoxy-phenyl)-acetate hydrochloride (1:1) obtained in Example 243.2 was converted into (RS)-(4-carbamimidoyl-phenylamino)-(3-cyclopentylaminomethyl-5-ethoxy-phenyl)-acetic acid; MS: 411 ([M+H]$^+$).

249.be

In analogy to Example 75, the ethyl (RS)-[3-(1H-benzoimidazol-2-yl)-5-ethoxy-phenyl]-(4-carbamimidoyl-phenylamino)-acetate hydrochloride (1:1) obtained in Example 244.3 was converted into (RS)-[3-(1H-benzoimidazol-2-yl)-5-ethoxy-phenyl]-(4-carbamimidoyl-phenylamino)-acetic acid; MS: 430 ([M+H]$^+$).

249.bf

In analogy to Example 75, the ethyl (RS)-(4-carbamimidoyl-phenylamino)-[3-ethoxy-5-(1H-imidazol-2-yl)-phenyl]-acetate hydrochloride (1:1) obtained in Example 245.2 was converted into (RS)-(4-carbamimidoyl-phenylamino)-[3-ethoxy-5-(1H-imidazol-2-yl)-phenyl]-acetic acid; MS: 380 ([M+H]$^+$).

249.bg

In analogy to Example 75, the mixture of ethyl (RS)- and (SR)-(4-carbamimidoyl-phenylamino)-[3-ethoxy-5-[(RS)-3-methyl-4,5-dihydro-isoxazol-5-yl]-phenyl]-acetate hydrochloride (1:1) obtained in Example 246.4 was converted into a mixture of (RS)- and (SR)-(4-carbamimidoyl-phenylamino)-[3-ethoxy-5-[(RS)-3-methyl-4,5-dihydro-isoxazol-5-yl]-phenyl]-acetic acid; MS: 397 ([M+H]$^+$).

249.bh

In analogy to Example 75, the ethyl (RS)-(4-carbamimidoyl-phenylamino)-[3-ethoxy-5-(3-hydroxy-2-methyl-3H-imidazol-4-yl)-phenyl]-acetate hydrochloride (1:1) obtained in Example 247.2 was converted into (RS)-(4-carbamimidoyl-phenylamino)-[3-ethoxy-5-(3-hydroxy-2-methyl-3H-imidazol-4-yl)-phenyl]-acetic acid; MS: 410 ([M+H]$^+$).

249.bj

In analogy to Example 75, the ethyl (RS)-(4-carbamimidoyl-phenylamino)-[3-ethoxy-5-(2-methyl-3H-imidazol-4-yl)-phenyl]-acetate hydrochloride (1:1) obtained in Example 248.2 was converted into (RS)-(4-carbamimidoyl-phenylamino)-[3-ethoxy-5-(2-methyl-3H-imidazol-4-yl)-phenyl]-acetic acid; MS: 394 ([M+H]$^+$).

Example 250

250.1

In analogy to Example 18.1, the methyl (RS)-(4-cyano-phenylamino)-(3-ethoxy-5-hydroxy-phenyl)-acetate obtained in Example 124.1 was converted with 4-hydroxy-N-methylpiperidine, diethyl azodicarboxylate and triphenylphosphine in THF into methyl (RS)-(4-cyano-phenylamino)-[3-ethoxy-5-(1-methyl-piperidin-4-yloxy)-phenyl]-acetate; MS: 424 ([M+H]$^+$).

250.2

In analogy to Example 6.2, the methyl (RS)-(4-cyano-phenylamino)-[3-ethoxy-5-(1-methyl-piperidin-4-yloxy)-phenyl]-acetate obtained in Example 250.1 was converted into methyl (RS)-(4-carbamimidoyl-phenylamino)-[3-ethoxy-5-(1-methyl-piperidin-4-yloxy)-phenyl]-acetate hydrochloride (1:1); MS: 441 ([M+H]$^+$).

Example 251

251.1

3,5-Bis-(tert-butyl-dimethyl-silanyloxy)-2-fluoro-benzaldehyde was prepared from 4-fluoro-phenol according to Chem. Pharm. Bull. 1990, 38, 2939–2946.

251.2

A mixture of the 3,5-bis-(tert-butyl-dimethyl-silanyloxy)-2-fluoro-benzaldehyde (3.0 g, 7.8 mmol) obtained in Example 251.1, potassium fluoride (1.81 g, 31.2 mmol), methyl iodide (1.17 ml, 18.7 mmol) and DMF (25 ml) was stirred for 2 h. at room temperature. Water (25 ml) was added and the mixture was extracted with diethyl ether. The organic phase was washed with water, dried, filtered and concentrated. The residue was purified by chromato-graphy (SiO$_2$, cyclohexane/EtOAc 18:1=>1:1). There was obtained 0.87 g (60%) of 2-fluoro-3,5-dimethoxy-benzaldehyde as a colorless solid.

251.3

In analogy to Example 1.1, the 2-fluoro-3,5-dimethoxy-benzaldehyde obtained in Example 251.2 was converted with 4-aminobenzonitrile and benzyl isonitrile in EtOH into ethyl (RS)-(4-cyano-phenylamino)-(2-fluoro-3,5-dimethoxy-phenyl)-acetate; MS: 358 ([M]$^+$).

251.4

In analogy to Example 6.2, the ethyl (RS)-(4-cyano-phenylamino)-(2-fluoro-3,5-dimethoxy-phenyl)-acetate obtained in Example 251.3 was converted into ethyl (RS)-(4-carbamimidoyl-phenylamino)-(2-fluoro-3,5-dimethoxy-phenyl-acetate hydrochloride (1:1); MS: 376 ([M+H]$^+$).

Example 252

252.1

In analogy to Example 251.2, the 3,5-bis-(tert-butyl-dimethyl-silanyloxy)-2-fluoro-benzaldehyde obtained in Example 251.1 was converted with potassium fluoride and ethyl iodide in DMF into 3,5-diethoxy-2-fluoro-benzaldehyde.

252.2

In analogy to Example 1.1, the 3,5-diethoxy-2-fluoro-benzaldehyde obtained in Example 252.1 was converted with 4-aminobenzonitrile and benzyl isonitrile in EtOH into ethyl (RS)-(4-cyano-phenylamino)-(3,5-diethoxy-2-fluoro-phenyl)-acetate; MS: 386 ([M]$^+$).

252.3

In analogy to Example 6.2, the ethyl (RS)-(4-cyano-phenylamino)-(3,5-diethoxy-2-fluoro-phenyl)-acetate obtained in Example 252.2 was converted into ethyl (RS)-(4-carbamimidoyl-phenylamino)-(3,5-diethoxy-2-fluoro-phenyl)-acetate hydrochloride (1:1); MS: 404 ([M+H]$^+$).

Example 253

253.a

In analogy to Example 75, the ethyl (RS)-(4-carbamimidoyl-phenylamino)-[3-ethoxy-5-(1-methyl-piperidin-4-yloxy)-phenyl]-acetate hydrochloride (1:1) obtained in Example 252.3 was converted into (RS)-(4-carbamimidoyl-phenylamino)-[3-ethoxy-5-(1-methyl-piperidin-4-yloxy)-phenyl]-acetic acid; MS: 427 ([M+H]$^+$).

253.b

In analogy to Example 70, the ethyl (RS)-(4-carbamimidoyl-phenylamino)-(2-fluoro-3,5-dimethoxy-phenyl-acetate hydrochloride (1:1) obtained in Example 251.4 was converted into (RS)-(4-carbamimidoyl-phenylamino)-(2-fluoro-3,5-dimethoxy-phenyl)-acetic acid; MS: 348 ([M+H]$^+$).

253.c

In analogy to Example 70, the ethyl (RS)-(4-carbamimidoyl-phenylamino)-(3,5-diethoxy-2-fluoro-phenyl)-acetate hydrochloride (1:1) obtained in Example 252.3 was converted into (RS)-(4-carbamimidoyl-phenylamino)-(3,5-diethoxy-2-fluoro-phenyl)-acetic acid; MS: 376 ([M+H]$^+$)

Example 254

254.1

In analogy to Example 64.1, 4-hydroxy-5-isopropyl-2-methyl-benzaldehyde (obtained by formylating thymol with TiCl$_4$/dichloromethyl methyl ether, Chem. Z. 1990, 114, 144) was converted with isopropyl iodide and K$_2$CO$_3$ in DMF into 4-isopropoxy-5-isopropyl-2-methyl-benzaldehyde.

254.2

In analogy to Example 1.1, the 4-isopropoxy-5-isopropyl-2-methyl-benzaldehyde obtained in Example 253.1 was converted with 4-aminobenzonitrile and benzyl isonitrile in EtOH into ethyl (RS)-(4-cyano-phenylamino)-(4-isopropoxy-5-isopropyl-2-methyl-phenyl)-acetate; MS: 394 ([M]$^+$).

254.3

In analogy to Example 6.2, the ethyl (RS)-(4-cyano-phenylamino)-(4-isopropoxy-5-isopropyl-2-methyl-phenyl)-acetate obtained in Example 253.2 was converted into ethyl (RS)-(4-carbamimidoyl-phenylamino)-(4-isopropoxy-5-isopropyl-2-methyl-phenyl)-acetate hydrochloride (1:1).

Example 255

255.1

The ethyl (RS)-(4-cyano-phenylamino)-(4-isopropoxy-5-isopropyl-2-methyl-phenyl)-acetate (921 mg, 2.34 mmol) obtained in Example 254.2 was dissolved in CH$_2$Cl$_2$ and cooled to −78° C. A 1M solution of BBr$_3$ in CH$_2$Cl$_2$ (9.4 ml, 9.4 mmol) was slowly added dropwise. After 15 min. the reaction mixture was left to warm to 0° C. and was stirred for 1.5 h. at 0° C. Ice-water (30 ml) was added and the mixture was stirred for 10 min. at 0° C. The organic phase was separated and the aqueous phase was extracted with CH$_2$Cl$_2$. The organic phase was dried, filtered and concentrated. The crude product was dissolved in acetone, Cs$_2$CO$_3$ (918 mg, 2.76 mmol) and iodoacetamide (447 mg, 2.41 mmol) were added and the mixture was stirred for 6 h. at room temperature. A dilute aqueous solution of KHSO$_4$ was added and the mixture was extracted with CH$_2$Cl$_2$. The organic phase was dried, filtered and concentrated, and the residue was purified by chromatography (SiO$_2$, hexane/EtOAc 1:1=>1:2). There were obtained 704 mg, (73%) of ethyl (RS)-(4-cyano-phenylamino)-(4-carbamoylmethoxy-5-isopropyl-2-methyl-phenyl)-acetate as a colorless foam.

255.2

In analogy to Example 6.2, the ethyl (RS)-(4-cyano-phenylamino)-(4-carbamoylmethoxy-5-isopropyl-2-methyl-phenyl)-acetate obtained in Example 255.1 was converted into ethyl (RS)-(4-carbamimidoyl-phenylamino)-(4- carbamoylmethoxy-5-isopropyl-2-methyl-phenyl)-acetate hydrochloride (1:1); MS: 427 ([M+H]$^+$).

Example 256

256.a

In analogy to Example 75, the ethyl (RS)-(4-carbamimidoyl-phenylamino)-(4-isopropoxy-5-isopropyl-2-methyl-phenyl)-acetate hydrochloride (1:1) obtained in Example 254.3 was converted into (RS)-(4-carbamimidoyl-phenylamino)-(4-isopropoxy-5-isopropyl-2-methyl-phenyl)-acetic acid; MS: 384 ([M+H]$^+$).

256.b

In analogy to Example 75, the ethyl (RS)-(4-carbamimidoyl-phenylamino)-(4-carbamoylmethoxy-5-isopropyl-2-methyl-phenyl)-acetate hydrochloride (1:1) obtained in Example 255.2 was converted into (RS)-(4-carbamimidoyl-phenylamino)-(4-carbamoylmethoxy-5-isopropyl-2-methyl-phenyl)-acetic acid; MS: 399 ([M+H]$^+$).

Example 257

257.1

In analogy to Example 1.1., piperonal was reacted with 4-aminobenzonitrile and benzyl isonitrile using ethanol in place of methanol. There was obtained ethyl (RS)-benzo[1,3]-dioxol-5-yl-(4-cyano-phenylamino)-acetate, MS (ISP) m/z 325 (M+H)+, 347 (M+Na)$^+$.

257.2

In analogy to Example 1.2., ethyl (RS)-benzo[1,3]dioxol-5-yl-(4-cyano-phenylamino)-acetate was hydrolyzed with lithium hydroxide to (RS)-benzo[1,3]dioxol-5-yl-(4-cyano-phenylamino)-acetic acid; MS (ISP) m/z 297 (M+H)$^+$, 314 (M+NH4)$^+$.

257.3

In analogy to Example 1.3., (RS)-benzo[1,3]dioxol-5-yl-(4-cyano-phenylamino)-acetic acid was converted with hydroxylamine hydrochloride and triethylamine into (E)- and/or (Z)-(RS)-benzo[1,3]dioxol-5-yl-[4-(N-hydroxycarbamimidoyl)-phenylamino]-acetic acid; MS (ISP) m/z 330 (M+H)$^+$.

Example 258

In analogy to Example 3, (E)- and/or (Z)-(RS)-benzo[1,3]dioxol-5-yl-[4-(N-hydroxycarbamimidoyl)-phenylamino]-acetic acid (see Example 257.3) was hydrogenated with Raney-nickel to (RS)-benzo[1,3]dioxol-5-yl-(4-carbamimidoyl-phenylamino)-acetate; MS (ISP) m/z 314 (M+H)$^+$.

Example 259

259.1

In analogy to Example 1.1., 3-fluoro-p-anisaldehyde was reacted with 4-aminobenzonitrile and benzyl isonitrile using ethanol in place of methanol. There was obtained ethyl (RS)-(4-cyano-phenylamino)-(3-fluoro-4-methoxy-phenyl)-acetate; MS (EI) m/z 328 M$^+$.

259.2

In analogy to Example 1.2., ethyl (RS)-(4-cyano-phenylamino)-(3-fluoro-4-methoxy-phenyl)-acetate was hydrolyzed with lithium hydroxide to (RS)-(4-cyano-phenylamino)-(3-fluoro-4-methoxy-phenyl)-acetic acid; MS (ISP) m/z 300 (M+H)$^+$, 318 (M+NH4)$^+$.

259.3

In analogy to Example 1.3., (RS)-(4-cyano-phenylamino)-(3-fluoro-4-methoxy-phenyl)-acetic acid was converted with hydroxylamine hydrochloride and triethylamine into (E)- and/or (Z)-(RS)-(3-fluoro-4-methoxy-phenyl)-[4-(N-hydroxycarbamimidoyl)-phenylamino]-acetic acid; MS (ISP) m/z 334 (M+H)$^+$.

Example 260

In analogy to Example 3, (E)- and/or (Z)-(RS)-(3-Fluoro-4-methoxy-phenyl)-[4-(N-hydroxycarbamimidoyl)-phenylamino]-acetic acid (see Example 259.3) was hydrogenated with Raney-nickel to (RS)-(4-carbamimidoyl-phenylamino)-(3-fluoro-4-methoxy-phenyl)-acetic acid; MS (ISP) m/z 318 (M+H)$^+$.

Example 261

261.1

In analogy to Example 1.1., 1,4-benzodioxan-6-carboxaldehyde was reacted with 4-aminobenzonitrile and benzyl isonitrile using ethanol in place of methanol. There was obtained ethyl (RS)-(4-cyano-phenylamino)-(2,3-dihydro-benzo[1,4]dioxin-6-yl)-acetate; MS (ISP) m/z 339 (M+H)$^+$, 361 (M+Na)$^+$.

261.2

In analogy to Example 1.2. ethyl (RS)-(4-cyano-phenylamino)-(2,3-dihydro-benzo[1,4]-dioxin-6-yl)-acetate was hydrolyzed with lithium hydroxide to (RS)-(4-cyano-phenylamino)-(2,3-dihydro-benzo[1,4]dioxin-6-yl)-acetic acid; MS (ISN) m/z 3309 (M–H)$^-$.

261.3

In analogy to Example 1.3. (RS)-(4-cyano-phenylamino)-(2,3-dihydro-benzo[1,4]dioxin-6-yl)-acetic acid was converted with hydroxylamine hydrochloride and triethylamine into (RS)(2,3-dihydro-benzo[1,4]dioxin-6-yl)-[4-(N-hydroxycarbamimidoyl)-phenylamino]-acetic acid; MS (ISP) m/z 344 (M+H)$^+$.

Example 262

In analogy to Example 3, (RS)(2,3-dihydro-benzo[1,4]dioxin-6-yl)-[4-(N-hydroxycarbamimidoyl)-phenylamino]-acetic acid (see Example 261.3) was hydrogenated with Raney-nickel to (RS)-(4-carbamimidoyl-phenylamino)-(2,3-dihydro-benzo[1,4]dioxin-6-yl)-acetic acid; MS (ISP) m/z 328 (M+H)$^+$.

Example 263

In analogy to Example 1.1., 3-hydroxymethyl-4-isopropoxy-benzaldehyde was reacted with 4-aminobenzonitrile and toluene-4-sulphonylmethyl isocyanide using ethanol in place of methanol. There was obtained ethyl (RS)-[4-(N-hydroxycarbamimidoyl)-phenylamino]-(3-hydroxymethyl-4-isopropoxy-phenyl)-acetate; MS (ISP) m/z 402 (M+H)$^+$.

Example 264

In analogy to Example 3, ethyl (RS)-[4-(N-hydroxycarbamimidoyl)-phenylamino]-(3-hydroxymethyl-4-isopropoxy-phenyl)-acetate (see Example 263) was hydrogenated with Raney-nickel to ethyl (RS)-(4-carbamimidoyl-phenylamino)-(3-hydroxymethyl-4-isopropoxy-phenyl)-acetate; MS (ISP) m/z 386 (M+H)$^+$.

Example 265

In analogy to Example 75, ethyl (RS)-(4-carbamimidoyl-phenylamino)-(3-hydroxymethyl-4-isopropoxy-phenyl)-acetate (see Example 264) was hydrolyzed with lithium hydroxide to (RS)-(4-carbamimidoyl-phenylamino)-(3-hydroxymethyl-4-isopropoxy-phenyl)-acetic acid. The product was crystallized from water; MS (ISP) m/z 358 (M+H)$^+$, 375, (M+NH4)$^+$.

Example 266

266.1

In analogy to Example 1.1., was 4-isopropoxy-3-methoxymethyl-benzaldehyde with 4-aminobenzonitrile and toluene-4-sulphonylmethyl isocyanide using ethanol in place of methanol. There was obtained ethyl (RS)-(4-cyano-phenylamino)-(4-isopropoxy-3-methoxymethyl-phenyl)-acetate; MS (ISP) m/z 405 (M+Na)$^+$.

266.2

In analogy to Example 6.2, ethyl (RS)-(4-cyano-phenylamino)-(4-isopropoxy-3-methoxymethyl-phenyl)-acetate was converted in a Pinner reaction into ethyl (RS)-(4-carbamimidoyl-phenylamino)-(4-isopropoxy-3-methoxymethyl-phenyl)-acetate hydrochloride (1:1); MS (ISP) m/z 400 (M+H)$^+$.

Example 267

In analogy to Example 75, ethyl (RS)-(4-carbamimidoyl-phenylamino)-(4-isopropoxy-3-methoxymethyl-phenyl)-acetate hydrochloride (1:1) (see Example 266.2) was hydrolyzed with lithium hydroxide to (RS)-(4-carbamimidoyl-phenylamino)-(4-isopropoxy-3-methoxymethyl-phenyl)-acetic acid. The product was crystallized from water; MS (ISP) m/z 372 (M+H)$^+$.

Example 268

268.1

In analogy to Example 1.1., 3,4-dichlorobenzaldehyde was reacted with 4-aminobenzonitrile and benzyl isonitrile using ethanol in place of methanol. There was obtained ethyl (RS)-(4-cyano-phenylamino)-(3,4-dichloro-phenyl)-acetate; MS (ISP) m/z 349.3 (M+H)$^+$, 366.1 (M+NH4)$^+$.

268.2

In analogy to Example 6.2, ethyl (RS)-(4-cyano-phenylamino)-(3,4-dichloro-phenyl)-acetate was converted in a Pinner reaction into ethyl (RS)-(4-carbamimidoyl-phenylamino)-(3,4-dichloro-phenyl)-acetate; MS (ISP) m/z 366.2 (M+H)$^+$.

Example 269

In analogy to Example 75, ethyl (RS)-(4-carbamimidoyl-phenylamino)-(3,4-dichloro-phenyl)-acetate (see Example 268.2) was hydrolyzed with lithium hydroxide to (RS)-(4-carbamimidoyl-phenylamino)-(3,4-dichloro-phenyl)-acetic acid; MS (ISP) m/z 338.1 (M+H)$^+$.

Example 270

270.1

In analogy to Example 1.1., ethyl (2-formyl-4-trifluoromethoxy-phenoxy)-acetate was reacted with 4-aminobenzonitrile and benzyl isonitrile using ethanol in place of methanol. There was obtained ethyl (RS)-(4-cyano-phenylamino)-(2-ethoxycarbonylmethoxy-5-trifluoromethoxy-phenyl)-acetate; MS (ISP) m/z 467 (M+H)$^+$, 489 (M+Na)$^+$.

270.2

In analogy to Example 1.2., ethyl (RS)-(4-cyano-phenylamino)-(2-ethoxycarbonylmethoxy-5-trifluoromethoxy-phenyl)-acetate was hydrolyzed with lithium hydroxide to (RS)-(2-carboxymethoxy-5-trifluoromethoxy-phenyl)-(4-cyano-phenylamino)-acetic acid; MS (ISP) m/z 411 (M+H)$^+$, 433 (M+Na)$^+$.

270.3

In analogy to Example 1.3., (RS)-(2-carboxymethoxy-5-trifluoromethoxy-phenyl)-(4-cyano-phenylamino)-acetic acid was converted with hydroxylamine hydrochloride and triethylamine into (E)- and/or (Z)-(RS)-(2-carboxymethoxy-5-trifluoromethoxy-phenyl)-[4-(N-hydroxycarbamimidoyl)-phenylamino]-acetic acid; MS (ISP) m/z 444 (M+H)$^+$, 466 (M+Na)$^+$.

Example 271

In analogy to Example 3, (E)- and/or (Z)-(RS)-(2-carboxymethoxy-5-trifluoromethoxy-phenyl)-[4-(N-hydroxycarbamimidoyl)-phenylamino]-acetic acid (see Example 270.3) was hydrogenated with Raney-Nickel to (RS)-(4-carbamimidoyl-phenylamino)-(2-carboxymethoxy-5-trifluoromethoxy-phenyl)-acetic acid; MS (ISP) m/z 428 (M+H)$^+$.

Example 272

272.1

In analogy to Example 12.1, 5-chlorosalicylaldehyde was converted with bromoethanol into 5-chloro-2-(2-hydroxy-ethoxy)-benzaldehyde; MS (EI) m/z 200 M$^+$.

272.2

In analogy to Example 1.1., 5-chloro-2-(2-hydroxy-ethoxy)-benzaldehyde was reacted with 4-aminobenzonitrile and toluene-4-sulphonylmethyl isocyanide using ethanol in place of methanol. There was obtained ethyl (RS)-[5-chloro-2-(2-hydroxy-ethoxy)-phenyl]-(4-cyano-phenylamino)-acetate; MS (ISN) m/z 373 (M−H)$^-$.

272.3

In analogy to Example 6.2, ethyl (RS)-[5-chloro-2-(2-hydroxy-ethoxy)-phenyl]-(4-cyano-phenylamino)-acetate was converted in a Pinner reaction into ethyl (RS)-(4-carbamimidoyl-phenylamino)-[5-chloro-2-(2-hydroxy-ethoxy)-phenyl]-acetate hydrochloride (1:1); MS (ISP) m/z 392 (M+H)$^+$.

Example 273

In analogy to Example 75, ethyl (RS)-(4-carbamimidoyl-phenylamino)-[5-chloro-2-(2-hydroxy-ethoxy)-phenyl]-acetate hydrochloride (1:1) (see Example 272.3) was hydrolyzed with lithium hydroxide to (RS)-(4-carbamimidoyl-phenylamino)-[5-chloro-2-(2-hydroxy-ethoxy)-phenyl]-acetic acid; MS (ISP) m/z 364 (M+H)$^+$.

Example 274

274.1

In analogy to Example 1.1., 5-methoxypiperonal was reactedwith 4-aminobenzonitrile and benzyl isonitrile using ethanol in place of methanol. There was obtained ethyl (RS)-(4-cyano-phenylamino)-(7-methoxy-benzo[1,3]dioxol-5-yl)-acetate; MS (ISP) m/z 355 (M+H)$^+$, 377 (M+Na)$^+$.

274.2

In analogy to Example 1.2., ethyl (RS)-(4-cyano-phenylamino)-(7-methoxy-benzo[1,3]dioxol-5-yl)-acetate was hydrolyzed with lithium hydroxide to (RS)-(4-cyano-phenylamino)-(7-methoxy-benzo[1,3]dioxol-5-yl)-acetic acid; MS (ISN) m/z 325 (M−H)$^-$.

274.3

In analogy to Example 1.3., (RS)-(4-cyano-phenylamino)-(7-methoxy-benzo[1,3]dioxol-5-yl)-acetic acid was converted with hydroxylamine hydrochloride and triethylamine into (E)- and/or (Z)-(RS)-[4-(N-hydroxycarbamimidoyl)-phenylamino]-(7-methoxy-benzo[1,3]-dioxol-5-yl)-acetic acid; MS (ISP) m/z 360 (M+H)$^+$, 382 (M+Na)$^+$.

Example 275

In analogy to Example 3, (E)- and/or (Z)-(RS)-[4-(N-hydroxycarbamimidoyl)-phenylamino]-(7-methoxy-benzo[1,3]dioxol-5-yl)-acetic acid (see Example 270.3) was hydrogenated with Raney-Nickel to (RS)-(4-carbamimidoyl-phenylamino)-(7-methoxy-benzo[1,3]dioxol-5-yl)-acetic acid; MS (ISP) m/z 344 (M+H)$^+$.

Example 276

276.1
In analogy to Example 12.1, 3,5-dichlorosalicylaldehyde was converted with tert-butyl bromoacetate in methyl ethyl ketone under reflux within 4 hours into tert-butyl (2,4-dichloro-6-formyl-phenoxy)-acetate; MS (EI) m/z 304(M) 248/250 (M-tert.butyl).

276.2
In analogy to Example 1.1., tert-butyl (2,4-dichloro-6-formyl-phenoxy)-acetate was reacted with 4-amino-N-hydroxybenzamidine and benzyl isonitrile. There was obtained methyl (RS)-(2-tert-butoxycarbonylmethoxy-3,5-dichloro-phenyl)-[4-(N-hydroxycarbamimidoyl)-phenylamino]-acetate; MS (ISP) m/z 498.2 (M+H)$^+$, 520.2 (M+Na)$^+$.

Example 277

In analogy to Example 75, methyl (RS)-(2-tert-butoxycarbonylmethoxy-3,5-dichloro-phenyl)-[4-(N-hydroxycarbamimidoyl)-phenylamino]-acetate was hydrolyzed with lithium hydroxide to (RS)-(2-carboxymethoxy-3,5-dichloro-phenyl)-[4-(N-hydroxycarbamimidoyl)-phenylamino]-acetic acid; the crude product was purified by treatment with THF and acetone; MS (ISP) m/z 428.4 (M+H)$^+$, 450.3 (M+Na)$^+$.

Example 278

3.7 g of finely powdered lithium carbonate were added to a solution of 1.96 g of methyl (RS)-(2-tert-butoxycarbonylmethoxy-3,5-dichloro-phenyl)-[4-(N-hydroxycarbamimidoyl)-phenylamino]-acetate (see Example 276.2) in 200 ml of THF and 100 ml of water. The suspension was stirred for 8 hours at 55–60° C. The reaction mixture was then concentrated and the aqueous suspension remaining was neutralized with 100 ml 1N HCl. The precipitate was filtered off, washed with water and dried overnight at 50° C. in a high vacuum. There were obtained 1.59 g of (RS)-(2-tert-butoxycarbonylmethoxy-3,5-dichloro-phenyl)-[4-(N-hydroxycarbamimidoyl)-phenylamino]-acetic acid; MS (ISP) m/z 484.3 (M+H)$^+$, 506.2 (M+Na)$^+$.

Example 279

In analogy to Example 3, (RS)-(2-tert-butoxycarbonylmethoxy-3,5-dichloro-phenyl)-[4-(N-hydroxycarbamimidoyl)-phenylamino]-acetic acid (see Example 278) was hydrogenated with Raney-nickel to (RS)-(2-tert-butoxycarbonylmethoxy-3,5-dichloro-phenyl)-(4-carbamimidoyl-phenylamino)-acetic acid; MS (ISP) m/z 468.2 (M+H)$^+$, 490.2 (M+Na)$^+$.

Example 280

In analogy to Example 75, (RS)-(2-tert-butoxycarbonylmethoxy-3,5-dichloro-phenyl)-(4-carbamimidoyl-phenylamino)-acetic acid (see Example 279) was hydrolyzed with lithium hydroxide to (RS)-(4-carbamimidoyl-phenylamino)-(2-carboxymethoxy-3,5-dichloro-phenyl)-acetic acid; MS (ISP) m/z 412.3 (M+H)$^+$, 468.1 (M–H+Ni)$^+$.

Example 281

281.1
In analogy to Example 12.1, 5-bromo-2-hydroxy-3-methoxy-benzaldehyde was converted with tert-butyl bromoacetate in methyl ethyl ketone under reflux within 3 hours into ethyl (4-bromo-2-formyl-6-methoxy-phenoxy)-acetate; MS (EI) m/z 316/318 M$^+$.

282.2
In analogy to Example 1.1., ethyl (4-bromo-2-formyl-6-methoxy-phenoxy)-acetate was reacted with 4-aminobenzonitrile and toluene-4-sulphonylmethyl isocyanide using ethanol in place of methanol. There was obtained ethyl (RS)-(5-bromo-2-ethoxycarbonylmethoxy-3-methoxy-phenyl)-(4-cyano-phenylamino)-acetate; MS (ISP) m/z 491/493 (M+H)$^+$, 513/515 (M+Na)$^+$.

282.3
In analogy to Example 1.2., ethyl (RS)-(5-bromo-2-ethoxycarbonylmethoxy-3-methoxy-phenyl)-(4-cyano-phenylamino)-acetate was hydrolyzed with lithium hydroxide to (RS)-(5-bromo-2-carboxymethoxy-3-methoxy-phenyl)-(4-cyano-phenylamino)-acetic acid; MS (ISN) m/z 433/435 (M–H)$^-$.

282.4
In analogy to Example 1.3., (RS)-(5-bromo-2-carboxymethoxy-3-methoxy-phenyl)-(4-cyano-phenylamino)-acetic acid was converted with hydroxylamine hydrochloride and triethylamine into (E)- and/or (Z)-(RS)-(5-bromo-2-carboxymethoxy-3-methoxy-phenyl)-[4-(N-hydroxycarbamimidoyl)-phenylamino]-acetic acid; MS (ISP) m/z 468/470 (M+H)$^+$, 490/492 (M+Na)$^+$.

Example 282

In analogy to Example 3, (E)- and/or (Z)-(RS)-(5-bromo-2-carboxymethoxy-3-methoxy-phenyl)-[4-(N-hydroxycarbamimidoyl)-phenylamino]-acetic acid (see Example 281.4) was hydrogenated with Raney-nickel to (RS)-(5-bromo-2-carboxymethoxy-3-methoxy-phenyl)-(4-carbamimidoyl-phenylamino)-acetic acid; MS (ISP) m/z 452/454 (M+H)$^+$.

Example 283

283.1
In analogy to Example 1.1., ethyl (4-chloro-2-formyl-6-methoxy-phenoxy)-acetate was reacted with 4-aminobenzonitrile and toluene-4-sulphonylmethyl isocyanide using ethanol in place of methanol. There was obtained ethyl (RS)-(5-chloro-2-ethoxycarbonylmethoxy-3-methoxy-phenyl)-(4-cyano-phenylamino)-acetate; MS (ISN) m/z 445/447 (M–H)$^-$.

283.2
In analogy to Example 6.2, ethyl (RS)-(5-chloro-2-ethoxycarbonylmethoxy-3-methoxy-phenyl)-(4-cyano-phenylamino)-acetate was converted in a Pinner reaction into ethyl (RS)-(4-carbamimidoyl-phenylamino)-(5-chloro-2-ethoxycarbonylmethoxy-3-methoxy-phenyl)-acetate hydrochloride (1:1); MS (ISP) m/z 464/466 (M+H)$^+$.

Example 284

In analogy to Example 75, ethyl (RS)-(4-carbamimidoyl-phenylamino)-(5-chloro-2-ethoxycarbonylmethoxy-3-methoxy-phenyl)-acetate hydrochloride (1:1) (see Example 283.2) was hydrolyzed with lithium hydroxide to (RS)-(4-carbamimidoyl-phenylamino)-(2-carboxymethoxy-5-chloro-3-methoxy-phenyl)-acetic acid; MS (ISP) m/z 408/410 (M+H)$^+$, 430/432 (M+Na)$^+$.

Example 285

285.1
In analogy to Example 12.1, 3,5-dichlorosalicylaldehyde was converted with iodoethanol in ethyl methyl ketone under reflux within 18 hours into 3,5-dichldro-2-(2-hydroxy-ethoxy)-benzaldehyde; MS (EI) m/z 234/236(M$^+$).

285.2
In analogy to Example 1.1., 3,5-dichloro-2-(2-hydroxy-ethoxy)-benzaldehyde was reacted with 4-amino-N- hydroxybenzamidine and benzyl isonitrile. There was obtained ethyl (RS)-[3,5-dichloro-2-(2-hydroxy-ethoxy)-phenyl]-[4-(N-hydroxycarbamimidoyl)-phenylamino]-acetate; MS (ISP) m/z 442.3 (M+H)$^+$, 464.1 (M+Na)$^+$.

Example 286

In analogy to Example 75, ethyl (RS)-[3,5-dichloro-2-(2-hydroxy-ethoxy)-phenyl]-[4-(N-hydroxycarbamimidoyl)-phenylamino]-acetate (see Example 285.2) was hydrolyzed with lithium hydroxide to (RS)-[3,5-dichloro-2-(2-hydroxy-ethoxy)-phenyl]-[4-(N-hydroxycarbamimidoyl)-phenylamino]-acetic acid; the crude product was purified by chromatography, MS (ISP) m/z 414.2 (M+H)$^+$, 436.3 (M+Na)$^+$.

Example 287

In analogy to Example 3, (RS)-[3,5-dichloro-2-(2-hydroxy-ethoxy)-phenyl]-[4-(N-hydroxycarbamimidoyl)-phenylamino]-acetic acid (see Example 286) was hydrogenated with Raney-nickel to (RS)-(4-carbamimidoyl-phenylamino)-[3,5-dichloro-2-(2-hydroxy-ethoxy)-phenyl]-acetic acid; MS (ISP) m/z 398.2 (M+H)$^+$, 420.2 (M+Na)$^+$.

Example 288

288.1

In analogy to Example 12.1, 3,5-dichlorosalicylaldehyde was reacted with tert-butyl bromoacetate in ethyl methyl ketone under reflux within 2 hours into tert-butyl (2,4-dibromo-6-formyl-phenoxy)-acetate; MS (EI) m/z 394((M) 338/340 (M-tert.butyl).

288.2

In analogy to Example 1.1., tert-butyl (2,4-dibromo-6-formyl-phenoxy)-acetate was reacted with 4-amino-N-hydroxybenzamidine and benzyl isonitrile. There was obtained ethyl (RS)-(3,5-dibromo-2-tert-butoxycarbonylmethoxy-phenyl)-[4-(N-hydroxycarbamimidoyl)-phenylamino]-acetate.

Example 289

In analogy to Example 75, ethyl (RS)-(3,5-dibromo-2-tert-butoxycarbonylmethoxy-phenyl)-[4-(N-hydroxycarbamimidoyl)-phenylamino]-acetate (see Example 288.2) was hydrolyzed with lithium hydroxide to (RS)-(3,5-dibromo-2-carboxymethoxy-phenyl)-[4-(N-hydroxycarbamimidoyl)-phenylamino]-acetic acid; MS (ISP) m/z 518.0 (M+H)$^+$, 540.1 (M+Na)$^+$.

Example 290

In analogy to Example 3, (RS)-(3,5-dibromo-2-carboxymethoxy-phenyl)-[4-(N-hydroxycarbamimidoyl)-phenylamino]-acetic acid (see Example 289) was hydrogenated with Raney-nickel to (RS)-(4-carbamimidoyl-phenylamino)-(3,5-dibromo-2-carboxymethoxy-phenyl)-acetic acid; MS (ISP) m/z 502.0 (M+H)$^+$.

Example 291

291.1

In analogy to Example 12.1, 5-bromo-2-hydroxy-3-methoxy-benzaldehyde was converted with bromoethanol in DMF at 85° C. wuthin 5 hours into 5-bromo-2-(2-hydroxy-ethoxy)-3-methoxy-benzaldehyde; MS (EI) m/z 274/276 M$^+$.

291.2

In analogy to Example 1.1., 5-bromo-2-(2-hydroxy-ethoxy)-3-methoxy-benzaldehyde was reacted with 4-aminobenzonitrile and toluene-4-sulphonylmethyl isocyanide using ethanol in place of methanol. There was obtained ethyl (RS)-[5-bromo-2-(2-hydroxy-ethoxy)-3-methoxy-phenyl]-(4-cyano-phenylamino)-acetate; MS (ISP) m/z 449/451 (M+H)$^+$, 471/473 (M+Na)$^+$.

291.3

In analogy to Example 6.2, ethyl (RS)-[5-bromo-2-(2-hydroxy-ethoxy)-3-methoxy-phenyl]-(4-cyano-phenylamino)-acetate was converted in a Pinner reaction into ethyl (RS)-[5-bromo-2-(2-hydroxy-ethoxy)-3-methoxy-phenyl]-(4-carbamimidoyl-phenylamino)-acetate hydrochloride (1:1); MS (ISP) m/z 466/468 (M+H)$^+$.

Example 292

In analogy to Example 75, ethyl (RS)-[5-bromo-2-(2-hydroxy-ethoxy)-3-methoxy-phenyl]-(4-carbamimidoyl-phenylamino)-acetate hydrochloride (1:1) (see Example 291.3) was hydrolyzed with lithium hydroxide to (RS)-[5-bromo-2-(2-hydroxy-ethoxy)-3-methoxy-phenyl]-(4-carbamimidoyl-phenylamino)-acetic acid; MS (ISP) m/z 438/440 (M+H)$^+$.

Example 293

293.1

A solution of 5.0 g of 3,5-dichlorosalicylaldehyde in 50 ml of DMF was treated with 3.23 g of potassium-tert.-butylate and 6.6 g of allyl iodide and stirred under argon at 65° C. After 2 hours the reaction mixture was concentrated, treated with ice-water and extracted with ethyl acetate. The organic phases were dried over sodium sulphate and concentrated. The residue was chrromatographed over silica gel and gave 5.5 g of 2-allyloxy-3,5-dichloro-benzaldehyde; MS (EI) m/z 230/232 M$^+$.

293.2

In analogy to Example 1.1., 2-allyloxy-3,5-dichloro-benzaldehyde was reacted with 4-aminobenzonitrile and toluene-4-sulphonylmethyl isocyanide using ethanol in place of methanol. There was obtained ethyl (RS)-(2-allyloxy-3,5-dichloro-phenyl)-(4-cyano-phenylamino)-acetate; MS (EI) m/z 404/406 M$^+$.

293.3

In analogy to Example 6.2, ethyl (RS)-(2-allyloxy-3,5-dichloro-phenyl)-(4-cyano-phenylamino)-acetate was converted in a Pinner reaction into ethyl (RS)-(2-allyloxy-3,5-dichloro-phenyl)-(4-carbamimidoyl-phenylamino)-acetate hydrochloride (1:1); MS (ISP) m/z 422/424 (M+H)$^+$.

Example 294

In analogy to Example 75, ethyl (RS)-(2-allyloxy-3,5-dichloro-phenyl)-(4-carbamimidoyl-phenylamino)-acetate hydrochloride (1:1) (see Example 293.3) was hydrolyzed with lithium hydroxide to (RS)-(2-allyloxy-3,5-dichloro-phenyl)-(4-carbamimidoyl-phenylamino)-acetic acid; MS (ISP) m/z 394/396 (M+H)$^+$.

Example 295

A solution of 300 mg of ethyl (RS)-(2-allyloxy-3,5-dichloro-phenyl)-(4-carbamimidoyl-phenylamino)-acetate hydrochloride (1:1) (see Example 293.3) in 5 ml of ethanol was treated with hydrogen in ther presence of a catalytic amount of platinum dioxide for 45 minutes while stirring. The reaction mixture was suction filtered over Speedex. The filtrate was concentrated and gave 270 mg of ethyl (RS)-(4-carbamimidoyl-phenylamino)-(3,5-dichloro-2-hydroxy-phenyl)-acetate hydrochloride (1:1); MS (ISP) m/z 382/384 (M+H)$^+$.

Example 296

In analogy to Example 75, ethyl (RS)-(4-carbamimidoyl-phenylamino)-(3,5-dichloro-2-hydroxy-phenyl)-acetate hydrochloride (1:1) (see Example 295) was hydrolyzed with lithium hydroxide to (RS)-(4-carbamimidoyl-phenylamino)-(3,5-dichloro-2-hydroxy-phenyl)-acetic acid; MS (ISP) m/z 354/356 (M+H)⁺.

Example 297

A solution of 275 mg of ethyl (RS)-(2-allyloxy-3,5-dichloro-phenyl)-(4-carbamimidoyl-phenylamino)-acetate hydrochloride (1: 1) (see Example 293.3) in 5 ml of ethanol was hydrogenatedpin the presence of a catalytic amount of palladium on calcium carbonate for 30 minutes while stirring. The reaction mixture was suction filtered over Speedex. The filtrate was concentrated and gave, after chromatographic separation over silica gel, 210 mg of ethyl (RS)-(4-carbamimidoyl-phenylamino)-(3,5-dichloro-2-propoxy-phenyl)-acetate hydrochloride (1:1), MS (ISP) m/z 424/426 (M+H)⁺.

Example 298

In analogy to Example 75, ethyl (RS)-(4-carbamimidoyl-phenylamino)-(3,5-dichloro-2-propoxy-phenyl)-acetate hydrochloride (1:1) (see Example 297) was hydrolyzed with lithium hydroxide to (RS)-(4-carbamimidoyl-phenylamino)-(3,5-dichloro-2-propoxy-phenyl)-acetic acid; MS (ISP) m/z 396/398 (M+H)⁺.

Example 299

299.1
In analogy to Example 293.1, 3,5-dichlorosalicylaldehyde was converted with diethylene glycol in DMF at 100° C. within 16 hours into 3,5-dichloro-2-[2-(2-hydroxy-ethoxy)-ethoxy]-benzaldehyde; MS (EI) m/z 278 (M), 190 (M-88).

299.2
In analogy to Example 1.1., 3,5-dichloro-2-[2-(2-hydroxy-ethoxy)-ethoxy]-benzaldehyde was reacted with 4-aminobenzonitrile and benzyl isonitrile using ethanol in place of methanol. There was obtained ethyl (RS)-(4-cyano-phenylamino)-{3,5-dichloro-2-[2-(2-hydroxy-ethoxy)-ethoxy]-phenyl}-acetate; MS (ISP) m/z 453.2 (M+H)⁺, 475.2 (M+Na)⁺.

299.2
In analogy to Example 6.2, ethyl (RS)-(4-cyano-phenylamino)-{3,5-dichloro-2-[2-(2-hydroxy-ethoxy)-ethoxy]-phenyl}-acetate was converted in a Pinner reaction into ethyl (RS)-(4-carbamimidoyl-phenylamino)-{3,5-dichloro-2-[2-(2-hydroxy-ethoxy)-ethoxy]-phenyl}-acetate hydrochloride; MS (ISP) m/z 470.2 (M+H)⁺, 492.2 (M+Na)⁺.

Example 300

In analogy to Example 75, ethyl (RS)-(4-carbamimidoyl-phenylamino)-{3,5-dichloro-2-[2-(2-hydroxy-ethoxy)-ethoxy]-phenyl}-acetate hydrochloride (see Example 299.3) was hydrolyzed with lithium hydroxide to (RS)-(4-carbamimidoyl-phenylamino)-{3,5-dichloro-2-[2-(2-hydroxy-ethoxy)-ethoxy]-phenyl}-acetic acid; MS (ISP) m/z 442.3 (M+H)⁺, 464.3 (M+Na)⁺.

Example 301

301.1
In analogy to Example 293.1, 5-bromo-3-ethyl-salicylaldehyde (Reg.No. 57704-12-8) was converted with 2-iodoethanol in DMF at 80° C. within 6 hours into 5-bromo-3-ethyl-2-(2-hydroxy-ethoxy)-benzaldehyde; MS (ISN) m/z 451.0 (M–H)⁺.

301.2
In analogy to Example 1.1., 5-bromo-3-ethyl-2-(2-hydroxy-ethoxy)-benzaldehyde was reacted with 4-aminobenzonitrile and benzyl isonitrile using ethanol in place of methanol. There was obtained ethyl (RS)-[5-bromo-3-ethyl-2-(2-hydroxy-ethoxy)-phenyl]-(4-cyano-phenylamino)-acetate; MS (ISP) m/z 449.3 (M+H)⁺, 471.0 (M+Na)⁺.

301.3
In analogy to Example 6.2, ethyl (RS)-[5-bromo-3-ethyl-2-(2-hydroxy-ethoxy)-phenyl]-(4-cyano-phenylamino)-acetate was converted in a Pinner reaction into ethyl (RS)-[5-bromo-3-ethyl-2-(2-hydroxy-ethoxy)-phenyl]-(4-carbamimidoyl-phenylamino)-acetate hydrochloride; MS (ISP) m/z 464.3.466.3 (M+H)⁺.

Example 302

In analogy to Example 75, ethyl (RS)-[5-bromo-3-ethyl-2-(2-hydroxy-ethoxy)-phenyl]-(4-carbamimidoyl-phenylamino)-acetate hydrochloride (see Example 301.3) was hydrolyzed with lithium hydroxide to (RS)-[5-bromo-3-ethyl-2-(2-hydroxy-ethoxy)-phenyl]-(4-carbamimidoyl-phenylamino)-acetic acid; MS (ISP) m/z 436.2, 438.3 (M+H)⁺, 458.3, 460.4 (M+Na)⁺.

Example 303

303.1
In analogy to Example 293.1, 3-bromo-5-chloro-salicylaldehyde was converted with 2-iodo-O-tetrahydropyranylethanol (Reg.No. 96388-83-9) in DMF at 80° C. within 4 hours into (RS)-3-bromo-5-chloro-2-[2-(tetrahydro-pyran-2-yloxy)-ethoxy]-benzaldehyde; MS (EI) m/z 362 (M), 261 (M-99).

303.2
In analogy to Example 1.1., (RS)-3-bromo-5-chloro-2-[2-(tetrahydro-pyran-2-yloxy)-ethoxy]-benzaldehyde was reacted with 4-aminobenzonitrile and benzyl isonitrile using ethanol in place of methanol. There was obtained ethyl (RS)-[3-bromo-5-chloro-2-(2-hydroxy-ethoxy)-phenyl]-(4-cyano-phenylamino)-acetate; MS (EI) m/z 454 (M), 379 (M-75,).

303.3
In analogy to Example 6.2 ethyl (RS)-[3-bromo-5-chloro-2-(2-hydroxy-ethoxy)-phenyl]-(4-cyano-phenylamino)-acetate was converted in a Pinner reaction into ethyl (RS)-[3-bromo-5-chloro-2-(2-hydroxy-ethoxy)-phenyl]-(4-carbamimidoyl-phenylamino)-acetate hydrochloride converted, MS (ISP) m/z 472.0 (M+H)⁺, 494.0 (M+Na)⁺.

Example 304

In analogy to Example 75, ethyl (RS)-[3-bromo-5-chloro-2-(2-hydroxy-ethoxy)-phenyl]-(4-carbamimidoyl-phenylamino)-acetate hydrochloride (see Example 303.3) was hydrolyzed with lithium hydroxide to (RS)-[3-bromo-5-chloro-2-(2-hydroxy-ethoxy)-phenyl]-(4-carbamimidoyl-phenylamino)-acetic acid; MS (ISP) m/z 442/444.2 (M+H)⁺, 464/466.1 (M+Na)⁺.

Example 305

305.1
In analogy to Example 293.1, 5-chloro-6-hydroxy-m-anisaldehyde (Reg.No. 90110-33-1) was converted with 2-iodoethanol in DMF at 70° C. within 3 hours into 3-chloro-2-(2-hydroxy-ethoxy)-5-methoxy-benzaldehyde; MS (EI) m/z 230 M⁺.

305.2
In analogy to Example 1.1., 3-chloro-2-(2-hydroxy-ethoxy)-5-methoxy-benzaldehyde was reacted with 4-aminobenzonitrile and toluene-4-sulphonylmethyl isocyanide using ethanol in place of methanol. There was obtained ethyl (RS)-[3-chloro-2-(2-hydroxy-ethoxy)-5-methoxy-phenyl]-(4-cyano-phenylamino)-acetate; MS (ISP) m/z 405 (M+H)$^+$, 427 (M+Na)$^+$.
305.3

In analogy to Example 6.2, ethyl (RS)-[3-chloro-2-(2-hydroxy-ethoxy)-5-methoxy-phenyl]-(4-cyano-phenylamino)-acetate was converted in a Pinner reaction into ethyl (RS)-(4-carbamimidoyl-phenylamino)-[3-chloro-2-(2-hydroxy-ethoxy)-5-methoxy-phenyl]-acetate hydrochloride (1:1); MS (ISP) m/z 422 (M+H)$^+$.

Example 306

In analogy to Example 75, ethyl (RS)-(4-carbamimidoyl-phenylamino)-[3-chloro-2-(2-hydroxy-ethoxy)-5-methoxy-phenyl]-acetate hydrochloride (1:1) (see Example 305.3) was hydrolyzed with lithium hydroxide to (RS)-(4-carbamimidoyl-phenylamino)-[3-chloro-2-(2-hydroxy-ethoxy)-5-methoxy-phenyl]-acetic acid; MS (ISP) m/z 394 (M+H)$^+$.

Example 307

307.1

In analogy to Example 293.1, 3,5-dichlorosalicylaldehyde was converted with 2-iodoacetamide in DMF at 70° C. within 4 hours into 2-(2,4-dichloro-6-formyl-phenoxy)-acetamide; MS (EI) m/z 247 (M),189 (M-58).

307.2

In analogy to Example 1.1., 2-(2,4-dichloro-6-formyl-phenoxy)-acetamide was reacted with 4-aminobenzonitrile and benzyl isonitrile. There was obtained methyl (RS)-(2-carbamoylmethoxy-3,5-dichloro-phenyl)-(4-cyano-phenylamino)-acetate; MS (ISP) m/z 408.2 (M+H)$^+$, 430.3 (M+Na)$^+$.

307.3

In analogy to Example 6.2, methyl (RS)-(2-carbamoylmethoxy-3,5-dichloro-phenyl)-(4-cyano-phenylamino)-acetate converted in a Pinner reaction into methyl (RS)-(4-carbamimidoyl-phenylamino)-(2-carbamoylmethoxy-3,5-dichloro-phenyl)-acetate hydrochloride; MS (ISP) m/z 425.4 (M+H)$^+$, 427.1 (M+Na)$^+$.

Example 308

In analogy to Example 75, methyl (RS)-(4-carbamimidoyl-phenylamino)-(2-carbamoylmethoxy-3,5-dichloro-phenyl)-acetate hydrochloride (see Example 307.3) was hydrolyzed with lithium hydroxide to (RS)-(4-carbamimidoyl-phenylamino)-(2-carbamoylmethoxy-3,5-dichloro-phenyl)-acetic acid; MS (ISP) m/z 411.3 (M+H)$^+$.

Example 309

309.1

In analogy to Example 293.1, 3,5-dichlorosalicylaldehyde was converted with 2-chloro-N,N-dimethylacetamide in DMF at 100° C. within 3 hours into 2-(2,4-dichloro-6-formyl-phenoxy)-N,N-dimethyl-acetamide; MS (EI) m/z 275, (M),240 (M–Cl).

309.2

In analogy to Example 1.1., 2-(2,4-dichloro-6-formyl-phenoxy)-N,N-dimethyl-acetamide was reacted with 4-aminobenzonitrile and benzyl isonitrile. There was obtained methyl (RS)-(4-cyano-phenylamino)-(3,5-dichloro-2-dimethylcarbamoylmethoxy-phenyl)-acetate; MS (EI) m/z 435 (M), 376 (M-59l).

309.3

In analogy to Example 6.2, methyl (RS)-(4-cyano-phenylamino)-(3,5-dichloro-2-dimethylcarbamoylmethoxy-phenyl)-acetate was converted in a Pinner reaction into methyl (RS)-(4-carbamimidoyl-phenylamino)-(3,5-dichloro-2-dimethylcarbamoylmethoxy-phenyl)-acetate hydrochloride; MS (ISP) m/z 453.4 (M+H)$^+$, 475.2 (M+Na)$^+$.

Example 310

In analogy to Example 75, methyl (RS)-(4-carbamimidoyl-phenylamino)-(3,5-dichloro-2-dimethylcarbamoylmethoxy-phenyl)-acetate hydrochloride (see Example 309.3) was hydrolyzed with lithium hydroxide to (RS)-(4-carbamimidoyl-phenylamino)-(3,5-dichloro-2-dimethylcarbamoylmethoxy-phenyl)-acetic acid; MS (ISP) m/z 439.3 (M+H)$^+$, 461.1 (M+Na)$^+$.

Example 311

311.1

In analogy to Example 293.1, 3,5-dichlorosalicylaldehyde was converted with 2-chloro-N-cyclopropylacetamide in DMF at 100° C. within 4 hours into N-cyclopropyl-2-(2,4-dichloro-6-formyl-phenoxy)-acetamide; MS (ISP) m/z 288.1 (M+H)$^+$, 310.0 (M+Na)$^+$.

311.2

In analogy to Example 1.1., N-cyclopropyl-2-(2,4-dichloro-6-formyl-phenoxy)-acetamide was reacted with 4-aminobenzonitrile and benzyl isonitrile. There was obtained methyl (RS)-(4-cyano-phenylamino)-(3,5-dichloro-2-cyclopropylcarbamoylmethoxy-phenyl)-acetate; MS (ISP) m/z 448.31 (M+H)$^+$, 470.3 (M+Na)$^+$.

311.3

In analogy to Example 6.2, methyl (RS)-(4-cyano-phenylamino)-(3,5-dichloro-2-cyclopropylcarbamoylmethoxy-phenyl)-acetate was converted in a Pinner reaction into methyl (RS)-(4-carbamimidoyl-phenylamino)-(3,5-dichloro-2-cyclopropylcarbamoylmethoxy-phenyl)-acetate hydrochloride; MS (ISP) m/z 465.2 (M+H)$^+$, 487.2 (M+Na)$^+$.

Example 312

In analogy to Example 75, methyl (RS)-(4-carbamimidoyl-phenylamino)-(3,5-dichloro-2-cyclopropylcarbamoylmethoxy-phenyl)-acetate hydrochloride (see Example 311.3) was hydrolyzed with lithium hydroxide to (RS)-(4-carbamimidoyl-phenylamino)-(3,5-dichloro-2-cyclopropylcarbamoylmethoxy-phenyl)-acetic acid; MS (ISP) m/z 451.3 (M+H)$^+$.

Example 313

313.1

61 mg of potassium chlorate and 0.5 ml of a 2.5% osmium tetroxide solution in tert.-butanol were added to a solution of 202 mg of ethyl (RS)-(2-allyloxy-3,5-dichloro-phenyl)-(4-cyano-phenylamino)-acetate (see Example 293.2) in 5 ml of acetone and 1.5 ml of water. The reaction mixture was stirred for 16 hours at room temperature, then concentrated. and extractedwith ice-water/chloroform. The organic phases were concentrated and the residue was chromatographed over silica gel. There were obtained 170 mg of a mixture of ethyl (RS)- and (SR)-(4-cyano-phenylamino)-[3,5-dichloro-2-[(RS)-2,3-dihydroxy-propoxy]-phenyl]-acetate; MS (ISP) m/z 439/441 (M+H)$^+$, 461/463 (M+Na)$^+$.

313.2

In analogy to Example 6.2, a mixture of ethyl (RS)- and (SR)-(4-cyano-phenylamino)-[3,5-dichloro-2-[(RS)-2,3-dihydroxy-propoxy]-phenyl]-acetate was converted in a Pinner reaction into a mixture of ethyl (RS)- and (SR)-(4- carbamimidoyl-phenylamino)-[3,5-dichloro-2-[(RS)-2,3-dihydroxy-propoxy]-phenyl]-acetate hydrochloride (1:1); MS (ISP) m/z 4561458 (M+H)$^+$.

Example 314

In analogy to Example 75, a mixture of ethyl (RS)- and (SR)-(4-carbamimidoyl-phenylamino)-[3,5-dichloro-2-[(RS)-2,3-dihydroxy-propoxy]-phenyl]-acetate hydrochloride (1:1) (see Example 311.3) was hydrolyzed with lithium hydroxide to a mixture of (RS)- and (SR)-(4-carbamimidoyl-phenylamino)-[3,5-dichloro-2-[(RS)-2,3-dihydroxy-propoxy]-phenyl]-acetic acid; MS (ISP) m/z 428/430 (M+H)$^+$.

Example 315

315.1

In analogy to Example 12.1, was 3.5-dibromosalicylaldehyde was converted with iodoethanol in ethyl methyl ketone under reflux within 18 hours into 3,5-dibromo-2-(2-hydroxy-ethoxy)-benzaldehyde; MS (EI) m/z 324 (M), 280 (M-44).

315.2

In analogy to Example 1.1., 3,5-dibromo-2-(2-hydroxy-ethoxy)-benzaldehyde was reacted with 4-aminobenzonitrile and benzyl isonitrile using ethanol in place of methanol. There was obtained ethyl (RS)-(4-cyano-phenylamino)-[3,5-dibromo-2-(2-hydroxy-ethoxy)-phenyl]-acetate.

315.3

In analogy to Example 1.2., ethyl (RS)-(4-cyano-phenylamino)-[3,5-dibromo-2-(2-hydroxy-ethoxy)-phenyl]-acetate was hydrolyzed with lithium hydroxide to (RS)-(4-cyano-phenylamino)-[3,5-dibromo-2-(2-hydroxy-ethoxy)-phenyl]-acetic acid; MS (ISN) m/z 469.0 (M−H)$^-$, 425.1(M-CO$_2$).

315.4

In analogy to Example 6.2, (RS)-(4-cyano-phenylamino)-[3,5-dibromo-2-(2-hydroxy-ethoxy)-phenyl]-acetic acid was converted in a Pinner reaction into methyl (RS)-(4-carbamimidoyl-phenylamino)-[3,5-dibromo-2-(2-hydroxy-ethoxy)-phenyl]-acetate hydrochloride; MS (ISP) m/z 502.1 (M+H)$^+$.

Example 316

In analogy to Example 75, methyl (RS)-(4-carbamimidoyl-phenylamino)-[3,5-dibromo-2-(2-hydroxy-ethoxy)-phenyl]-acetate hydrochloride (see Example 315.4) was hydrolyzed with lithium hydroxide to (RS)-(4-carbamimidoyl-phenylamino)-[3,5-dibromo-2-(2-hydroxy-ethoxy)-phenyl]-acetic acid; MS (ISP) m/z 488.1 (M+H)$^+$, 510.1 (M+Na)$^+$.

Example 317

317.1

In analogy to Example 293.1, 5-chloro-3-ethyl-salicylaldehyde was converted with 2-iodoethanol at 75° C. within 6 hours into 5-chloro-3-ethyl-2-(2-hydroxy-ethoxy)-benzaldehyde; MS (EI) m/z 228 (M), 210 (M-H$_2$O).

317.2

In analogy to Example 1.1., 5-chloro-3-ethyl-2-(2-hydroxy-ethoxy)-benzaldehyde was reacted with 4-aminobenzonitrile and benzyl isonitrile. There was obtained methyl (RS)-[5-chloro-3-ethyl-2-(2-hydroxy-ethoxy)-phenyl]-(4-cyano-phenylamino)-acetate; MS (ISP) m/z 389.3 (M+H)$^+$, 411.3 (M+Na)$^+$.

317.3

In analogy to Example 6.2, methyl (RS)-[5-chloro-3-ethyl-2-(2-hydroxy-ethoxy)-phenyl]-(4-cyano-phenylamino)-acetate was converted in a Pinner reaction into (RS)-(4-carbamimidoyl-phenylamino)-[5-chloro-3-ethyl-2-(2-hydroxy-ethoxy)-phenyl]-acetate hydrochloride; MS (ISP) m/z 406.4 (M+H)$^+$.

Example 318

In analogy to Example 75, methyl (RS)-(4-carbamimidoyl-phenylamino)-[5-chloro-3-ethyl-2-(2-hydroxy-ethoxy)-phenyl]-acetate hydrochloride (see Example 338.3) was hydrolyzed with lithium hydroxide to (RS)-(4-carbamimidoyl-phenylamino)-[5-chloro-3-ethyl-2-(2-hydroxy-ethoxy)-phenyl]-acetic acid; MS (ISP) m/z 392.2 (M+H)$^+$, 414.3 (M+Na)$^+$.

Example 319

319.1

In analogy to Example 18.1, 5-chloro-3-iodo-salicylaldehyde was converted with diisopropyl azodicarboxylate (DIAD) and 2-benzyloxyethanol in a Mitsonobu reaction into 2-(2-benzyloxy-ethoxy)-5-chloro-3-iodo-benzaldehyde; MS (EI) m/z 416 (M), 198 (M-H$_2$O).

319.2

In analogy to Example 1.1., 2-(2-benzyloxy-ethoxy)-5-chloro-3-iodo-benzaldehyde was reacted with 4-aminobenzonitrile and toluene-4-sulphonylmethyl isocyanide. There was obtained methyl (RS)-[2-(2-benzyloxy-ethoxy)-5-chloro-3-iodo-phenyl]-(4-cyano-phenylamino)-acetate, MS (EI) m/z 576 (M), 517 (M-COOCH$_3$).

319.3

In analogy to Example 6.2, methyl (RS)-[2-(2-benzyloxy-ethoxy)-5-chloro-3-iodo-phenyl]-(4-cyano-phenylamino)-acetate was converted in a Pinner reaction into methyl (RS)-[2-(2-benzyloxy-ethoxy)-5-chloro-3-iodo-phenyl]-(4-carbamimidoyl-phenylamino)-acetate hydrochloride; MS (ISP) m/z 594.1 (M+H)$^+$, 615.9 (M+Na)$^+$.

Example 320

In analogy to Example 75, methyl (RS)-[2-(2-benzyloxy-ethoxy)-5-chloro-3-iodo-phenyl]-(4-carbamimidoyl-phenylamino)-acetate hydrochloride (see Example 319.3) was hydrolyzed with lithium hydroxide to (RS)-[2-(2-benzyloxy-ethoxy)-5-chloro-3-iodo-phenyl]-(4-carbamimidoyl-phenylamino)-acetic acid; MS (ISP) m/z 580.0 (M+H)$^+$, 601.9 (M+Na)$^+$.

Example 321

321.1

In analogy to Example 293.1, 5-chloro-3-iodo-salicylaldehyde (Reg.No. 215124-03-1) was converted with 1-(tert-butyldimethylsilyloxy)-2-iodoethane (Reg.No. 101166-65-8) in dimethylacetamide at 60° C. within 6 hours into 2-[2-(tert-butyl-dimethyl-silanyloxy)-ethoxy]-5-chloro-3-iodo-benzaldehyde; MS (EI) m/z 439 (M−1), 383 (M-t-butyl).

321.2

In analogy to Example 1.1., 2-[2-(tert-butyl-dimethyl-silanyloxy)-ethoxy]-5-chloro-3-iodo-benzaldehyde was reacted with 4-aminobenzonitrile and toluene-4-sulphonylmethyl isocyanide. There was obtained methyl (RS)-[5-chloro-2-(2-hydroxy-ethoxy)-3-iodo-phenyl]-(4-cyano-phenylamino)-acetate, MS (EI) m/z 486 (M+1), 427 (M-COOCH$_3$).

321.3

In analogy to Example 6.2 methyl (RS)-[5-chloro-2-(2-hydroxy-ethoxy)-3-iodo-phenyl]-(4-cyano-phenylamino)-acetate was converted in a Pinner reaction into methyl (RS)-(4-carbamimidoyl-phenylamino)-[5-chloro-2-(2- hydroxy-ethoxy)-3-iodo-phenyl]-acetate hydrochloride; MS (ISP) m/z 504.1 (M+H)+.

Example 322

In analogy to Example 75, methyl (RS)-(4-carbamimidoyl-phenylamino)-[5-chloro-2-(2-hydroxy-ethoxy)-3-iodo-phenyl]-acetate hydrochloride (see Example 321.3) was hydrolyzed with lithium hydroxide to (RS)-(4-carbamimidoyl-phenylamino)-[5-chloro-2-(2-hydroxy-ethoxy)-3-iodo-phenyl]-acetic acid; MS (ISP) m/z 490.2 (M+H)+, 512.1 (M+Na)+.

Example 323

323.1

A solution of 119.9 ml of 2-ethylphenol in 500 ml of chlorobenzene was treatedwith 126.9 g of iodine and 134.5 g of copper(II) chloride and stirred under reflux for 5.5 hours. After cooling the reaction mixture was filtered and the residue was washed with methylene chloride. The combined filtrates were washed with aqueous sodium thiosulphate solution and ice-water. The organic phases were dried over sodium sulphate and concentrated. The residue was crystallized from hexane and gave 79.3 g of 2-ethyl-4-iodo-phenol. The mother liquor was chromatographed over silica gel and gave a further 41 g of 2-ethyl-4-iodo-phenol; MS (EI) m/z 248 (M).

323.2

A solution of 19.5 g of 2-ethyl-4-iodo-phenol in 150 ml of DMF was treated portionwise at 0° C. over 15 minutes with 9.37 g of potassium tert.-butylate versetzt and the mixture was stirred for 30 minutes. Then, about 100 ml of solvent were removed in a high vacuum. The residue was treated dropwise at 0° C. over 1 hour with 12.66 g of chloromethyl methyl ether and then poured into ice-water and extracted with ether-hexane (1:2). The organic phases were washed with sodium chloride solution and water and concentrated. The residue was chromatographed over silica gel and gave 21.8 g of 2-ethyl-4-iodo-1-methoxymethoxy-benzene; MS (EI) m/z 292 (M).

323.3

A solution of cyclopropylmagnesium bromide, freshly prepared from 2.49 g of magnesium and 13.3 g of cyclopropyl bromide in 40 ml of THF, was treated with 1.2 g of bistriphenyl-phosphine-nickel chloride and at 35–45° C. within 20 minutes with a solution of 20.8 g of 2-ethyl-4-iodo-1-methoxymethoxy-benzene in 40 ml of toluene. After stirring for 2 hours the reaction mixture was poured into aqueous ammonium chloride solution and extracted with ether. The organic phases were washed with water, saturated aqueous sodium bicarbonate solution and sodium chloride solution, dried over magnesium sulphate and concentrated. The residue was chromatographed over silica gel and gave 12.7 g of 4-cyclopropyl-2-ethyl-1-methoxymethoxy-benzene; MS (EI) m/z 206 (M), 176 (M-CH$_2$O).

323.4

A solution of 12.0 g of 4-cyclopropyl-2-ethyl-1-methoxymethoxy-benzene in 240 ml of 2N acetic acid was stirred for 24 hours at 90° C. The reaction mixture was poured into ice-water and extracted with dichloromethane. The organic phases were washed with water, saturated aqueous sodium bicarbonate solution and sodium chloride solution, dried over magnesium sulphate and concentrated. The residue was chromatographed over silica gel and gave 8.7 g of 4-cyclopropyl-2-ethyl-phenol; MS (EI) m/z 162 (M), 147 (M-CH$_3$).

323.5

In analogy to Example 89.1, 4-cyclopropyl-2-ethyl-phenol was formylated to 5-cyclopropyl-3-ethyl-2-hydroxy-benzaldehyde; MS (EI) m/z 190 (M), 175, (M-CH$_3$).

323.6

In analogy to Example 293.1, 5-cyclopropyl-3-ethyl-2-hydroxy-benzaldehydewas converted with 2-iodoethanol at 60° C. within 6 hours into 5-cyclopropyl-3-ethyl-2-(2-hydroxy-ethoxy)-benzaldehyde; MS (EI) m/z 234 (M), 216 (M-H$_2$O).

323.7

In analogy to Example 1.1., 5-cyclopropyl-3-ethyl-2-(2-hydroxy-ethoxy)-benzaldehyde was reacted with 4-aminobenzonitrile and benzyl isonitrile. There was obtained methyl (RS)-(4-cyano-phenylamino)-[5-cyclopropyl-3-ethyl-2-(2-hydroxy-ethoxy)-phenyl]-acetate; MS (ISP) m/z 395.4 (M+H)+, 417.4 (M+Na)+.

323.8

In analogy to Example 6.2, methyl (RS)-(4-cyano-phenylamino)-[5-cyclopropyl-3-ethyl-2-(2-hydroxy-ethoxy)-phenyl]-acetate was converted in a Pinner reaction into (RS)-(4-carbamimidoyl-phenylamino)-[5-cyclopropyl-3-ethyl-2-(2-hydroxy-ethoxy)-phenyl]-acetate hydrochloride; MS (ISP) m/z 412.2 (M+H)+.

Example 324

In analogy to Example 75, methyl (RS)-(4-carbamimidoyl-phenylamino)-[5-cyclopropyl-3-ethyl-2-(2-hydroxy-ethoxy)-phenyl]-acetate hydrochloride (see Example 336.3) was hydrolyzed with lithium hydroxide to (RS)-(4-carbamimidoyl-phenylamino)-[5-cyclopropyl-3-ethyl-2-(2-hydroxy-ethoxy)-phenyl]-acetic acid; MS (ISP) m/z 398.4 (M+H)+, 420.4 (M+Na)+.

Example 325

325.1

In analogy to Example 293.1, 5-bromo-3-ethyl-salicylaldehyde (Reg.No. 57704-12-8) was converted with 2-iodoacetamide in dimethylacetamide at 40° C. within 2 hours into 2-(4-bromo-2-ethyl-6-formyl-phenoxy)-acetamide; MS (EI) m/z 285 (M), 241 (M-CONH$_2$).

325.2

In analogy to Example 1.1., 2-(4-bromo-2-ethyl-6-formyl-phenoxy)-acetamide was reacted with 4-aminobenzonitrile and benzyl isonitrile. There was obtained methyl (RS)-(5-bromo-2-carbamoylmethoxy-3-ethyl-phenyl)-(4-cyano-phenylamino)-acetate; MS (ISP) m/z 446.2 (M+H)+, 468.1 (M+Na)+.

Example 326

In analogy to Example 75, methyl (RS)-(5-bromo-2-carbamoylmethoxy-3-ethyl-phenyl)-(4-carbamimidoyl-phenylamino)-acetate hydrochloride (see Example 325.3) was hydrolyzed with lithium hydroxide to (RS)-(5-bromo-2-carbamoylmethoxy-3-ethyl-phenyl)-(4-carbamimidoyl-phenylamino)-acetic acid; MS (ISP) m/z 449, 451.3 (M+H)+, 471.1 (M+Na)+.

Example 327

327.1

In analogy to Example 18.1, 5-chloro-3-iodo-salicylaldehyde was converted with diisopropyl azodicarboxylate (DIAD) and ethyl 2-hydroxymethacrylate in a Mitsonobu reaction into 2-(4-chloro-2-formyl-6-iodo-phenoxy)-ethyl 2-methyl-acrylate; MS (EI) m/z 394 (M), 281 (M–113).

327.2

In analogy to Example 1.1., 2-(4-chloro-2-formyl-6-iodo-phenoxy)-ethyl 2-methyl-acrylate was reacted with 4-aminobenzonitrile and toluene-4-sulphonylmethyl isocyanide. There was obtained 2-{4-chloro-2-[(4-cyanophenylamino)-methoxycarbonyl-methyl]-6-iodo-phenoxy}-ethyl (RS)-2-methyl-acrylate; MS (ISP) m/z 555.1 (M+H)⁺, 576.9 (M+Na)⁺.

327.3

1.99 g of allyltributyltin and 0.35 g of tetrakis (triphenylphosphine)palladium were added to a solution of 1.66 g of 2-{4-chloro-2-[(4-cyano-phenylamino)-methoxycarbonyl-methyl]-6-iodo-phenoxy}-ethyl (RS)-2-methyl-acrylate in 15 ml of absolutem dimethylacetamide and the mixture was stirred at 90° C. for 2.5 hours. Then, the mixture was concentrated in a high vacuum. The residue was treated with ice-water and extracted with ethyl acetate. The organic phases were washed with sodium chloride solution and water and concentrated. The residue was chromatographed over silica gel and gave 1.3 g of 2-{2-allyl-4-chloro-6-[(4-cyano-phenylamino)-methoxycarbonyl-methyl]-phenoxy}-ethyl (RS)-2-methyl-acrylate.

327.4

In analogy to Example 6.2, was 2-{2-allyl-4-chloro-6-[(4-cyano-phenylamino)-methoxy-carbonyl-methyl]-phenoxy}-ethyl (RS)-2-methyl-acrylate was converted in a Pinner reaction into 2-{2-allyl-6-[(4-carbamimidoyl-phenylamino)-methoxycarbonyl-methyl]-4-chloro-phenoxy}-ethyl (RS)-2-methyl-acrylate hydrochloride; MS (ISP) m/z 486.3 (M+H)⁺.

Example 328

In analogy to Example 75,2-{2-allyl-6-[(4-carbamimidoyl-phenylamino)-methoxycarbonyl-methyl]-4-chloro-phenoxy}-ethyl (RS)-2-methyl-acrylate hydrochloride (see Example 327.3) was hydrolyzed with lithium hydroxide to (RS)-[3-allyl-5-chloro-2-(2-hydroxy-ethoxy)-phenyl]-(4-carbamimidoyl-phenylamino)-acetic acid; MS (ISP) m/z 404.4 (M+H)⁺, 426.4 (M+Na)⁺.

Example 329

329.1

A solution of 30.0 g of 5-ethyl-salicylaldehyde (Reg.No. 52411-35-5) in 500 ml of DMF was treated with 36.0 g of sodium iodide and 67.6 g of Chloroamine T and stirred for one hour at room temperature. The reaction mixture was concentrated in a high vacuum, poured into ice-water, made acid with 2N hydrochloric acid and extracted with ethyl acetate. The organic phases were washed with aqueous sodium thiosulphate solution, saturated sodium chloride solution and ice-water, dried over sodium sulphate and concentrated. The residue was taken up in ether-hexane (1:1) and filtered. The filtrate was concentrated and gave 45.8 g of 5-ethyl-2-hydroxy-3-iodo-benzaldehyde; MS (EI) m/z 276 M⁺.

329.2

In analogy to Example 18.1, 5-ethyl-2-hydroxy-3-iodo-benzaldehyde was converted with DIAD and 2-benzyloxyethanol in a Mitsonobu reaction into 2-(2-benzyloxy-ethoxy)-5-ethyl-3-iodo-benzaldehyde; MS (EI) m/z 410 M⁺.

329.3

In analogy to Example 1.1., 2-(2-benzyloxy-ethoxy)-5-ethyl-3-iodo-benzaldehyde was reacted with 4-aminobenzonitrile and toluene-4-sulphonylmethyl isocyanide using ethanol in place of methanol. There was obtained ethyl (RS)-[2-(2-benzyloxy-ethoxy)-5-ethyl-3-iodo-phenyl]-(4-cyano-phenylamino)-acetate; MS (ISP) m/z 585 (M+H)⁺.

329.4

A solution of 7.1 g of ethyl (RS)-[2-(2-benzyloxy-ethoxy)-5-ethyl-3-iodo-phenyl]-(4-cyano-phenylamino)-acetate in 50 ml of dichloromethane was treated with 7.29 g of iodotrimethylsilane. After 12 hours at room temperature the same amount of iodotrimethylsilane was added and the mixture was stirred for 18 hours at room temperature. Then, ethanol was added. The reaction mixture was concentrated, poured on to ice/aqueous sodium bisulphite solution and extracted with ethyl acetate. The organic phases were washed with aqueous sodium hydrogen carbonate solution and ice-water, dried over sodium sulphate and concentrated. Crystallization of the residue gave 3.8 g of ethyl (RS)-(4-cyano-phenylamino)-[5-ethyl-2-(2-hydroxy-ethoxy)-3-iodo-phenyl]-acetate. Chromatography of the mother liquor on silica gel gave an additional 1.83 g of product; MS (ISP) m/z 495 (M+H)⁺, 517 (M+Na)⁺.

329.5

In analogy to Example 293.3, ethyl (RS)-(4-cyano-phenylamino)-[5-ethyl-2-(2-hydroxy-ethoxy)-3-iodo-phenyl]-acetate was converted with allyltributyltin and tetrakis(triphenyl-phosphine)palladium in a Stille reaction into ethyl (RS)-[3-allyl-5-ethyl-2-(2-hydroxy-ethoxy)-phenyl]-(4-cyano-phenylamino)-acetate; MS (ISP) m/z 409 (M+H)⁺.

329.6

In analogy to Example 6.2, ethyl (RS)-[3-allyl-5-ethyl-2-(2-hydroxy-ethoxy)-phenyl]-(4-cyano-phenylamino)-acetate was converted in a Pinner reaction into ethyl (RS)-[3-allyl-5-ethyl-2-(2-hydroxy-ethoxy)-phenyl]-(4-carbamimidoyl-phenylamino)-acetate hydrochloride; MS (ISP) m/z 426 (M+H)⁺.

Example 330

In analogy to Example 75, ethyl (RS)-[3-allyl-5-ethyl-2-(2-hydroxy-ethoxy)-phenyl]-(4-carbamimidoyl-phenylamino)-acetate hydrochloride (see Example 329.3) was hydrolyzed with lithium hydroxide to (RS)-[3-allyl-5-ethyl-2-(2-hydroxy-ethoxy)-phenyl]-(4-carbamimidoyl-phenylamino)-acetic acid; MS (ISP) m/z 398 (M+H)⁺.

Example 331

331.1

In analogy to Example 293.1, 3,5-diiodosalicylaldehyde was converted with 2-iodo-O-tetrahydropyranylethanol (Reg.No. 96388-83-9) in DMF at 80° C. within 6 hours into (RS)-3,5-diiodo-2-[2-(tetrahydro-pyran-2-yloxy)-ethoxy]-benzaldehyde; MS (EI) m/z 502 M⁺.

331.2

In analogy to Example 1.1., (RS)-3,5-diiodo-2-[2-(tetrahydro-pyran-2-yloxy)-ethoxy]-benzaldehyde was reacted with 4-aminobenzonitrile and toluene-4-sulphonylmethyl isocyanide. There was obtained methyl (RS)-(4-cyano-phenylamino)-[2-(2-hydroxy-ethoxy)-3,5-diiodo-phenyl]-acetate, MS (ISP) m/z 579 (M+H)⁺.

331.3

In analogy to Example 6.2, methyl (RS)-(4-cyano-phenylamino)-[2-(2-hydroxy-ethoxy)-3,5-diiodo o-phenyl]-acetate was converted in a Pinner reaction into (4-carbamimidoyl-phenylamino)-[2-(2-hydroxy-ethoxy)-3,5-diiodo-phenyl]-acetate hydrochloride; MS (ISP) m/z 596 (M+H)⁺.

331.4

In analogy to Example 327.3, ethyl (4-carbamimidoyl-phenylamino)-[2-(2-hydroxy-ethoxy)-3,5-diiodo o-phenyl]-acetate hydrochloride was reacted with tributylvinylstannane and tetrakis(triphenylphosphine)palladium in a Stille reaction and, after concentration, the crude mixture was chromatographed over silica gel. There was obtained methyl (RS)-4-carbamimidoyl-phenylamino)-[2-(2-hydroxyethoxy)-3,5-divinyl-phenyl]-acetate hydrochloride; MS (ISP) m/z 396 (M+H)+.

Example 332

In analogy to Example 75, methyl (RS)-(4-carbamimidoyl-phenylamino)-[2-(2-hydroxy-ethoxy)-3,5-divinyl-phenyl]-acetate hydrochloride (see Example 327.3) was hydrolyzed with lithium hydroxide to (RS)-(4-carbamimidoyl-phenylamino)-[2-(2-hydroxy-ethoxy)-3,5-divinyl-phenyl]-acetic acid; MS (ISP) m/z 382 (M+H)+, 404 (M+Na)+.

Example 333

333.1

In analogy to Example 293.3, 2-{4-chloro-2-[(4-cyano-phenylamino)-methoxycarbonyl-methyl]-6-iodo-phenoxy}-ethyl (RS)-2-methyl-acrylate (see Example 327.2) was converted with tributyl(phenylethynyl)tin and tetrakis(triphenylphosphine)palladium in a Stille reaction into 2-{4-chloro-2-[(4-cyano-phenylamino)-methoxycarbonyl-methyl]-6-phenylethynyl-phenoxy}-ethyl (RS)-2-methyl-acrylate; MS (ISP) m/z 529.2 (M+H)+, 551.0 (M+Na)+.

333.2

In analogy to Example 6.2, 2-{4-chloro-2-[(4-cyano-phenylamino)-methoxycarbonyl-methyl]-6-phenylethynyl-phenoxy}-ethyl (RS)-2-methyl-acrylate was converted in a Pinner reaction into 2-{2-[(4-carbamimidoyl-phenylamino)-methoxycarbonyl-methyl]-4-chloro-6-phenylethynyl-phenoxy}-ethyl (RS)-2-methyl-acrylate hydrochloride; the product was purified by chromatography over silica gel; MS (ISP) m/z 546.3 (M+H)+.

Example 334

In analogy to Example 6.2, 2-{4-chloro-2-[(4-cyano-phenylamino)-methoxycarbonyl-methyl]-6-phenylethynyl-phenoxy}-ethyl (RS)-2-methyl-acrylate (see Example 333.1) was subjected to a Pinner reaction and methyl (RS)-(4-carbamimidoyl-phenylamino)-[5-chloro-2-(2-hydroxy-ethoxy)-3-phenylethynyl-phenyl]-acetate hydrochloride was isolated as a byproduct by chromatography over silica gel; MS (ISP) m/z 478.3 (M+H)+.

Example 335

In analogy to Example 75, 2-{2-[(4-carbamimidoyl-phenylamino)-methoxycarbonyl-methyl]-4-chloro-6-phenylethynyl-phenoxy}-ethyl (RS)-2-methyl-acrylate hydrochloride (see Example 333.2) was hydrolyzed with lithium hydroxide to (RS)-(4-carbamimidoyl-phenylamino)-[5-chloro-2-(2-hydroxy-ethoxy)-3-phenylethynyl-phenyl]-acetic acid; MS (ISP) m/z 464.2 (M+H)+, 486.1 (M+Na)+.

Example 336

A solution of 210 mg of 2-{2-[(4-carbamimidoyl-phenylamino)-methoxycarbonyl-methyl]-4-chloro-6-phenylethynyl-phenoxy}-ethyl (RS)-2-methyl-acrylate hydrochloride (see Example 333.2) in 5 ml of methanol and 5 ml of THF was hydrogenated in the presence of a catalytic amount of Raney-nickel for 5 hours while stirring at room temperature. The reaction mixture was suction filtered over a filter aid. The filtrate was concentrated and, after lyophilization from water, gave 190 mg of 2-{2-[(4-carbamimidoyl-phenylamino)-methoxycarbonyl-methyl]-4-chloro-6-styryl-phenoxy}-ethyl (RS)-Z-isobutyrate hydrochloride, MS (ISP) m/z 550.2 (M+H)+.

Example 337

In analogy to Example 75, 2-{2-[(4-carbamimidoyl-phenylamino)-methoxycarbonyl-methyl]-4-chloro-6-styryl-phenoxy}-ethyl (RS)-Z-isobutyrate hydrochloride (see Example 336) was hydrolyzed with lithium hydroxide to (RS)-Z-(4-carbamimidoyl-phenylamino)-[5-chloro-2-(2-hydroxy-ethoxy)-3-styryl-phenyl]-acetic acid; MS (ISP) m/z 466.3 (M+H)+.

Example 338

In analogy to Example 29.2, 2-{2-[(4-carbamimidoyl-phenylamino)-methoxycarbonyl-methyl]-4-chloro-6-phenylethynyl-phenoxy}-ethyl (RS)-2-methyl-acrylate hydrochloride (see Example 333.2) was hydrogenated in methanol/dioxan to 2-{2-[(4-carbamimidoyl-phenylamino)-methoxycarbonyl-methyl]-4-chloro-6-phenethyl-phenoxy}-ethyl (RS)-isobutyrate hydrochloride; MS (ISP) m/z 552.4 (M+H)+.

Example 339

In analogy to Example 75, 2-{2-[(4-carbamimidoyl-phenylamino)-methoxycarbonylmethyl]-4-chloro-6-phenethyl-phenoxy}-ethyl (RS)-isobutyrate hydrochloride (see Example 338) was hydrolyzed with lithium hydroxide to (RS)-(4-carbamimidoyl-phenylamino)-[5-chloro-2-(2-hydroxy-ethoxy)-3-phenethyl-phenyl]-acetic acid; MS (ISP) m/z 468.3 (M+H)+.

Example 340

340.1

In analogy to Example 18.1, 5-ethyl-2-hydroxy-3-iodo-benzaldehyde (see Example 329.1) was converted with DIAD and 2-hydroxyethyl methyacrylate in a Mitsonobu reaction into 2-(4-ethyl-2-formyl-6-iodo-phenoxy)-ethyl 2-methyl-acrylate; MS (EI) m/z 388.2 (M), 358.9 (M-CH$_2$O).

340.2

In analogy to Example 1.1., 2-(4-ethyl-2-formyl-6-iodo-phenoxy)-ethyl 2-methyl-acrylate was reacted with 4-aminobenzonitrile and benzyl isocyanide. There was obtained 2-{2-[(4-cyano-phenylamino)-methoxycarbonyl-methyl]-4-ethyl-6-iodo-phenoxy}-ethyl (RS)-2-methyl-acrylate; MS (ISP) m/z 549.1 (M+H)+, 571.2 (M+Na)+.

340.3

In analogy to Example 327.3, 2-{2-[(4-cyano-phenylamino)-methoxycarbonyl-methyl]-4-ethyl-6-iodo-phenoxy}-ethyl (RS)-2-methyl-acrylate was converted with tributyl(phenylethynyl)stannane and tetrakis(triphenylphosphine)palladium in a Stille reaction into 2-{2-[(4-cyano-phenylamino)-methoxycarbonyl-methyl]-4-ethyl-6-phenylethynyl-phenoxy}-ethyl (RS)-2-methyl-acrylate; MS (ISP) m/z 523.3 (M+H)+, 545.3 (M+Na)+.

340.4

In analogy to Example 6.2, 2-{2-[(4-cyano-phenylamino)-methoxycarbonyl-methyl]-4-ethyl-6-phenylethynyl-phenoxy}-ethyl (RS)-2-methyl-acrylate was converted in a Pinner reaction into 2-{2-[(4-carbamimidoyl-phenylamino)-methoxycarbonyl-methyl]-4-ethyl-6-phenylethynyl-phenoxy}-ethyl (RS)-2-methyl-acrylate hydrochloride; the product was purified by chromatography over silica gel; MS (ISP) m/z 540.3 (M+H)+.

Example 341

In analogy to Example 6.2, 2-{2-[(4-cyano-phenylamino)-methoxycarbonyl-methyl]-4-ethyl-6-phenylethynyl-phenoxy}-ethyl (RS)-2-methyl-acrylate (see Example 340.4) was subjected to a Pinner reaction and methyl (RS)-(4-carbamimidoyl-phenylamino)-[5-ethyl-2-(2-hydroxy-ethoxy)-3-phenylethynyl-phenyl]-acetate

Example 342

In analogy to Example 75, methyl (RS)-(4-carbamimidoyl-phenylamino)-[5-ethyl-2-(2-hydroxy-ethoxy)-3-phenylethynyl-phenyl]-acetate hydrochloride (see Example 341) was hydrolyzed with lithium hydroxide to (RS)-(4-carbamimidoyl-phenylamino)-[5-ethyl-2-(2-hydroxy-ethoxy)-3-phenylethynyl-phenyl]-acetic acid hydrochloride; MS (ISP) m/z 458.4 (M+H)$^+$, 480.3 (M+Na)$^+$.

Example 343

343.1

In analogy to Example 89.1, 2-ethyl-4-iodo-phenol (see Example 323.1) was formulated to 3-ethyl-2-hydroxy-5-iodo-benzaldehyde; MS (EI) m/z 276 M$^+$.

343.2

In analogy to Example 18.1, 3-ethyl-2-hydroxy-5-iodo-benzaldehyde was converted with DIAD and 2-benzylethanol in a Mitsonobu reaction into 2-(2-benzyloxy-ethoxy)-3-ethyl-5-iodo-benzaldehyde; MS (EI) m/z 410 M$^+$.

343.3

In analogy to Example 1.1., 2-(2-benzyloxy-ethoxy)-3-ethyl-5-iodo-benzaldehyde was reacted with 4-aminobenzonitrile and toluene-4-sulphonylmethyl isocyanide. There was obtained ethyl (RS)-[2-(2-benzyloxy-ethoxy)-3-ethyl-5-iodo-phenyl]-(4-cyano-phenylamino)-acetate; MS (ISP) m/z 585 (M+H)$^+$, 607 (M+Na)$^+$.

343.3

In analogy to Example 6.2, ethyl (RS)-[2-(2-benzyloxy-ethoxy)-3-ethyl-5-iodo-phenyl]-(4-cyano-phenylamino)-acetate was converted in a Pinner reaction into ethyl (RS)-[2-(2-benzyloxy-ethoxy)-3-ethyl-5-iodo-phenyl]-(4-carbamimidoyl-phenylamino)-acetate hydrochloride; the product was purified by chromatography over silica gel; MS (ISP) m/z 602 (M+H)$^+$.

343.5

In analogy to Example 329.4, ethyl (RS)-[2-(2-benzyloxy-ethoxy)-3-ethyl-5-iodo-phenyl]-(4-carbamimidoyl-phenylamino)-acetate hydrochloride was converted with trimethylsilyl iodide into ethyl (RS)-(4-carbamimidoyl-phenylamino)-[3-ethyl-2-(2-hydroxy-ethoxy)-5-iodo-phenyl]-acetate hydrochloride; MS (ISP) m/z 512 (M+H)$^+$.

343.6

In analogy to Example 327.3, ethyl (RS)-(4-carbamimidoyl-phenylamino)-[3-ethyl-2-(2-hydroxy-ethoxy)-5-iodo-phenyl]-acetate hydrochloride was converted with tributylvinylstannane and tetrakis(triphenylphosphine)palladium in a Stille reaction into ethyl (RS)-(4-carbamimidoyl-phenylamino)-[3-ethyl-2-(2-hydroxy-ethoxy)-5-vinyl-phenyl]-acetate hydrochloride; MS (ISP) m/z 412 (M+H)$^+$.

Example 344

In analogy to Example 75, ethyl (RS)-(4-carbamimidoyl-phenylamino)-[3-ethyl-2-(2-hydroxy-ethoxy)-5-vinyl-phenyl-acetate hydrochloride (see Example 343.6) was hydrolyzed with lithium hydroxide to (RS)-(4-carbamimidoyl-phenylamino)-[3-ethyl-2-(2-hydroxy-ethoxy)-5-vinyl-phenyl]-acetic acid; MS (ISP) m/z 384 (M+H)$^+$.

Example 345

345.1

In analogy to Example 327.3, 2-{2-[(4-cyano-phenylamino)-methoxycarbonyl-methyl]-4-ethyl-6-iodo-phenoxy}-ethyl (RS)-2-methyl-acrylate (see Example 342.2) was converted with tributylethynylstannane and tetrakis(triphenylphosphine)palladium in a Stille reaction into 2-{2-[(4-cyano-phenylamino)-methoxycarbonyl-methyl]-4-ethyl-6-ethynyl-phenoxy}-ethyl (RS)-2-methyl-acrylate; MS (ISP) m/z 447.4 (M+H)$^+$, 469.4 (M+Na)$^+$.

345.2

In analogy to Example 6.2, 2-{2-[(4-cyano-phenylamino)-methoxycarbonyl-methyl]-4-ethyl-6-ethynyl-phenoxy}-ethyl (RS)-2-methyl-acrylate was converted in a Pinner reaction into 2-[2-[(4-carbamimidoyl-phenylamino)-methoxycarbonyl-methyl]-6-(1-chloro-vinyl)-4-ethyl-phenoxy]-ethyl (RS)-2-methyl-acrylate hydrochloride; the product was purified by chromatography over silica gel; MS (ISP) m/z 500.3 (M+H)$^+$.

Example 346

In analogy to Example 6.2, 2-{2-[(4-cyano-phenylamino)-methoxycarbonyl-methyl]-4-ethyl-6-ethynyl-phenoxy}-ethyl (RS)-2-methyl-acrylate (see Example 343.1) was subjected to a Pinner reaction and methyl (RS)-(4-carbamimidoyl-phenylamino)-[3-(1-chloro-vinyl)-5-ethyl-2-(2-hydroxy-ethoxy)-phenyl]-acetate hydrochloride was isolated as a byproduct after chromatography over silica gel; MS (ISP) m/z 432.3 (M+H)$^+$.

Example 347

In analogy to Example 75, 2-[2-[(4-carbamimidoyl-phenylamino)-methoxycarbonyl-methyl]-6-(1-chloro-vinyl)-4-ethyl-phenoxy]-ethyl (RS)-2-methyl-acrylate hydrochloride (see Example 345.2) was hydrolyzed with lithium hydroxide to (RS)-(4-carbamimidoyl-phenylamino)-[3-(1-chloro-vinyl)-5-ethyl-2-(2-hydroxy-ethoxy)-phenyl]-acetic acid; MS (ISP) m/z 418.2 (M+H)$^+$, 440.2 (M+Na)$^+$.

Example 348

348.1

In analogy to Example 327.3, 2-{2-[(4-cyano-phenylamino)-methoxycarbonyl-methyl]-4-ethyl-6-iodo-phenoxy}-ethyl (RS)-2-methyl-acrylate (see Example 340.2) was converted with tributyl(1-ethoxyvinyl)stannane and tetrakis(triphenylphosphine)palladium in a Stille reaction into 2-[2-[(4-cyano-phenylamino)-methoxycarbonyl-methyl]-6-(1-ethoxy-vinyl)-4-ethyl-phenoxy]-ethyl (RS)-2-methyl-acrylate; MS (ISP) m/z 493.2 (M+H)$^+$, 515.2 (M+Na)$^+$.

348.2

In analogy to Example 6.2, 2-[2-[(4-cyano-phenylamino)-methoxycarbonyl-methyl]-6-(1-ethoxy-vinyl)-4-ethyl-phenoxy]-ethyl (RS)-2-methyl-acrylate was converted in a Pinner reaction into 2-{2-acetyl-6-[(4-carbamimidoyl-phenylamino)-methoxycarbonyl-methyl]-4-ethyl-phenoxy}-ethyl (RS)-2-methyl-acrylate hydrochloride; the product was purified by chromatography over silica gel; MS (ISP) m/z 482.4 (M+H)$^+$, 512.3 (M+Na)$^+$.

Example 349

In analogy to Example 75, 2-{2-acetyl-6-[(4-carbamimidoyl-phenylamino)-methoxycarbonyl-methyl]-4-ethyl-phenoxy}-ethyl (RS)-2-methyl-acrylate hydrochloride (see Example 348.2) was hydrolyzed with lithium hydroxide to (RS)-[3-acetyl-5-ethyl-2-(2-hydroxy-ethoxy)-phenyl]-(4-carbamimidoyl-phenylamino)-acetic acid; MS (ISP) m/z 400.4 (M+H)$^+$, 422.3 (M+Na)$^+$.

Example 350

In analogy to Example 29.2, 2-{2-[(4-carbamimidoyl-phenylamino)-methoxycarbonyl-methyl]-4-ethyl-6-phenylethynyl-phenoxy}-ethyl (RS)-2-methyl-acrylate hydrochloride (see Example 340.4) was hydrogenated in methanol/dioxan to 2-{2-[(4-carbamimidoyl-phenylamino)-methoxycarbonyl-methyl]-4-ethyl-6-phenethyl-phenoxy}-ethyl (RS)-isobutyrate hydrochloride; MS (ISP) m/z 546.3 (M+H)$^+$.

Example 351

In analogy to Example 75, 2-{2-[(4-carbamimidoyl-phenylamino)-methoxycarbonyl-methyl]-4-ethyl-6-phenethyl-phenoxy}-ethyl (RS)-isobutyrate hydrochloride (see Example 350) was hydrolyzed with lithium hydroxide to (RS)-(4-carbamimidoyl-phenylamino)-[5-ethyl-2-(2-hydroxy-ethoxy)-3-phenethyl-phenyl]-acetic acid; MS (ISP) m/z 462.2 (M+H)$^+$, 484.3 (M+Na)$^+$.

Example 352

352.1

Analogously to Example 124.1, methyl (RS)-(4-benzyloxy-3-ethoxy-phenyl)-(4-cyano-phenylamino)-acetate (Example 2b) was hydrogenated to (RS)-(4-cyano-phenylamino)-(3-ethoxy-4-hydroxy-phenyl)-acetate.

352.2

0.3 mmol of the phenol obtained in Example 352.1. were dissolved in 1000 µl of DMF and treated with a small amount of sodium iodide and then with 0.3 mmol of potassium tert-butylate. After the addition of 0.3 mmol of 3-methyl-butyl bromide the mixture was left to react for 6 hours at room temperature. Subsequently, 50 µl of formic acid were added, the reaction mixture was filtered and the reaction product was purified by preparative HPLC (RP18, 20% to 95% acetonitrile). There was thus obtained methyl (RS)-(4-cyano-phenylamino)-[3-ethoxy-4-(3-methyl-butoxy)-phenyl]-acetate.

352.3

60 mg of the material obtained according to Example 352.2. were dissolved in 400 µl of chloroform and 1500 µl of dry hydrochloric acid in methanol (w(HCl)=27%). The mixture was left to react for 5 hours at room temperature and was then concentrated. The residue was dissolved in 500 µl of THF and 1500 µl of dry 2 molar ammonia in ethanol and heated for 5 hours to 45° C. Subsequently, 500 µl of 2 molar sodium hydroxide solution were added at room temperature. After 30 minutes the reaction mixture was neutralized with 200 µl of formic acid and concentrated. The residue was dissolved in formic acid and subjected to preparative HPLC (RP18, 10% to 95% acetonitrile). There was thus obtained (R,S)-(4-carbamimidoyl-phenylamino)-[3-ethoxy-4-(3-methyl-butoxy)-phenyl]-acetic acid.

Example 353

The following products were obtained according to the procedure described in Example 352 by using the corresponding alkyl bromides:

353.a.
  By using 3-phenoxy-propyl bromide via methyl (RS)-(4-cyano-phenylamino)-[3-ethoxy-4-(3-phenoxy-propoxy)-phenyl]-acetate there was obtained (R,S)-(4-carbamimidoyl-phenylamino)-[3-ethoxy-4-(3-phenoxy-propoxy)-phenyl]-acetic acid;

353.b.
  by using 2-cyclohexyl-ethyl bromide via (RS)-(4-cyano-phenylamino)-[4-(2-cyclohexyl-ethoxy)-3-ethoxy-phenyl]-acetate there was obtained (R,S)-(4-carbamimidoyl-phenylamino)-[4-(2-cyclohexyl-ethoxy)-3-ethoxy-phenyl]-acetic acid;

353.c.
  by using 2-phenoxy-ethyl bromide via (RS)-(4-cyano-phenylamino)-[3-ethoxy-4-(2-phenoxy-ethoxy)-phenyl]-acetate there was obtained (R,S)-(4-carbamimidoyl-phenylamino)-[3-ethoxy-4-(2-phenoxy-ethoxy)-phenyl]-acetic acid.

Example 354

354.1

0.3 mmol of the phenol obtained in Example 352.1 was dissolved in 1000 µl of DMF and treated with 0.6 mmol of potassium carbonate and subsequently with 0.3 mmol of 2-bromo-2'-methoxyacetophenone. The mixture was left to react for 5 h. at 60° C. and was then filtered. 50 µl of formic acid were added to the filtrate and the mixture was subsequently subjected to preparative HPLC (RP18, 20% to 95% acetonitrile). There was thus obtained methyl (R,S)-(4-cyano-phenylamino)-{3-ethoxy-4-[2-(2-methoxy-phenyl)-2-oxo-ethoxy]-phenyl}-acetate.

354.2.

Analogously to the procedure described obtained in Example 352.3, from the product obtained above there was obtained (R,S)-(4-carbamimidoyl-phenylamino)-{3-ethoxy-4-[2-(2-methoxy-phenyl)-2-oxo-ethoxy]-phenyl}-acetic acid.

Example 355

The following products were obtained according to the procedure described in Example 354 by using the corresponding alkyl bromides:

355.a
  By using 2-bromo-4'-methoxyacetophenone via (RS)-(4-cyano-phenylamino)-{3-ethoxy-4-[2-(4-methoxy-phenyl)-2-oxo-ethoxy]-phenyl}-acetate there was obtained (R,S)-(4-carbamimidoyl-phenylamino)-{3-ethoxy-4-[2-(4-methoxy-phenyl)-2-oxo-ethoxy]-phenyl}-acetic acid;

355.b
  By using 4-(2-oxo-pentyl)-bromide via (RS)-(4-cyano-phenylamino-[3-ethoxy-4-(2-oxo-pentyloxy)-phenyl]-acetate there was obtained (R,S)-(4-carbamimidoyl-phenylamino)-[3-ethoxy-4-(2-oxo-pentyloxy)-phenyl]-acetic acid.

Example 356

356.1

131 mg (0.5 mmol) of triphenylphosphine were dissolved in 650 µl of tetrahydrofuran and cooled to 0° C. under argon. 78 µl (0.5 mmol) of diethyl azodicarboxylate dissolved in 650 µl of tetrahydrofuran were added to this solution and the mixture was left to react for 1 h. Subsequently, 0.5 mmol of 2-(4-fluorophenyl)-ethanol dissolved in 500 µl of dioxan and 0.33 mmol of the phenol prepared in Example 124.1. in 700 µl of tetrahydrofuran were added. The reaction mixture was left to react for 2 hours at room temperature and was then subjected to preparative HPLC (RP18, 20% to 95% acetonitrile). There was thus obtained ethyl (R,S)-(4-cyano-phenylamino)-{3-ethoxy-5-[2-(4-fluoro-phenyl)-ethoxy]-phenyl}-acetate.

356.2.

Analogously to the procedure described in Example 352.3 from the product obtained above there was obtained (R,S)-(4-carbamimidoyl-phenylamino)-{3-ethoxy-5-[2-(4-fluoro-phenyl)-ethoxy]-phenyl}-acetic acid.

Example 357

The following products were obtained according to the procedure described in Example 356 by using the corresponding alcohols:

357.a
- By using (RS)-3-hydroxy-tetrahydrofuran via a mixture of ethyl (R,S)-(4-cyano-phenylamino)-[5-ethyl-2-[(RS)-(tetrahydro-furan-3-yloxy)]-phenyl]-acetate there was obtained a mixture of (R,S)-(4-carbamimidoyl-phenylamino)-[5-ethyl-2-[(RS)-(tetrahydro-furan-3-yloxy)]-phenyl]-acetic acid;

357.b
- by using tetrahydro-4H-pyran-4-ol via ethyl (R,S)-(4-cyano-phenylamino)-[5-ethyl-2-(tetrahydro-pyran-4-yloxy)-phenyl]-acetate there was obtained (R,S)-(4-carbamimidoyl-phenylamino)-[5-ethyl-2-(tetrahydro-pyran-4-yloxy)-phenyl]-acetic acid;

357.c
- by using 2-(hydroxymethyl)-pyridine via ethyl (R,S)-(4-cyano-phenylamino)-[5-ethyl-2-(pyridin-2-ylmethoxy)-phenyl]-acetate there was obtained (R,S)-(4-carbamimidoyl-phenylamino)-[5-ethyl-2-(pyridin-2-ylmethoxy)-phenyl]-acetic acid;

357.d
- by using N-(2-hydroxyethyl)-2-pyrrolidone via ethyl (R,S)-(4-cyano-phenylamino)-{5-ethyl-2-[2-(2-oxo-pyrrolidin-1-yl)-ethoxy]-phenyl}-acetate there was obtained (R,S)-(4-carbamimidoyl-phenylamino)-{5-ethyl-2-[2-(2-oxo-pyrrolidin-1-yl)-ethoxy]-phenyl}-acetic acid.

Example 358

The following products were obtained according to the procedure described in Example 352.2 and 352.3 from the phenol obtained according to Example 124 and the corresponding alkyl bromides:

358.a
- By using 4-bromo-1-butene via methyl (R,S)-(3-but-3-enyloxy-5-ethoxy-phenyl)-(4-cyano-phenylamino)-acetate there was obtained (R,S)-(3-but-3-enyloxy-5-ethoxy-phenyl)-(4-carbamimidoyl-phenylamino)-acetic acid;

358.b
- by using 1-bromo-3-methylbutane via methyl (R,S)-(4-cyano-phenylamino)-[3-ethoxy-5-(3-methyl-butoxy)-phenyl]-acetate there was obtained (R,S)-(4-carbamimidoyl-phenylamino)-[3-ethoxy-5-(3-methyl-butoxy)-phenyl]-acetic acid;

358.c
- by using bromomethylcyclohexane via methyl (R,S)-(4-cyano-phenylamino)-(3-cyclohexylmethoxy-5-ethoxy-phenyl)-acetate there was obtained (R,S)-(4-carbamimidoyl-phenylamino)-(3-cyclohexylmethoxy-5-ethoxy-phenyl)-acetic acid;

358.d
- by using 1-butyl bromide via methyl (R,S)-(3-butoxy-5-ethoxy-phenyl)-(4-cyano-phenylamino)-acetate there was obtained (R,S)-(3-butoxy-5-ethoxy-phenyl)-(4-carbamimidoyl-phenylamino)-acetic acid;

358.e
- by using 2-bromoethyl methyl ether via methyl (R,S)-(4-cyano-phenylamino)-[3-ethoxy-5-(2-methoxy-ethoxy)-phenyl]-acetate there was obtained (R,S)-(4-carbamimidoyl-phenylamino)-[3-ethoxy-5-(2-methoxy-ethoxy)-phenyl]-acetic acid;

358.f
- by using 3-phenoxy-propyl bromide via methyl (R,S)-(4-cyano-phenylamino)-[3-ethoxy-5-(3-phenoxy-propoxy)-phenyl]-acetate there was obtained (R,S)-(4-carbamimidoyl-phenylamino)-[3-ethoxy-5-(3-phenoxy-propoxy)-phenyl]-acetic acid;

358.g
- by using 2-cyclohexyl ethyl bromide via methyl (R,S)-(4-cyano-phenylamino)-[3-(2-cyclohexyl-ethoxy)-5-ethoxy-phenyl]-acetate there was obtained (R,S)-(4-carbamimidoyl-phenylamino)-[3-(2-cyclohexyl-ethoxy)-5-ethoxy-phenyl]-acetic acid;

358.h
- by using cyclopropylmethyl bromide via (R,S)-(4-cyano-phenylamino)-(3-cyclopropylmethoxy-5-ethoxy-phenyl)-acetate there was obtained (R,S)-(4-carbamimidoyl-phenylamino)-(3-cyclopropylmethoxy-5-ethoxy-phenyl)-acetic acid;

358.j
- by using 2-phenoxy-ethyl-bromide via methyl (R,S)-(4-cyano-phenylamino)-[3-ethoxy-5-(2-phenoxy-ethoxy)-phenyl]-acetate there was obtained (R,S)-(4-carbamimidoyl-phenylamino)-[3-ethoxy-5-(2-phenoxy-ethoxy)-phenyl]-acetic acid;

358.k
- by using 1-hexyl bromide via methyl (R,S)-(4-cyano-phenylamino)-(3-ethoxy-5-hexyloxy-phenyl)-acetate there was obtained (R,S)-(4-carbamimidoyl-phenylamino)-(3-ethoxy-5-hexyloxy-phenyl)-acetic acid.

Example 359

The following products were obtained according to the procedure described in Example 354.1 and 354.2 from the phenol obtained according to Example 124 and the corresponding alkyl bromides:

359.a
- By using 2-bromo-acetophenone via methyl (R,S)-(4-cyano-phenylamino)-[3-ethoxy-5-(2-oxo-2-phenyl-ethoxy)-phenyl]-acetate there was obtained (R,S)-(4-carbamimidoyl-phenylamino)-[3-ethoxy-5-(2-oxo-2-phenyl-ethoxy)-phenyl]-acetic acid;

359.b
- by using 2-bromo-2'-methoxy-acetophenone via methyl (R,S)-(4-cyano-phenylamino)-{3-ethoxy-5-[2-(2-methoxy-phenyl)-2-oxo-ethoxy]-phenyl}-acetate there was obtained (R,S)-(4-carbamimidoyl-phenylamino)-{3-ethoxy-5-[2-(2-methoxy-phenyl)-2-oxo-ethoxy]-phenyl}-acetic acid;

359.c
- by using 2-bromo-4'-methoxy-acetophenone via methyl (R,S)-(4-cyano-phenylamino)-{3-ethoxy-5-[2-(4-methoxy-phenyl)-2-oxo-ethoxy]-phenyl}-acetate there was obtained (R,S)-(4-carbamimidoyl-phenylamino)-{3-ethoxy-5-[2-(4-methoxy-phenyl)-2-oxo-ethoxy]-phenyl}-acetic acid;

359.d
- by using 3-methyl-2-oxo-butyl-bromide via methyl (R,S)-(4-cyano-phenylamino)-[3-ethoxy-5-(3-methyl-2-oxo-butoxy)-phenyl]-acetate there was obtained (R,S)-(4-carbamimidoyl-phenylamino)-[3-ethoxy-5-(3-methyl-2-oxo-butoxy)-phenyl]-acetic acid;

359.e
- by using 4-methyl-2-oxo-pentyl-bromide via methyl (R,S)-(4-cyano-phenylamino)-[3-ethoxy-5-(4-methyl- 2-oxo-pentyloxy)-phenyl]-acetate there was obtained (R,S)-(4-carbamimidoyl-phenylamino)-[3-ethoxy-5-(4-methyl-2-oxo-pentyloxy)-phenyl]-acetic acid;

359.f
by using 2-oxo-pentyl-bromide via (R,S)-(4-carbamimidoyl-phenylamino)-[3-ethoxy-5-(2-oxo-pentyloxy)-phenyl]-acetate there was obtained (R,S)-(4-carbamimidoyl-phenylamino)-[3-ethoxy-5-(2-oxo-pentyloxy)-phenyl]-acetic acid;

359.g
by using 2-oxo-butyl-bromide via (R,S)-(4-cyano-phenylamino)-[3-ethoxy-5-(2-oxo-butoxy)-phenyl]-acetate there was obtained (R,S)-(4-carbamimidoyl-phenylamino)-[3-ethoxy-5-(2-oxo-butoxy)-phenyl]-acetic acid.

Example 360

The following products were obtained according to the procedure described in Example 354.1 and 354.2 from the phenol obtained according to Example 148 and the corresponding alcohols:

360.a
by using 2-methylthio-ethanol via methyl (R,S)-(4-cyano-phenylamino)-[5-ethyl-2-(2-methylsulphanyl-ethoxy)-3-propyl-phenyl]-acetate there was obtained (R,S)-(4-carbamimidoyl-phenylamino)-[5-ethyl-2-(2-methylsulphanyl-ethoxy)-3-propyl-phenyl]-acetic acid;

360.b
by using 4-(hydroxymethyl)-pyridine via methyl (R,S)-(4-cyano-phenylamino)-[5-ethyl-3-propyl-2-(pyridin-4-ylmethoxy)-phenyl]-acetate there was obtained (R,S)-(4-carbamimidoyl-phenylamino)-[5-ethyl-3-propyl-2-(pyridin-4-ylmethoxy)-phenyl]-acetic acid;

360.c
by using benzyl alcohol via methyl (R,S)-(2-benzyloxy-5-ethyl-3-propyl-phenyl)-(4-cyano-phenylamino)-acetate there was obtained (R,S)-(2-benzyloxy-5-ethyl-3-propyl-phenyl)-(4-carbamimidoyl-phenylamino)-acetic acid;

360.d
by using 3-furanmethanol via methyl (R,S)-(4-cyano-phenylamino)-[5-ethyl-2-(furan-3-ylmethoxy)-3-propyl-phenyl]-acetate there was obtained (R,S)-(4-carbamimidoyl-phenylamino)-[5-ethyl-2-(furan-3-ylmethoxy)-3-propyl-phenyl]-acetic acid;

360.e
by using 3-(hydroxymethyl)-pyridine via methyl (R,S)-(4-cyano-phenylamino)-[5-ethyl-3-propyl-2-(pyridin-3-ylmethoxy)-phenyl]-acetate there was obtained (R,S)-(4-carbamimidoyl-phenylamino)-[5-ethyl-3-propyl-2-(pyridin-3-ylmethoxy)-phenyl]-acetic acid;

360.f
by using 4-methyl-5-thiazolyl-ethanol via methyl (R,S)-(4-cyano-phenylamino)-{5-ethyl-2-[2-(4-methyl-thiazol-5-yl)-ethoxy]-3-propyl-phenyl}-acetate there was obtained (R,S)-(4-carbamimidoyl-phenylamino)-{5-ethyl-2-[2-(4-methyl-thiazol-5-yl)-ethoxy]-3-propyl-phenyl}-acetic acid;

360.g
by using cyclopentanol via methyl (R,S)-(4-carbamimidoyl-phenylamino)-(2-cyclopentyloxy-5-ethyl-3-propyl-phenyl)-acetate there was obtained (R,S)-(4-carbamimidoyl-phenylamino)-(2-cyclopentyloxy-5-ethyl-3-propyl-phenyl)-acetic acid;

360.h
by using (hydroxymethyl)-cyclopropane via methyl (R,S)-(4-cyano-phenylamino)-(2-cyclopropylmethoxy-5-ethyl-3-propyl-phenyl)-acetate there was obtained (R,S)-(4-carbamimidoyl-phenylamino)-(2-cyclopropylmethoxy-5-ethyl-3-propyl-phenyl)-acetic acid;

360.j
by using (hydroxymethyl)-cyclohexane via methyl (R,S)-(4-cyano-phenylamino)-(2-cyclo-hexylmethoxy-5-ethyl-3-propyl-phenyl)-acetate there was obtained (R,S)-(4-carbamimidoyl-phenylamino)-(2-cyclohexylmethoxy-5-ethyl-3-propyl-phenyl)-acetic acid;

360.k
by using (hydroxymethyl)-cyclopentane via methyl (R,S)-(4-cyano-phenylamino)-(2-cyclopentylmethoxy-5-ethyl-3-propyl-phenyl)-acetate there was obtained (R,S)-(4-carbamimidoyl-phenylamino)-(2-cyclopentylmethoxy-5-ethyl-3-propyl-phenyl)-acetic acid;

360.l
by using 2-(3-fluorophenyl)-ethanol via methyl (R,S)-(4-cyano-phenylamino)-15-ethyl-2-[2-(3-fluoro-phenyl)-ethoxy]-3-propyl-phenyl}-acetate there was obtained (R,S)-(4-carbamimidoyl-phenylamino)-{5-ethyl-2-[2-(3-fluoro-phenyl)-ethoxy]-3-propyl-phenyl}-acetic acid;

360.m
by using 2-(hydroxymethyl)-pyridine via methyl (R,S)-(4-cyano-phenylamino)-[5-ethyl-3-propyl-2-(pyridin-2-ylmethoxy)-phenyl]-acetate there was obtained (R,S)-(4-carbamimidoyl-phenylamino)-[5-ethyl-3-propyl-2-(pyridin-2-ylmethoxy)-phenyl]-acetic acid;

360.n
by using 2-isopropoxy-ethanol via methyl (R,S)-(4-cyano-phenylamino)-[5-ethyl-2-(2-isopropoxy-ethoxy)-3-propyl-phenyl]-acetate there was obtained (R,S)-(4-carbamimidoyl-phenylamino)-[5-ethyl-2-(2-isopropoxy-ethoxy)-3-propyl-phenyl]-acetic acid;

360.o
by using 2-methoxy-ethanol via methyl (R,S)-(4-cyano-phenylamino)-[5-ethyl-2-(2-methoxy-ethoxy)-3-propyl-phenyl]-acetate there was obtained (R,S)-(4-carbamimidoyl-phenylamino)-[5-ethyl-2-(2-methoxy-ethoxy)-3-propyl-phenyl]-acetic acid;

360.p
by using 2-(2-fluorophenyl)-ethanol via methyl (R,S)-(4-cyano-phenylamino)-{5-ethyl-2-[2-(2-fluoro-phenyl)-ethoxy]-3-propyl-phenyl}-acetate there was obtained (R,S)-(4-carbamimidoyl-phenylamino)-{5-ethyl-2-[2-(2-fluoro-phenyl)-ethoxy]-3-propyl-phenyl}-acetic a 360.q
by using 2-(4-fluorophenyl)- ethanol via methyl (R,S)-(4-cyano-phenylamino)-{5-ethyl-2-[2-(4-fluoro-phenyl)-ethoxy]-3-propyl-phenyl}-acetate there was obtained (R,S)-(4-carbamimidoyl-phenylamino)-{5-ethyl-2-[2-(4-fluoro-phenyl)-ethoxy]-3-propyl-phenyl}-acetic acid;

360.r
by using tetrahydro-4H-pyran-4-ol via methyl (R,S)-(4-cyano-phenylamino)-[5-ethyl-3-propyl-2-(tetrahydro-pyran-4-yloxy)-phenyl]-acetate there was obtained (R,S)-(4-carbamimidoyl-phenylamino)-[5-ethyl-3-propyl-2-(tetrahydro-pyran-4-yloxy)-phenyl]-acetic acid;

360.s
  by using 2,5-difluoro-benzyl alcohol via methyl (R,S)-(4-cyano-phenylamino)-[2-(2,5-difluoro-benzyloxy)-5-ethyl-3-propyl-phenyl]-acetate there was obtained (R,S)-(4-carbamimidoyl-phenylamino)-[2-(2,5-difluoro-benzyloxy)-5-ethyl-3-propyl-phenyl]-acetic acid;

360.t
  by using 3,4-difluoro-benzyl alcohol via methyl (R,S)-(4-cyano-phenylamino)-[2-(3,4-difluoro-benzyloxy)-5-ethyl-3-propyl-phenyl]-acetate there was obtained (R,S)-(4-carbamimidoyl-phenylamino)-[2-(3,4-difluoro-benzyloxy)-5-ethyl-3-propyl-phenyl]-acetic acid;

360.u
  by using (RS)-1-isopropyl-3-pyrrolidinol via a mixture of methyl (RS) and (SR)-(4-cyano-phenylamino)-[5-ethyl-2-[(RS)-(1-isopropyl-pyrrolidin-3-yloxy)]-3-propyl-phenyl]-acetate there was obtained a mixture of (RS) and (SR)-(4-carbamimidoyl-phenylamino)-[5-ethyl-2-[(RS)-(1-isopropyl-pyrrolidin-3-yloxy)]-3-propyl-phenyl]-acetic acid;

360.v
  by using (RS)-3-hydroxy-tetrahydrofuran via a mixture of methyl (RS) and (SR)-(-(4-cyano-phenylamino)-[5-ethyl-3-propyl-2-[(RS)-(tetrahydro-furan-3-yloxy)]-phenyl]-acetate there was obtained a mixture of (RS) and (SR)-(4-carbamimidoyl-phenylamino)-[5-ethyl-3-propyl-2-[(RS)-(tetrahydro-furan-3-yloxy)]-phenyl]-acetic acid;

360.w
  by using (RS)-tetrahydro-3-furanmethanol via a mixture of methyl (R,S) and (SR)-(4-cyano-phenylamino)-[5-ethyl-3-propyl-2-[(RS)-(tetrahydro-furan-3-ylmethoxy)]-phenyl]-acetate there was obtained a mixture of (R,S) and (SR)-(4-carbamimidoyl-phenylamino)-[5-ethyl-3-propyl-2-[(RS)-(tetrahydro-furan-3-ylmethoxy)-phenyl]-acetic acid;

Example 361

The following products were obtained according to the procedure described in Example 354.1 and 354.2 from the phenol obtained according to Example 134.3 and the corresponding alcohols:

361.a
  By using 3,4-difluoro-benzyl alcohol via methyl (R,S)-(4-cyano-phenylamino)-[2-(3,4-difluoro-benzyloxy)-5-ethyl-phenyl]-acetate there was obtained (R,S)-(4-carbamimidoyl-phenylamino)-[2-(3,4-difluoro-benzyloxy)-5-ethyl-phenyl]-acetic acid;

361.b
  by using 2-methylthio-ethanol via methyl (R,S)-(4-cyano-phenylamino)-[5-ethyl-2-(2-methylsulphanyl-ethoxy)-phenyl]-acetate there was obtained (R,S)-(4-carbamimidoyl-phenylamino)-[5-ethyl-2-(2-methylsulphanyl-ethoxy)-phenyl]-acetic acid;

361.c
  by using 4-(hydroxymethyl)-pyridine via methyl (R,S)-(4-cyano-phenylamino)-[5-ethyl-2-(pyridin-4-ylmethoxy)-phenyl]-acetate there was obtained (R,S)-(4-carbamimidoyl-phenylamino)-[5-ethyl-2-(pyridin-4-ylmethoxy)-phenyl]-acetic acid;

361.d
  by using 3-furanmethanol via methyl (R,S)-(4-cyano-phenylamino)-[5-ethyl-2-(furan-3-ylmethoxy)-phenyl]-acetate there was obtained (R,S)-(4-carbamimidoyl-phenylamino)-[5-ethyl-2-(furan-3-ylmethoxy)-phenyl]-acetic acid;

361.e
  by using 3-(hydroxymethyl)-pyridine via methyl (R,S)-(4-cyano-phenylamino)-[5-ethyl-2-(pyridin-3-ylmethoxy)-phenyl]-acetate there was obtained (R,S)-(4-carbamimidoyl-phenylamino)-[5-ethyl-2-(pyridin-3-ylmethoxy)-phenyl]-acetic acid;

361.f
  by using cyclopentanol via methyl (R,S)-(4-cyano-phenylamino)-(2-cyclopentyloxy-5-ethyl-phenyl)-acetate there was obtained (R,S)-(4-carbamimidoyl-phenylamino)-(2-cyclopentyloxy-5-ethyl-phenyl)-acetic acid;

361.g
  by using (hydroxymethyl)-cyclopropane via methyl (R,S)-(4-cyano-phenylamino)-(2-cyclopropylmethoxy-5-ethyl-phenyl)-acetate there was obtained (R,S)-(4-carbamimidoyl-phenylamino)-(2-cyclopropylmethoxy-5-ethyl-phenyl)-acetic acid;

361.h
  by using (hydroxymethyl)-cyclopentane via methyl (R,S)-(4-cyano-phenylamino)-(2-cyclopentylmethoxy-5-ethyl-phenyl)-acetate there was obtained (R,S)-(4-carbamimidoyl-phenylamino)-(2-cyclopentylmethoxy-5-ethyl-phenyl)-acetic acid;

361.i
  by using 2-(3-fluorophenyl)-ethanol via methyl (R,S)-(4-cyano-phenylamino)-{5-ethyl-2-(2-(3-fluoro-phenyl)-ethoxy]-phenyl}-acetate there was obtained (R,S)-(4-carbamimidoyl-phenylamino)-{5-ethyl-2-[2-(3-fluoro-phenyl)-ethoxy]-phenyl}-acetic acid;

361.k
  by using 2-propargyl alcohol via methyl (R,S)-(4-cyano-phenylamino)-(5-ethyl-2-prop-2-ynyloxy-phenyl)-acetate there was obtained (R,S)-(4-carbamimidoyl-phenylamino)-(5-ethyl-2-prop-2-ynyloxy-phenyl)-acetic acid;

361.l
  by using 2-(2-fluorophenyl)-ethanol via methyl (R,S)-(4-cyano-phenylamino)-{5-ethyl-2-[2-(2-fluoro-phenyl)-ethoxy-phenyl]-acetate there was obtained (R,S)-(4-carbamimidoyl-phenylamino)-{5-ethyl-2-[2-(2-fluoro-phenyl)-ethoxy]-phenyl}-acetic acid;

361.m
  by using 2-(4-fluorophenyl)-ethanol via methyl (R,S)-(4-cyano-phenylamino)-15-ethyl-2-[2-(4-fluoro-phenyl)-ethoxy]-phenyl}-acetate there was obtained (R,S)-(4-carbamimidoyl-phenylamino)-{5-ethyl-2-[2-(4-fluoro-phenyl)-ethoxy]-phenyl}-acetic acid;

361.n
  by using 2,5-difluoro-benzyl alcohol via methyl (R,S)-(4-cyano-phenylamino)-[2-(2,5-difluoro-benzyloxy)-5-ethyl-phenyl-acetate there was obtained (R,S)-(4-carbamimidoyl-phenylamino)-[2-(2,5-difluoro-benzyloxy)-5-ethyl-phenyl]-acetic acid;

361.o
  by using 2,5-difluoro-benzyl alcohol via methyl (R,S)-(4-cyano-phenylamino)-[2-(2,5-difluoro-benzyloxy)-5-ethyl-phenyl]-acetate there was obtained (R,S)-(4-carbamimidoyl-phenylamino)-[2-(2,5-difluoro-benzyloxy)-5-ethyl-phenyl]-acetic acid;

361.p
  by using (RS)-1-isopropyl-3-pyrrolidinol via a mixture of methyl (RS) and (SR)-(4-cyano-phenylamino)-[5- ethyl-2-[(RS)-(1-isopropyl-pyrrolidin-3-yloxy)]-phenyl]-acetate there was obtained a mixture of (RS) and (SR)-(4-carbamimidoyl-phenylamino)-[5-ethyl-2-[(RS)-(1-isopropyl-pyrrolidin-3-yloxy)]-phenyl]-acetic acid;

361.q by using (RS)-tetrahydro-3-furanmethanol via a mixture of methyl (RS) and (SR)-(4-cyano-phenylamino)-[5-ethyl-2-[(RS)-(tetrahydro-furan-3-ylmethoxy)]-phenyl]-acetate there was obtained a mixture of (RS) and (SR)-(4-carbamimidoyl-phenylamino)-[5-ethyl-2-[(RS)-(tetrahydro-furan-3-ylmethoxy)]-phenyl]-acetic acid;

361.r by using (RS)-(2-fluorophenyl)-methyl-carbinol via a mixture of methyl (RS) and (SR)-(4-cyano-phenylamino)-{5-ethyl-2-[(RS)-[1-(2-fluoro-phenyl)-ethoxy]]-phenyl}-acetate there was obtained a mixture of (RS) and (SR)-(4-carbamimidoyl-phenylamino)-{5-ethyl-2-[(RS)-[1-(2-fluoro-phenyl)-ethoxy]]-phenyl}-acetic acid.

Example 362

The following products were obtained according to the procedure described in Example 354.1 and 354.2 from the phenol obtained according to Example 124 and the corresponding alcohols:

362.a

By using 2-methylthio-ethanol via methyl (R,S)-(4-cyano-phenylamino)-[3-ethoxy-5-(2-methylsulphanyl-ethoxy)-phenyl]-acetate there was obtained (R,S)-(4-carbamimidoyl-phenylamino)-3-ethoxy-5(2-methylsulphanyl-ethoxy)-phenyl]-acetic acid;

362.b by using 4-(hydroxymethyl)-pyridine via methyl (R,S)-(4-cyano-phenylamino)-[3-ethoxy-5-(pyridin-4-ylmethoxy)-phenyl]-acetate there was obtained (R,S)-(4-carbamimidoyl-phenylamino)-[3-ethoxy-5-(pyridin-4-ylmethoxy)-phenyl]-acetic acid;

362.c by using 4-methyl-5-thiazolyl-ethanol via methyl (R,S)-(4-cyano-phenylamino)-{3-ethoxy-5-[2-(4-methyl-thiazol-5-yl)-ethoxy]-phenyl}-acetate there was obtained (R,S)-(4-carbamimidoyl-phenylamino)-{3-ethoxy-5-[2-(4-methyl-thiazol-5-yl)-ethoxy]-phenyl}-acetic acid;

362.d by using (hydroxymethyl)-cyclopentane via methyl (R,S)-(4-cyano-phenylamino)-(3-cyclopentylmethoxy-5-ethoxy-phenyl)-acetate there was obtained (R,S)-(4-carbamimidoyl-phenylamino)-(3-cyclopentylmethoxy-5-ethoxy-phenyl)-acetic acid;

362.e by using 2-(3-fluorophenyl)-ethanol via methyl (R,S)-(4-cyano-phenylamino)-{3-ethoxy-5-[2-(3-fluoro-phenyl)-ethoxy]-phenyl}-acetate there was obtained (R,S)-(4-carbamimidoyl-phenylamino)-{3-ethoxy-5-[2-(3-fluoro-phenyl)-ethoxy]-phenyl}-acetic acid;

362.f by using 2-(hydroxymethyl)-pyridine via methyl (R,S)-(4-cyano-phenylamino)-[3-ethoxy-5-(pyridin-2-ylmethoxy)-phenyl]-acetate there was obtained (R,S)-(4-carbamimidoyl-phenylamino)-[3-ethoxy-5-(pyridin-2-ylmethoxy)-phenyl]-acetic acid;

362.g by using 2-isopropoxy-ethanol via methyl (R,S)-(4-cyano-phenylamino)-[3-ethoxy-5-(2-isopropoxy-ethoxy)-phenyl]-acetate there was obtained (R,S)-(4-carbamimidoyl-phenylamino)-[3-ethoxy-5-(2-isopropoxy-ethoxy)-phenyl]-acetic acid;

362.h by using propargyl alcohol via methyl (R,S)-(4-cyano-phenylamino)-(3-ethoxy-5-prop-2-ynyloxy-phenyl)-acetate there was obtained (R,S)-(4-carbamimidoyl-phenylamino)-(3-ethoxy-5-prop-2-ynyloxy-phenyl)-acetic acid;

362.j by using 2-(2-fluorophenyl)-ethanol via methyl (R,S)-(4-cyano-phenylamino)-{3-ethoxy-5-[2-(2-fluoro-phenyl)-ethoxy]-phenyl}-acetate there was obtained (R,S)-(4-carbamimidoyl-phenylamino)-{3-ethoxy-5-[2-(2-fluoro-phenyl)-ethoxy]-phenyl}-acetic acid;

362.k by using 2-indanol via methyl (R,S)-(4-cyano-phenylamino)-[3-ethoxy-5-(indan-2-yloxy)-phenyl]-acetate there was obtained (R,S)-(4-carbamimidoyl-phenylamino)-[3-ethoxy-5-(indan-2-yloxy)-phenyl]-acetic acid;

362.l by using tetrahydro-4H-pyran-4-ol via methyl (R,S)-(4-cyano-phenylamino)-[3-ethoxy-5-(tetrahydro-pyran-4-yloxy)-phenyl]-acetate there was obtained (R,S)-(4-carbamimidoyl-phenylamino)-[3-ethoxy-5-(tetrahydro-pyran-4-yloxy)-phenyl]-acetic acid.

Example A: Pharmaceutical Composition I

|  | Per tablet |
| --- | --- |
| Active substance | 200 mg |
| Microcrystalline cellulose | 155 mg |
| Maize starch | 25 mg |
| Talc | 25 mg |
| Hydroxypropylmethylcellulose | 20 mg |
|  | 425 mg |

Example B: Pharmaceutical Composition II

|  | Per Capsule |
| --- | --- |
| Active substance | 100.0 mg |
| Maize starch | 20.0 mg |
| Lactose | 95.0 mg |
| Talc | 4.5 mg |
| Magnesium stearate | 0.5 mg |
|  | 220.0 mg |

Upon reading the present specification, various alternative embodiments may become obvious to the skilled artisan. These embodiments are to be considered within the scope and spirit of the invention that is only to be limited by the claims that follow and their equivalents.

What is claimed is:

1. A compound of the formula:

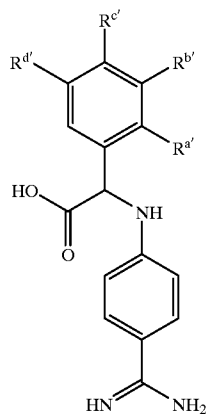

wherein, $R^{a'}$ is flourine;
$R^{b'}$ is alkoxy;
$R^{c'}$ is hydrogen; and
$R^{d'}$ is alkoxy;

or a hydrate or solvate thereof, or a physiologically usable salt of one of the mentioned compounds.

2. A compound of the formula:

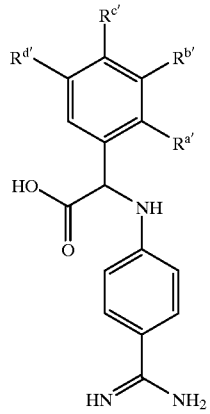

wherein, $R^{a'}$ is hydroxyethoxy;
$R^{b'}$ is hydrogen;
$R^{c'}$ is alkoxy; and
$R^{d'}$ is alkoxy;

or a hydrate or solvate thereof, or a physiologically usable salt of one of the mentioned compounds.

3. The compound in accordance with claim 2, which is (RS)-(4-carbamimidoyl-phenylamino)-[4,5-diethoxy-2-(2-hydroxy-ethoxy)-phenyl]-acetic acid.

4. A compound of the formula:

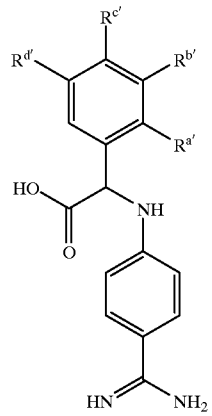

wherein, $R^{a'}$ is carbamoylmethoxy;
$R^{b'}$ is hydrogen;
$R^{c'}$ is alkoxy; and
$R^{d'}$ is alkoxy;

or a hydrate or solvate thereof, or a physiologically usable salt of one of the mentioned compounds.

5. A compound of the formula:

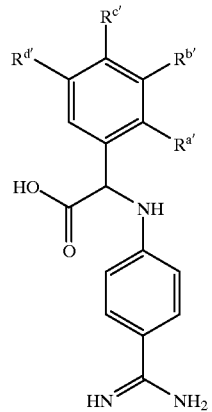

wherein, $R^{a'}$ is hydrogen;
$R^{b'}$ is alkoxy;
$R^{c'}$ is dialkylaminoalkoxy; and
$R^{d'}$ is hydrogen;

or a hydrate or solvate thereof, or a physiologically usable salt of one of the mentioned compounds.

6. The compound in accordance with claim 5, which is (RS)-(4-carbamimidoyl-phenylamino)-[4-(2-dimethylamino-ethoxy)-3-ethoxy-phenyl]-acetic acid.

7. A compound of the formula:

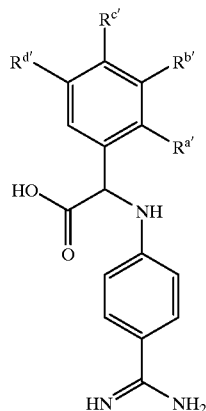

wherein, $R^{a'}$ is hydrogen;
$R^{b'}$ is alkoxy;
$R^{c'}$ is hydroxyalkoxy; and
$R^{d'}$ is hydrogen;

or a hydrate or solvate thereof, or a physiologically usable salt of one of the mentioned compounds.

8. The compound in accordance with claim 7, which is (RS)- and (SR)-(4-carbamimidoyl-phenylamino)-[3-ethoxy-4-[(RS)-2-hydroxy-1-methyl-ethoxy]-phenyl]-acetic acid.

9. A compound of the formula:

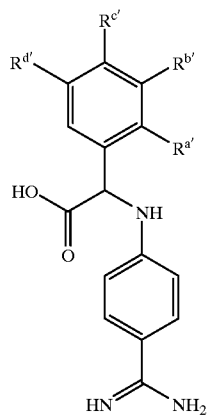

wherein, $R^{a'}$ is hydrogen;
$R^{b'}$ is alkoxy;
$R^{c'}$ is alkoxy; and
$R^{d'}$ is hydrogen;

or a hydrate or solvate thereof, or a physiologically usable salt of one of the mentioned compounds.

10. A compound of the formula:

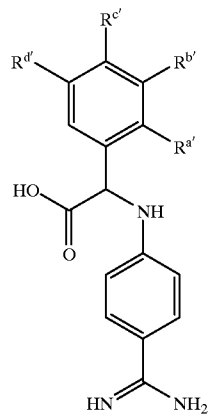

wherein, $R^{a'}$ is hydrogen;
$R^{b'}$ is alkoxy;
$R^{c'}$ is hydrogen; and
$R^{d'}$ is alkoxy;

or a hydrate or solvate thereof, or a physiologically usable salt of one of the mentioned compounds.

11. A compound of the formula:

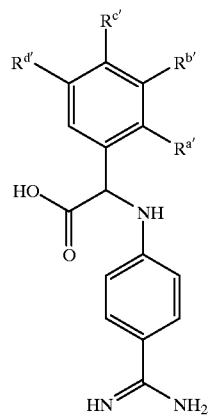

wherein, $R^{a'}$ is hydrogen;
$R^{b'}$ is alkoxy;
$R^{c'}$ is hydroxyalkoxy; and
$R^{d'}$ is hydrogen;

or a hydrate or solvate thereof, or a physiologically usable salt of one of the mentioned compounds.

12. The compound in accordance with claim 11, which is (RS)-(4-carbamimidoyl-phenylamino)-[3-ethoxy-4-(2-hydroxy-ethoxy)-phenyl]-acetic acid.

13. A compound of the formula:

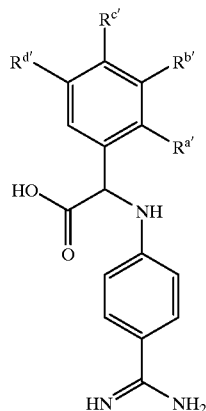

wherein, $R^{a'}$ is hydrogen;

$R^{b'}$ is hydroxycycloalkoxy;

$R^{c'}$ is hydrogen; and $R^{d'}$ is alkoxy;

or a hydrate or solvate thereof, or a physiologically usable salt of one of the mentioned compounds.

14. The compound in accordance with claim 13, which is (RS)- and (SR)-(4-carbamimidoyl-phenylamino)-[3-ethoxy-5-[(1-RS,2RS)-2-hydroxy-cyclopentyloxy]-phenyl]-acetic acid.

15. The compound in accordance with claim 13, which is (RS)- and (SR)-(4-carbamimidoyl-phenylamino)-[3-ethoxy-5-[(1RS,2RS)-2-hydroxy-cyclohexyloxy]-phenyl]-acetic acid.

16. A compound of the formula:

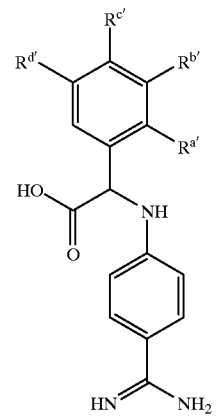

wherein, $R^{a'}$ is hydrogen;

$R^{b'}$ is hydroxyalkoxy;

$R^{c'}$ is alkoxy; and $R^{d'}$ is alkoxy;

or a hydrate or solvate thereof, or a physiologically usable salt of one of the mentioned compounds.

17. The compound in accordance with claim 16, which is (RS)-(4-carbamimidoyl-phenylamino)-[4,5-diethoxy-2-(3-hydroxy-propoxy)-phenyl]-acetic acid.

18. The compound in accordance with claim 1, which is (RS)-(4-carbamimidoyl-phenylamino)-(2-fluoro-3,5-dimethoxy-phenyl)-acetic acid.

19. The compound in accordance with claim 1, which is (RS)-(4-carbamimidoyl-phenylamino)-(3,5-diethoxy-2-fluoro-phenyl)-acetic acid.

20. The compound in accordance with claim 4, which is (RS)-(4-carbamimidoyl-phenylamino)-(2-carbamoylmethoxy-4,5-diethoxy-phenyl)-acetic acid.

21. The compound in accordance with claim 9, which is (RS)-(4-carbamimidoyl-phenylamino)-(3-ethoxy-4-methoxy-phenyl)-acetic acid hydrochloride.

22. The compound in accordance with claim 10, which is (RS)-(4-carbamimidoyl-phenylamino)-3,5-diethoxy-phenyl)-acetic acid.

* * * * *